United States Patent
Tlsty et al.

(10) Patent No.: US 12,332,245 B2
(45) Date of Patent: Jun. 17, 2025

(54) CANCER BIOMARKERS AND METHODS OF USE THEREOF

(71) Applicant: THE REGENTS OF THE UNIVERSITY OF CALIFORNIA, Oakland, CA (US)

(72) Inventors: Thea D. Tlsty, San Francisco, CA (US); Hal K. Berman, Toronto (CA); Mona L. Gauthier, Toronto (CA); Bob Y. Liu, San Francisco, CA (US); Colleen A. Fordyce, San Francisco, CA (US); Curtis R. Pickering, San Francisco, CA (US); Paul A. Reynolds, San Francisco, CA (US); Nancy Dumont, San Francisco, CA (US); Geoffrey M. Benton, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/664,006

(22) Filed: May 18, 2022

(65) Prior Publication Data

US 2023/0204591 A1 Jun. 29, 2023

Related U.S. Application Data

(63) Continuation of application No. 15/284,349, filed on Oct. 3, 2016, which is a continuation of application No. 12/373,047, filed as application No. PCT/US2007/015584 on Jul. 3, 2007, now abandoned.

(60) Provisional application No. 60/830,960, filed on Jul. 14, 2006.

(51) Int. Cl.
*C12Q 1/68* (2018.01)
*G01N 33/574* (2006.01)

(52) U.S. Cl.
CPC . *G01N 33/57492* (2013.01); *G01N 33/57415* (2013.01)

(58) Field of Classification Search
None
See application file for complete search history.

(56) References Cited

U.S. PATENT DOCUMENTS

| | | |
|---|---|---|
| 4,318,846 A | 3/1982 | Khanna et al. |
| 4,415,732 A | 11/1983 | Caruthers et al. |
| 4,458,066 A | 7/1984 | Caruthers et al. |
| 4,591,570 A | 5/1986 | Chang |
| 4,605,735 A | 8/1986 | Miyoshi et al. |
| 4,683,195 A | 7/1987 | Mullis et al. |
| 4,683,202 A | 7/1987 | Mullis |
| 4,757,141 A | 7/1988 | Fung et al. |
| 4,889,818 A | 12/1989 | Gelfand et al. |
| 4,947,210 A | 8/1990 | Nagata et al. |
| 5,091,652 A | 2/1992 | Mathies et al. |
| 5,143,854 A | 9/1992 | Pirrung et al. |
| 5,171,695 A | 12/1992 | Ekins |
| 5,185,439 A | 2/1993 | Arnold, Jr. et al. |
| 5,223,409 A | 6/1993 | Ladner et al. |
| 5,242,828 A | 9/1993 | Bergstrom et al. |
| 5,283,174 A | 2/1994 | Arnold et al. |
| 5,288,644 A | 2/1994 | Fodor et al. |
| 5,292,658 A | 3/1994 | Cormier et al. |
| 5,313,264 A | 5/1994 | Ivarsson et al. |
| 5,322,770 A | 6/1994 | Gelfand |
| 5,324,633 A | 6/1994 | Fodor et al. |
| 5,399,491 A | 3/1995 | Kacian et al. |
| 5,403,484 A | 4/1995 | Ladner et al. |
| 5,409,818 A | 4/1995 | Davey et al. |
| 5,418,144 A | 5/1995 | Cormier et al. |
| 5,432,049 A | 7/1995 | Fischer et al. |
| 5,445,934 A | 8/1995 | Fodor et al. |
| 5,470,710 A | 11/1995 | Weiss et al. |
| 5,486,452 A | 1/1996 | Gordon et al. |
| 5,492,806 A | 2/1996 | Drmanac et al. |
| 5,498,538 A | 3/1996 | Kay et al. |
| 5,503,980 A | 4/1996 | Cantor |
| 5,510,270 A | 4/1996 | Fodor et al. |
| 5,516,637 A | 5/1996 | Huang et al. |
| 5,525,464 A | 6/1996 | Drmanac et al. |
| 5,532,128 A | 7/1996 | Eggers et al. |
| 5,538,848 A | 7/1996 | Livak et al. |
| 5,545,531 A | 8/1996 | Rava et al. |
| 5,547,732 A | 8/1996 | Edwards et al. |

(Continued)

FOREIGN PATENT DOCUMENTS

| | | |
|---|---|---|
| AU | 2007/2763055 | 1/2008 |
| AU | 2011/248632 | 12/2012 |

(Continued)

OTHER PUBLICATIONS

U.S. Appl. No. 17/652,466, filed Feb. 24, 2022, Bremer.
Allred et al., "Adjuvant tamoxifen reduces subsequent breast cancer in women with estrogen receptor-positive ductal carcinoma in situ: A study based on NSABP protocol B-24". J Clin Oncol. 2012; vol. 30, No. 12, pp. 1268-1273.
Breastcancer.org, "New Guidelines Say Lumpectomy Margins Can Be Small as Long as Tumor Has No Ink on It". 2 pages; (Mar. 12, 2018) available at https://www.breastcancer.org/research-news/20140402. This reference is a webpage and the date apparent on the webpage is listed herewith. However, the webpage may have been available, in some form, prior to this date.

(Continued)

*Primary Examiner* — Celine X Qian
(74) *Attorney, Agent, or Firm* — KNOBBE, MARTENS, OLSON & BEAR, LLP

(57) ABSTRACT

The present invention provides detection methods for detecting a pre-cancerous epithelial cell signature. The present invention further provides reagents for use in the detection methods. A subject detection method is useful in various imaging, diagnostic, prognostic, and patient monitoring methods, which are also provided.

21 Claims, 45 Drawing Sheets

Specification includes a Sequence Listing.

(56) References Cited

U.S. PATENT DOCUMENTS

| | | |
|---|---|---|
| 5,547,839 A | 8/1996 | Dower et al. |
| 5,554,517 A | 9/1996 | Davey et al. |
| 5,556,752 A | 9/1996 | Lockhart et al. |
| 5,571,698 A | 11/1996 | Ladner et al. |
| 5,578,832 A | 11/1996 | Trulson et al. |
| 5,580,732 A | 12/1996 | Grossman et al. |
| 5,585,481 A | 12/1996 | Arnold, Jr. et al. |
| 5,593,839 A | 1/1997 | Hubbell et al. |
| 5,599,695 A | 2/1997 | Pease et al. |
| 5,625,033 A | 4/1997 | Kay et al. |
| 5,631,734 A | 5/1997 | Stern et al. |
| 5,648,211 A | 7/1997 | Fraiser et al. |
| 5,658,727 A | 8/1997 | Barbas et al. |
| 5,661,028 A | 8/1997 | Foote |
| 5,667,988 A | 9/1997 | Barbas et al. |
| 5,683,888 A | 11/1997 | Campbell |
| 5,723,591 A | 3/1998 | Livak et al. |
| 5,736,330 A | 4/1998 | Fulton |
| 5,741,668 A | 4/1998 | Ward et al. |
| 5,744,312 A | 4/1998 | Mamone et al. |
| 5,760,951 A | 6/1998 | Dixon et al. |
| 5,777,079 A | 7/1998 | Tsien et al. |
| 5,786,146 A | 7/1998 | Herman et al. |
| 5,800,992 A | 9/1998 | Fodor et al. |
| 5,804,387 A | 9/1998 | Cormack et al. |
| 5,807,522 A | 9/1998 | Brown et al. |
| 5,849,481 A | 12/1998 | Urdea et al. |
| 5,851,829 A | 12/1998 | Marasco et al. |
| 5,874,304 A | 2/1999 | Zolotukhin et al. |
| 5,876,146 A | 3/1999 | Deaver et al. |
| 5,876,930 A | 3/1999 | Livak et al. |
| 5,876,995 A | 3/1999 | Bryan |
| 5,904,915 A | 5/1999 | Fujibayashi et al. |
| 5,925,558 A | 7/1999 | Tsien et al. |
| 5,948,899 A | 9/1999 | Arnold et al. |
| 5,965,371 A | 10/1999 | Marasco et al. |
| 5,981,180 A | 11/1999 | Chandler |
| 6,004,745 A | 12/1999 | Arnold et al. |
| 6,007,996 A | 12/1999 | McNamara et al. |
| 6,057,107 A | 5/2000 | Fulton |
| 6,063,603 A | 5/2000 | Davey et al. |
| 6,171,797 B1 | 1/2001 | Perbost |
| 6,180,351 B1 | 1/2001 | Cattell |
| 6,197,599 B1 | 3/2001 | Chin et al. |
| 6,225,047 B1 | 5/2001 | Hutchens et al. |
| 6,232,072 B1 | 5/2001 | Fisher |
| 6,242,266 B1 | 6/2001 | Schleifer et al. |
| 6,320,196 B1 | 11/2001 | Dorsel et al. |
| 6,323,043 B1 | 11/2001 | Caren et al. |
| 6,329,209 B1 | 12/2001 | Wagner et al. |
| 6,331,393 B1 | 12/2001 | Laird et al. |
| 6,355,934 B1 | 3/2002 | Osgood et al. |
| 6,579,684 B2 | 6/2003 | Price et al. |
| 6,610,484 B1 | 8/2003 | Hung |
| 6,797,393 B2 | 9/2004 | Qiao et al. |
| 6,919,211 B1 | 7/2005 | Fodor et al. |
| 7,011,949 B2 | 3/2006 | Amorese et al. |
| 7,081,340 B2 * | 7/2006 | Baker ............... C12N 15/1003 435/6.16 |
| 7,112,404 B2 | 9/2006 | Laird et al. |
| 7,186,512 B2 | 3/2007 | Martienssen et al. |
| 7,446,185 B2 | 11/2008 | Nelson |
| 7,452,727 B2 | 11/2008 | Henning et al. |
| 11,543,411 B2 | 1/2023 | Bremer et al. |
| 11,821,900 B2 | 11/2023 | Bremer |
| 2002/0197676 A1 | 12/2002 | Lukyanov et al. |
| 2003/0225528 A1 | 12/2003 | Baker |
| 2003/0225529 A1 | 12/2003 | Ecker et al. |
| 2005/0032085 A1 | 2/2005 | Labas et al. |
| 2006/0063190 A1 | 3/2006 | Fischer et al. |
| 2006/0129331 A1 | 6/2006 | Akilesh et al. |
| 2006/0275844 A1 | 12/2006 | Linke et al. |
| 2007/0009915 A1 | 1/2007 | Wang |
| 2007/0077582 A1 | 4/2007 | Slepnev |
| 2007/0105133 A1 | 5/2007 | Clarke et al. |
| 2010/0003189 A1 | 1/2010 | Tlsty et al. |
| 2010/0068717 A1 | 3/2010 | Badve et al. |
| 2010/0158894 A1 | 6/2010 | Umemura |
| 2011/0183333 A1 | 7/2011 | Martin et al. |
| 2012/0003639 A1 | 1/2012 | Kerlikowske et al. |
| 2013/0317083 A1 | 11/2013 | Rigoutsos |
| 2017/0184601 A1 | 6/2017 | Tlsty et al. |
| 2017/0350895 A1 | 12/2017 | Bremer et al. |
| 2022/0187301 A1 | 6/2022 | Bremer |
| 2022/0260569 A1 | 8/2022 | Bremer |
| 2023/0136619 A1 | 5/2023 | Bremer et al. |

FOREIGN PATENT DOCUMENTS

| | | |
|---|---|---|
| AU | 2013/205536 | 5/2013 |
| AU | 2013/205531 | 11/2016 |
| CA | 2657576 | 1/2008 |
| EP | 0244210 | 11/1989 |
| EP | 0204157 | 10/1990 |
| EP | 0245071 | 1/1992 |
| EP | 0329822 | 6/1994 |
| EP | 0373203 | 8/1994 |
| EP | 0721016 | 7/1996 |
| EP | 0728520 | 5/2001 |
| EP | 0785280 | 4/2003 |
| EP | 0799897 | 6/2006 |
| EP | 2041574 | 4/2009 |
| EP | 2442108 | 4/2012 |
| EP | 2442109 | 4/2012 |
| EP | 2450710 | 5/2012 |
| EP | 2564200 | 3/2013 |
| EP | 3227687 | 10/2017 |
| EP | 3508854 | 7/2019 |
| WO | WO 1991/02814 | 3/1991 |
| WO | WO 1992/15673 | 9/1992 |
| WO | WO 1995/00669 | 1/1995 |
| WO | WO 1995/07463 | 3/1995 |
| WO | WO 1995/21265 | 8/1995 |
| WO | WO 1995/22058 | 8/1995 |
| WO | WO 1995/35505 | 12/1995 |
| WO | WO 1996/31622 | 10/1996 |
| WO | WO 1997/02357 | 1/1997 |
| WO | WO 1997/10365 | 3/1997 |
| WO | WO 1997/27317 | 7/1997 |
| WO | WO 1997/292212 | 8/1997 |
| WO | WO 1998/14605 | 4/1998 |
| WO | WO 1998/26277 | 6/1998 |
| WO | WO 1999/39210 | 8/1999 |
| WO | WO 1999/49019 | 9/1999 |
| WO | WO 1999/51773 | 10/1999 |
| WO | WO 2000/04382 | 1/2000 |
| WO | WO 2000/04389 | 1/2000 |
| WO | WO 2000/04390 | 1/2000 |
| WO | WO 2000/54046 | 9/2000 |
| WO | WO 2000/56934 | 9/2000 |
| WO | WO 2001/14425 | 3/2001 |
| WO | WO 2001/40803 | 6/2001 |
| WO | WO 2002/019767 | 3/2002 |
| WO | WO 2000/63701 | 6/2002 |
| WO | WO 2005/038051 | 4/2005 |
| WO | WO 2005/083429 | 9/2005 |
| WO | WO 2008/008284 | 1/2008 |
| WO | WO 2011/139721 | 11/2011 |
| WO | WO 2016/090323 | 6/2016 |
| WO | WO 2020/056338 | 3/2020 |

OTHER PUBLICATIONS

Chivukula et al., "Ductal Carcinoma In Situ: One Size Does Not Fit All". Women's Health. Sep. 2010:669-672.

Cuzick et al., Effect of tamoxifen and radiotherapy in women with locally excised ductal carcinoma in situ: long-term results from the UK/ANZ DCIS trial, The Lancet Oncology, vol. 12, Issue 1, pp. 21-29, 2011.

Declaration By Troy Bremer in U.S. Appl. No. 15/529,966, filed Feb. 2, 2021.

Fisher et al., "Prevention of invasive breast cancer in women with ductal carcinoma in situ: An update of the National Surgical

(56) References Cited

OTHER PUBLICATIONS

Adjuvant Breast and Bowel Project experience". Semin Oncol., Aug. 1, 2001; vol. 28, No. 4, pp. 400-418.
Lari et al., "Biological Markers in DCIS and Risk of Breast Recurrence: A Systematic Review". J Cancer, 2011: vol. 2, pp. 232-261.
Marsh K. et al., "Frequent Alterations of Cell Cycle Regulators in Early-Stage Breast Lesions as Detected By Immunohistochemistry". Br J Cancer, 1998; vol. 77, No. 9, pp. 1460-1468.
Picarsic et al., Predictors of invasive breast cancer or DCIS recurrence in estrogen receptor positive (ER+) and estrogen receptor negative (ER-) ductal carcinoma in situ (DCIS) patients with and without associated invasive carcinoma (IC) (Journal of Clinical Oncology, 2009, 27, No. 15_Suppl; Abstract E11523).
Picarsic et al., Role of Transcription Factors [FOXA1,GATA-3] in Predicting Outcomes in Recurrent Ductal Carcinoma-In-Situ (DCIS) or Invasive Carcinoma (IC) in DCIS Patients on Core Needle Biopsies of Breast. Cancer Res (2009) 69 (24_Supplement): 2115.
Siewertsz van Reesema L. et al., "SIAH and EGFR; Two RAS Pathway Biomarkers are Highly Prognostic in Locally Advanced and Metastatic Breast Cancer". EBioMedicine. Sep. 1, 2016;11: 183-198.
Solin, L. J. et al., "A Multigene Expression Assay to Predict Local Recurrence Risk for Ductal Carcinoma In Situ of the Breast". J Nat Cancer Inst., May 15, 2013; 105(10): 701-710.
Vicini et al., "Biosignatures to Optimize Adjuvant Radiation Therapy Use in Patients with DCIS with High Risk Clinicopathologic Features". American Society of Radiation Oncology Annual Meeting 2021, 2 pages.
Wärnberg et al., "Abstract GS5-08: A Validation of DCIS Biiological Risk Profile in a Randomised Study for Radiation Therapy with 20 Year Follow-up (SweDCIS)". Cancer Res. Feb. 15, 2018; Abstract.
Yang M. et al., "Microinvasive ductal carcinoma {T1 mic) of the breast. The clinicopathological profile and immunohistochemical features of 28 cases". Pathol Inter'l. 2003; vol. 53, pp. 422-428.
Response to U.S. Office Action dated Sep. 24, 2014, filed Mar. 23, 2015 in U.S. Appl. No. 12/373,047.
Response to U.S. Office Action dated May 29, 2015, filed Nov. 20, 2015 in U.S. Appl. No. 12/373,047.
Response to U.S. Office Action dated Mar. 11, 2022, filed Aug. 5, 2022 in U.S. Appl. No. 15/284,349.
U.S. Office Action dated Apr. 11, 2014 in U.S. Appl. No. 13/094,729.
Response (Supplemental) to Office Action dated Jul. 23, 2015, filed on Apr. 14, 2016 in U.S. Appl. No. 13/094,729.
U.S. Office Action dated Jan. 18, 2022, received in U.S. Appl. No. 13/094,729.
Response to Office Action dated Jan. 18, 2022, filed Jun. 21, 2022 in U.S. Appl. No. 13/094,729.
U.S. Office Action dated Aug. 15, 2022, received in U.S. Appl. No. 13/094,729.
Response to U.S. Office Action dated Dec. 7, 2021, filed Feb. 9, 2022 in U.S. Appl. No. 15/529,966.
U.S. Office Action dated Mar. 1, 2022 in U.S. Appl. No. 15/529,966.
Response to U.S. Office Action dated Mar. 1, 2022 filed Aug. 25, 2022 in U.S. Appl. No. 15/529,966.
U.S. Office Action dated Jun. 14, 2022 in U.S. Appl. No. 17/652,471.
Response to Restriction Requirement dated Jun. 14, 2022, filed Aug. 10, 2022 in U.S. Appl. No. 17/652,471.
U.S. Office Action dated Aug. 30, 2022 in U.S. Appl. No. 17/652,471.
Canadian Office Action dated May 2, 2022 in CA Application No. 2657576.
Response to European Office Action dated Jul. 18, 2011, filed Jan. 26, 2012 in EP Application No. 07810252.2.
Response to European Office Action dated Aug. 11, 2014, filed May 20, 2015 in EP Application No. 07810252.2.
Response to European Search Report dated Jun. 27, 2012, filed Jan. 24, 2013 in EP Application No. 11188923.4.
Response to Office Action dated Feb. 18, 2013, filed Aug. 26, 2013 in EP Application No. 11188923.4.
Response to European Office Action dated Jul. 15, 2014, filed Apr. 29, 2015 in EP Application No. 11188923.4.
Response to European Office Action dated May 18, 2015, filed Sep. 18, 2015 in EP Application No. 11188923.4.
Response to European Office Action dated May 12, 2016, filed Nov. 22, 2016 in EP Application No. 11188923.4.
Response to European Office Action dated Jun. 12, 2017, filed Oct. 17, 2017 in EP Application No. 11188923.4.
Response to European Office Action dated Feb. 23, 2018, filed Sep. 4, 2018 in EP Application No. 11188923.4.
Response to European Office Action dated Nov. 29, 2018, filed Apr. 9, 2019 in EP Application No. 11188923.4.
Response to European Office Action dated Sep. 16, 2019, filed Jan. 21, 2020 in EP Application No. 11188923.4.
Response to Extended Search Report dated Mar. 20, 2012, filed Februay 7, 2013 in EP Application No. 11188925.9.
Response to European Office Action dated Mar. 4, 2013, filed Sep. 13, 2013 in EP Application No. 11188925.9.
Response to Extended Search Report dated Mar. 20, 2012, filed Februay 7, 2013 in EP Application No. 11188926.7.
Response to European Office Action dated Mar. 4, 2013, filed Sep. 13, 2013 in European Application No. 11188926.7.
Response to European Office Action dated Sep. 26, 2013, filed Jul. 2, 2014 in EP Application No. 11188926.7.
European Office Action dated Apr. 13, 2022 in EP Application No. 20190672.4.
Partial European Search Report dated Jun. 30, 2022 in EP Application No. EP 19859855.9.
Response to Japanese Office Action dated Apr. 8, 2014, filed Jul. 8, 2014 in JP Application No. 2009- 520751.
File History, U.S. Appl. No. 13/094,729, filed Apr. 26, 2011.
File History, U.S. Appl. No. 17/275,406, filed Mar. 11, 2021.
File History, U.S. Appl. No. 17/652,471, filed Feb. 24, 2021.
Bouvier-Labit, C., et al., "P16 and P19 MRNA expression in neuroglial tumours: Correlation with KI67 proliferation index, neuropathology and applied neurobiology," 1999, vol. 25, pp. 408-416.
Canadian Office Action dated May 1, 2020, in Canadian Application 2,797,585.
Darling, Maria L. Rosenfield et al., "Atypical ductal hyperplasia and ductal carcinoma in situ as revealed by large-core needle breast biopsy: Results of surgical excision," American Journal of Roentgenology, 2000, vol. 175, pp. 1341-1346.
Response to European Office Action Response filed Apr. 23, 2019 in European Patent Application No. EP15865163.8.
Response to U.S. Office Action filed Jun. 28, 2019 in U.S. Appl. No. 15/529,966.
Response to U.S Office Action filed Oct. 17, 2019 in U.S. Appl. No. 15/529,966.
Wiechmann. L et al., "The molecular journey from ductal carcinoma in situ to invasive breast cancer," American Cancer Society, 2008, vol. 112, pp. 2130-2142.
Zhou et al., "Tumor Markers Predicting Recurrence Type after a Primary Ductal Carcinoma In Situ", Cancer Research, vol. 71, No. 24, P4-10-01, Dec. 1, 2012, XP055643824.
Zhou et al., "A Comparison of Tumor Biology in Primary Ductal Carcinoma In Situ Recurring as Invasive Carcinoma versus a New In Situ", International Journal of Breast Cancer, vol. 2013, Jan. 1, 2013, pp. 1-8, XP055643823.
Response to Canadian Office Action dated (Dec. 15, 2014), filed Jun. 10, 2015 received in Canadian Appl. No. 2,657,576.
Response to Canadian Office Action dated (Dec. 19, 2016), filed Feb. 24, 2017 received in Canadian Appl. No. 2,657,576.
Response to Canadian Office Action dated (Jun. 21, 2017), filed Dec. 19, 2017 received in Canadian Appl. No.2,657,576.
Response to Canadian Office Action dated (May 31, 2018), filed Nov. 27, 2019 in Canadian Patent Application Np. 2,657,576.
Response to Canadian Office Action dated (Apr. 21, 2017), filed Oct. 20, 2017 Canadian Application No. 2,797,585.
Response to Canadian Office Action dated (Dec. 1, 2017), filed Jun. 1, 2018 in Canadian Application 2,797, 585.
Response to Canadian Office Action dated (Jun. 7, 2019), filed Dec. 9, 2019 in Canadian Application 2,797,585.

(56) References Cited

OTHER PUBLICATIONS

Response to Canadian Office Action dated (May 1, 2020), filed Nov. 2, 2020 in Canadian Application 2,797,585.
Declaration by Troy Bremer and Exhibits (A-G) in U.S. Appl. No. 13/094,729, dated Nov. 9, 2020.
Notice of Allowance in U.S. Appl. No. 15/529,966, dated Jun. 1, 2021.
Response to Office Action dated Dec. 21, 2020 Response Filed Jan. 18, 2021 in European Patent Application No. EP 15865163.8.
U.S. Office Action dated Jun. 22, 2020 in U.S. Appl. No. 15/529,966.
U.S. Office Action dated Mar. 2, 2020 in U.S. Appl. No. 15/529,966.
Response to Office Action dated Mar. 15, 2021 filed on Jun. 14, 2021 in U.S. Appl. No. 13/094,729.
Final Office Action dated Mar. 15, 2021 in U.S. Appl. No. 13/094,729.
European Office Action dated Jun. 11, 2021 in European Patent Application No. 18209239.5.
Office Action Response filed on Feb. 22, 2018 in U.S. Appl. No. 15/529,966 in 11 pages.
Office Action Response filed on Aug. 16, 2018 in U.S. Appl. No. 15/529,966 in 15 pages.
Office Action Response filed on May 29, 2020 in U.S. Appl. No. 15/529,966 in 15 pages.
Office Action Response filed on Feb. 3, 2021 in U.S. Appl. No. 15/529,966 in 19 pages.
Response to European Office Action filed May 28, 2020 in European Patent Application No. EP15865163.8.
Response to Office Action (dated Nov. 10, 2014) Filed Jul. 19, 2016, in Australian Patent Application No. 2013205531.
Canadian Office Action dated Dec. 9, 2015, received in Canadian Appl. No. 2,657,576.
Response to Canadian Office Action dated (Dec. 9, 2015), filed Jun. 9, 2016 received in Canadian Appl. No. 2,657,576.
Canadian Office Action dated Jun. 30, 2020, received in Canadian Appl. No. 2,657,576.
Canadian Office Action dated Jun. 14, 2021, received in Canadian Appl. No. 2,657,576.
Response to Office Action dated Sep. 17, 2013 filed on Mar. 14, 2014 in U.S. Appl. No. 13/094,729.
Response to Office Action dated Apr. 11, 2014 filed on Jul. 11, 2014 in U.S. Appl. No. 13/094,729.
Response to Office Action dated Jul. 23, 2015 filed on Jan. 21, 2016 in U.S. Appl. No. 13/094,729.
Response to Office Action dated Apr. 27, 2016 filed on Sep. 27, 2016 in U.S. Appl. No. 13/094,729.
Response to Office Action dated Dec. 5, 2017 filed on Mar. 6, 2017 in U.S. Appl. No. 13/094,729.
Response to Office Action dated Mar. 24, 2017 filed on Jun. 26, 2017 in U.S. Appl. No. 13/094,729.
Response to Office Action dated Mar. 16, 2018 filed on Jun. 14, 2018 in U.S. Appl. No. 13/094,729.
Response to Office Action dated Sep. 26, 2018 filed on Feb. 25, 2019 in U.S. Appl. No. 13/094,729.
Response to Office Action dated Mar. 29, 2019 filed on Jul. 1, 2019 in U.S. Appl. No. 13/094,729.
Response to Office Action dated Oct. 8, 2019 filed on Feb. 11, 2020 in U.S. Appl. No. 13/094,729.
U.S. Office Action dated Jun. 8, 2020, received in U.S. Appl. No. 13/094,729.
Response to Office Action dated Jun. 8, 2020 filed on Nov. 9, 2020 in U.S. Appl. No. 13/094,729.
Response to Australian Office Action dated Sep. 19, 2013 filed on Jun. 3, 2015 in Australian Application No. 2011248632.
Canadian Office Action dated Dec. 1, 2017, Canadian Application No. 2,797,585.
Response to Canadian Office Action dated Dec. 1, 2017, Filed Jun. 12, 2018, Canadian Application No. 2,797,585.
Canadian Office Action dated Jun. 7, 2019, Canadian Application No. 2,797,585.
Response to Canadian Office Action dated Jun. 7, 2019, Filed Dec. 9, 2019 Canadian Application No. 2,797,585.
Response to European Office Action dated Sep. 30, 2014, Filed Aug. 16, 2016 European Application No. 11721599.6.
Response to European Office Action dated Mar. 6, 2017, Filed Jul. 4, 2017 European Application No. 11721599.6.
Response to European Office Action dated Apr. 19, 2018, Filed Jun. 18, 2018 European Application No. 11721599.6.
Office Action dated Aug. 3, 2021 received in U.S. Appl. No. 13/094,729 in 32 pages.
Canadian Office Action dated Apr. 7, 2021 Canadian Application No. 2,797,585.
Wood, The Role of Clinical Trials in Changing Therapy for Ductal Carcinoma In Situ. Annals of Surgical Oncology, 2004; 11 (1):24S-27S. (Year: 2004).
Boughey et al. Current Treatment and Clinical Trial Developments for Ductal Carcinoma In Situ of the Breast Boughey et al. The Oncologist; 2007;12:1276-1287. (Year: 2007).
Response to Canadian Office Action dated Apr. 7, 2021, Filed Oct. 7, 2021, Canadian Application No. 2,797,585.
Response to Canadian Office Action dated Jun. 14, 2021, filed Nov. 8, 2021 in Canadian Appl. No. 2,657,576.
Response to Office Action dated Jan. 29, 2021 filed on Dec. 10, 2021 in European Patent Application No. 20190672.4 in 5 pages.
Response to Office Action dated Aug. 3, 2021 filed on Dec. 2, 2021 in U.S. Appl. No. 13/094,729.
Office Action dated Dec. 7, 2021 in U.S. Appl. No. 15/529,966.
Response to European Search Reported dated Mar. 19, 2019 filed on Jan. 9, 2020 in European Patent Application No. 18209239.5.
Response to Office Action dated Jun. 11, 2021 filed Dec. 8, 2021 in European Patent Application No. 18209239.5.
Dunne et al., Effect of Margin Status on Local Recurrence After Breast Conservation and Radiation Therapy for Ductal Carcinoma In Situ, Journal of Clinical Oncology, vol. 27, No. 10, 2009.
Office Action Response filed on Oct. 30, 2020 in Canadian Patent Application No. 2657576 in 63 pages.
Office Action Response filed on Dec. 10, 2020 in Canadian Patent Application No. 2797585 in 46 pages.
Office Action dated Dec. 21, 2020 received in European Patent Application No. EP15865163.8 in 3 pages.
Office Action Response Filed Jan. 18, 2021 in European Patent Application No. EP15865163.8 in 3 pages.
Office Action dated Jan. 29, 2021 received in European Patent Application No. 20190672.4 in 9 pages.
Office Action Response and declaration filed on Feb. 3, 2021 in U.S. Appl. No. 15/529,966 in 23 pages.
Office Action dated Mar. 15, 2021 received in U.S. Appl. No. 13/094,729 in 32 pages.
Office Action Response and declaration filed on Nov. 9, 2020 in U.S. Appl. No. 13/094,729 in 21 pages.
Affymetrix Solutions for Cancer Analysis Data Sheet, dated 2005.
Boland (British Journal of Cancer 2004 vol. 90 pp. 423-429) (Year: 2004).
Burstein (The New England Journal of Medicine vol. 350 No 14 pp. 1430-1441 2004) (Year: 2004).
Cheng et al (Journal of the National Cancer Institute, 1997, 89: 1356-1360).
Ernster et al., "Detection of DCIS in women undergoing screening Mammography", J. Natl Cancer vol. 94 No. 20, pp. 1546-1954 (2002).
European Office Action dated Aug. 5, 2009 in corresponding European Patent Application No. 07810252.2.
European Office Action dated Nov. 25, 2019 in European Application No. 15 865 163.8.
European Search Report dated Mar. 19, 2019 in European Patent Application No. 18209239.5.
Extended European Search Report dated Sep. 21, 2018 in European Patent Application No. 15865163.8.
International Search Report dated Sep. 19, 2008 in International Application No. PCT-US07/15584.
International Search report and written opinion dated Dec. 5, 2019 in international application No. PCT/US19/51128.
March (British Journal of Cancer 1998 vol. 77 No 9 pp. 1460-1468) (Year: 1998).

(56) References Cited

OTHER PUBLICATIONS

Marsh, KL et al., "Loss of heterozygosity at chromosome 9p in ductal carcinoma in situ and invasive carcinoma of the breast," British Journal of Cancer, 1998, vol. 77, No. 9, pp. 1439-1447.
Mohsin (Modern Pathology 2004 vol. 17 pp. 1545-1554) (Year: 2004).
Office Action dated Nov. 10, 2014 in Australian Patent Application No. 2013205531.
Office Action dated Nov. 10, 2014 in Australian Patent Application No. 2013205536.
Office Action dated Feb. 23, 2018 in European Patent Application No. 11188923.4.
Prelude Press Release dated Aug. 2, 2018 entitled Journal of Clinical Cancer Res arch Publication Demonstrates that DCISionRT® Provides Prognostic and Predictive Power for Assessing a Patient's DCIS Risk.
Response to Office Action (dated Jun. 23, 2011) filed Sep. 23, 2011 in U.S. Appl. No. 12/373,047.
Response to US Office Action (dated Apr. 10, 2012) filed Jul. 9, 2012 in related U.S. Appl. No. 12/373,047.
Response to Australian Office Action (dated Jul. 25, 2012) filed Mar. 14, 2014 in corresponding Australian Application No. 2007273055.
Response to Australian Office Action (dated Mar. 25, 2014) filed Apr. 9, 2014 in corresponding Australian Application No. 2007273055.
Response to Canadian Office Action (dated Nov. 20, 2013) filed May 20, 2014 in corresponding Canadian Application No. 2657576.
Response to European Office Action (dated Aug. 5, 2009) filed May 17, 2010 in corresponding European Application No. 07810252.2.
Response to European Office Action (dated May 31, 2010) filed Nov. 25, 2010 in corresponding European Application No. 07810252.2.
Response to European Office Action (dated Dec. 8, 2010) filed Jun. 14, 2011 in corresponding European Application No. 07810252.2.
Response to European Office Action (dated Sep. 20, 2013) filed Jun. 30, 2014 in corresponding European Application No. 11188923.4.
Response to European Office Action (dated Sep. 26, 2013) filed Jul. 2, 2014 in corresponding European Application No. 11188925.9.
Response to European Office Action (dated Sep. 26, 2013) filed Jul. 2, 2014 in corresponding European Application No. 11188926.7.
Response to Japanese Office Action (dated Jan. 8, 2013) filed Jul. 5, 2013 in corresponding Japanese Application No. 2009-520751.
Response to European Communication pursuant to Rules 161 (1) and 162 EPC (dated Dec. 7, 2012) filed Jun. 5, 2013 in corresponding European Application No. 11721599.6.
Response to U.S. Office Action dated (Apr. 11, 2014), filed Jul. 11, 2014 received in U.S. Appl. No. 13/094,729.
Response to U.S. Office Action dated (Jul. 23, 2015), filed Jan. 21, 2016 in U.S. Appl. No. 13/094,729.
Response to U.S. Office Action dated (Sep. 17, 2013), filed Mar. 14, 2014 received in U.S. Appl. No. 13/094,729.
Response to U.S. Office Action dated (Apr. 27, 2016), filed Sep. 27, 2016 received in U.S. Appl. No. 13/094,729.
Response to U.S. Office Action dated (Dec. 5, 2016), filed Mar. 6, 2017 received in U.S. Appl. No. 13/094,729.
Response to U.S. Office Action dated (Mar. 24, 2017), Filed Jul. 19, 2017, received in U.S. Appl. No. 13/094,729.
Response to U.S. Office Action dated (Mar. 16, 2018), Filed Jun. 14, 2018, in U.S. Appl. No. 13/094,729.
Response to U.S. Office Action dated (Sep. 26, 2018), filed Feb. 25, 2019 in U.S. Appl. No. 13/094,729.
Response to U.S. Office Action dated (Mar. 29, 2019), filed Jul. 1, 2019, in U.S. Appl. No. 13/094,729.
Response to U.S. Office Action dated (Oct. 8, 2019), filed Feb. 11, 2020 in U.S. Appl. No. 13/094,729.
Response to Canadian Office Action dated (Nov. 20, 2013), filed May 20, 2014 received in Canadian Appl. No. 2,657,576.
Salido (Breast Cancer Research 2005 vol. 7 R267-R273) (Year: 2005).
Sendur, et al., Cardiotoxicity of Novel HER2-Targeted Therapies, Current Medical Research and Opinion, vol. 29, No. 8, pp. 1015-1024, 2013.
Steinman (Annals of Clinical and Laboratory Science vol. 37 No. 2 2007 pp. 127-134) (Year: 2007).
Office Action in Canadian Patent Application Np. 2,657,576, dated Jun. 30, 2020.
Office Action in Canadian Application 2,797,585, dated May 1, 2020.
Office Action in U.S. Appl. No. 13/094,729, dated Jun. 8, 2020.
Office Action in U.S. Appl. No. 15/529,966, dated Jun. 22, 2020.
Response to Office Action in European Patent Application No. EP15865163.8, filed May 28, 2020.
Response to European Search Report dated Mar. 19, 2019 in European Patent Application No. 18209239.5, filed Jan. 9, 2020.
Response to Office Action dated Sep. 16, 2019 in European Patent Application No. 1188923.4, filed Jan. 21, 2020.
Office Action dated Sep. 16, 2019 in European Application No. 11188923.4.
Office Action dated Oct. 8, 2019 in U.S. Appl. No. 13/094,729.
Office Action dated Jun. 7, 2019 in Canadian Application No. 2797585.
Office Action dated Jul. 17, 2019 in U.S. Appl. No. 15/529,966.
Dedeoğlu, Analysis of Differentially expressed genes in breast Cancer: brca1-induced gene expression Profiles and meta- analysis gene Signature, Thesis Submitted to Bilkent University, (2009).
European Search Reported dated Mar. 13, 2019 in European Patent Application No. 1820939.5.
Long-Term Results Show that Radiation Therapy After Lumpectomy to Remove DCIS Reduces Recurrence Risk, Published Oct. 4, 2013 < https://www.breastcancer.org/research-news/20131004> Applicants note that the webpage was printed on Mar. 12, 2018, and has a publication date of 2011, however, the webpage may have been available, in some form, prior to this date.
Older Women Diagnosed with DCIS or Early-Stage Disease Have Excellent Prognosis, Published Mar. 16, 2011 < https://www.breastcancer.org/research-news/20110316> Applicants note that the webpage was printed on Mar. 12, 2018, and has a publication date of 2011, however, the webpage may have been available, in some form, prior to this date.
Office Action dated May 31, 2018 in Canadian Patent Application Np. 2,657,576.
Office Action dated Sep. 26, 2018 in U.S. Appl. No. 13/094,729.
Office Action dated Nov. 29, 2018 in European Patent Application No. 1188923.4.
Office Action dated Mar. 18, 2019 in U.S. Appl. No. 15/529,966.
Office Action dated Mar. 29, 2019 in U.S. Appl. No. 13/094,729.
Supplementary European Search Report dated Sep. 21, 2018 in European Patent Application Np: 15865163.8.
Wolf et al., FOXA1: Growth Inhibitor and a Favorable Prognostic Factor in Human Breast Cancer, Int. J. Cancer, vol. 120, pp. 1013-1022, (2006).
File History, U.S. Appl. No. 15/529,966, filed May 25, 2017.
Office Action Dated Apr. 19, 2018 in European Patent Application Np. 11721599.6.
Albergaria, et al. Expression of FOXA1 and GATA-3 in Breast Cancer: The Prognostic Significance in Hormone Receptor-Negative Tumors, Breast Cancer Research, vol. 11 No. 3, pp. 1-15 (2009).
Badve et al., FOXA 1 Expression 1n Breast Cancer Correlation with Luminal Subtype A and 34 Survival, Clin Cancer Res, vol. 13, pp. 4415-4421, Aug. 1, 2007.
Bartova, M, et al., COX-2, p16 and Ki67 Expression in DCIS, Microinvasive and Early Invasive Breast Carcinoma with Extensive Intraductal Component, Bratislava Medical Journal, vol. 115, No. , pp. 445-45, (2014).
Behling, K et al., Increased SIAH Expression Predicts Ductal Carcinoma in situ (DCIS) Progression to Invasive Carcinoma, Breast Cancer Research and Treatment, vol. 129, No. 3, pp. 717-724, (2010).
Chan et al., The expression of the ubiquitin ligase SIAH2 (seven in absentia homolog 2) is mediated through gene copy number in

(56) References Cited

OTHER PUBLICATIONS breast cancer and is associated with a basal-like phenotype and p53 expression, Breast Cancer Res, vol. 13, R19, Feb. 9, 2011.
Crawford et al., "Histologically normal human mammary epithelia with silenced p16(INK4a) overexpress COX-2, promoting a premalignant program," Cancer Cell 2004;5(3):263-73.
Extended European Search Report dated Aug. 5, 2009, received in European Patent Appl. No. 07810252.2.
Gorringe, K, et al. Ductal Carcinoma In Situ Biology, Biomarkers and Diagnosis, Frontiers in Oncology, vol. 7, Article, 248, pp. 1-14, (2017).
Hammond et al., American Society of Clinical Oncology/College of American Pathologists Guideline Recommendations for Immunohistochemical Testing of Estrogen and Progesterone Receptors in Breast Cancer (Unabridged Version), Arch Pathol Lab Med, vol. 134, e48, Jul. 1, 2010.
Horimoto et al., Low FOXA 1 expression predicts good response to neo-adjuvant chemotherapy resulting in good outcomes for luminal HER2-negative breast cancer cases, British Journal of Cancer, vol. 112, pp. 345-351, Epub Nov. 25, 2014.
International Search Report & Written Opinion, dated Feb. 16, 2016, in International Application PCT/US2015/064115.
Kerlikowske et al., "Biomarker Expression and Risk of Subsequent Tumors after Initial Ductal Carcinoma in situ Diagnosis", J Natl Cancer Inst, vol. 102 No. 9, pp. 627-637 (May 5, 2010).
Kerlikowske et al., "Characteristics associated with recurrence among women with ductal carcinoma in situ treated by lumpectomy", J. Natl Cancer Inst, vol. 95 No. 22, pp. 1692-1702 (2003).
Lee et al., Context-Specific Regulation of NF-kB Target Gene Expression by EZH2 in Breast Cancers, Mol Cell, vol. 43, pp. 798-810, Sep. 2, 2011.
Muggerud, A., et al., Molecular Diversity in Ductal Carcinoma in situ (DCIS) and Early Invasive Breast Cancer, Molecular Oncology, vol. 4, No. 4, pp. 357-368, (2010).
Office Action dated May 31, 2010, received in European Patent Appl. No. 07810252.2.
Office Action dated Dec. 7, 2012 in European Application No. 11721599.6.
Office Action dated Sep. 19, 2013 in Australian Application No. 2011248632.
Office Action dated Sep. 26, 2013 in European Patent Application No. 11188926.7.
Office Action dated Apr. 8, 2014 in received in Japanese Appl. No. 2009-520751 (with English translation).
Office Action dated Dec. 1, 2017 in Canadian Application 2,797,585.
Office Action dated Mar. 16, 2018 in U.S. Appl. No. 13/094,729.
Office Action dated Oct. 23, 2017 in U.S. Appl. No. 15/529,966.
Office Action dated Mar. 16, 2018 in U.S. Appl. No. 15/529,966.
Partial European Search Report received in European Patent Application No. EP 11 18 8923, filed Jul. 3, 2007.
Partial European Search Report dated May 23, 2018 in European Patent Application No. EP 15865163.8.
Yu, K. et al. Gene Expression Patterns of Tumor progression in Different Breast Cancer Molecular Subtypes from an Asian-Chinese Population, Proc. Amer. Association Cancer Res., vol. 25, (2004).
Zhou, W, Aspects of Progression in Breast Carcinoma, From Ductal Carcinoma in Situ to Invasive Cancer, Acta Universitatis Asupaliensis Uppsala, Separtmentt of Surgical Sciences, Akademiska sjukhuset, SE-751 85, Uppsala, Sweden,, (2012).
Annual Meeting of Japanese Society of National Medical Service, 2005, 59th, 357-763.
Arbiser, JL. "Molecular regulation of angiogenesis and tumorigenesis by signal transduction pathways: evidence of predictable and reproducible patterns of synergy in diverse neoplasms", Semin Cancer Biol. 14 (2004) 81-91.
Chan, E. Integrating Transcriptomics and Proteomics. Drug Discovery and Development, Apr. 1, 2006, 6(3) 20-26.
Chow, L.W.C., et al., "Study of COX-2, Ki67, and p53 expression to predict effectiveness of 5-flurouracil, epirubicin and cyclophosphamide with celecoxib treatment in breast cancer patients", Biomedicine & Pharmacotherapy, vol. 59, pp. S298-S301, 2005.
Davies et al., "Correlation between Cyclooxygenase-2 Expression and Angiogenesis in Human Breast Cancer", Clinical Cancer Research, vol. 9, pp. 2651-2656, Jul. 2003.
Di Vinci et al., "p16INK4a Promoter Methylation and Protein Expression in Breast Fibroadenoma and Carcinoma," Int. J. Cancer, 2005, pp. 414-421, vol. 114.
Dwek et al. Proteome and glycosylation mapping identifies post-translational modifications associated with aggressive breast cancer. Proteomics 2001, 1, 756-762.
European Publication received in European Patent Application No. EP 11 18 8923, filed Jul. 3, 2007.
European Publication received in European Patent Application No. EP 11 18 8925, filed Jul. 3, 2007.
European Publication received in European Patent Application No. EP 11 18 8926, filed Jul. 3, 2007.
European Search Report received dated Jun. 27, 2012 received in European Patent Application No. 11188923.4, filed on Jul. 3, 2007.
European Search Report received in European Patent Application No. EP 11 18 8925, filed Jul. 3, 2007.
European Search Report received in European Patent Application No. EP 11 18 8926, filed Jul. 3, 2007.
Expression Probeset Details for HG-U133A:201930_S_AT (This document was printed from the world wide web at www.affymetrix.com/analysis/netaffx/fullrecord.affx?pk=HG-U133A:210930_S_AT on Sep. 11, 2013. The original publication date is unknown.).
Faratian et al., "Membranous and cytoplasmic staining of Ki67 is Associated with HER2 and ER Status in Invasive Breast Carcinoma." Histopathology 54.2 (Jan. 2009): 254-257.
File History, U.S. Appl. No. 12/373,047, filed May 13, 2009.
File History, U.S. Appl. No. 15/284,349, filed Oct. 3, 2016.
Gauthier et al., "Abrogated Response to Cellular Stress Identifies DCIS Associated with Subsequent Tumor Events and Defines Basal-like Breast Tumors." Cancer Cell. 12.5 (Nov. 2007): 479-491.
Gauthier et al., "p38 Regulates Cycloxygenase-2 in Human Mammary Epithelial Cells and is Activated in Premalignant Tissue", Cancer Res , vol. 65, No. 5, pp. 1792-1799, Mar. 1, 2005.
Hoshikawa et al. Hypoxia induces different genes in the lungs of rats compared with mice. Physiol. Genomics 12: 209-219, 2003.
International Search Report and Written Opinion dated Sep. 14, 2011, from International Application No. PCT/US2011/034005, filed Apr. 26, 2011.
Iorio et al., "MicroRNA Gene Expression Deregulation in Human Breast Cancer", Cancer Res, vol. 65, No. 16, pp. 7065-7070, Aug. 15, 2005.
Kenny et al., "Quantification of Cellular Proliferation in Tumor and Normal Tissues of Patients with Breast Cancer by [$^{18}$F]Fluorothymidine-Positron Emission Tomography Imaging: Evaluation of Analytical Methods", Cancer Res, vol. 65, No. 21, pp. 10104-10112, Nov. 1, 2005.
Kepple, J et al., "The receptor expression pattern in ductal carcinoma in situ predicts recurrence", The American Journal of Surgery, 192 (2006) 68-71.
Mylonas et al., "Expression of Her2/neu, Steroid Receptors (ER and PR), Ki67 and p53 in Invasive Mammary Ductal Carcinoma Associated with Ductal Carcinoma in Situ (DCIS) Versus Invasive Breast Cancer Alone." Anticancer Research. 25.3A (May 2005): 1719-1723.
Office Action dated Dec. 8, 2010, received in European Patent Appl. No. 07810252.2.
Office Action dated Jul. 18, 2011, received in European Patent Application No. 07810252.2.
Office Action dated Feb. 9, 2012 received in European Patent Application No. 07 810 252.2.
Office Action dated Dec. 12, 2012 received in European Patent Appl. No. 07810252.2-2401.
Office Action dated Oct. 17, 2013 in European Patent Application No. 07810252.2.
Office Action dated Aug. 11, 2014, received in European Application No. 07810252.2.
Office Action dated Jun. 16, 2015 in European Patent Application No. 07810252.2.

(56) References Cited

OTHER PUBLICATIONS

Office Action dated Jul. 25, 2012, received in Australian Patent Application No. 2007273055, filed on Jul. 3, 2007.
Office Action dated Mar. 25, 2014, received in Australian Application No. 2007273055.
Office Action dated Nov. 11, 2014 in Australian Patent Application No. 2013205531.
Office Action dated Nov. 11, 2014 in Australian Patent Application No. 2013205536.
Office Action dated Nov. 20, 2013, received in Canadian Appl. No. 2,657,576.
Office Action, dispatch date Jan. 8, 2013, received in Japanese Patent Appl. No. 2009-520751, and translation.
Office Action dated Mar. 10, 2014, received in Japanese Appl. No. 2009-520751 (with English translation).
Office Action dated Oct. 24, 2014, received in Japanese Appl. No. 2009-520751 (with English translation).
Office Action dated Feb. 18, 2013, received in European Application No. 11188923.4, 6 pages.
Office Action dated Sep. 20, 2013 in European Application No. 11188923.4.
Office Action dated Jul. 15, 2014, received in European Application No. 11188923.4.
Office Action dated May 18, 2015 in European Patent Application No. 11188923.4.
Office Action dated Mar. 4, 2013, received in European Application No. 11188925.9, 6 pages.
Office Action dated Sep. 26, 2013 in European Application No. 11188925.9.
Office Action dated Jul. 15, 2014, received in European Application No. 11188925.9.
Office Action dated May 18, 2015 in European Patent Application No. 11188925.9.
Office Action Dated Mar. 4, 2013, received in European Application No. 11188926.7, 5 pages.
Office Action dated Jul. 15, 2014, received in European Application No. 11188926.7.
Office Action dated May 18, 2015 in European Patent Application No. 11188926.7.
Office Action dated Sep. 17, 2013, received in U.S. Appl. No. 13/094,729.
Office Action dated Apr. 11, 2014, received in U.S. Appl. No. 13/094,729.
Office Action dated Jul. 23, 2015 in U.S. Appl. No. 13/094,729.
Perrone et al., "COX-2 Expression in DCIS: Correlation with VEGF, HER-2/neu, Prognostic Molecular Markers and Clinicopathological Features." Histopathology. 46.5 (May 2005): 561-568.
Plon, S.E., "Screening and Clinical Implications for BRCA1 and BRCA2 Mutation Carriers", Journal of Mammary Gland Biology and Neoplasia, vol. 3, No. 4, pp. 377-387, 1998.
Ruiz et al., "Tissue Microarrays for Comparing Molecular Features with Proliferation Activity in Breast Cancer," Int. J. Cancer, 2006, pp. 2190-2194, vol. 118.
Schorr et al., "Are the Pure In Situ Breast Ductal Carcinomas and Those Associated with Invasive Carcinoma the Same?" Applied Immunohistochemistry and Molecular Morphology 18.1 (Jan. 2010): 51-54.
Stoll, B.A., "Premalignant Breast Lesions: Role for Biological Markers in Predicting Progression to Cancer", European Journal of Cancer, vol. 35, No. 5, pp. 693-697, 1999.
Ushijama et al. Genes involved in breast cancers. Nippon Rinsho, Mar. 2006, 64(3): 432-436 (partial).
Tlsty et al., "Genetic and Epigenetic Changes in Mammary Epithelial Cells May Mimic Early Events in Carcinogenesis", Journal of Mammary Gland Biology and Neoplasia, vol. 9, No. 3, pp. 263-274, Jul. 2004.
Tuomisto et al., "Analysis of gene and protein expression during monocyte-macrophage differentiation and cholesterol loading-cDNA and protein array study", Atherosclerosis, vol. 180, pp. 283-291, 2005.
Van Der Groep et al., "Molecular Profile of Ductal Carcinoma in situ of the Breast in BRCA1 and BRCA2 germline mutation carriers." Journal of Clinical Pathology. 62.10 (Oct. 2009): 926-930.
Whitehead et al. Variation in tissue-specific gene expression among natural populations. Genome Biology 2005, 6:R13, in 14 pages.
Witkiewicz, A. et al., "Associate of RB/p16-Pathway Perturbations with DCIS Recurrence" The American Journal of Psychology, vol. 179, No. 3, Sep. 2011.
Office Action dated Jun. 23, 2011 in U.S. Appl. No. 12/373,047.
Office Action dated Apr. 10, 2012 in U.S. Appl. No. 12/373,047.
Office Action dated Sep. 24, 2014 in U.S. Appl. No. 12/373,047.
Office Action dated May 29, 2015 in U.S. Appl. No. 12/373,047.
Office Action dated Jun. 3, 2016 in U.S. Appl. No. 12/373,047.
Office Action dated Dec. 15, 2014 in Canadian Application No. 2657576.
Office Action dated Dec. 19, 2016 in Canadian Application No. 2,657,576.
Office Action dated Jun. 21, 2017 in Canadian Application 2,657,576.
Office Action dated May 12, 2016 in European Application No. 11188923.4.
Office Action dated Jun. 12, 2017 in European Application No. 11188923.4.
Office Action dated Apr. 27, 2016, received in U.S. Appl. No. 13/094,729.
Office Action dated Dec. 5, 2016, received in U.S. Appl. No. 13/094,729.
Office Action dated Mar. 24, 2017, received in U.S. Appl. No. 13/094,729.
Office Action dated Apr. 21, 2017 in Canadian Application 2,797,585.
Office Action dated Sep. 30, 2014 in European Application No. 11721599.6.
Office Action dated Apr. 15, 2016 in European Application No. 11721599.6.
Office Action dated Mar. 6, 2017 in European Application No. 11721599.6.
Nofech-Mozes et al., "Biological Markers Predictive of Invasive Recurrence in DCIS", Clinical Medicine: Oncology, vol. 2, pp. 7-18, 2008.
Patani et al., "Current management of DCIS: a review", Breast Cancer Res Treat, vol. 111, pp. 1-10, 2008.
Provenzano et al., "Biological Markers that predict clinical recurrence in ductal carcinoma in situ of the breast", European Journal of Cancer 39, pp. 622-630, 2003.
Boland et al.(British Journal of Cancer, 2004, vol. 90, pp. 423-429). (Year: 2004).
Joyce et al (Investigative Ophthalmology & Visual Science, 2005, vol. 45, No. 5, pp. 1340-1348) (Year: 2005).
Belvisi et al.(British Journal of Pharmacology 1997, vol. 120, pp. 910-916).
Declaration By Troy Bremer in U.S. Appl. No. 13/094,729, dated Feb. 13, 2023.
Tsikitis et al., "Biology of Ductal Carcinoma in Situ Classification Based on Biologic Potential," Am J Clin Oncol. 2006; 29: 305-310.
U.S. Office Action dated Nov. 9, 2022 in U.S. Appl. No. 15/284,349.
Response to U.S. Office Action dated Nov. 9, 2022, filed Mar. 2, 2023 in U.S. Appl. No. 15/284,349.
Response to Office Action Dated Aug. 15, 2022, filed Feb. 14, 2023 in U.S. Appl. No. 13/094,729.
U.S. Notice of Allowance dated Nov. 2, 2022 in U.S. Appl. No. 15/529,966.
Response to U.S. Office Action dated Aug. 30, 2022, filed Feb. 24, 2023 in U.S. Appl. No. 17/652,471.
U.S. Office Action dated Mar. 9, 2023 in U.S. Appl. No. 17/652,471.
Response to Canadian Office Action dated May 2, 2022, filed Sep. 2, 2022 and supplemental Response, filed Sep. 14, 2022 in CA Application No. 2657576.
Response to European Office Action dated Apr. 13, 2022, filed Jan. 18, 2023 in EP Application No. 20190672.4.

(56) References Cited

OTHER PUBLICATIONS

Office Action dated Nov. 2, 2022 received in EP Application No. 15865163.8 in 7 pages.
Response to European Office Action dated Nov. 2, 2022, filed Mar. 10, 2023 in EP Application No. EP15865163.8.
Extended European Search Report dated Oct. 20, 2022, received in European Patent Appl. No. 19859855.9.
U.S. Office Action dated May 9, 2023 in U.S. Appl. No. 15/284,349.
Japanese Office Action with translation, dated Aug. 17, 2023 in JP Application No. 2021-539476.
Response to U.S. Office Action dated May 9, 2023, filed Aug. 9, 2023 in U.S. Appl. No. 15/284,349.
Response to U.S. Office Action dated Mar. 9, 2023, filed Jun. 16, 2023 in U.S. Appl. No. 17/652,471.
Response to EP Communication (70(2) and 70a(2) EPC, dated Nov. 8, 2022, filed May 12, 2023 in European Patent Appl. No. 19859855.9.
Chen et al., Discordant Protein and mRNA Expression in Lung Adenocarcinomas. Mol Cell Proteo. Apr. 1, 2002; 1(4): 304-313.
Fish et al., Assessment of Treatment for Patients with Primary Ductal Carcinoma in situ in the Breast. Annals Surg Oncol. Dec. 1998;5: 724-732.
Henriksen et al., Semi-quantitative Scoring of Potentially Predictive Markers for Endocrine Treatment of Breast Cancer: A Comparison Between Whole Sections and Tissue Microarrays. J Clin Path. Apr. 1, 2007;60(4): 397-404.
Mack et al., Relationship of New Histological Categorization of Ductal Carcinoma in situ of the Breast with Size and the Immunohistochemical Expression of p53, c-erb B2, bcl-2, and ki-67. Human Pathol. Aug. 1, 1997;28(8): 974-979.
Shah et al., The Clinical Utility of DCISionRT® on Radiation Therapy Decision Making in Patients with Ductal Carcinoma in situ Following Breast-conserving Surgery. Annals Surg Oncol. Oct. 1, 2021: 5974-5984.
U.S. Office Action dated Jun. 15, 2023, received in U.S. Appl. No. 13/094,729.
U.S. Notice of Allowance dated Sep. 7, 2023 in U.S. Appl. No. 17/652,471.
U.S. Notice of Allowance dated Oct. 18, 2023 in U.S. Appl. No. 17/652,471.
U.S. Restriction Requirement dated Nov. 8, 2023 in U.S. Appl. No. 17/652,466.
U.S. Office Action dated Dec. 20, 2023 in U.S. Appl. No. 15/284,349.
Response to U.S. Office Action Dated Dec. 20, 2023, filed Jun. 18, 2024 in U.S. Appl. No. 15/284,349.
Response to Office Action Dated Jun. 15, 2023, filed Sep. 14, 2023 in U.S. Appl. No. 13/094,729.
U.S. Notice of Allowance dated Jun. 6, 2024, received in U.S. Appl. No. 13/094,729.
U.S. Office Action dated Feb. 16, 2024 in U.S. Appl. No. 17/275,406.
Response to U.S. Office Action Dated Feb. 16, 2024, filed Apr. 15, 2024 in U.S. Appl. No. 17/275,406.
Response to Japanese Office Action Dated Aug. 17, 2023, filed Feb. 20, 2024 in JP Application No. 2021-539476.
U.S. Office Action dated Oct. 21, 2024 in U.S. Appl. No. 15/284,349.
Declaration By Troy Bremer in U.S. Appl. No. 13/094,729, dated Jun. 18, 2024.
Shono et al., "Cyclooxygenase-2 Expression in Human Gliomas: Prognostic Significance and Molecular Correlations", Cancer Res. Jun. 1, 2001;61(11): 4375-4381.
Response to U.S. Office Action Dated Nov. 8, 2023 filed Mar. 28, 2024 in U.S. Appl. No. 17/652,466.
U.S. Office Action dated May 9, 2024 in U.S. Appl. No. 17/652,466.
Response to U.S. Office Action Dated May 9, 2024 filed Oct. 8, 2024 in U.S. Appl. No. 17/652,466.
Japanese Final Office Action dated Jun. 4, 2024 in JP Application No. 2021-539476.
Response/Appeal to Japanese Office Action Dated Jun. 4, 2024, filed Oct. 3, 2024 in JP Application No. 2021-239476.
European Office Action dated Nov. 27, 2024 in EP Application No. 18209239.5.
U.S. Notice of Allowance dated Mar. 31, 2025, received in U.S. Appl. No. 13/094,729.
U.S. Office Action dated Apr. 1, 2025 in U.S. Appl. No. 17/275,406.
U.S. Notice of Allowance dated Apr. 22, 2025, received in U.S. Appl. No. 17/652,466.

* cited by examiner

Cells in CD73⁺CD90⁻ population exhibit p16$^{INK4a}$-promoter hypermethylation

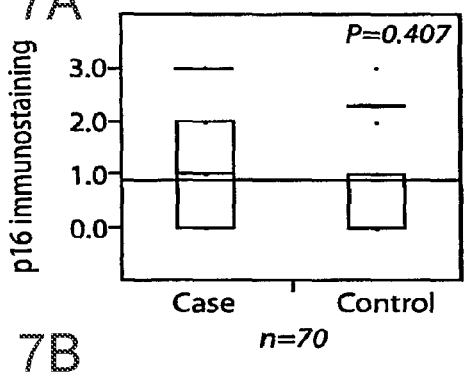
Fig. 7A
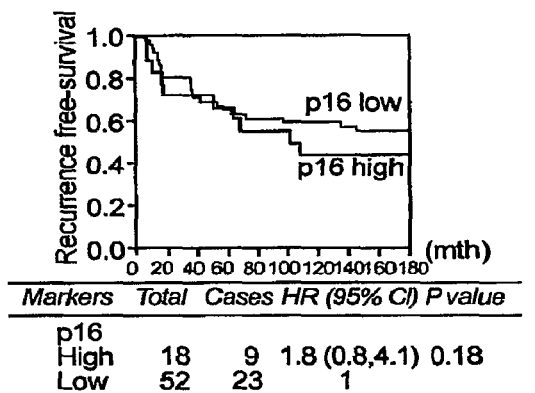
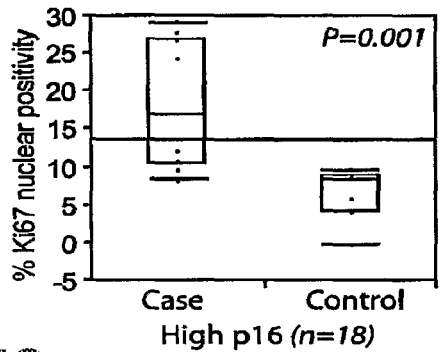
Fig. 7B
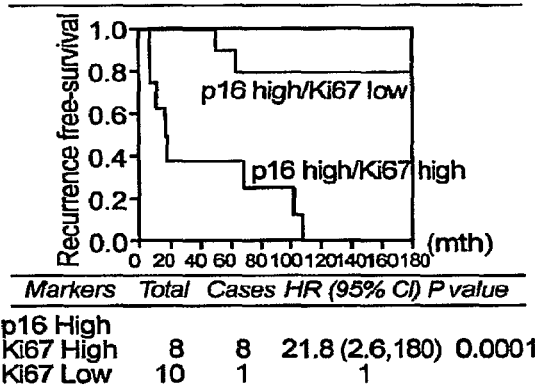
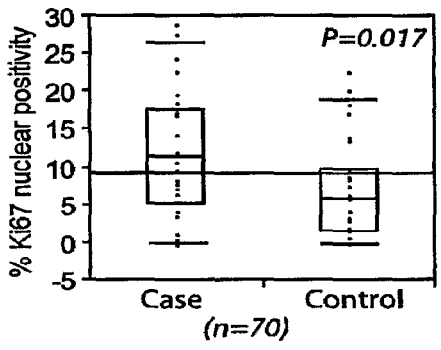
Fig. 7C
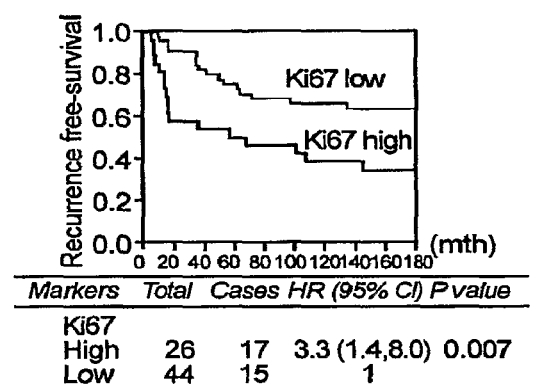
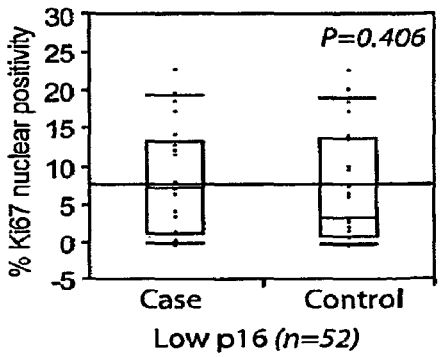
Fig. 7D
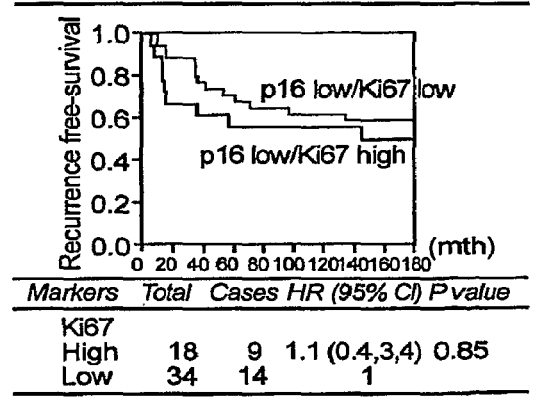

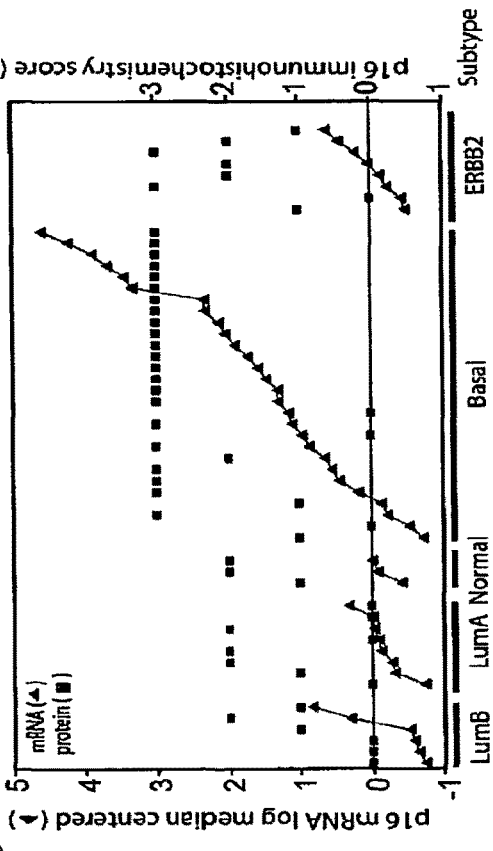
Fig. 8A
Fig. 8B
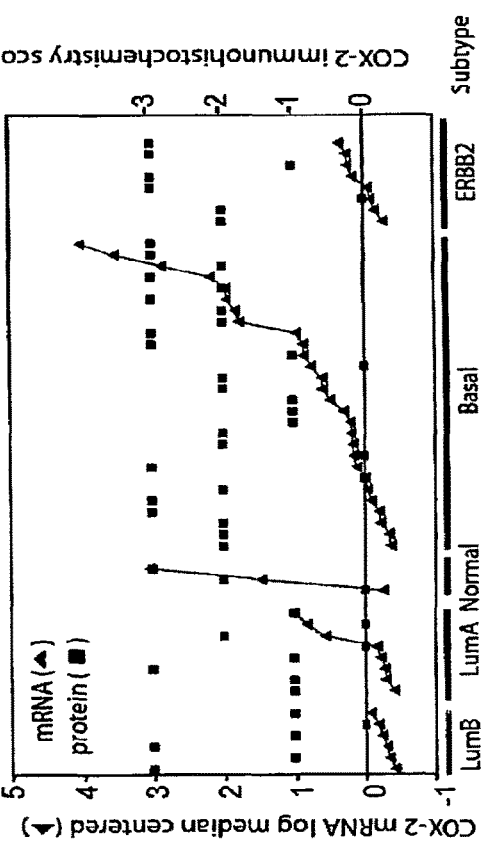
Fig. 8C
Fig. 8D

Fig. 9A
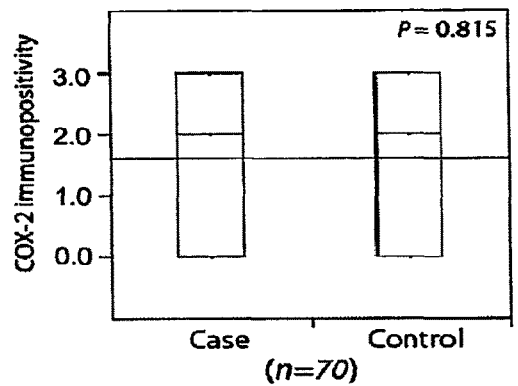
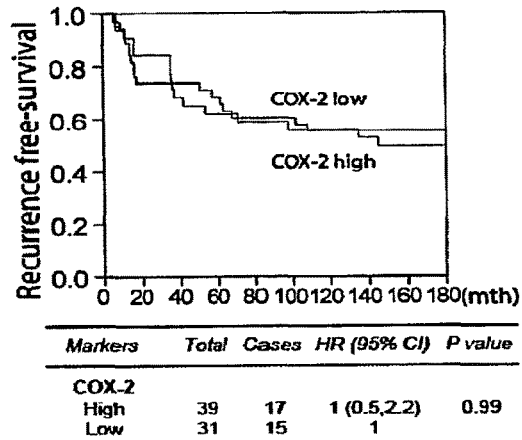
Fig. 9B
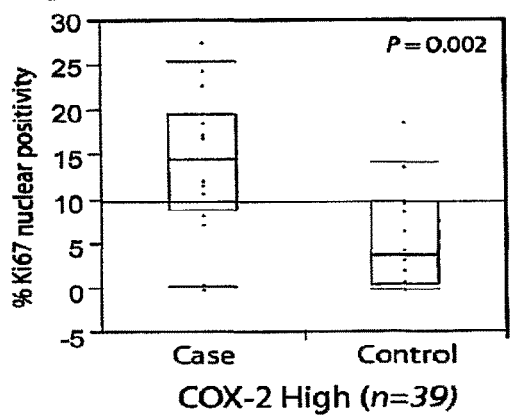
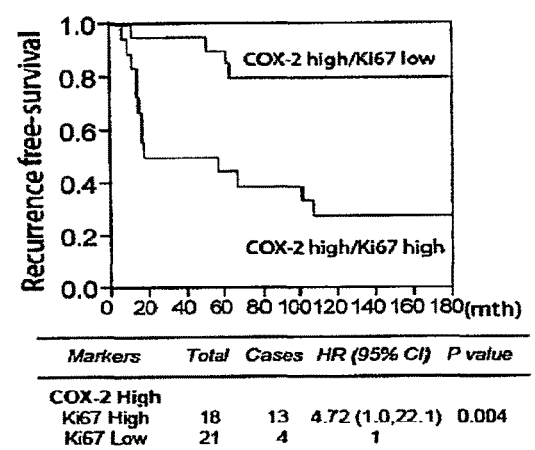
Fig. 9C
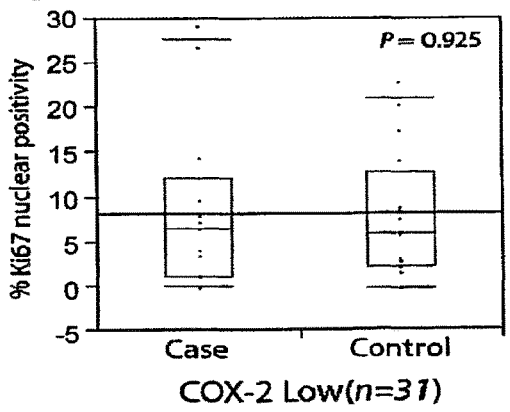
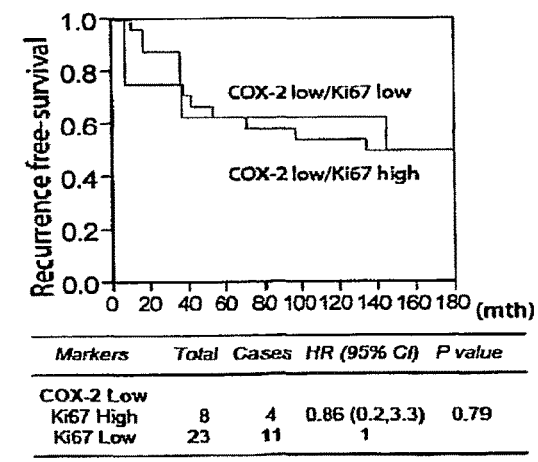

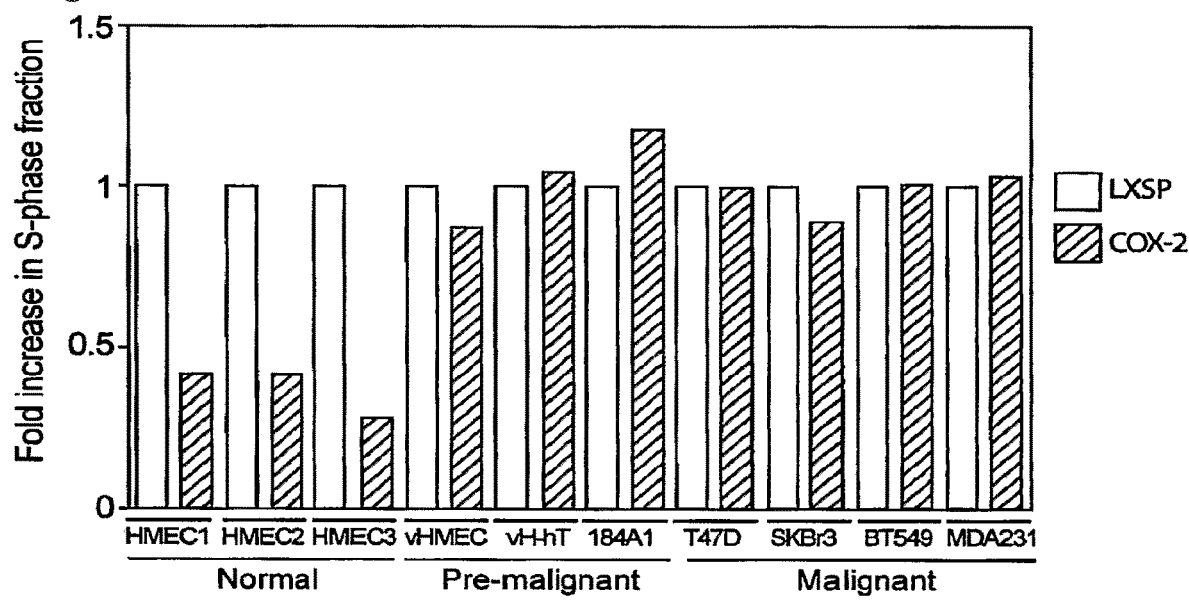
Fig. 11A
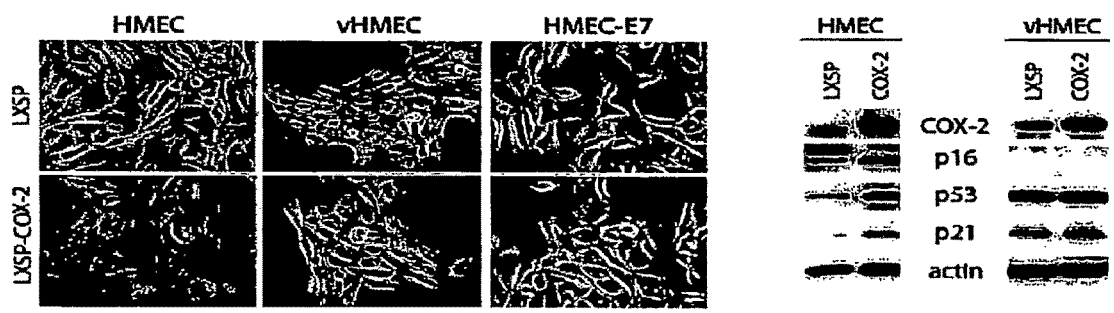
Fig. 11B
Fig. 11C

FIG. 14

| NAME | fold | absolute value |
|---|---|---|
| AA399473::tissue factor pathway inhibitor 2 | 25.1045372 | 25.1045372 |
| AA936757::heparin-binding growth factor binding protein | 21.44376905 | 21.44376905 |
| AA447835::small proline-rich protein 1B (cornifin) | 16.60194318 | 16.60194318 |
| AA456394::four and a half LIM domains 1 | 14.21973815 | 14.21973815 |
| "AA598974::cell division cycle 2, G1 to S and G2 to M" | 11.26586192 | 11.26586192 |
| R40057 prominin (mouse)-like 1 | -11.08709008 | 11.08709008 |
| "AA775616::secreted phosphoprotein 1 (osteopontin, bone sialoprotein I, early T-lymphocyte activation 1)" | -10.04318206 | 10.04318206 |
| "T49159::plasminogen activator inhibitor, type II (arginine-serpin)" | 8.858119257 | 8.858119257 |
| H50095::KIAA0698 gene product (Hephaestin) | -8.516280514 | 8.516280514 |
| H50095::KIAA0698 gene product | -8.516280514 | 8.516280514 |
| "AA454743::protease, serine, 9 (neurosin)" | -8.432625426 | 8.432625426 |
| AA401035::mitogen-activated protein kinase 4 | -6.841962776 | 6.841962776 |
| "AA031513::matrix metalloproteinase 7 (matrilysin, uterine)" | -6.804722548 | 6.804722548 |
| AA461065::mercaptopyruvate sulfurtransferase | 6.634633035 | 6.634633035 |
| AA187351::ribonucleotide reductase M2 polypeptide | 6.494071798 | 6.494071798 |
| W93717::KIAA0008 gene product (cell cycle regulated homologue of dlg1) | 6.249098219 | 6.249098219 |
| AA598794::connective tissue growth factor | -6.038140704 | 6.038140704 |
| H72122::ectodermal-neural cortex (with BTB-like domain) | -5.9679533 | 5.9679533 |
| "AA458969::diacylglycerol kinase, zeta (104kD)" | -5.495154899 | 5.495154899 |
| R80217::prostaglandin-endoperoxide synthase 2 (prostaglandin G/H synthase and cyclooxygenase) | 5.144260808 | 5.144260808 |
| "AA936768::interleukin 1, alpha" | 5.045721885 | 5.045721885 |
| "AA877166::myosin regulatory light chain 2, smooth muscle isoform" | -4.872192804 | 4.872192804 |
| N22272::UDP glycosyltransferase 8 (UDP- | -4.845603928 | 4.845603928 |

FIG. 14 (cont.)

| NAME | fold | absolute value |
|---|---|---|
| galactose ceramide galactosyltransferase) | | |
| "N92901::fatty acid binding protein 4, adipocyte" | 4.810206255 | 4.810206255 |
| T80924::alpha-1-antichymotrypsin | -4.764822463 | 4.764822463 |
| "AA862465::alpha-2-glycoprotein 1, zinc" | -4.647980295 | 4.647980295 |
| AA460685::apoptosis inhibitor 4 (survivin) | 4.552530703 | 4.552530703 |
| "AA700832::retinol-binding protein 1, cellular" | -4.535504506 | 4.535504506 |
| "AA775091::delta sleep inducing peptide, immunoreactor" | 4.269652426 | 4.269652426 |
| AA682423::monoamine oxidase B | -4.201035336 | 4.201035336 |
| AA449336::Homo sapiens protein regulator of cytokinesis 1 (PRC1) mRNA | 4.198455177 | 4.198455177 |
| "AA504943::crystallin, alpha B" | -4.132210222 | 4.132210222 |
| "H99676::collagen, type VI, alpha 1" | -4.05317844 | 4.05317844 |
| AA155913::matrix Gla protein | -3.902101541 | 3.902101541 |
| AA873060::leukemia-associated phosphoprotein p18 (stathmin) | 3.899798373 | 3.899798373 |
| AA478542::A kinase (PRKA) anchor protein (gravin) 12 | -3.897631892 | 3.897631892 |
| AA228130::PC4 and SFRS1 interacting protein 1 | 3.832234873 | 3.832234873 |
| W47179::cathepsin B | -3.811231038 | 3.811231038 |
| AA630734::seryl-tRNA synthetase | 3.743009977 | 3.743009977 |
| N66132::H.sapiens mRNA for rTS beta protein | 3.7394194 | 3.7394194 |
| "R76553::Homo sapiens a disintegrin-like and metalloprotease (reprolysin type) with thrombospondin type 1 motif, 1 (ADAMTS1), mRNA" | -3.709675654 | 3.709675654 |
| "AA663995::minichromosome maintenance deficient (mis5, S. pombe) 6" | 3.666333409 | 3.666333409 |
| AA706968::ZW10 interactor | 3.625717217 | 3.625717217 |
| "T77595::hexabrachion (tenascin C, cytotactin)" | -3.5875639 | 3.5875639 |
| "AA701455::centromere protein F (350/400kD, mitosin)" | 3.56459009 | 3.56459009 |
| AA456975::apolipoprotein D | -3.514345204 | 3.514345204 |
| R25377::DEK gene | 3.445705985 | 3.445705985 |
| "R93124::aldo-keto reductase family 1, member C1 (dihydrodiol dehydrogenase 1; 20-alpha (3-alpha)-hydroxysteroid dehydrogenase)" | 3.428526848 | 3.428526848 |
| AA877815::KIAA0353 protein | -3.419786107 | 3.419786107 |

FIG. 14 (cont.)

| NAME | fold | absolute value |
|---|---|---|
| AA894927::asparagine synthetase | 3.418607599 | 3.418607599 |
| AA464691::DKFZP564I1922 protein | -3.386188595 | 3.386188595 |
| AA453783::Homo sapiens mRNA; cDNA DKFZp564B1264 (from clone DKFZp564B1264) | 3.351931997 | 3.351931997 |
| N70776::frizzled (Drosophila) homolog 1 | -3.324394529 | 3.324394529 |
| R60343::5' nucleotidase (CD73) | 3.301872358 | 3.301872358 |
| H17696::myelin basic protein | -3.292975972 | 3.292975972 |
| "AA045326::protein tyrosine phosphatase, receptor type, J" | -3.262815628 | 3.262815628 |
| H45711::Kruppel-like factor 4 (gut) | 3.233755054 | 3.233755054 |
| H56655::desmin | -3.225395716 | 3.225395716 |
| H56655::desmin | -3.225395716 | 3.225395716 |
| AA071486::serine/threonine kinase 12 (aurora b) | 3.222269301 | 3.222269301 |
| AA434342::proline arginine-rich end leucine-rich repeat protein | 3.191334035 | 3.191334035 |
| N69049::frizzled (Drosophila) homolog 7 | -3.182534525 | 3.182534525 |
| AA677706::lactotransferrin | -3.085611058 | 3.085611058 |
| AA825491::interferon regulatory factor 4 | 3.054019023 | 3.054019023 |
| "AA481745::Homo sapiens clone 23763 unknown mRNA, partial cds" | -2.981367604 | 2.981367604 |
| AA598653::osteoblast specific factor 2 (fasciclin I-like) | -2.964948654 | 2.964948654 |
| AA598653::osteoblast specific factor 2 (fasciclin I-like) | -2.964948654 | 2.964948654 |
| AA446027::early growth response 2 (Krox-20 (Drosophila) homolog) | -2.963765696 | 2.963765696 |
| AA424560::Homo sapiens mRNA full length insert cDNA clone EUROIMAGE 248114 | -2.961183797 | 2.961183797 |
| AA406449::damage-specific DNA binding protein 2 (48kD) | 2.953451608 | 2.953451608 |
| AA430504::ubiquitin carrier protein E2-C | 2.937032834 | 2.937032834 |
| AA450265::proliferating cell nuclear antigen | 2.927663883 | 2.927663883 |
| "AA936799::matrix metalloproteinase 2 (gelatinase A, 72kD gelatinase, 72kD type IV collagenase)" | -2.889141496 | 2.889141496 |
| "N53172::Human orphan G protein-coupled receptor (RDC1) mRNA, partial cds" | -2.854775432 | 2.854775432 |
| "AA136707::procollagen-lysine, 2-oxoglutarate 5-dioxygenase (lysine | -2.847604647 | 2.847604647 |

FIG. 14 (cont.)

| NAME | fold | absolute value |
|---|---|---|
| hydroxylase) 2" | | |
| AA487488::claudin 7 | -2.84276597 | 2.84276597 |
| "AA488324::budding uninhibited by benzimidazoles 1 (yeast homolog), beta" | 2.839079872 | 2.839079872 |
| AA069372::forkhead box D1 | 2.811814744 | 2.811814744 |
| AA682321::NIMA (never in mitosis gene a)-related kinase 2 | 2.769233968 | 2.769233968 |
| R62612::fibronectin 1 | -2.73243452 | 2.73243452 |
| "AA284260::keratin, hair, acidic, 4" | 2.73095183 | 2.73095183 |
| "AA633747::collagen, type VI, alpha 2" | -2.725106606 | 2.725106606 |
| H86812::heparan sulfate (glucosamine) 3-O-sulfotransferase 1 | 2.693989899 | 2.693989899 |
| "H64346::syndecan 2 (heparan sulfate proteoglycan 1, cell surface-associated, fibroglycan)" | -2.620685626 | 2.620685626 |
| N64374::KIAA0537 gene product | -2.603583125 | 2.603583125 |
| AA452095::chromosome-associated polypeptide C | 2.597279354 | 2.597279354 |
| "AA284668::plasminogen activator, urokinase" | 2.590492527 | 2.590492527 |
| "AA700904::CDC45 (cell division cycle 45, S.cerevisiae, homolog)-like" | 2.568998924 | 2.568998924 |
| AA114250::KIAA0512 gene product | -2.560317371 | 2.560317371 |
| AA858026::protein C inhibitor (plasminogen activator inhibitor III) | -2.55868225 | 2.55868225 |
| "AA459401::protease, serine-like, 1" | -2.554026376 | 2.554026376 |
| R32025::Homo sapiens mRNA full length insert cDNA clone EUROIMAGE 248114 | -2.546989913 | 2.546989913 |
| W86653::FK506-binding protein 5 | 2.533953197 | 2.533953197 |
| R26960::peripheral myelin protein 22 | -2.518041355 | 2.518041355 |
| "N45138::transforming growth factor, beta 2" | -2.51222351 | 2.51222351 |
| H19439::Down syndrome candidate region 1-like 1 | -2.511269 | 2.511269 |
| "AA775415::SMT3 (suppressor of mif two 3, yeast) homolog 2" | 2.507695209 | 2.507695209 |
| "AA451684::CD1D antigen, d polypeptide" | 2.492166748 | 2.492166748 |
| "H38804::BUB3 (budding uninhibited by benzimidazoles 3, yeast) homolog" | 2.465751636 | 2.465751636 |
| AA683041::neuronal pentraxin II | -2.464588284 | 2.464588284 |
| "AA448157::cytochrome P450, subfamily I (dioxin-inducible), polypeptide 1 (glaucoma 3, primary infantile)" | -2.454709669 | 2.454709669 |

FIG. 14 (cont.)

| NAME | fold | absolute value |
|---|---|---|
| H15662::KIAA0291 protein (unknown gene) | -2.453909951 | 2.453909951 |
| T97925::Homo sapiens clone 24921 mRNA sequence | -2.446537625 | 2.446537625 |
| W86876::KIAA0320 protein (Talin 2) | -2.4404992 | 2.4404992 |
| "AA450189::enolase 2, (gamma, neuronal)" | -2.423743905 | 2.423743905 |
| "H75632::basic helix-loop-helix domain containing, class B, 2" | -2.420770171 | 2.420770171 |
| AA633549::ribonucleotide reductase M1 polypeptide | 2.415913901 | 2.415913901 |
| AA496283::Thy-1 cell surface antigen | -2.406606635 | 2.406606635 |
| "AA451904::epididymis-specific, whey-acidic protein type, four-disulfide core" | -2.40390552 | 2.40390552 |
| N49403::KIAA0779 protein (unknown gene) | -2.402313608 | 2.402313608 |
| AA448755::cell division cycle 25B | 2.401628573 | 2.401628573 |
| AA625995::zinc finger protein 9 (a cellular retroviral nucleic acid binding protein) | 2.395489468 | 2.395489468 |
| "H90431::adrenergic, beta-2-, receptor, surface" | 2.389455711 | 2.389455711 |
| W68396::SNF-1 related kinase | 2.38689572 | 2.38689572 |
| W58092::tropomyosin 1 (alpha) | -2.36317485 | 2.36317485 |
| AA099568::uridine phosphorylase | 2.362734406 | 2.362734406 |
| H54752::replication factor C (activator 1) 4 (37kD) | 2.362483555 | 2.362483555 |
| T72877::interleukin 1 receptor antagonist | 2.35434789 | 2.35434789 |
| AA454668::prostaglandin-endoperoxide synthase 1 (prostaglandin G/H synthase and cyclooxygenase) | 2.353591061 | 2.353591061 |
| AA504625::kinesin-like 1 | 2.347033686 | 2.347033686 |
| H21041::activating transcription factor 3 | 2.344604735 | 2.344604735 |
| "AA099153::tissue inhibitor of metalloproteinase 3 (Sorsby fundus dystrophy, pseudoinflammatory)" | -2.34309237 | 2.34309237 |
| "T70109::succinate dehydrogenase complex, subunit A, flavoprotein (Fp)" | 2.326465691 | 2.326465691 |
| N73611::transcription factor Dp-1 | 2.320180588 | 2.320180588 |
| "R43605::KIAA0293 protein (Homeobox protein Cux-2, Cut-like 2, CUTL2)" | -2.31587695 | 2.31587695 |
| "R83277::origin recognition complex, subunit 1 (yeast homolog)-like" | 2.300497316 | 2.300497316 |
| AA430032::pituitary tumor-transforming 1 | 2.298871048 | 2.298871048 |
| "R52796::interleukin 13 receptor, alpha 2" | 2.29456853 | 2.29456853 |

FIG. 14 (cont.)

| NAME | fold | absolute value |
|---|---|---|
| "T49530::Homo sapiens lipase, endothelial (LIPG) mRNA" | -2.292266614 | 2.292266614 |
| "AA430540::collagen, type IV, alpha 2" | -2.284580694 | 2.284580694 |
| "T60048::actin, gamma 2, smooth muscle, enteric" | -2.283519459 | 2.283519459 |
| R24543::guanine nucleotide regulatory protein (oncogene) | 2.283367229 | 2.283367229 |
| H21943::thymopoietin | 2.277802635 | 2.277802635 |
| "R55303::nerve growth factor receptor (TNFR superfamily, member 16)" | -2.257950649 | 2.257950649 |
| AA486653::CD81 antigen (target of antiproliferative antibody 1) | 2.25023157 | 2.25023157 |
| AA157018::stromal interaction molecule 1 | -2.244449253 | 2.244449253 |
| "AA486275::protease inhibitor 2 (anti-elastase), monocyte/neutrophil" | 2.244321338 | 2.244321338 |
| AA279188::a disintegrin and metalloprotease domain 8 | 2.243999876 | 2.243999876 |
| AA598517::keratin 8 | -2.231186932 | 2.231186932 |
| "AA029299::potassium large conductance calcium-activated channel, subfamily M, beta member 1" | -2.23019652 | 2.23019652 |
| "AA155695::transcobalamin I (vitamin B12 binding protein, R binder family)" | -2.228716978 | 2.228716978 |
| AA010065::CDC28 protein kinase 2 | 2.227440864 | 2.227440864 |
| "AA634006::actin, alpha 2, smooth muscle, aorta" | -2.223991274 | 2.223991274 |
| "H99816::procollagen-lysine, 2-oxoglutarate 5-dioxygenase (lysine hydroxylase) 2" | -2.220866263 | 2.220866263 |
| "W72679::highly expressed in cancer, rich in leucine heptad repeats" | 2.216495458 | 2.216495458 |
| AA478724::insulin-like growth factor binding protein 6 | 2.210194178 | 2.210194178 |
| W58342::putative gene product | -2.20856153 | 2.20856153 |
| H15445::H.sapiens mRNA for SEX gene | -2.207907192 | 2.207907192 |
| R10382::protein C inhibitor (plasminogen activator inhibitor III) | -2.201079581 | 2.201079581 |
| "T69926::myosin, heavy polypeptide 9, non-muscle" | -2.19458309 | 2.19458309 |
| W72207::cystatin A (stefin A) | 2.194373639 | 2.194373639 |
| AA256502::proprotein convertase subtilisin/kexin type 5 | -2.192297707 | 2.192297707 |
| AA486082::serum/glucocorticoid regulated kinase | -2.190102026 | 2.190102026 |

FIG. 14 (cont.)

| NAME | fold | absolute value |
|---|---|---|
| AA459292::CDC28 protein kinase 1 | 2.184734765 | 2.184734765 |
| H14810::Homo sapiens mRNA; cDNA DKFZp434G012 (from clone DKFZp434G012) | -2.184162721 | 2.184162721 |
| R02346::small nuclear ribonucleoprotein 70kD polypeptide (RNP antigen) | -2.183170823 | 2.183170823 |
| AA455786::minichromosome maintenance deficient (S. cerevisiae) 3 | 2.177381743 | 2.177381743 |
| AA496796::chondrocyte-derived ezrin-like protein | -2.172279362 | 2.172279362 |
| T55446::high density lipoprotein binding protein (vigilin) | -2.162011595 | 2.162011595 |
| "W94714::6-phosphofructo-2-kinase/fructose-2,6-biphosphatase 3" | -2.159099985 | 2.159099985 |
| N50079::Opa-interacting protein 2 | 2.144050953 | 2.144050953 |
| "AA457738::Human 12S RNA induced by poly(rI), poly(rC) and Newcastle disease virus" | 2.13349192 | 2.13349192 |
| H53658::DKFZP564M2423 protein | 2.128483049 | 2.128483049 |
| AA485371::bone marrow stromal cell antigen 2 | -2.12600365 | 2.12600365 |
| W91879::Homo sapiens vav 3 oncogene (VAV3) mRNA | -2.12594386 | 2.12594386 |
| AA476543::similar to rat HREV107 | -2.123668929 | 2.123668929 |
| H29592::KIAA0377 gene product (histidine acid phosphatase) | 2.122666643 | 2.122666643 |
| AA663986::fibrillarin | 2.119545692 | 2.119545692 |
| "AA865469::Tubulin, alpha, brain-specific" | -2.117094751 | 2.117094751 |
| "T49146::ATP synthase, subunit b-like" | -2.115189237 | 2.115189237 |
| "H57180::phospholipase C, gamma 2 (phosphatidylinositol-specific)" | -2.114150608 | 2.114150608 |
| "AA427732::solute carrier family 12 (potassium/chloride transporters), member 7" | -2.110424989 | 2.110424989 |
| AA425602::zona pellucida glycoprotein 3A (sperm receptor) | -2.108977702 | 2.108977702 |
| AA401137::lipocalin 2 (oncogene 24p3) | -2.108086866 | 2.108086866 |
| R19158::serine/threonine kinase 15 (aurora a) | 2.107888005 | 2.107888005 |
| "N53380::protein kinase C, mu" | -2.10158732 | 2.10158732 |
| "H82081::rab3 GTPase-activating protein, non-catalytic subunit (150kD)" | -2.101115333 | 2.101115333 |
| AA012867::ADP-ribosylation factor 6 | 2.09991978 | 2.09991978 |

FIG. 14 (cont.)

| NAME | fold | absolute value |
|---|---|---|
| AA629262::polo (Drosophia)-like kinase | 2.095503346 | 2.095503346 |
| "AA480995::methylene tetrahydrofolate dehydrogenase (NAD+ dependent), methenyltetrahydrofolate cyclohydrolase" | 2.094144257 | 2.094144257 |
| N23406::MCF.2 cell line derived transforming sequence | 2.092396607 | 2.092396607 |
| N35907::KIAA0830 protein | -2.086631581 | 2.086631581 |
| "AA487797::ribonuclease, RNase A family, 1 (pancreatic)" | -2.086434909 | 2.086434909 |
| "protein tyrosine phosphatase, non-receptor type 7 isoform 2" | -2.082463705 | 2.082463705 |
| AA169814::sorting nexin 2 | 2.080004707 | 2.080004707 |
| "W68220::KIAA0101 gene product (casein kinase 1, gamma 1)" | 2.079536635 | 2.079536635 |
| T59658::Homo sapiens mRNA; cDNA DKFZp586P1622 (from clone DKFZp586P1622) | 2.079465389 | 2.079465389 |
| AA454098::kinesin-like 5 (mitotic kinesin-like protein 1) | 2.079461548 | 2.079461548 |
| AA452627::endothelin receptor type A | 2.07633863 | 2.07633863 |
| AA010158::glutamyl-prolyl-tRNA synthetase | 2.07342368 | 2.07342368 |
| AA504266::stromal antigen 2 | -2.066711339 | 2.066711339 |
| "H59203::CDC6 (cell division cycle 6, S. cerevisiae) homolog" | 2.055668511 | 2.055668511 |
| "AA676804::CCAAT/enhancer binding protein (C/EBP), gamma" | 2.049280881 | 2.049280881 |
| AA431408::DKFZP566D193 protein | 2.042963559 | 2.042963559 |
| "AA482251::phosphatidylinositol-4-phosphate 5-kinase, type I, gamma" | -2.041992847 | 2.041992847 |
| W74602::TEA domain family member 4 | 2.039490562 | 2.039490562 |
| "T69359::mannose-binding lectin (protein C) 2, soluble (opsonic defect)" | 2.03809328 | 2.03809328 |
| R33755::glutathione S-transferase pi | 2.028376501 | 2.028376501 |
| AA211446::Homo sapiens mRNA full length insert cDNA clone EUROIMAGE 180147 | -2.02679478 | 2.02679478 |
| AA464601::tetraspan 5 | 2.021238206 | 2.021238206 |
| N70773::development and differentiation enhancing factor 2 | 2.017450098 | 2.017450098 |
| "H20547::potassium inwardly-rectifying channel, subfamily J, member 6" | -2.014104484 | 2.014104484 |
| AA436406::N-myristoyltransferase 1 | -2.013115219 | 2.013115219 |
| "AA043334::small nuclear RNA activating | 2.009674037 | 2.009674037 |

FIG. 14 (cont.)

| NAME | fold | absolute value |
|---|---|---|
| complex, polypeptide 3, 50kD" | | |
| H99415::A kinase (PRKA) anchor protein 2 | -2.002624963 | 2.002624963 |
| "W49619::cadherin 2, N-cadherin (neuronal)" | -1.995322534 | 1.995322534 |
| "W49619::cadherin 2, N-cadherin (neuronal)" | -1.995322534 | 1.995322534 |
| AA416628::Homo sapiens mRNA; cDNA DKFZp564C2063 (from clone DKFZp564C2063) | -1.982452761 | 1.982452761 |
| AA018372::glutamate dehydrogenase 1 | 1.977179619 | 1.977179619 |
| R66310::peptidylglycine alpha-amidating monooxygenase | -1.970973902 | 1.970973902 |
| AA456008::transmembrane protein | -1.969522436 | 1.969522436 |
| AA630449::epididymal secretory protein (19.5kD) | -1.962778749 | 1.962778749 |
| AA159311::KIAA1090 (Wolf-Hirschhorn syndrome candidate 1) | -1.961900222 | 1.961900222 |
| H45376::nel (chicken)-like 2 | -1.953255857 | 1.953255857 |
| R38539::fibroblast growth factor 2 (basic) | -1.947635639 | 1.947635639 |
| "AA011057::lectin, galactoside-binding, soluble, 7 (galectin 7)" | -1.943164707 | 1.943164707 |
| N74662::DKFZP564B147 protein | 1.939624332 | 1.939624332 |
| "AA128561::collagen, type XVII, alpha 1" | 1.934590933 | 1.934590933 |
| AA192268::KIAA0892 protein | 1.931364415 | 1.931364415 |
| "AA521232::ras-related C3 botulinum toxin substrate 2 (rho family, small GTP binding protein Rac2)" | 1.929301347 | 1.929301347 |
| AA703652::slit (Drosophila) homolog 3 | -1.92415973 | 1.92415973 |
| "R66139::small inducible cytokine subfamily D (Cys-X3-Cys), member 1 (fractalkine, neurotactin)" | -1.922713842 | 1.922713842 |
| "AA868929::troponin T1, skeletal, slow" | 1.921673212 | 1.921673212 |
| "H29897::phospholipase C, beta 4" | -1.919274065 | 1.919274065 |
| T49652::arachidonate 5-lipoxygenase-activating protein | -1.917007338 | 1.917007338 |
| "AA916325::aldo-keto reductase family 1, member C3 (3-alpha hydroxysteroid dehydrogenase, type II)" | 1.914338217 | 1.914338217 |
| AA490210::tropomyosin 1 (alpha) | -1.912242355 | 1.912242355 |
| "W55872::nuclear factor of kappa light polypeptide gene enhancer in B-cells inhibitor, alpha" | 1.904327253 | 1.904327253 |
| "AA426025::Homer, neuronal immediate | -1.894217323 | 1.894217323 |

FIG. 14 (cont.)

| NAME | fold | absolute value |
|---|---|---|
| early gene, 2" | | |
| "R06438::myosin, light polypeptide kinase" | -1.890475337 | 1.890475337 |
| AA464540::ribosome binding protein 1 (dog 180kD homolog) | -1.885955163 | 1.885955163 |
| AA024832::Homo sapiens mRNA; cDNA DKFZp586I0324 (from clone DKFZp586I0324) | -1.876500492 | 1.876500492 |
| AA488341::cathepsin Z | -1.871330147 | 1.871330147 |
| R01139::ribosomal protein L10a | 1.869509089 | 1.869509089 |
| N22552::forkhead box C1 | -1.867762593 | 1.867762593 |
| T57556::histidine triad nucleotide-binding protein | 1.865648407 | 1.865648407 |
| AA293860::mitogen-activated protein kinase kinase kinase 4 | -1.862818445 | 1.862818445 |
| "AA129736::non-metastatic cells 5, protein expressed in (nucleoside-diphosphate kinase)" | -1.862716369 | 1.862716369 |
| N78902::leptin receptor | 1.862421207 | 1.862421207 |
| "AA456131::carbonic anhydrase VB, mitochondrial" | -1.857206911 | 1.857206911 |
| AA460270::midline 1 (Opitz/BBB syndrome) | -1.8567218 | 1.8567218 |
| AA101875::chondroitin sulfate proteoglycan 2 (versican) | -1.85637627 | 1.85637627 |
| AA004823::death associated transcription factor 1 | -1.846052726 | 1.846052726 |
| "AA461456::collagen, type V, alpha 2" | -1.843117455 | 1.843117455 |
| "R09069::glucan (1,4-alpha-), branching enzyme 1 (glycogen branching enzyme, Andersen disease, glycogen storage disease type IV)" | -1.838745632 | 1.838745632 |
| "H22136::guanylate cyclase 1, soluble, alpha 3" | -1.83462588 | 1.83462588 |
| H97597::glioma pathogenesis-related protein | -1.834069588 | 1.834069588 |
| R38117::peflin | 1.831104076 | 1.831104076 |
| "AA148736::syndecan 4 (amphiglycan, ryudocan)" | -1.830459617 | 1.830459617 |
| AA857163::amphiregulin (schwannoma-derived growth factor) | 1.830409053 | 1.830409053 |
| W49781::leupaxin | -1.830232215 | 1.830232215 |
| AA417881::bleomycin hydrolase | 1.828637476 | 1.828637476 |
| "AA455940::KIAA0473 (DnaJ (Hsp40) | -1.827130139 | 1.827130139 |

FIG. 14 (cont.)

| NAME | fold | absolute value |
|---|---|---|
| homolog, subfamily C, member 6)" | | |
| AA452556::translocating chain-associating membrane protein | -1.826217382 | 1.826217382 |
| "W72033::ras homolog gene family, member I" | -1.8165783 | 1.8165783 |
| "AA405569::fibroblast activation protein, alpha" | -1.813897645 | 1.813897645 |
| AA115876::protease inhibitor 12 (neuroserpin) | -1.812967111 | 1.812967111 |
| AA521346::serine threonine protein kinase | -1.807083774 | 1.807083774 |
| AA521346::serine threonine protein kinase | -1.807083774 | 1.807083774 |
| "H70099::mannosyl (alpha-1,6-)-glycoprotein beta-1,2-N-acetylglucosaminyltransferase" | -1.806767875 | 1.806767875 |
| AA430512::protease inhibitor 9 (ovalbumin type) | 1.80511413 | 1.80511413 |
| N72259::cornichon-like | 1.799000155 | 1.799000155 |
| AA424629::latent transforming growth factor beta binding protein 2 | -1.79888994 | 1.79888994 |
| "T70198::adaptor-related protein complex 2, mu 1 subunit" | -1.796760465 | 1.796760465 |
| N20798::v-kit Hardy-Zuckerman 4 feline sarcoma viral oncogene homolog | -1.793765791 | 1.793765791 |
| R83000::basic transcription factor 3 | 1.793052693 | 1.793052693 |
| "AA278240::DNA segment, numerous copies, expressed probes (GS1 gene)" | -1.791686812 | 1.791686812 |
| T72171::thyroxin-binding globulin | -1.791481075 | 1.791481075 |
| "AA262080::solute carrier family 12 (sodium/potassium/chloride transporters), member 2" | -1.79001533 | 1.79001533 |
| AA284568::calponin 2 | -1.789404816 | 1.789404816 |
| AA496359::immediate early protein | 1.782262434 | 1.782262434 |
| "H19246::Human clone 23575 mRNA, partial cds" | -1.780160228 | 1.780160228 |
| N78895::KIAA0429 gene product | 1.777754156 | 1.777754156 |
| "H61449::carboxypeptidase N, polypeptide 2, 83kD" | 1.775661534 | 1.775661534 |
| AA458578::KIAA0439 (NEDD4L) | -1.774870149 | 1.774870149 |
| AA455935::Homo sapiens mRNA; cDNA DKFZp564H1916 (from clone DKFZp564H1916) | -1.77406873 | 1.77406873 |
| "R79082::protein tyrosine phosphatase, receptor type, K" | -1.769900054 | 1.769900054 |
| AA043501::v-maf musculoaponeurotic | -1.769495004 | 1.769495004 |

FIG. 14 (cont.)

| NAME | fold | absolute value |
|---|---|---|
| fibrosarcoma (avian) oncogene homolog | | |
| "R59579::prostaglandin D2 synthase (21kD, brain)" | -1.768359484 | 1.768359484 |
| "AA129135::solute carrier family 29 (nucleoside transporters), member 1" | -1.767360435 | 1.767360435 |
| AA405804::lysyl oxidase-like 1 | -1.761855997 | 1.761855997 |
| AA465355::U3 snoRNP-associated 55-kDa protein | 1.761593274 | 1.761593274 |
| "AA865878::actin related protein 2/3 complex, subunit 4 (20 kD)" | -1.760623555 | 1.760623555 |
| AA454215::Homo sapiens clone 23631 mRNA sequence | -1.756250944 | 1.756250944 |
| AA455591::EphB3 | -1.755881896 | 1.755881896 |
| AA172400::retinoic acid induced 3 | -1.755523531 | 1.755523531 |
| AA235332::Ras suppressor protein 1 | -1.752923057 | 1.752923057 |
| "AA019482::creatine kinase, mitochondrial 1 (ubiquitous)" | 1.749064804 | 1.749064804 |
| R26224::membrane-anchored glycoprotein (metastasis and invasion) | -1.742689614 | 1.742689614 |
| "AA454080::inhibitor of DNA binding 4, dominant negative helix-loop-helix protein" | -1.741951911 | 1.741951911 |
| AA102053::tyrosyl-tRNA synthetase | 1.740725446 | 1.740725446 |
| AA496541::KIAA0317 gene product | -1.740526232 | 1.740526232 |
| H26182::neuronal PAS domain protein 2 | -1.738499631 | 1.738499631 |
| T53298::insulin-like growth factor binding protein 7 | -1.736479706 | 1.736479706 |
| AA278402::actin binding protein; macrophin (microfilament and actin filament cross-linker protein) | -1.730557891 | 1.730557891 |
| "AA017526::collagen, type IX, alpha 3" | -1.725062621 | 1.725062621 |
| AA262504::eyes absent (Drosophila) homolog 3 | 1.724477676 | 1.724477676 |
| H00817::lysophospholipase I | 1.724301851 | 1.724301851 |
| AA427561::heparan sulfate proteoglycan 2 (perlecan) | -1.722998438 | 1.722998438 |
| AA055523::calmodulin-like 3 | -1.71815583 | 1.71815583 |
| AA071473::matrilin 2 | -1.71758378 | 1.71758378 |
| AA625890::myosin VI | -1.71645818 | 1.71645818 |
| "AA598487::phosphoribosylglycinamide formyltransferase, phosphoribosylglycinamide synthetase, phosphoribosylaminoimidazole synthetase" | 1.712079868 | 1.712079868 |
| W65461::dual specificity phosphatase 5 | 1.709460116 | 1.709460116 |

FIG. 14 (cont.)

| NAME | fold | absolute value |
|---|---|---|
| AA130870::microtubule-associated protein 4 | -1.708404772 | 1.708404772 |
| AA149527::KIAA0947 protein | -1.70738839 | 1.70738839 |
| "H65395::proteasome (prosome, macropain) activator subunit 2 (PA28 beta)" | 1.702879771 | 1.702879771 |
| W90128::X-box binding protein 1 | 1.701305235 | 1.701305235 |
| W68169::platelet-derived growth factor beta polypeptide (simian sarcoma viral (v-sis) oncogene homolog) | -1.699720045 | 1.699720045 |
| H96235::v-ets avian erythroblastosis virus E26 oncogene homolog 2 | 1.698626929 | 1.698626929 |
| R38619::fucose-1-phosphate guanylyltransferase | -1.697542671 | 1.697542671 |
| H51554::superkiller viralicidic activity 2 (S. cerevisiae homolog)-like | -1.694599351 | 1.694599351 |
| AA496984::KIAA1071 protein (angiomotin) | -1.694402549 | 1.694402549 |
| N51499::A kinase (PRKA) anchor protein 2 | -1.692171779 | 1.692171779 |
| N54123::KIAA0349 protein | -1.689199914 | 1.689199914 |
| R14822::RAN binding protein 1 | 1.689084163 | 1.689084163 |
| H51066::Homo sapiens mRNA for leptin receptor gene-related protein | -1.688194996 | 1.688194996 |
| R10973::tumor susceptibility gene 101 | -1.685851894 | 1.685851894 |
| AA464630::thrombospondin 1 | -1.680830935 | 1.680830935 |
| AA457330::calpain-like protease | -1.676730701 | 1.676730701 |
| R43334::KIAA0410 (Nucleoporin like 1) | -1.674641473 | 1.674641473 |
| "R66447::v-myc avian myelocytomatosis viral related oncogene, neuroblastoma derived" | -1.67320822 | 1.67320822 |
| "AA070226::selenoprotein P, plasma, 1" | -1.673037255 | 1.673037255 |
| H13300::insulin-like growth factor 1 receptor | -1.670870172 | 1.670870172 |
| AA489569::keratin 7 | -1.670236137 | 1.670236137 |
| W95636::glypican 4 | -1.669209299 | 1.669209299 |
| R83837::v-yes-1 Yamaguchi sarcoma viral related oncogene homolog | 1.66837629 | 1.66837629 |
| "AA447600::Homo sapiens clone 628 unknown mRNA, complete sequence" | 1.66783433 | 1.66783433 |
| "AA460731::collagen, type I, alpha 1" | -1.667595918 | 1.667595918 |
| H73590::immunoglobulin mu | 1.667503303 | 1.667503303 |
| "AA772816::Human acidic 82 kDa protein mRNA, complete cds" | 1.66549315 | 1.66549315 |

FIG. 14 (cont.)

| NAME | fold | absolute value |
|---|---|---|
| "AA001449::pleiotrophin (heparin binding growth factor 8, neurite growth-promoting factor 1)" | -1.66495619 | 1.66495619 |
| H73724::cyclin-dependent kinase 6 | -1.664382722 | 1.664382722 |
| AA496691::dystroglycan 1 (dystrophin-associated glycoprotein 1) | -1.664179985 | 1.664179985 |
| "AA076063::Homo sapiens mRNA for caldesmon, 3' UTR" | -1.66408493 | 1.66408493 |
| AA293653::phosphoprotein enriched in astrocytes 15 | -1.663540838 | 1.663540838 |
| "AA432271::protein kinase, AMP-activated, beta 1 non-catalytic subunit" | -1.662274271 | 1.662274271 |
| T52325::DKFZP586B2022 protein | -1.662204365 | 1.662204365 |
| R26707::Human Chromosome 16 BAC clone CIT987SK-A-363E6 | 1.66093671 | 1.66093671 |
| AA459588::H.sapiens seb4D mRNA | -1.660518704 | 1.660518704 |
| "AA443982::protein phosphatase 1, catalytic subunit, alpha isoform" | 1.65857939 | 1.65857939 |
| W77812::cisplatin resistance associated | 1.65681729 | 1.65681729 |
| N79761::DNA-dependent protein kinase catalytic subunit-interacting protein 2 | -1.655595342 | 1.655595342 |
| W80739::Homo sapiens clone 24590 mRNA sequence | -1.655490727 | 1.655490727 |
| N51740::KIAA0879 protein | -1.655092575 | 1.655092575 |
| W69106::chromobox homolog 3 (Drosophila HP1 gamma) | 1.654964431 | 1.654964431 |
| AA430382::nucleoside phosphorylase | 1.654869156 | 1.654869156 |
| AA159194::FAT tumor suppressor (Drosophila) homolog | -1.654638058 | 1.654638058 |
| AA459390::Homo sapiens mRNA; cDNA DKFZp586O2223 (from clone DKFZp586O2223) | -1.651595485 | 1.651595485 |
| AA434159::chromosome 19 open reading frame 3 | -1.650843389 | 1.650843389 |
| AA872704::ribosomal protein S25 | 1.649528226 | 1.649528226 |
| AA167375::KIAA0530 protein | 1.646649919 | 1.646649919 |
| AA456616::ribosomal protein S5 | 1.645372813 | 1.645372813 |
| AA488618::transcription factor CP2 | 1.645239368 | 1.645239368 |
| AA775447::alpha-2-macroglobulin | -1.643579834 | 1.643579834 |
| "AA678280::adaptor-related protein complex 3, beta 1 subunit" | 1.641655187 | 1.641655187 |
| H88599::predicted osteoblast protein | -1.639757216 | 1.639757216 |
| T56013::3-hydroxy-3-methylglutaryl-Coenzyme A synthase 1 (soluble) | -1.637856741 | 1.637856741 |

FIG. 14 (cont.)

| NAME | fold | absolute value |
|---|---|---|
| AA857035::biliverdin reductase B (flavin reductase (NADPH)) | 1.637722601 | 1.637722601 |
| N46419::Homo sapiens mRNA for synaptogyrin 3 | -1.635967979 | 1.635967979 |
| N59532::aminomethyltransferase (glycine cleavage system protein T) | -1.635151256 | 1.635151256 |
| "H16813::protein phosphatase, EF hand calcium-binding domain 1" | 1.634199427 | 1.634199427 |
| AA489602::heat shock protein 75 | 1.633235318 | 1.633235318 |
| AA291412::KIAA0077 protein | -1.632389996 | 1.632389996 |
| N64862::FYN-binding protein (FYB-120/130) | 1.632057516 | 1.632057516 |
| AA130235::KIAA0567 protein | 1.630180461 | 1.630180461 |
| "AA608515::Homo sapiens NADH dehydrogenase (ubiquinone) 1 alpha subcomplex, 5 (13kD, B13) (NDUFA5) mRNA" | 1.629360871 | 1.629360871 |
| AA136054::ATP citrate lyase | -1.627584586 | 1.627584586 |
| AA702548::Homo sapiens clone 24988 mRNA sequence | 1.626216641 | 1.626216641 |
| "T71284::complement component 1, q subcomponent, beta polypeptide" | -1.622771191 | 1.622771191 |
| "H50345::succinate dehydrogenase complex, subunit A, flavoprotein (Fp)" | 1.622421311 | 1.622421311 |
| "AA405190::Homo sapiens signal sequence receptor, gamma (translocon-associated protein gamma) (SSR3), mRNA" | -1.621467924 | 1.621467924 |
| "AA405190::Homo sapiens signal sequence receptor, gamma (translocon-associated protein gamma) (SSR3), mRNA" | -1.621467924 | 1.621467924 |
| N50247::myotubularin related protein 6 | 1.620565098 | 1.620565098 |
| "AA669674::eukaryotic translation initiation factor 3, subunit 6 (48kD)" | 1.619333572 | 1.619333572 |
| "W45165::capping protein (actin filament) muscle Z-line, beta" | -1.618113612 | 1.618113612 |
| AA455896::glypican 1 | -1.617076741 | 1.617076741 |
| AA489752::cyclin G2 | 1.614468287 | 1.614468287 |
| AA018569::KIAA0073 protein | 1.614324525 | 1.614324525 |
| "AA485426::interferon (alpha, beta and omega) receptor 2" | -1.614263941 | 1.614263941 |
| H56109::clone 686 protein | -1.613082972 | 1.613082972 |
| "AA701933::CUG triplet repeat,RNA-binding protein 2" | -1.61295904 | 1.61295904 |

FIG. 14 (cont.)

| NAME | fold | absolute value |
|---|---|---|
| AA777192::polymerase (RNA) II (DNA directed) polypeptide I (14.5kD) | 1.612023379 | 1.612023379 |
| AA669603::membrane protein of cholinergic synaptic vesicles | -1.61193276 | 1.61193276 |
| AA599072::Homo sapiens clone 24422 mRNA sequence | -1.610200981 | 1.610200981 |
| AA702185::aryl hydrocarbon receptor nuclear translocator | -1.609959826 | 1.609959826 |
| N24824::v-kit Hardy-Zuckerman 4 feline sarcoma viral oncogene homolog | -1.608542982 | 1.608542982 |
| "T84633::interferon, alpha-inducible protein (clone IFI-6-16)" | 1.608043797 | 1.608043797 |
| N24113::dual specificity phosphatase 3 (vaccinia virus phosphatase VH1-related) | -1.60698528 | 1.60698528 |
| AA598670::ubiquitin-activating enzyme E1 (A1S9T and BN75 temperature sensitivity complementing) | -1.605446973 | 1.605446973 |
| R60995::coagulation factor C (Limulus polyphemus) homology (cochlin) | 1.60536823 | 1.60536823 |
| "T73556::fatty-acid-Coenzyme A ligase, long-chain 1" | -1.602286078 | 1.602286078 |
| N90109::nucleolin | 1.601119446 | 1.601119446 |
| R19306::nuclear factor I/X (CCAAT-binding transcription factor) | -1.600528721 | 1.600528721 |
| AA608548::SET translocation (myeloid leukemia-associated) | 1.59920726 | 1.59920726 |
| "AA121387::Homo sapiens mRNA for KIAA0560 protein, complete cds" | 1.598638358 | 1.598638358 |
| "AA443510::polymerase (DNA directed), delta 2, regulatory subunit (50kD)" | 1.596301871 | 1.596301871 |
| "AA677167::Homo sapiens mRNA for KIAA0481 protein, complete cds" | -1.59488141 | 1.59488141 |
| H53024::calumenin | -1.593284462 | 1.593284462 |
| AA405769::phosphoenolpyruvate carboxykinase 1 (soluble) | -1.593274881 | 1.593274881 |
| "R91503::ATP-binding cassette, sub-family C (CFTR/MRP), member 2" | 1.591931725 | 1.591931725 |
| AA127116::heterogeneous nuclear ribonucleoprotein A1 | 1.591154581 | 1.591154581 |
| "AA669042::actinin, alpha 1" | -1.590721798 | 1.590721798 |
| W02265::translational inhibitor protein p14.5 | 1.590452022 | 1.590452022 |
| "W02204::solute carrier family 24 (sodium/potassium/calcium exchanger), member 1" | -1.589666867 | 1.589666867 |

FIG. 14 (cont.)

| NAME | fold | absolute value |
|---|---|---|
| AA047443::LIM domain-containing preferred translocation partner in lipoma | -1.589582191 | 1.589582191 |
| "R26046::Homo sapiens clone 23711 unknown mRNA, partial cds" | 1.588478859 | 1.588478859 |
| H01820::KIAA0981 protein | -1.587697544 | 1.587697544 |
| "AA485226::vitamin D (1,25-dihydroxyvitamin D3) receptor" | 1.58596982 | 1.58596982 |
| "AA158035::pyridoxal (pyridoxine, vitamin B6) kinase" | 1.582681016 | 1.582681016 |
| T60109::GTP-binding protein homologous to Saccharomyces cerevisiae SEC4 | -1.582664055 | 1.582664055 |
| "R73003::solute carrier family 16 (monocarboxylic acid transporters), member 4" | -1.581034398 | 1.581034398 |
| W74533::latrophilin | -1.580716387 | 1.580716387 |
| AA053035::Homo sapiens mRNA; cDNA DKFZp586M1418 (from clone DKFZp586M1418) | 1.580365479 | 1.580365479 |
| H41165::ribosomal protein S19 | 1.580337076 | 1.580337076 |
| "AA598815::proteasome (prosome, macropain) subunit, alpha type, 5" | 1.579194098 | 1.579194098 |
| R44822::phosphoribosyl pyrophosphate synthetase-associated protein 1 | -1.579163692 | 1.579163692 |
| "AA417816::protein kinase C, nu" | 1.577960477 | 1.577960477 |
| AA452981::fibulin 2 | -1.576429031 | 1.576429031 |
| AA706987::UDP-N-acetyl-alpha-D-galactosamine:polypeptide N-acetylgalactosaminyltransferase 1 (GalNAc-T1) | 1.576058985 | 1.576058985 |
| AA463924::DNA segment on chromosome X (unique) 522 expressed sequence | -1.575620627 | 1.575620627 |
| AA101299::antiquitin 1 | -1.575529635 | 1.575529635 |
| "W07798::collagen, type XVIII, alpha 1" | -1.57530752 | 1.57530752 |
| H99883::KIAA0828 protein | -1.575289547 | 1.575289547 |
| R71440::collagen-binding protein 2 (colligen 2) | -1.57524205 | 1.57524205 |
| "H65030::phospholipase A2, group VII (platelet-activating factor acetylhydrolase, plasma)" | -1.573523254 | 1.573523254 |
| AA043412::peptidylprolyl isomerase C (cyclophilin C) | -1.573185026 | 1.573185026 |
| AA609783::Homo sapiens mRNA; cDNA DKFZp586A0618 (from clone DKFZp586A0618) | -1.572743449 | 1.572743449 |
| AA031398::src homology three (SH3) and | 1.5712933 | 1.5712933 |

FIG. 14 (cont.)

| NAME | fold | absolute value |
|---|---|---|
| cysteine rich domain | | |
| AA677257::thiopurine S-methyltransferase | 1.570840483 | 1.570840483 |
| H71857::ribosomal protein S23 | -1.570734858 | 1.570734858 |
| "AA425437::immunoglobulin superfamily, member 3" | -1.570636887 | 1.570636887 |
| "W67174::Human beta-1D integrin mRNA, cytoplasmic domain, partial cds" | 1.569071248 | 1.569071248 |
| AA454970::KIAA0204 gene product | 1.568644063 | 1.568644063 |
| AA486728::vinculin | -1.568097757 | 1.568097757 |
| R42763::KIAA0319 gene product | -1.564622344 | 1.564622344 |
| AA431773::Homo sapiens clone 23716 mRNA sequence | -1.562149145 | 1.562149145 |
| "AA621201::solute carrier family 30 (zinc transporter), member 3" | -1.561012145 | 1.561012145 |
| "AA669758::nucleophosmin (nucleolar phosphoprotein B23, numatrin)" | 1.559888337 | 1.559888337 |
| N39229::Human Chromosome 16 BAC clone CIT987SK-A-211C6 | 1.559829194 | 1.559829194 |
| T63971::KIAA0758 protein | -1.559543814 | 1.559543814 |
| "AA598513::protein tyrosine phosphatase, receptor type, F" | -1.558491016 | 1.558491016 |
| "AA776294::Rab geranylgeranyltransferase, alpha subunit" | 1.558057399 | 1.558057399 |
| H54023::leukocyte immunoglobulin-like receptor 2 | -1.557682941 | 1.557682941 |
| AA046650::putative nuclear protein | -1.557316657 | 1.557316657 |
| AA629909::glycyl-tRNA synthetase | 1.557200102 | 1.557200102 |
| "AA490213::transducer of ERBB2, 1" | 1.557162683 | 1.557162683 |
| AA460599::Jun activation domain binding protein | 1.556547909 | 1.556547909 |
| R00595::ribosomal protein L7a | -1.556213335 | 1.556213335 |
| "AA455369::solute carrier family 9 (sodium/hydrogen exchanger), isoform 1 (antiporter, Na+/H+, amiloride sensitive)" | -1.556062009 | 1.556062009 |
| AA732931::syntaxin 4A (placental) | 1.55283088 | 1.55283088 |
| T72336::partner of Ral-binding protein 1 | -1.552445937 | 1.552445937 |
| "H24329::guanylate cyclase 1, soluble, alpha 3" | -1.551165227 | 1.551165227 |
| H10964::peroxisomal biogenesis factor 12 | -1.551107653 | 1.551107653 |
| "AA495846::ras homolog gene family, member B" | -1.550788081 | 1.550788081 |
| "AA018676::protein kinase, AMP-activated, gamma 1 non-catalytic subunit" | 1.550102129 | 1.550102129 |
| R08891::KIAA0676 (GTPase-activating | -1.549787074 | 1.549787074 |

FIG. 14 (cont.)

| NAME | fold | absolute value |
|---|---|---|
| protein GYP2) | | |
| "AA291972::Homo sapiens herpesvirus entry mediator B (poliovirus receptor-related 2) (HVEB), mRNA" | -1.548754346 | 1.548754346 |
| "AA644129::Fanconi anemia, complementation group A" | 1.547495295 | 1.547495295 |
| R70685::jagged1 (Alagille syndrome) | -1.547288914 | 1.547288914 |
| AA430050::KIAA0729 protein | -1.546767815 | 1.546767815 |
| AA442040::Clathrin assembly lymphoid-myeloid leukemia gene | -1.544781235 | 1.544781235 |
| AA190339::dual specificity phosphatase 3 (vaccinia virus phosphatase VH1-related) | -1.543309482 | 1.543309482 |
| AA427891::activated p21cdc42Hs kinase | -1.542956007 | 1.542956007 |
| AA488087::FK506-binding protein 9 (63 kD) | -1.542776909 | 1.542776909 |
| "N30428::nuclear receptor subfamily 3, group C, member 1" | 1.542641398 | 1.542641398 |
| H73727::ribosomal protein S14 | 1.542484352 | 1.542484352 |
| AA633993::cell division cycle 10 (homologous to CDC10 of S. cerevisiae) | 1.54159252 | 1.54159252 |
| N63623::KIAA0471 (RAB GTPase activating protein 1-like) | -1.541259727 | 1.541259727 |
| AA291556::Homo sapiens ras inhibitor (RIN1) mRNA | 1.541198509 | 1.541198509 |
| W58032::frizzled-related protein | -1.540448103 | 1.540448103 |
| AA148230::Tat-interacting protein (30kD) | -1.540213069 | 1.540213069 |
| N29585::KIAA0934 protein | -1.539942583 | 1.539942583 |
| N92519::E2F transcription factor 3 | -1.537359962 | 1.537359962 |
| AA402207::eyes absent (Drosophila) homolog 2 | -1.536366609 | 1.536366609 |
| AA190789::KIAA0746 protein | -1.535761944 | 1.535761944 |
| AA496804::sperm specific antigen 2 | -1.535121028 | 1.535121028 |
| "AA775445::platelet-activating factor acetylhydrolase, isoform Ib, alpha subunit (45kD)" | -1.534418265 | 1.534418265 |
| AA478273::APEX nuclease (multifunctional DNA repair enzyme) | 1.533464674 | 1.533464674 |
| AA490617::vaccinia related kinase 2 | 1.531022678 | 1.531022678 |
| "AA630016::chaperonin containing TCP1, subunit 8 (theta)" | -1.530728652 | 1.530728652 |
| AA458965::natural killer cell transcript 4 | -1.530057192 | 1.530057192 |
| N73761::dihydropyrimidinase | -1.529746375 | 1.529746375 |
| T67066::Homo sapiens clone 24590 mRNA sequence | -1.52969689 | 1.52969689 |

FIG. 14 (cont.)

| NAME | fold | absolute value |
|---|---|---|
| AA458622::BH-protocadherin (brain-heart) | -1.529690169 | 1.529690169 |
| T64469::p8 protein (candidate of metastasis 1) | -1.5288471 | 1.5288471 |
| AA046679::Homo sapiens clone TUA8 Cri-du-chat region mRNA | -1.528652626 | 1.528652626 |
| AA428139::KIAA0936 protein | -1.527437597 | 1.527437597 |
| AA443177::signal recognition particle 72kD | 1.527310506 | 1.527310506 |
| H23021::retinoblastoma-binding protein 8 | -1.52549385 | 1.52549385 |
| AA487589::methionine aminopeptidase; eIF-2-associated p67 | 1.525055432 | 1.525055432 |
| R70518::tumor necrosis factor alpha-inducible cellular protein containing leucine zipper domains; Huntingtin interacting protein L | -1.524434172 | 1.524434172 |
| "AA481026::SWI/SNF related, matrix associated, actin dependent regulator of chromatin, subfamily a, member 2" | 1.524196811 | 1.524196811 |
| R41691::Homo sapiens clone IMAGE 30714 | 1.523348098 | 1.523348098 |
| W95595::corneodesmosin | -1.523238781 | 1.523238781 |
| AA504442::KIAA0029 protein | -1.522313752 | 1.522313752 |
| N26645::Homo sapiens clone 24723 mRNA sequence | -1.521265502 | 1.521265502 |
| H06296::ELL gene (11-19 lysine-rich leukemia gene) | -1.520910382 | 1.520910382 |
| R38201::opioid-binding protein/cell adhesion molecule-like | 1.520308092 | 1.520308092 |
| "AA670429::secretory granule, neuroendocrine protein 1 (7B2 protein)" | -1.517795225 | 1.517795225 |
| N47111::5-hydroxytryptamine (serotonin) receptor 2C | -1.51754042 | 1.51754042 |
| AA486435::chondrocyte-derived ezrin-like protein | -1.515243691 | 1.515243691 |
| AA464612::Homo sapiens mRNA; cDNA DKFZp564H0223 (from clone DKFZp564H0223) | 1.514615397 | 1.514615397 |
| N48000::Homo sapiens mRNA; cDNA DKFZp586L141 (from clone DKFZp586L141) | -1.514598185 | 1.514598185 |
| "AA135813::thymosin, beta 4, X chromosome" | -1.513601015 | 1.513601015 |
| AA478078::KIAA0134 gene product | 1.512984846 | 1.512984846 |
| AA425450::glycoprotein (transmembrane) | -1.512853995 | 1.512853995 |

FIG. 14 (cont.)

| NAME | fold | absolute value |
|---|---|---|
| nmb | | |
| N59721::CAG repeat domain | -1.510979805 | 1.510979805 |
| "AA126760::tubulin, gamma polypeptide" | 1.5106382 | 1.5106382 |
| N22178::nuclear DNA-binding protein | 1.510592862 | 1.510592862 |
| AA490546::thymine-DNA glycosylase | -1.509981112 | 1.509981112 |
| "R88246::adrenergic, beta, receptor kinase 1" | 1.508727493 | 1.508727493 |
| AA156571::alanyl-tRNA synthetase | 1.507793887 | 1.507793887 |
| AA054287::RNA binding motif protein 3 | 1.505933997 | 1.505933997 |
| AA447774::cytochrome c-1 | 1.504519145 | 1.504519145 |
| H99843::quinolinate phosphoribosyltransferase (nicotinate-nucleotide pyrophosphorylase (carboxylating)) | 1.503295161 | 1.503295161 |
| "AA634103::thymosin, beta 4, X chromosome" | -1.502312964 | 1.502312964 |

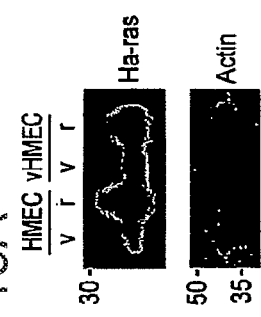
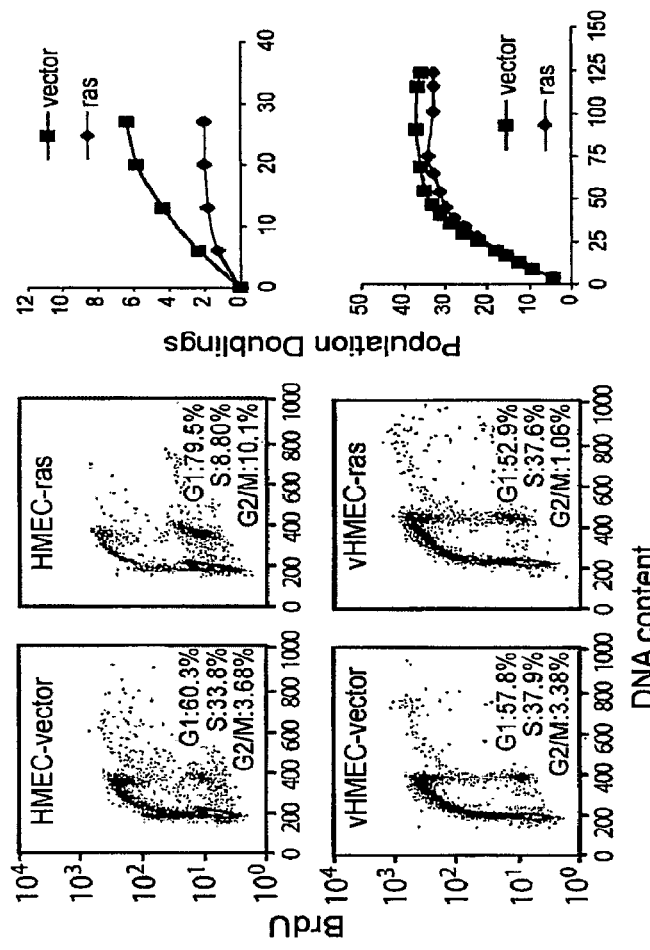
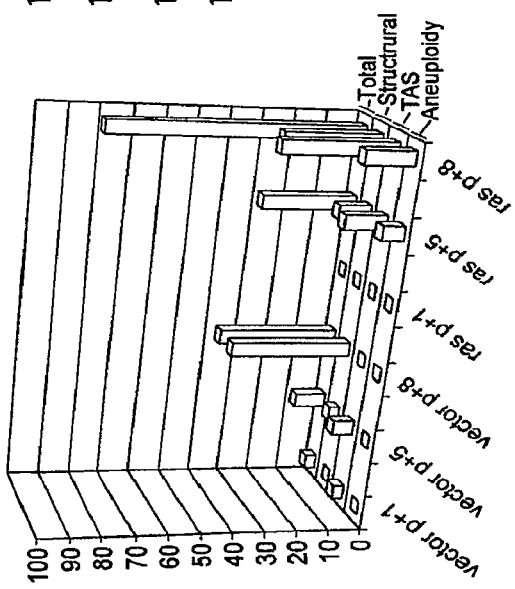
Fig. 15A
Fig. 15B
Fig. 15C

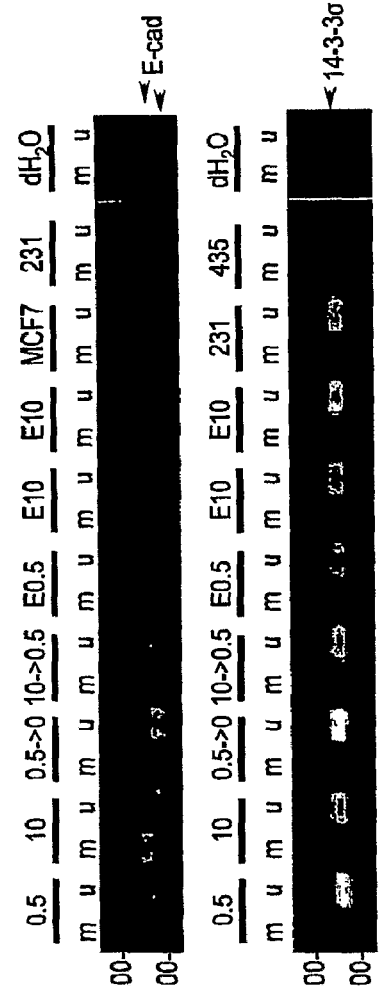
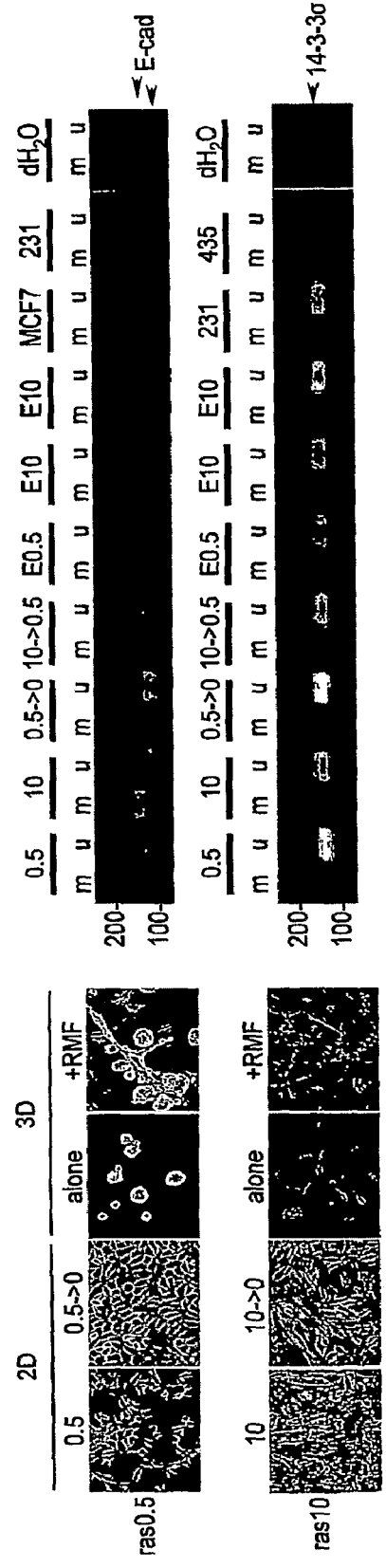
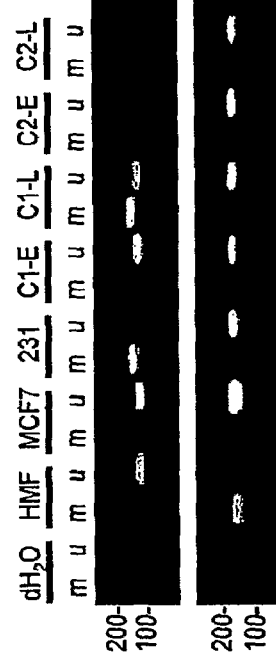
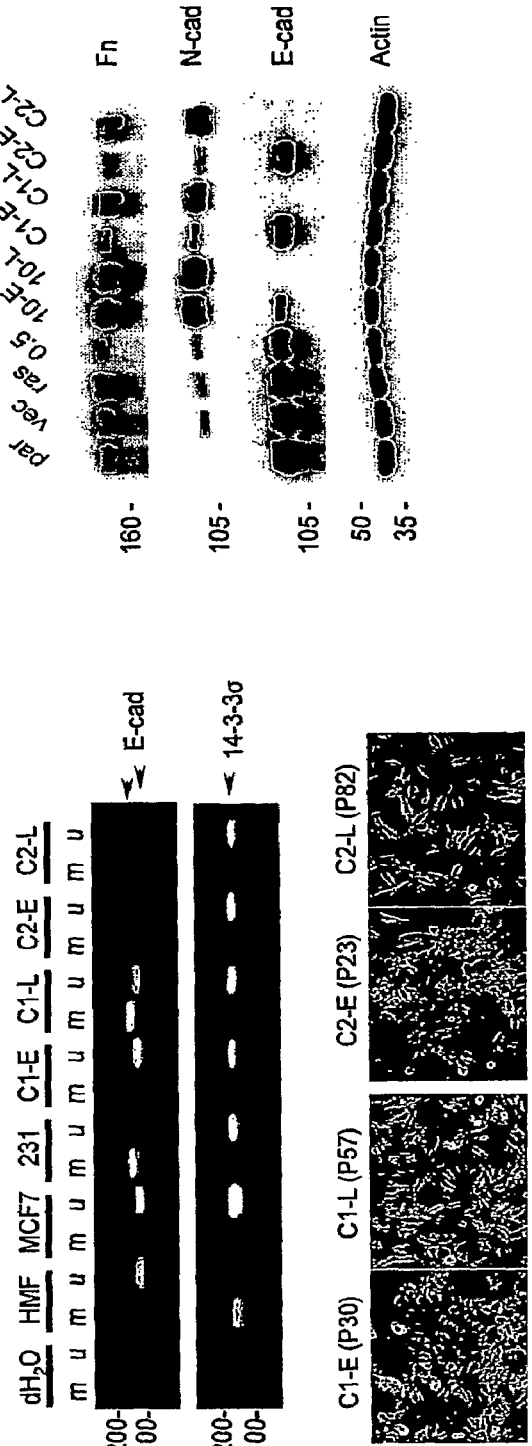

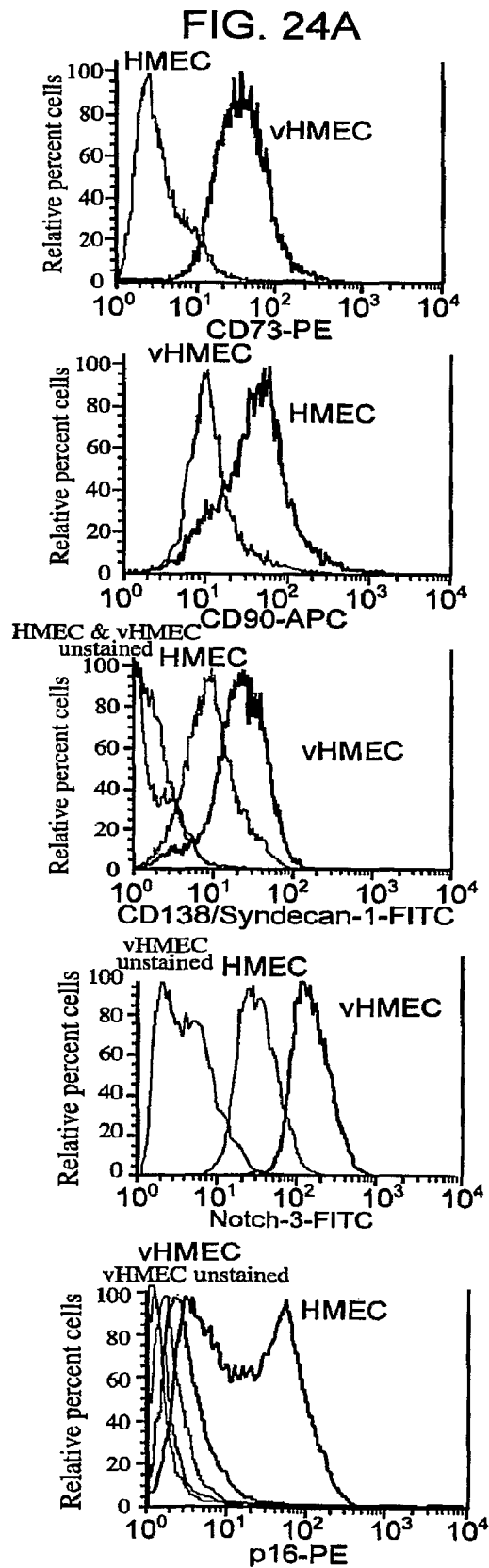

CANCER BIOMARKERS AND METHODS OF USE THEREOF

STATEMENT REGARDING FEDERALLY SPONSORED R&D

This invention was made with government support under grants no. R01 CA122024, P50 CA058207 and R01 CA097214, awarded by the National Institutes of Health (National Cancer Institute). The government has certain rights in the invention.

REFERENCE TO SEQUENCE LISTING

The present application includes a Sequence Listing in electronic format. The Sequence Listing is provided as a file entitled SEQLIST_UC102_001C2.txt, created and last saved on Jul. 22, 2022, which is 15,304 bytes in size, and is updated by a file entitled REPLACEMENTSEQLIST_UC102_001C2.txt, created and last saved on Sep. 13, 2022, which is 15,301 bytes in size. The information in the electronic format of the Sequence Listing is incorporated herein by reference in its entirety.

BACKGROUND

Cancer, like many diseases, is not the result of a single, well-defined cause, but rather can be viewed as several diseases, each caused by different aberrations in informational pathways, that ultimately result in apparently similar pathologic phenotypes. Identification of polynucleotides that correspond to genes that are differentially expressed in cancerous, pre-cancerous, or low metastatic potential cells relative to normal cells of the same tissue type, provides the basis for diagnostic tools, facilitates drug discovery by providing for targets for candidate agents, and further serves to identify therapeutic targets for cancer therapies that are more tailored for the type of cancer to be treated.

LITERATURE

Crawford et al. (2004) *Cancer Cell* 5:263; McDermott et al. (2006) *PLoS Biol.* 4:e51; Berman et al. (2005) *Cold Spring Harbor Symp. Quant. Biol.* 70:317; Gauthier et al. (2005) *Cancer Res.* 65:1792; Shim et al. (2003) *Cancer Res.* 63:2347; Hoist et al. (2003) *Cancer Res.* 63:1596; Tlsty et al. (2004) *J. Mammary Gland Biol. Neoplasia* 9:263; Kruger et al. (1991) *Br. J. Cancer* 63:114-118.

SUMMARY OF THE INVENTION

The present invention provides detection methods for detecting a pre-cancerous epithelial cell signature. The present invention further provides reagents for use in the detection methods. A subject detection method is useful in various imaging, diagnostic, prognostic, and patient monitoring methods, which are also provided.

BRIEF DESCRIPTION OF THE DRAWINGS

FIGS. 7A-D depict correlation of p16 overexpression, coupled with proliferation, with increased risk of subsequent tumor events among women with ductal carcinoma in situ (DCIS).

FIGS. 8A-D depict concordance between p16 or COX-2 mRNA and protein expression in tumors.

FIGS. 9A-C depict the correlation between COX-2 overexpression, coupled with proliferation, with increased risk of subsequent tumor events among women with DCIS.

FIGS. 11A-C depict the relationship between overexpression of COX-2, in the absence or presence of proliferation, and p16/Rb dysfunction.

FIG. 14 depicts mRNAs that are over-expressed or under-expressed in vHMEC, compared to normal HMEC.

FIGS. 15A-C depict immunoblot analysis (FIG. 15A), cell cycle analysis (FIG. 15B), and chromosome analysis (FIG. 15C) of vHMEC comprising a control expression vector or a Ha-rasV 12 expression vector.

FIGS. 17A-D depict the effect of extracellular signaling and intracellular ras activation on cellular morphology and methylation in HMEC.

FIGS. 24A-C depict marker analysis of vHMEC and HMEC.

DEFINITIONS

Figure 1:
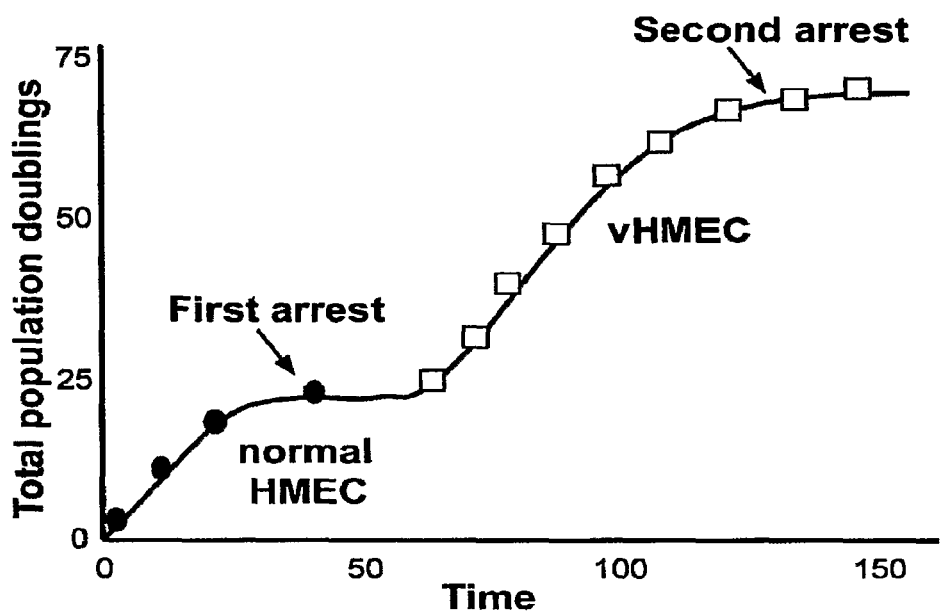
FIG. 1 is a growth curve of normal human mammary epithelial cells (HMEC) and variant human mammary epithelial cells (vHMEC).
Figure 2A:
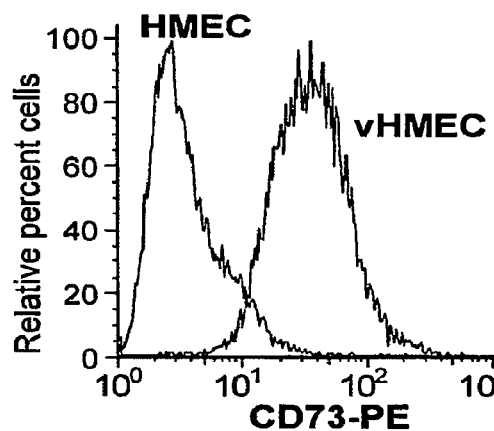
FIG. 2 depicts fluorescence activated cell sorting (FACS) analysis of CD73, CD90, CD138, and Notch receptor-3 expression on vHMEC and HMEC cells.
Figure 2B:
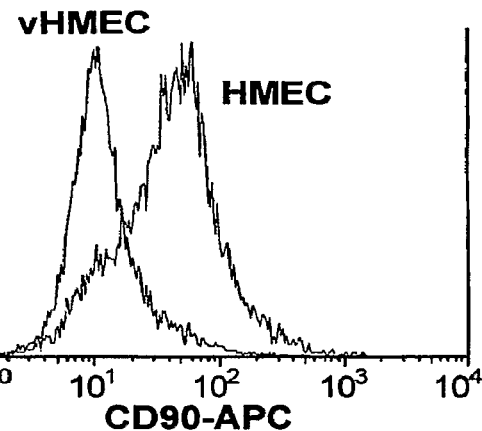
Figure 2C:
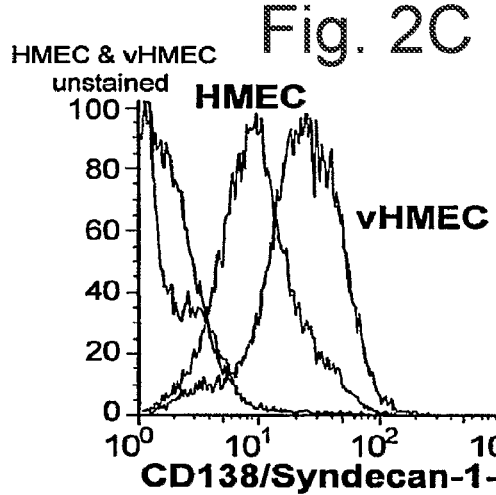
Figure 2D:
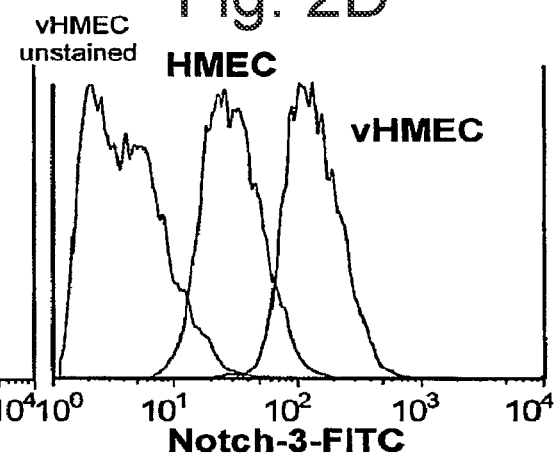

A "gene product" is a biopolymeric product that is expressed or produced by a gene, such as a peptide or protein. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e., cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "polynucleotide" refers to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) *Cell* 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) *Nucl. Acids Res.* 24:1841-1848; Chaturvedi et al. (1996) *Nucl. Acids Res.* 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids (Pooga et al *Curr Cancer Drug Targets.* (2001) 1:231-9).

The term "capture agent" refers to an agent that binds a target molecule through an interaction that is sufficient to permit the agent to bind and concentrate the target molecule from a homogeneous mixture of different molecules. The binding interaction is typically mediated by an affinity region of the capture agent. Typical capture agents include any moiety that can specifically bind to a target molecule. In certain embodiments, a polypeptide, e.g., an antibody protein, may be employed. Capture agents usually "specifically bind" a target molecule. Accordingly, the term "capture agent" refers to a molecule or a multi-molecular complex which can specifically bind a target molecule, e.g., a phosphorylated polypeptide, with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{10-11}$ M, less than about $10^{-12}$ M, to up to about $10^{-16}$ M) without significantly binding to other molecules.

The term "specific binding" refers to the ability of a capture agent to preferentially bind to a particular target molecule that is present in a homogeneous mixture of different target molecule. In certain embodiments, a specific binding interaction will discriminate between desirable and undesirable target molecules in a sample, typically more than about 10 to 100-fold or more (e.g., more than about 1000- or 10,000-fold).

The term "capture agent/target complex" is a complex that results from the specific binding of a capture agent with a target, i.e., a "binding partner pair". A capture agent and an target for the capture agent will usually specifically bind to each other under "conditions suitable for specific binding", where such conditions are those conditions (in terms of salt concentration, pH, detergent, protein concentration, temperature, etc.) which allow for binding to occur between capture agents and targets to bind in solution. Such conditions, particularly with respect to proteins and antibodies, include those described in Harlow and Lane (Antibodies: A Laboratory Manual Cold Spring Harbor Laboratory, Cold Spring Harbor, N.Y. (1989)) and Ausubel, et al (Short Protocols in Molecular Biology, 5th ed., Wiley & Sons, 2002).

As used herein, "binding partners" and equivalents thereof refer to pairs of molecules that can be found in a capture agent/target complex, i.e., exhibit specific binding with each other.

The phrase "surface-bound capture agent" refers to a capture agent that is immobilized on a surface of a substrate. In certain embodiments, the capture agent employed herein may be present on a surface of the same support, e.g., in the form of an array.

The term "pre-determined" refers to an element whose identity is known prior to its use. An element may be known by name, sequence, molecular weight, its function, or any other attribute or identifier. In some embodiments, the term "polypeptide of interest", i.e., a known polypeptide that is of interest, is used synonymously with the term "pre-determined polypeptide".

The term "antibody protein" is used herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Types of antibodies, including antibody isotypes, monoclonal antibodies and antigen-binding fragments thereof (e.g., Fab, Fv, scFv, and Fd fragments, chimeric antibodies, humanized antibodies, single-chain antibodies, etc) are known and need not be described in any further detail.

A polynucleotide "derived from" or "specific for" a designated sequence, such as a target sequence of a target nucleic acid, refers to a polynucleotide sequence which comprises a contiguous sequence of approximately at least about 6 nucleotides, at least about 8 nucleotides, at least about 10-12 nucleotides, or at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientation relative to the original polynucleotide.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.govBLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a eDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W, Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms.

Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50. ° C. or about 55° C. to about 60° C.; or, a salt concentration of about 0.15 M NaCl at 72° C. for about 15 minutes; or, a salt concentration of about 0.2×SSC at a temperature of at least about 50° C. or about 55. ° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37. ° C. (for 14-base oligos), 48. ° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tin) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A "DNA-dependent DNA polymerase" is an enzyme that synthesizes a complementary DNA copy from a DNA template. Examples include DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from E. coli and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. RNA degradation mediated by an RNAse H may result in separation of RNA from a RNA:DNA complex, or the RNAse H may cut the RNA at various locations such that portions of the RNA melt off or permit enzymes to unwind portions of the RNA.

As used herein, the term "target nucleic acid region" or "target nucleic acid" or "target molecules" refers to a nucleic acid molecule with a "target sequence" to be detected (e.g., in a method involving nucleic acid hybridization and/or amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with its use in synthesis of primer extension products, and are in many embodiments in the range of between 8 nucleotides and 100 nucleotides (nt) in length, such as 10 nt to 75 nt, 15 nt to 60 nt, 15 nt to 40 nt, 18 nt to 30 nt, 20 nt to 40 nt, 21 nt to 50 nt, 22 nt to 45 nt, 25 nt to 40 nt, and so on, e.g., in the range of between 18 nt and 40 nt, between 20 nt and 35 nt, between 21 and 30 nt in length, inclusive, and any length between the stated ranges. Primers can be in the range of between 10-50 nucleotides long, such as 15-45, 18-40, 20-30, 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are in many embodiments in the range of between 8 nt and 100 nt in length, such as 8 to 75 nt, 10 to 74 nt, 12 to 72 nt, 15 to 60 nt, 15 to 40 nt, 18 to 30 nt, 20 to 40 nt, 21 to 50 nt, 22 to 45 nt, 25 to 40 nt in length, and so on, e.g., in the range of between 18-40 nt, 20-35 nt, or 21-30 nt in length, and any length between the stated ranges. In some embodiments, a probe is in the range of between 10-50 nucleotides long, such as 15-45, 18-40, 20-30, 21-28, 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TAQMAN™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

Probes and primers contemplated herein include those useful in various amplification and/or detection systems, including those in which primers and probes are provided as bi-functional molecules. Exemplary amplification and/or detection systems include Sunrise™ primer-based systems, Molecular Beacons, the Taqman™ system, an Amplifluor™ hairpin primer-based system, a Scorpions technology (e.g., bi-functional molecules containing a PCR primer element covalently linked to a probe element), and a Light Upon Extension or LUX™-based system. Further exemplary detection systems include those based on a melt-curve analysis, and using intercalating dyes such as the fluorescent dye SYBR Green.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

An "array," includes any one, two-dimensional or substantially two-dimensional (as well as a three-dimensional) arrangement of addressable regions bearing a particular chemical moiety or moieties (e.g., polynucleotide or oligonucleotide sequences (nucleic acids), polypeptides (e.g., proteins such antibodies) associated with that region. In the broadest sense, arrays are arrays of polymeric binding agents, where the polymeric binding agents may be any of: polypeptides, proteins (e.g., antibodies), nucleic acids, synthetic mimetics of such polymeric binding agents, etc. In some embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). In other embodiments, the arrays are arrays of polypeptides, e.g., proteins or fragments thereof, antibodies, and the like.

Any given substrate may carry one, two, four or more or more arrays disposed on a front surface of the substrate. Depending upon the use, any or all of the arrays may be the same or different from one another and each may contain multiple spots or features. An array can contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, from 5.0 μm to 500 μm, or from 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other polymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, than 4 mm and less than 600 mm, or less than 400 mm; a width of more than 4 mm and less than 1 m, less than 500 mm, or less than 400 mm; and a thickness of more than 0.01 mm and less than 5.0 mm, more than 0.1 mm and less than 2 mm, or more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 urn or 633 nm.

Arrays can be fabricated using drop deposition from pulse jets of either polynucleotide precursor units (such as monomers) in the case of in situ fabrication, or the previously obtained polynucleotide. Such methods are described in detail in, for example, U.S. Pat. Nos. 6,242,266, 6,232,072, 6,180,351, 6,171,797, 6,323,043, and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (e.g., rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

A "scanner" is device for evaluating arrays. In scanners, an optical light source, particularly a laser light source, generates a light which is focused on the array and sequentially illuminates surface regions of known location (for example, a point or line) on an array substrate. The resulting signals from the surface regions are collected either employing the same lens used to focus the light onto the array or using a separate lens positioned to one side of the lens used to focus the onto the array. The collected signals may be then transmitted through appropriate spectral filters, to an optical detector. A recording device, such as a computer memory, records the detected signals and builds up a scan file of intensities as a function of position, or time as it relates to the position. In the case of spot illumination, such intensities, as a function of position, are typically referred to in the art as "pixels". Biopolymer arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorimeter. A number of different types of such devices are commercially available from different sources, such as such as Perkin-Elmer, Agilent, or Axon Instruments, etc., and examples of suitable scanners are described in U.S. Pat. Nos. 5,091,652; 5,760,951, 6,320,196 and 6,355,934.

The term "assessing" includes any form of measurement, and includes determining if an element is present or not. The terms "determining," "measuring," "evaluating," "assessing," and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "binds specifically," in the context of a specific binding reagent, e.g., in the context of antibody binding, refers to high avidity and/or high affinity binding of an antibody to a specific polypeptide i.e., epitope of a polypeptide, e.g., a CD73 polypeptide, a CD138 polypeptide, a notch receptor-3 polypeptide, a CD90 polypeptide, a BMI-1 polypeptide, or a Cox-2 polypeptide. For example, antibody binding to an epitope on a specific target gene product or fragment thereof is stronger than binding of the same antibody to any other epitope, particularly those which may be present in molecules in association with, or in the same sample, as the specific polypeptide of interest, e.g., binds more strongly to a specific target polypeptide than to any other epitopes so that by adjusting binding conditions the antibody binds almost exclusively to the specific target epitope and not to any other epitope, or to any other polypeptide which does not comprise the epitope. Antibodies that bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a target polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

A composition (e.g. a polynucleotide, polypeptide, antibody, or host cell) that is "isolated" or "in substantially isolated form" refers to a composition that is in an environment different from that in which the composition naturally occurs. For example, a polynucleotide that is in substantially isolated form is outside of the host cell in which the polynucleotide naturally occurs, and could be a purified fragment of DNA, could be part of a heterologous vector, or could be contained within a host cell that is not a host cell from which the polynucleotide naturally occurs. The term "isolated" does not refer to a genomic or eDNA library, whole cell total protein or mRNA preparation, genomic DNA preparation, or an isolated human chromosome. A composition which is in substantially isolated form is usually substantially purified.

As used herein, the term "substantially purified" refers to a compound (e.g., a polynucleotide, a polypeptide or an antibody, etc.) that is removed from its natural environment and is at least 60% free, 75% free, at least 90%, at least 95%, at least 98%, or at least 99% free from other components with which it is naturally associated. Thus, for example, a composition containing A is "substantially free of" B when at least 85% by weight of the total A+B in the composition is A. For example, A comprises at least about 90% by weight of the total of A+B in the composition, or at least about 95% or even 99% by weight. In the case of polynucleotides, "A" and "B" may be two different genes positioned on different chromosomes or adjacently on the same chromosome, or two isolated cDNA species, for example.

If one composition is "bound" to another composition, the compositions do not have to be in direct contact with each other. In other words, bonding may be direct or indirect, and, as such, if two compositions (e.g., a substrate and a polypeptide) are bound to each other, there may be at least one other composition (e.g., another layer) between to those compositions. Binding between any two compositions described herein may be covalent or non-covalent. The terms "bound" and "linked" are used interchangeably herein.

As used herein, "subject," "host," "patient," and "individual" are used interchangeably to refer to a mammal, e.g., a human, a non-human primate, ungulates, canines, felines, equines, and the like.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

As used herein, the term "a polypeptide associated with cancer" refers to a polypeptide encoded by a polynucleotide that is differentially expressed in a cancer cell.

The term "biological sample" encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment," "treating," "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells. Detection of pre-cancerous cells is of particular interest.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. A permanent genetic change is generally achieved by introduction of the DNA into the genome of the cell. Suitable methods of genetic modification include viral infection, transfection, conjugation, protoplast fusion, electroporation, particle gun technology, calcium phosphate precipitation, direct microinjection, and the like. A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, or a cell from a multicellular organism (e.g., a primary cell, a cell line) cultured as a unicellular entity, which eukaryotic cell can be, or has been, used as a recipient for a nucleic acid (e.g., an exogenous nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an epithelial cell" includes a plurality of such cells and reference to "the biomarker" includes reference to one or more biomarkers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides reagents and methods for detecting a pre-cancerous or cancerous epithelial cell. It has been found that certain signatures associated with mammary epithelial cells identify pre-cancerous cells, and indicate a level of risk that a malignant tumor will develop. Mammary epithelial cell signatures include, for example, the presence and/or levels and/or posttranslation modification of a protein or collection of proteins; the presence and/or level of a nucleic acid; and the integrity or methylation status or other parameter of a nucleic acid.

A variant mammary epithelial cell (vMEC) appears morphological normal, e.g., a vMEC is morphologically indistinguishable from a normal mammary epithelial cell. However, a vMEC has a "signature" that indicates its potential for developing into a cancerous cell, e.g., a vMEC is a pre-malignant cell. Thus, e.g., a vMEC signature distinguishes it from an MEC (e.g., a control, normal MEC that is not pre-malignant) by one or more of: 1) a lower than normal level of an mRNA, compared to the level of the mRNA in a MEC; 2) a higher than normal level of an mRNA, compared to the level of the mRNA in a MEC; 3) a lower than normal level of a protein, compared to the level of the protein in a MEC; 4) a higher than normal level of a protein, compared to the level of the protein in an MEC; 5) a higher level of a post-translationally modified protein, compared to the level of the post-translationally modified protein in an MEC; 6) an increased level of genomic DNA abnormalities, compared to the level found in an MEC; and 7) an increased level of methylation of a particular promoter(s), compared to the level of methylation of the promoter(s) in an MEC.

For example, an mRNA or a protein that is differentially expressed in a vMEC, compared to a control, normal MEC, is present in the vMEC at a level from about 1.5-fold to 100-fold higher or lower than the level of the mRNA or protein in a control, normal MEC, e.g., an mRNA or a protein that is differentially expressed in a vMEC is present in the vMEC at a level of from about 1.5-fold to about 2-fold, from about 2-fold to about 2.5-fold, from about 2.5-fold to about 5-fold, from about 5-fold to about 10-fold, from about 10-fold to about 15-fold, from about 15-fold to about 20-fold, from about 20-fold to about 25-fold, from about 25-fold to about 50-fold, from about 50-fold to about 75-fold, or from about 75-fold to about 100-fold, or more, higher or lower than the level of the mRNA or protein in a control, normal MEC. In some embodiments, a control, normal MEC is a primary MEC isolated from an individual, where the control, normal MEC is a CD73⁻ MEC, e.g., is substantially negative for CD73.

Methods for detecting a pre-cancerous or cancerous epithelial cell find use in various clinical settings, e.g., imaging methods, diagnostic methods, prognostic methods, and monitoring methods. Reagents suitable for use in a subject method include: 1) reagents that detect the presence and/or level of a selected protein or collection of proteins; 2) reagents that detect posttranslational modifications of gene expression-controlling proteins; 3) reagents that detect the level of a selected DNA; 4) reagents that detect the integrity of a selected DNA; 5) reagents that detect methylation status of a selected DNA; 6) reagents that detect the presence and/or a level of a selected mRNA or collection of mRNA; 7) reagents that detect the presence and/or level of a selected microRNA; 8) reagents for proteomics analyses; and 9) reagents for biological assays.

Reagents

As noted above, the present invention provides reagents for detecting a mammary epithelial cell signature that provides for identification of risk that a mammary epithelial cell will become malignant. These reagents are described in more detail below.

Reagents for Detecting a Mammary Epithelial Cell Signature

The present invention provides reagents for detecting a mammary epithelial cell (MEC) signature, e.g., an MEC signature that is indicative of a pre-cancerous MEC. An "MEC signature" includes, but is not limited to: 1) the presence and/or level of a selected protein or collection of proteins; 2) the presence or absence of a posttranslational modification of a selected protein or collection of proteins; 3) the presence of a chromatin modification; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

Suitable reagents include, but are not limited to, 1) reagents that detect the presence and/or level of a selected protein or collection of proteins; 2) reagents that detect posttranslational modifications of gene expression-controlling proteins; 3) reagents that detect the level of a selected DNA; 4) reagents that detect the integrity of a selected DNA; 5) reagents that detect methylation status of a selected DNA; 6) reagents that detect the presence and/or a level of a selected mRNA or collection of mRNA; 7) reagents that detect the presence and/or level of a selected microRNA; 8) reagents for proteomics analyses; and 9) reagents for use in biological assays.

Specific Binding Agents

Specific binding agents (also referred to as "capture agents") are provided, which are useful in a subject detection method, where specific binding agents include specific binding agents that detect the presence and/or level of a protein in an MEC, specific binding agents that detect the presence and/or levels of a selected posttranslationally modified protein, and the like. "Specific binding agents" include, e.g., antibodies, antigen-binding fragments of an antibody; an epitope-binding fragment of an antibody; or other protein that bind specifically to an epitope on a target polypeptide. The discussion below refers to antibody reagents. However, any specific binding agent is suitable for use. Hence, where the disclosure refers to "antibody reagents," other specific binding agents are also contemplated.

Antibody reagents are provided, which are useful in a subject detection method. In some embodiments, an antibody reagent detects the presence and/or levels of a selected protein or collection of proteins in an MEC. In other embodiments, an antibody reagent detects the presence and/or levels of a selected posttranslationally modified protein, e.g., a protein that controls gene expression.

A subject antibody reagent can be in substantially isolated form, e.g., in an environment other than its naturally-occurring environment. In some embodiments, a subject antibody reagent is a synthetic antibody reagent, or a recombinant antibody reagent. In some embodiments, the antibody reagents are immobilized on an insoluble support. In some embodiments, a panel of antibodies is provided, where a panel of antibodies is two or more different antibodies, each specific for a different polypeptide that comprises an MEC signature. The antibody reagents bind specifically to a selected target polypeptide or collection of selected target polypeptides.

Suitable antibody reagents include antibodies of any isotype; single-chain Fv; Fab; Fab; Fv; F(ab')$_2$; artificial antibodies; and the like. Suitable antibodies also include "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033. In some embodiments, the antibodies are monoclonal antibodies. In some embodiments, an antibody reagent is directly or indirectly detectably labeled.

Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. Other suitable detectable labels include fluorescent dyes, e.g., Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

In some embodiments, an antibody reagent comprises, covalently linked to the antibody reagent, a protein that provides for a detectable signal. Suitable proteins include, but are not limited to, fluorescent proteins and enzymes (e.g., β-galactosidase, luciferase, horse radish peroxidase, alkaline phosphatase, etc.). Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., Science 263(5148): 802-805 (Feb. 11, 1994); an enhanced GFP (EGFP), Clontech-Genbank Accession Number U55762); a blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3): 462-471 (1998); 3. Heim, R. and Tsien, R. Y. Curr. Biol. 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, and 5,925,558; a GFP from species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

Indirect labels include second antibodies specific for an antibody reagent, wherein the second antibody is labeled as described above; and members of specific binding pairs, e.g., biotin-avidin, and the like.

In some embodiments, the antibodies are immobilized on an insoluble support, e.g., in an antibody diagnostic device, in an antibody array, etc. Antibodies can be immobilized directly or indirectly (e.g., via a linker molecule) to an insoluble support for use in a diagnostic assay to detect a target polypeptide in a biological sample. An antibody reagent can be immobilized by covalent or non-covalent attachment to an insoluble support. Insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (RIA), and the like); sheets, e.g., nylon, nitrocellulose, and the like; and chips, e.g., $SiO_2$ chips such as those used in microarrays. Accordingly, the invention further provides assay devices comprising one or more antibody reagents attached to a solid support.

The present invention further provides an array of antibodies, e.g., monoclonal antibodies, attached to an insoluble support in an array. In some embodiments, a subject antibody array provides for detection of a target polypeptide that is indicative of a pre-cancerous epithelial cell.

Suitable antibodies are obtained by immunizing a host animal with peptides comprising all or a portion of a target protein. Suitable host animals include mouse, rat sheep, goat, hamster, rabbit, etc. The host animal will generally be from a different species than the immunogen where the immunogen is from a naturally occurring source, e.g., a human sample, where representative host animals include, but are not limited to, e.g., rabbits, goats, mice, etc.

Methods for producing and using antibody arrays are known in the art; and any known method can be used. See, e.g., U.S. Pat. No. 6,797,393.

In one embodiment, the antibody reagents are arranged in the form of an array. An array can be created by spotting captures agents onto a substrate (e.g., glass, nitrocellulose, etc.) and attaching those capture agents to the substrate. The antibody reagents can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena et al. (1995) *Science* 270(5235): 467-70; Shalon et al. (1996) *Genome Res*. 6(7):639-45, U.S. Pat. No. 5,807,522, EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734. The antibody reagents utilized in the arrays can be of varying types and can include, for example, antibodies, including antibody fragments, aptamers, avimers, or peptidomimetics.

Common physical substrates for making protein arrays include glass or silicon slides, magnetic particles or other micro beads, functionalized with aldehyde or other chemical groups to help immobilize proteins. The substrate can also be coated with PLL (polylysine), nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

The variables in the immobilization of proteins include: type of capture agent (e.g., antibody reagent), nature of surface (including any pretreatment prior to use), and the immobilization method. Both adsorption and covalent attachment have been used for protein arrays. Orientation of the capture agent is very important in presenting it to the ligand or the surface in a functional state. Although covalent attachment using a variety of chemically activated surfaces (e.g., aldehyde, amino, epoxy) as well as attachment by specific biomolecular interactions (e.g., biotin-streptavidin) provide a stable linkage and good reproducibility, chemical derivatization of the surface may alter the biological activity of the capture agent and/or may result in multi-site attachment.

In one embodiment, antibody arrays are made with a non-contact deposition printer. The printer uses thermal ink jet heads that can print many solutions simultaneously to produce hundreds of spots of 50-60 μm in diameter with a spacing of 150 μm between spots. The droplet volume ranges between 35 pL to 1.5 nL. The heating element is made out of TaAl or other suitable materials, and is capable of achieving temperatures that can vaporize a sufficient volume of printing buffer to produce a bubble that will push out a precise volume of the antibody solution on the substrate. Selection of printing buffer is important, in that the buffer accomplishes the following: increases printing efficiency (measure of the number of spots that are printed to the total number of spots that are attempted), reduces sample spreading, promotes uniform delivery, stabilizes the capture agents that are being printed, reduces sample drying, and increases the visibility of the printed spots. In addition to the printing buffer, other variables that affect printing include: size of the drops, the method of washing and drying the print head, and the speed at which the dispensing head moves. Various modifications may be within these conditions.

Antibody Reagents that Detect the Presence and/or Level of a Selected Protein or Collection of Proteins In some embodiments, a subject antibody (or panel of antibodies) detects the presence and/or level of a selected protein (or collection of proteins) produced by an MEC. Detection of the presence and/or level of a selected protein or collection of proteins produced by an MEC allows prediction of the likelihood that the MEC is pre-cancerous, e.g., will progress to form a tumor. For example, in some embodiments, a subject antibody or antibody array detects the presence and/or level of a selected target polypeptide, or collection of target polypeptides, that constitute a vMEC signature, e.g., the polypeptide(s) are present in a vMEC at a higher or lower than normal level, compared to a control, normal MEC (e.g., compared to a $CD73^-$ MEC).

Suitable antibodies include antibodies that bind specifically to a target polypeptide identified in FIG. 14. Suitable antibodies include antibodies that bind specifically to a target polypeptide selected from: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR, TRF2, activin, and MEK1/2. These proteins are discussed in greater detail below.

CD73 (also referred to as 5'-ribonucleotide phosphohydrolase) is a membrane-bound enzyme that catalyzes the conversion of AMP to bioactive adenosine at neutral pH; and also has functions independent of its enzyme activity. CD73 is expressed on various cells include endothelial cells, pericytes, follicular dendritic cells, and subsets of T cells. Amino acid sequences of human CD73 are known, and are presented in, e.g., GenBank Accession Nos. AAH65937, NP_002517, and AI40168.

CD90, also known as Thy-1, is a 25-37 kD, glycosylphosphatidylinositol-anchored, cell surface glycoprotein found on many cell types. Amino acid sequences of human CD90 are known, and are presented in, e.g., GenBank Accession Nos. P04216, AAG13904, AAH65559, and NP_006279. See also, Seki et al. (1985) *Proc. Natl. Acad. Sci. U.S.A.* 82:6657-6661.

CD138, also known as syndecan-1, is a transmembrane heparan sulfate proteoglycans. Amino acid sequences of human CD138 are known, and are presented in, e.g., GenBank Accession Nos. AAH08765, P18827, and NP_002988.

Notch3 (or "notch-3 receptor") is a membrane-spanning protein that comprises multiple tandem repeats of a calcium-binding, epidermal growth factor (EGF)-like domain. Amino acid sequences of human notch3 are known and are presented in, e.g., GenBank Accession Nos. AAB91371, AAC15789, AAC14346, and NP_000426.

COX-2 ("cyclooxygenase-2") is an enzyme that converts arachidonic acid to prostaglandin $H_2$. Amino acid sequences of human COX-2 are known, and are presented in, e.g., GenBank Accession Nos. AAA58433 and NP_000954.

Ki67 (also referred to as "Ki67 antigen") is a nuclear antigen expressed in proliferating cells but not in quiescent cells, and thus is used as a "proliferation marker" to measure proliferation of cells. Multiple isoforms of Ki67 have been identified. Ki67 includes multiple repeats of an approximately 22 amino acid motif, referred to as the "Ki67" motif. Schluter et al. (1993) *J. Cell Biol.* 123:513-522. Amino acid sequences of a 3256-amino acid isoform of human Ki-67 are known, and are presented in, e.g., GenBank Accession Nos. CAA46519, CAI16902, CAH73169, and EAW49178. Amino acid sequences of a 2896-amino acid isoform of human Ki-67 are known, and are presented in, e.g., GenBank Accession Nos. CAA46520, CAI16903, CAH73170, and EAW49179. Amino acid sequences of a 2801-amino acid isoform of human Ki-67 are known, and are presented in, e.g., GenBank Accession No. EAW49177.

p16 (also known as INK4a, MTS1, CDK4I, and cyclin dependent kinase inhibitor 2A) is a cyclin dependent kinase inhibitor. p16, a member of the INK4 family, binds to and inhibits cyclin-dependent kinase-4 (CDK4). Amino acid sequences of human p16 are known, and are presented in, e.g., GenBank Accession Nos. P42771 (156 amino acid form); NP 000068 (156 amino acid form); NP_478102 (173 amino acid form); and NP_478104 (116 amino acid form).

IGF2 (also known as somatomedin A) is a single chain polypeptide that shares amino acid sequence identity of about 47% with insulin. Amino acid sequences of 180 amino acid human IGF2 are known, and are presented in, e.g, GenBank Accession No. ABD93451, and GenBank Accession No. ABM83647.

YKL-40 is a secreted glycoprotein of the chitinase family. YKL-40 is a major secretory protein of human chondrocytes and synoviocytes. Hakala et al. J. Biol. Chem. 268 (34), 25803-25810 (1993). Amino acid sequences of human YKL-40 are known, and are presented in, e.g., GenBank Accession No. AAA16074; and U.S. Pat. No. 6,579,684.

Epidermal growth factor receptor (EGF-R) is also referred to as ErbB-1 or HER1. EGF-R is the cell-surface receptor for members of the epidermal growth factor family (EGF-family) of extracellular protein ligands. EGFR (epidermal growth factor receptor) exists on the cell surface and is activated by binding of its specific ligands, including epidermal growth factor and transforming growth factor α (TGFα). Amino acid sequences of human EGF-R are known, and are presented in, e.g., GenBank Accession Nos. AAG35786 (p110); and AAG35787 (p60).

c-jun is the cellular counterpart of the transforming protein of the chicken retrovirus ASV 17. Via a leucine zipper, c-Jun forms homodimers and heterodimers with Fos and other jun-related proteins which, together, comprise the AP-1 transcription factor that binds TPA response elements (TREs). c-Jun therefore mediates transcriptional regulation in response to a variety of stimulants. Amino acid sequences of human c-jun are known, and are presented in, e.g., GenBank Accession Nos. AAH68522 and NP_002219.

Proliferating cell nuclear antigen (PCNA) (also referred to as cyclin, or DNA polymerase delta auxiliary protein) is involved in DNA replication and repair. Amino acid sequences of human PCNA are known, and are presented in, e.g., GenBank Accession Nos. AAH00491 and NP_872590.

Cyclin B1 plays a role in cell cycle control. M-phase promoting factor or maturation promoting factor (MPF), the key regulator of the $G_2 \rightarrow M$ transition during the cell cycle, is regulated by phosphorylation of both of its component proteins: the serine/threonine protein kinase cdc2 and a B-type cyclin. Amino acid sequences of human cyclin B1 are known, and are presented in, e.g., GenBank Accession Nos. NP_114172, EAW51306, and AAP88038.

C-kit, also known as CD117, is a cytokine receptor expressed on the surface of hematopoietic stem cells as well as other cell types. C-kit is the receptor for the cytokine stem cell factor (SCF), also known as "steel factor" or "c-kit ligand." Amino acid sequences of human c-kit are known, and are presented in, e.g., GenBank Accession Nos. AAH71593 and AAC50968.

Signal Transducer and Activator of Transcription-3 (STAT3) is a member of a family of STATs. STATS are transcription factors that are phosphorylated by JAK kinases in response to cytokine activation of a cell surface receptor tyrosine kinases. Bromberg et al. (1999) *Cell* 98:295-303; and Ihle (2001) *Curr. Opin. Cell Biol.* 13:211-217. Amino acid sequences of human STAT3 are known, and are presented in, e.g., GenBank Accession Nos. NP_644805, NP_003141, NP_998827, and CAA10032.

The cyclin D1 proto-oncogene is an important regulator of G1 to S-phase transition and an important cofactor for several transcription factors in numerous cell types. Amino acid sequences of human cyclin D1 are known, and are presented in, e.g., GenBank Accession Nos. NP_444284, AAH23620, AAH25302, AAH01501, and AAH14078.

Phosphatidylinositol 3-kinases (PI3K) generate lipids that control a wide variety of intracellular signalling pathways. Mammals have eight distinct catalytic subunits and seven regulatory subunits. Catalytic subunit isoforms include p110α, p110β, p110δ, and p110γ. Amino acid sequences of human PI3K catalytic subunits are known, and are presented in, e.g., GenBank Accession Nos. NP_005017, 000329, and CAI15702 (p110δ); NP_006209, AAI13604, and P42336 (p110α); NP_002640, P48736, and AAH35683 (p110γ); and NP_006210, AAI14433, and P42338 (p110β). See also, Kang et al. (2006) *Proc. Natl. Acad. Sci. USA* 103:1289; and Vanhaesebroeck et al. (2005) *TRENDS Biochem. Sci.* 30:194.

Mitogen-activated protein (MAP) kinases (MAPK) are serine/threonine-specific protein kinases that respond to extracellular stimuli (e.g., mitogens) and regulate various cellular activities, such as gene expression, mitosis, differentiation, and cell survival/apoptosis. MAPK include MAPK1 (ERK2, MAPK1), MAPK3 (ERK1), MAPK6 (ERK3), MAPK7 (ERK7), MAPK8 (JNK1), MAPK9 (JNK2), MAPK10 (JNK3), MAPK11 (p38bMAPK), MAPK12 (p38gMAPK), MAPK13, and MAPK14 (p38 MAPK). Amino acid sequences of human MAPK are known, and are presented in, e.g., GenBank Accession Nos. NP_002736, NP_620407, and AAH99905 (MAPK1); AAH13992, P27361, EAW79912, EAW79912, EAW77913, EAW79914, and EAW79915 (MAPK3); NP_002739, AAH35492, and EAW77434 (MAPK6); NP_620603, NP_620601, and EAW50887 (MAPK7); AA130571, NP_620637, and NP_620635 (MAPK8); CAG38817, AAH32539, and AAY46156 (MAPK9); AAH65516, AAH51731, and P53779 (MAPK10); CAG30400, NP_002742, and AAH27933 (MAPK11); CAG30401, NP_002960, and AAH15741 (MAPK12); CAG46488, CA19690, and CAB08438 (MAPK13); CAG38743, AAH31574, and AAH00092 (MAPK14).

Mitogen-activated protein (MAP) kinases require dual phosphorylation on threonine and tyrosine residues in order to gain enzymatic activity. This activation is carried out by a family of enzymes known as MAP kinase kinases (MAPKKs, MKKs, or MEKs). MAPKK include MAP2K1 (MEK1), MAP2K2 (MEK2), MAP2K3 (MEK3), MAP2K4 (Mkk4, JNKK1), MAP2K5 (MEK5), MAP2K6 (MKK6), MAP2K7 (JNKK2). Amino acid sequences of human MAPKKs are known, and are presented in, e.g., GenBank Accession Nos. AAI39730, NP_002746, and Q02750 (MAP2K1); NP_109587, AAH18645, and P36507 (MAP2K2).

TRF2 is a telomere-binding protein. Telomere-binding proteins TRF1 and TRF2 interact with several other telomere regulators including T1N2, PTOP, POT1, and RAP1 to ensure proper maintenance of telomeres. TRF2 mediates t-loop formation and end protection. Liu et al. (2004) *J. Biol. Chem.* 279:51338. Amino acid sequences of human TRF2 (500 amino acids) are known, and are presented in, e.g., GenBank Accession Nos. NP_05643, Q15554, and AAB81135.

Activin A is a homodimer of the activin βA subunits. The activin βA monomer can also form a heterodimer with inhibin a, to produce the activin A antagonist, inhibin A. Amino acid sequences of human activin βA (426 amino acids) are known, and are presented in, e.g, GenBank Accession Nos. EAL24001, EAW94141, and AAH07858.

In some embodiments, the present invention provides an antibody panel, comprising two or more antibodies with specificity for two or more polypeptides that are differentially expressed in pre-cancerous epithelial cells or surrounding epithelial cells. In some embodiments, a subject antibody panel comprises antibody reagents that provide for detection of two, three, four, five, or all of CD73, CD138, notch receptor-3, CD90, BMI-1, and COX-2. In other embodiments, a subject antibody panel comprises antibody reagents that provide for detection of CD90 and CD73. In other embodiments, a subject antibody panel comprises antibody reagents that provide for detection of 1(i67 and COX-2. In other embodiments, a subject antibody panel comprises antibody reagents that provide for detection of Ki67 and p16. In other embodiments, a subject antibody panel comprises antibody reagents that provide for detection of Ki67, COX-2, and p16. In other embodiments, a subject antibody panel comprises antibody reagents that provide for detection of TRF2 and activin. In other embodiments, a subject antibody panel comprises antibody reagents that provide for detection of activin, and markers that are induced by activin.

Antibody Reagents that Detect the Presence and/or Level of Posttranslationally Modified Polypeptides In some embodiments, a subject antibody detects the presence and/or level of a posttranslationally modified polypeptide produced by an MEC. Posttranslationally modified polypeptides that are targets for a subject antibody reagent include histone deacetylase (HDAC) polypeptides. Posttranslational modifications of HDAC polypeptides include methylation and acetylation. In some embodiments, an antibody reagent specifically binds to an HDAC epitope(s) that is not modified, e.g., the antibody reagent binds specifically to an HDAC epitope that comprises only encoded amino acids. In other embodiments, an antibody reagent specifically binds to an acetylated HDAC polypeptide, e.g., the antibody reagents binds specifically to an HDAC epitope that is acetylated. In other embodiments, an antibody reagent specifically binds to a methylated HDAC polypeptide, e.g:, the antibody reagents binds specifically to an HDAC epitope that is methylated.

Antibody Reagents that Detect a Chromatin Modification

In some embodiments, an antibody reagent for use in a subject detection method includes an antibody reagent that detects a modification of one or more intracellular proteins. Modification of an intracellular protein includes, e.g., modification of chromatin, e.g., acetylation of chromatin by an HDAC (e.g., polycomb-group (PeG) protein modifications; histone modifications); etc. In some embodiments, an antibody reagent detects a chromatin epitope that is acetylated. In other embodiments, an antibody reagent detects a chromatin epitope that is deacetylated. In other embodiments, an antibody reagent detects a chromatin epitope that is methylated. In other embodiments, an antibody reagent detects a chromatin epitope that is demethylated.

Antibody Reagents that Detect Modification of an Extracellular Matrix Component

In some embodiments, an antibody reagent for use in a subject detection method includes an antibody reagent that detects a modification in an extracellular matrix (ECM) component. ECM modifications that can be detected using a subject antibody reagent include, but are not limited to, enzymatic cleavage of an ECM component into fragments; sulfation; removal of one or more sulfate groups; phosphorylation; dephosphorylation; glycosylation; deglycosylation; and the like. ECM includes, but is not limited to, collagen, fibronectin, elastin, laminin, etc.

Antibody Reagents that Detect Secretion and/or Release of a Molecule

In some embodiments, an antibody reagent for use in a subject detection method includes an antibody reagent that detects a secreted or released molecule from a cell, e.g., an MEC, a fibroblast that is cultured in vitro with a reporter epithelial cell, etc. Secreted or released molecules that can be detected using an antibody reagent include, e.g., proteins. MEC can also secrete one or more of a nucleic acid, a calcium ion, etc., and such molecules can be detected using other reagents, as described below.

Binding Reagents that Detect Methylated DNA

In some embodiments, a binding reagent for use in a subject detection method includes a binding reagent that detects methylated DNA, e.g., where the methylation status of a selected DNA provides an indication as to whether a cell, e.g., an MEC, is pre-cancerous. Binding reagents that detect methylated DNA are known in the art and include binding reagents that specifically bind a nucleotide sequence comprising a $C^{me}pG$ sequence, where $C^{me}$ is methylated cytosine. Suitable $C^{me}pG$-specific binding reagents include methylated-CpG binding domain proteins (MBD) (e.g., MECP2; MBD2; etc.); a methylated-CpG-binding domain of an MBD protein; an antibody reagent specific for a methylated-CpG; and the like. See, e.g., Yegnasubramanian et al. (2006) *Nucl. Acids Res.* 34:e19. Proteins containing a methyl-binding domain include, but are not limited to, MBD1, MBD2, MBD3, MBD4, MeCP1 and MeCP2. See, for example, Bird et al. (1999) *Cell* 99:451-454.

Specific Binding Reagent Panels

Specific binding reagent panels are provided. As noted above, in some embodiments, a specific binding reagents is an antibody; however, specific binding reagents other than antibodies are also contemplated. Where the disclosure refers to an "antibody reagent panel," it should be understood that the disclosure applies as well to panels of other specific binding reagents. Antibody reagent panels (specific binding reagent panels) are provided, where a subject antibody reagent panel includes two or more of: 1) an antibody reagent that provides for detection of the presence and/or level of a selected protein or collection of proteins, e.g., a selected protein or collection of proteins that provide for detection of a pre-cancerous MEC; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell, e.g., from an MEC, from a fibroblast that is cultured in vitro with a reporter epithelial cell, etc; and 6) a binding reagent that provides for detection of a methylated DNA.

In some embodiments, a subject antibody reagent panel includes two or more of: 1) two or more different antibody reagents that provide for detection of the presence and/or level of two or more selected proteins, e.g., two or more selected proteins that provide for detection of a pre-cancerous MEC; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more antibodies that bind specifically to two or more of the protein markers identified in FIG. 14. In some embodiments, a subject antibody reagent panel includes two or more of: 1) two or more different antibody reagents that provide for detection of the presence and/or level of two or more of CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more of: 1) two or more different antibody reagents that provide for detection of the presence and/or level of two or more of CD73, CD138, notch receptor-3, CD90, BMI-1, and COX-2; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more of: 1) two or more different antibody reagents that provide for detection of the presence and/or level of COX-2, Ki67, and p16; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell.; and 6) a binding reagent that provides for detection of a methylated DNA.

In some embodiments, a subject antibody reagent panel includes two or more of: 1) two or more different antibody reagents that provide for detection of the presence and/or level of TRF2 and activin; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell.; and 6) a binding reagent that provides for detection of a methylated DNA.

As noted above, in some embodiments, an antibody reagent panel comprises two or more antibody reagents immobilized onto an insoluble support. In some embodiments, a subject antibody reagent panel comprises an array of antibody reagents.

Nucleic Acid Reagents

The present invention provides nucleic acid reagents for use in a subject detection method (e.g., in a subject imaging method, a subject diagnostic method, a subject prognostic method, a subject method for determining efficacy of a treatment method, etc.). The nucleic acid reagents are in substantially isolated form, and can be synthetic or recombinant. The nucleic acid reagents include reagents that provide for one or more of: 1) detection of the level of a selected DNA; 2) detection of the integrity of a selected DNA; 3) detection of the methylation status of a selected DNA; 4) detection of the presence and/or a level of a selected mRNA or collection of mRNA; and 5) detection of the presence and/or level of a selected microRNA or collection of microRNAs.

Reagents for Detecting the Level of a Selected DNA

In some embodiments, a subject nucleic acid reagent provides for detection of the level of a selected DNA in an MEC. For example, in some embodiments, a selected DNA is amplified (e.g., present in greater than the normal copy number) in an MEC that is pre-cancerous. In other embodiments, a selected DNA is deleted (entirely or in part) in an MEC that is pre-cancerous. Suitable nucleic acid reagents for detecting the level of a selected DNA in an MEC include nucleic acid reagents that function as primers for nucleic acid amplification; nucleic acid reagents that function as nucleic acid probes; and the like. In some embodiments, one or more additional, non-nucleic acid, reagent is provided in a system for use in detecting the level of a selected DNA in an MEC. Such additional reagents include, for example, a restriction endonuclease that cuts at a site adjacent to and/or within an amplified region of a selected DNA; and the like. As an example, a subject system can include a restriction endonuclease that cuts at a site adjacent to and/or within an amplified region of a selected DNA; and a nucleic acid reagent that functions as a probe and provides for determination of the relative levels of the selected DNA in a test MEC, compared to one or more control MEC. Genomic loci that are amplified in a pre-cancerous MEC include loci in chromosome 14q. Genomic loci that are deleted in a pre-cancerous MEC include loci in chromosomes 3p, 4, 5, and 6q. Such amplifications and/or deletions can be detected by array profiling, by karyotyping, etc.

Reagents for Detecting the Integrity of a Selected DNA

In some embodiments, a subject nucleic acid reagent provides for detection of the integrity of a selected DNA in an MEC. For example, in some embodiments, a subject nucleic acid reagent provides for detection of one or more of: a translocation of a selected DNA, an inversion of a selected DNA, deletion of all or a portion of a selected DNA, and telomere integrity, in an MEC. Suitable nucleic acid reagents for detecting the integrity of a selected DNA in an MEC include nucleic acid reagents that function as primers for nucleic acid amplification; nucleic acid reagents that function as nucleic acid probes; and the like. In some embodiments, one or more additional, non-nucleic acid, reagent is provided in a system for use in detecting the integrity of a selected DNA in an MEC. Such additional reagents include, for example, a restriction endonuclease that cuts at a site adjacent to and/or within a selected DNA; and the like. As an example, a subject system can include a restriction endonuclease that cuts at a site adjacent to and at a site within a selected DNA; and a nucleic acid reagent that functions as a probe and provides for determination of the integrity of the selected DNA in a test MEC, compared to one or more control MEC.

Reagents that Provide for Detection of the Methylation Status of a Selected DNA

In some embodiments, a subject nucleic acid reagent provides for detection of the methylation status of a selected DNA in an MEC. Suitable nucleic acid reagents include nucleic acid reagents that function as primers for nucleic acid amplification; nucleic acid reagents that function as nucleic acid probes; and the like. Nucleic acid reagents can be used in a variety of methods to detect DNA methylation status, where suitable methods include, but are not limited to, methylation-specific polymerase chain reaction (MSP; Herman et al. (1996) *Proc. Natl. Acad. Sci. USA* 93:9821-9826); MethylLight (Eads et al. (2000) *Nucl. Acids Res.* 28:E32; and U.S. Pat. No. 6,331,393); HeavyMethyl (Cottrell et al. (2004) *Nucl. Acids Res.* 32:el 0); MethylQuant (Thomassin et al. (2004) *Nucl. Acids Res.* 32; e168; and the like.

A number of methods involve treatment of DNA with a bisulfite reagent, which converts unmethylated cytosines to uracils, leaving only methylated cytosines unchanged (see, e.g., WO 05/038051). Following bisulfite treatment, individual cytosine positions can be detected by a primer extension reaction (Gonzalgo and Jones (1997) *Nucleic Acids Res.* 25:2529-31; and WO 95/00669) or by enzymatic digestion (Xiong and Laird (1997) *Nucleic Acids Res.* 25: 2535-4). Alternatively, following bisulfite treatment, a methylation-specific polymerase chain reaction (PCR) can be carried out, using primers that bind either to methylated or unmethylated DNA only and that therefore selectively amplify only DNA with a defined methylation. MethylLight is a variation of MSP, and involves use of a methylation-specific real-time detection probe (MethylLight), which makes the assay both homogenous and quantitative. HeavyMethyl is also a variation on MSP. In the HeavyMethyl method, the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. When the blocker is not bound, the primer-binding site is accessible and the amplicon is generated. HeavyMethyl in combination with real-time detection with methylation-specific fluorogenic probes provides sensitive and specific detection of DNA methylation.

In some embodiments, a subject system will include, in addition to a nucleic acid reagent, one or more additional reagents, e.g., a methylation-sensitive restriction endonuclease (e.g., a restriction endonuclease that recognizes and cleaves a nucleic acid having a particular nucleotide sequence only when the sequence is unmethylated); a methylation-insensitive restriction endonuclease (e.g., a restriction endonuclease that recognizes and cleaves a nucleic acid having a particular nucleotide sequence, regardless of the methylation status of the nucleotide sequence); and the like. The term "methylation-sensitive enzyme" refers to a restriction enzymes that does not cleave DNA (or cleaves DNA poorly) if one or more nucleotides in its recognition site are methylated. Suitable methylation-sensitive and methylation-insensitive restriction endonucleases that are suitable for use include, but are not limited to, MboI, DpnII, HpaII, BsmBI, Sau3A, and ClaI.

Reagents that Provide for Detection of the Level and/or Presence of an mRNA

A subject nucleic acid reagent includes a nucleic acid probe, or collection of nucleic acid probes, that provides for detection of the presence and/or level of an mRNA (or a cDNA copy of an mRNA) in an MEC. In some embodiments, a subject nucleic acid reagent is a nucleic acid primer, or a collection of nucleic acid primers, that provides for detection of the presence and/or level of an mRNA (or a cDNA copy of an mRNA) in an MEC. For example, a subject nucleic acid reagent includes a nucleic acid probe, or collection of nucleic acid probes, a nucleic acid primer, or a collection of nucleic acid primers, that provides for detection of the presence and/or level of an mRNA (or a cDNA copy of an mRNA) that is differentially expressed in a pre-cancerous MEC. For example, an mRNA (or a cDNA copy) that is differentially expressed in a pre-cancerous MEC can be expressed at a level that is at least about 25%, at least about 50%, at least about 75%, at least about 100% (or 2-fold), at least about 5-fold, at least about 10-fold, at least about 50-fold, or at least about 100-fold, or more, higher than the level of the mRNA in a normal (non-pre-cancerous) MEC. As another example, an mRNA (or a cDNA copy) that is differentially expressed in a pre-cancerous MEC can be expressed at a level that is at least about 20%, at least about 30%, at least about 40%, at least about 50%, at least about 60%, at least about 70%, at least about 80%, or at least about 90% lower than the level of the mRNA in a normal (e.g., non-pre-cancerous) MEC.

Exemplary nucleic acid probes include probes that detect, in an MEC (e.g., a vMEC, or a normal MEC), one or more of the mRNA set forth in FIG. 14. Exemplary nucleic acid probes include probes that detect, in an MEC (e.g., a vMEC, or a normal MEC), one or more of the following mRNA (or cDNA copy of an mRNA): CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject nucleic acid reagent is a collection of nucleic acid probes that provides for detection of two or more of the following mRNA (or cDNA copy of an mRNA): CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject nucleic acid reagent is a collection of nucleic acid probes that provides for detection of the presence and/or level of two, three, four, five, or all of CD73, CD138, notch receptor-3, CD90, BMI-1, and COX-2 mRNAs (or cDNA copies of same). In other embodiments, a subject nucleic acid reagent is a collection of nucleic acid probes that provides for detection of the presence and/or level of Ki67, COX-2, and p16 mRNA (or cDNA copies of same).

Nucleic acid probes that are suitable for detecting the presence and/or level of an mRNA that is differentially expressed in a pre-cancerous MEC can have a length of from about 10 nucleotides to about 100 nucleotides (nt), e.g., from about 10 nt to about 15 nt, from about 15 nt to about 20 nt, from about 20 nt to about 25 nt, from about 25 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt.

Nucleic acids comprising nucleotide sequences encoding CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2 are known in the art; and can form the basis for the design and preparation of a nucleic acid reagent, or collection of nucleic acid reagents, including probes and primers. For example, nucleotide sequences encoding human CD73 are presented in GenBank Accession Nos. BC065937, NM_002526, and AL589666; nucleotide sequences encoding human CD90 are presented in GenBank Accession Nos. AF261093, NM_006288, and BC065559; nucleotide sequences encoding human CD138 are presented in GenBank Accession Nos. NM_002997, and BC008765; nucleotide sequences encoding human notch-3 receptor are presented in GenBank Accession Nos. U97669, AC004663, AH006054, and NM_000435; nucleotide sequences encoding human COX-2 are presented in GenBank Accession Nos. M90100, and NM_000963; nucleotide sequences encoding human Ki-67 are presented in GenBank Accession Nos. X65551, X65550, AL355529, and AL390236; nucleotide sequences encoding human p16 are presented in GenBank Accession Nos. NM_000077, NM_058195, and NM_058197; nucleotide sequences encoding human TRF2 are presented in GenBank Accession Nos NM_005652 and AF002999; and nucleotide sequences encoding human activin βA chain are presented in GenBank Accession Nos CH236951 and BC007858.

Reagents that Provide for Detection of the Presence and/or Level of a microRNA

In some embodiments, a subject nucleic acid reagent provides for detection of the presence and/or level of a microRNA that is expressed in a pre-cancerous MEC, e.g., that is differentially expressed in a pre-cancerous MEC, compared to a normal (non-precancerous MEC). MicroRNAs that can be detected using a subject nucleic acid reagent include, but are not limited to, mir 196b (HoxA9), (p14), 328, 30A-3P, 125b, 30E-3P, 680, 134, 604, 128b, 128a, 331, 520F, 299-3P, 520H, 510, 365, 520G, 9, 324-3P, 351, 125A, 764-5P, 302D, 520D, 652, 520C, 350, 585, 621, 542-5P, 560, 126, and 341. See, e.g., Griffiths-Jones et al. (2006) "miRBase: microRNA sequences, targets and gene nomenclature" *Nucleic Acids Res.* 34:D140-D144; GenBank Accession No. NT 007819; Kim et al. (2004) *Proc. Natl. Acad. Sci. USA* 101:360-365; Weber (2005) *FEBS J.* 272:59-73.

For specific microRNA sequences, see, e.g.: 1) 328: Kim et al. (2004) *Proc. Natl. Acad. Sci. USA* 101:360-365; and Weber (2005) *FEBS J.* 272:59-73; 2) 196b: Yekta et al. (2004) *Science* 304:594-596; 3) 30A-3p: Kasashima et al. ((2004) *Biochem. Biophys. Res. Comm.* 322:403-410; 4) 125b: Lee et al. (2005) *J. Biol. Chem.* 280:16635-16641; 5) 30e-3p: Kasashima et al. (2004) *Biochem. Biophys. Res. Comm.* 322:403-410; and Weber (2005) *FEBS J.* 272:59-73; 6) 680: Weber (2005) *FEBS J.* 272:59-73; and Fu et al. (2005) *FEBS Lett.* 579:3849-3854; 7) 134: Altuvia et al. (2005) *Nucl. Acids Res.* 33:2697-2706; and Suh et al. (2004) *Dev Biol.* 270:488-498; 8) 604: Cummins et al. (2006) *Proc Natl Acad Sci USA.* 103:3687-3692; 9) 128b: Lim et al. (2003) *Science* 299:1540; 10) 128a: Kasashima et al. ((2004) *Biochem. Biophys. Res. Comm.* 322:403-410; 11) 331: Kim et al. (2004) *Proc. Natl. Acad. Sci. USA* 101:360-365; and Weber (2005) *FEBS J.* 272:59-73; 12) 520F: Bentwich et al. (2005) *Nat. Genet.* 37:766-770; 13) 299-3P: Altuvia et al. (2005) *Nucl. Acids Res.* 33:2697-2706; and Weber (2005) *FEBS J.* 272:59-73; 14) 520H: Bentwich et al. (2005) *Nat. Genet.* 37:766-770; 15) 510: Bentwich et al. (2005) *Nat. Genet.* 37:766-770; 16) 365: Bentwich et al. (2005) *Nat. Genet.* 37:766-770; 17) 520G: Bentwich et al. (2005) *Nat. Genet.* 37:766-770; 18) 324-3P: Kim et al. (2004) *Proc. Natl. Acad. Sci. USA* 101:360-365; and Weber (2005) *FEBS J.* 272:59-73; 19) 125A: Lagos-Quintana et al. (2002) *Curr Biol.* 12:735-739; 20) 302D: Suh et al. (2004) *Dev Biol.* 270:488-498; 21) 520D: Bentwich et al. (2005) *Nat. Genet.* 37:766-770; 22) 652: 22) 652: Cummins et al. (2006) *Proc Natl Acad Sci USA.* 103:3687-3692; 23) 520C: Bentwich et al. (2005) *Nat. Genet.* 37:766-770; 24) 585: Cummins et al. (2006) *Proc Natl Acad Sci USA.* 103:3687-3692; 25) 621: Cummins et al. (2006) *Proc Natl Aced Sci USA.* 103:3687-3692; 26) 542-5p: Sewer et al. (2005) *BMC Bioinformatics.* 6:267; 27) 560: Cummins et al. (2006) *Proc Natl Acad Sci USA.* 103:3687-3692; and 28) 126: Lagos-Quintana et al. (2002) *Curr Biol.* 12:735-739.

A suitable sequence includes a stem-loop sequence; a mature sequence; a sequence complementary to a stem-loop sequence; and a sequence complementary to a mature sequence.

MicroRNA sequences include, e.g., 1) 328:
stem-loop sequence:
(SEQ ID NO: 1)
UGGAGUGGGGGGCAGGAGGGGCUCAGGGAGAAAGUGCAUACAGCCCCUGGCCCUCUC

UGCCCUUCCGUCCCCUG;

mature sequence:
(SEQ ID NO: 2)
CUGGCCCUCUCUGCCCUUCCGU;

-continued nucleotide sequence complementary to mature sequence:
(SEQ ID NO: 3)
5'-ACGGAAGGGCAGAGAGGGCCAG-3';

2) 196b:
stem-loop sequence:
(SEQ ID NO: 4)
ACUGGUCGGUGAUUUAGGUAGUUUCCUGUUGUUGGGAUCCACCUUUCUCUCGACAGCA

CGACACUGCCUUCAUUACUUCAGUUG;

mature sequence:
(SEQ ID NO: 5)
UAGGUAGUUUCCUGUUGUUGG;

nucleotide sequence complementary to mature sequence:
(SEQ ID NO: 6)
5'-CCAACAACAGGAAACTACCTA-3';

3) 30A-3P:
stem-loop sequence:
(SEQ ID NO: 7)
GCGACUGUAAACAUCCUCGACUGGAAGCUGUGAAGCCACAGAUGGGCUUUCAGUCGGA

UGUUUGCAGCUGC;

mature sequence:
(SEQ ID NO: 8)
UGUAAACAUCCUCGACUGGAAG;

nucleotide sequence complementary to mature sequence:
(SEQ ID NO: 9)
5'-CTTCCAGTCGAGGATGTTTACA-3';

4) 125b:
stem-loop sequence:
(SEQ ID NO: 10)
UGCGCUCCUCUCAGUCCCUGAGACCCUAACUUGUGAUGUUUACCGUUUAAAUCCACGGG

UUAGGCUCUUGGGAGCUGCGAGUCGUGCU;

mature sequence:
(SEQ ID NO: 11)
UCCCUGAGACCCUAACUUGUGA;

nucleotide sequence complementary to mature sequence:
(SEQ ID NO: 12)
5'-TCACAAGTTAGGGTCTCAGGGT-3';

5) 30e-3p:
stem-loop sequence:
(SEQ ID NO: 13)
GGGCAGUCUUUGCUACUGUAAACAUCCUUGACUGGAAGCUGUAAGGUGUUCAGAGGAG

CUUUCAGUCGGAUGUUUACAGCGGCAGGCUGCCA;

mature sequence:
(SEQ ID NO: 14)
CUUUCAGUCGGAUGUUUACAGC;

nucleotide sequence complementary to mature sequence:
(SEQ ID NO: 15)
5'-GCTGTAAACATCCGACTGAAAG-3';

6) 680:
stem-loop sequence:
(SEQ ID NO: 16)
CCUGCCGGGGCUAAAGUGCUGACAGUGCAGAUAGUGGUCCUCUCCGUGCUACCGCACUG

UGGGUACUUGCUGCUCCAGCAGG;

mature sequence:
mature sequence:
(SEQ ID NO: 17)
UAAAGUGCUGACAGUGCAGAU;

nucleotide sequence complementary to mature sequence:
(SEQ ID NO: 18)
5'-ATCTGCACTGTCAGCACTTTA-3';

-continued 7) 134:
stem-loop sequence:
(SEQ ID NO: 19)
CAGGGUGUGUGACUGGUUGACCAGAGGGGCAUGCACUGUGUUCACCCUGUGGGCCACC

UAGUCACCAACCCUC;

mature sequence:
(SEQ ID NO: 20)
UGUGACUGGUUGACCAGAGGG;

nucleotide sequence complementary to mature sequence:
(SEQ ID NO: 21)
5'-CCCTCTGGTCAACCAGTCACA-3';

8) 604:
stem-loop sequence:
(SEQ ID NO: 22)
AGAGCAUCGUGCUUGACCUUCCACGCUCUCGUGUCCACUAGCAGGCAGGUUUUCUGACA

CAGGCUGCGGAAUUCAGGACAGUGCAUCAUGGAGA;

mature sequence:
(SEQ ID NO: 23)
AGGCUGCGGAAUUCAGGAC;

nucleotide sequence complementary to mature sequence:
(SEQ ID NO: 24)
5'-GTCCTGAATTCCGCAGCCT-3';

9) 128b:
stem-loop sequence:
(SEQ ID NO: 25)
UGUGCAGUGGGAAGGGGGGCCGAUACACUGUACGAGAGUGAGUAGCAGGUCUCACAGU

GAACCGGUCUCUUUCCCUACUGUGUC;

mature sequence:
(SEQ ID NO: 26)
UCACAGUGAACCGGUCUCUUUC;

nucleotide sequence complementary to mature sequence:
(SEQ ID NO: 27)
5'-GAAAGAGACCGGTTCACTGTGA-3';

10) 128a:
stem-loop sequence:
(SEQ ID NO: 28)
UGAGCUGUUGGAUUCGGGGCCGUAGCACUGUCUGAGAGGUUUACAUUUCUCACAGUGA

ACCGGUCUCUUUUUCAGCUGCUUC;

mature sequence:
(SEQ ID NO: 29)
UCACAGUGAACCGGUCUCUUUU;

nucleotide sequence complementary to mature sequence:
(SEQ ID NO: 30)
5'-AAAAGAGACCGGTTCACTGTGA-3';

11) 331:
stem-loop sequence:
(SEQ ID NO: 31)
GAGUUUGGUUUUGUUUGGGUUUGUUCUAGGUAUGGUCCCAGGGAUCCCAGAUCAAACC

AGGCCCCUGGGCCUAUCCUAGAACCAACCUAAGCUC;

mature sequence:
(SEQ ID NO: 32)
GCCCCUGGGCCUAUCCUAGAA;

nucleotide sequence complementary to mature sequence:
(SEQ ID NO: 33)
5'-TTCTAGGATAGGCCCAGGGGC-3';

-continued 12) 520F:
stem-loop sequence:
(SEQ ID NO: 34)
UCUCAGGCUGUGACCCUCUAAAGGGAAGCGCUUUCUGUGGUCAGAAAGAAAAGCAAGU

GCUUCCUUUUAGAGGGUUACCGUUUGGGA;

mature sequence:
(SEQ ID NO: 35)
AAGUGCUUCCUUUUAGAGGGUU;

nucleotide sequence complementary to mature sequence:
(SEQ ID NO: 36)
5'-AACCCTCTAAAAGGAAGCACTT-3';

13) 299-3P:
stem-loop sequence:
(SEQ ID NO: 37)
AAGAAAUGGUUUACCGUCCCACAUACAUUUUGAAUAUGUAUGUGGGAUGGUAAACCGC

UUCUU;

mature sequence:
(SEQ ID NO: 38)
UAUGUGGGAUGGUAAACCGCUU;

nucleotide sequence complementary to mature sequence:
(SEQ ID NO: 39)
5'-AAGCGGTTTACCATCCCACATA-3';

14) 520H:
stem-loop sequence:
(SEQ ID NO: 40)
UCCCAUGCUGUGACCCUCUAGAGGAAGCACUUUCUGUUUGUUGUCUGAGAAAAAACAA

AGUGCUUCCCUUUAGAGUUACUGUUUGGGA;

mature sequence:
(SEQ ID NO: 41)
ACAAAGUGCUUCCCUUUAGAGU;

nucleotide sequence complementary to mature sequence:
(SEQ ID NO: 42)
5'-ACTCTAAAGGGAAGCACTTTGA-3';

15) 510:
stem-loop sequence:
(SEQ ID NO: 43)
GUGGUGUCCUACUCAGGAGAGUGGCAAUCACAUGUAAUUAGGUGUGAUUGAAACCUCU

AAGAGUGGAGUAACAC;

mature sequence:
(SEQ ID NO: 44)
UACUCAGGAGAGUGGCAAUCACA;

nucleotide sequence complementary to mature sequence:
(SEQ ID NO: 45)
5'-TGTGATTGCCACTCTCCTGAGTA-3';

16) 365:
stem-loop sequence:
(SEQ ID NO: 46)
ACCGCAGGGAAAAUGAGGGACUUUUGGGGGCAGAUGUGUUUCCAUUCCACUAUCAUAA

UGCCCCUAAAAAUCCUUAUUGCUCUUGCA;

mature sequence:
(SEQ ID NO: 47)
UAAUGCCCCUAAAAAUCCUUAU;

nucleotide sequence complementary to mature sequence:
(SEQ ID NO: 48)
5'-ATAAGGATTTTTAGGGGCATTA-3';

-continued 17) 520G:
stem-loop sequence:
(SEQ ID NO: 49)
UCCCAUGCUGUGACCCUCUAGAGGAAGCACUUUCUGUUUGUUGUCUGAGAAAAAACAA

AGUGCUUCCCUUUAGAGUGUUACCGUUUGGGA;

mature sequence:
(SEQ ID NO: 50)
ACAAAGUGCUUCCCUUUAGAGUGU;

nucleotide sequence complementary to mature sequence:
(SEQ ID NO: 51)
5'-ACACTCTAAAGGGAAGCACTTTGA-3';

18) 324-3P:
stem-loop sequence:
(SEQ ID NO: 52)
CUGACUAUGCCUCCCCGCAUCCCCUAGGGCAUUGGUGUAAAGCUGGAGACCCACUGCCC

CAGGUGCUGCUGGGGGUUGUAGUC;

mature sequence:
(SEQ ID NO: 53)
CCACUGCCCCAGGUGCUGCUGG;

nucleotide sequence complementary to mature sequence:
(SEQ ID NO: 54)
5'-CCAGCAGCACCTGGGGCAGTGG-3';

19) 125A:
stem-loop sequence:
(SEQ ID NO: 55)
UGCCAGUCUCUAGGUCCCUGAGACCCUUUAACCUGUGAGGACAUCCAGGGUCACAGGUG

AGGUUCUUGGGAGCCUGGCGUCUGGCC;

mature sequence:
(SEQ ID NO: 56)
UCCCUGAGACCCUUUAACCUGUG;

nucleotide sequence complementary to mature sequence:
(SEQ ID NO: 57)
5'-CACAGGTTAAAGGGTCTCAGGGT-3';

20) 302D:
stem-loop sequence:
(SEQ ID NO: 58)
CCUCUACUUUAACAUGGAGGCACUUGCUGUGACAUGACAAAAAUAAGUGCUUCCAUGU

UUGAGUGUGG;

mature sequence:
(SEQ ID NO: 59)
UAAGUGCUUCCAUGUUUGAGUGU;

nucleotide sequence complementary to mature sequence:
(SEQ ID NO: 60)
5'-ACACTCAAACATGGAAGCACTTA-3';

21) 520D:
stem-loop sequence:
(SEQ ID NO: 61)
UCUCAAGCUGUGAGUCUACAAAGGGAAGCCCUUUCUGUUGUCUAAAAGAAAAGAAAGU

GCUUCUCUUUGGUGGGUUACGGUUUGAGA;

mature sequence:
(SEQ ID NO: 62)
UCUACAAAGGGAAGCCCUUUCUG;

nucleotide sequence complementary to mature sequence:
(SEQ ID NO: 63)
5'-CAGAAAGGGCTTCCCTTTGTAGA-3';

-continued 22) 652:
stem-loop sequence:
(SEQ ID NO: 64)
ACGAAUGGCUAUGCACUGCACAACCCUAGGAGAGGGUGCCAUUCACAUAGACUAUAAU

UGAAUGGCGCCACUAGGGUUGUGCAGUGCACAACCUACAC;

mature sequence:
(SEQ ID NO: 65)
AAUGGCGCCACUAGGGUUGUGCA;

nucleotide sequence complementary to mature sequence:
(SEQ ID NO: 66)
5'-TGCACAACCCTAGTGGCGCCATT-3';

23) 520C:
stem-loop sequence:
(SEQ ID NO: 67)
UCUCAGGCUGUCGUCCUCUAGAGGGAAGCACUUUCUGUUGUCUGAAAGAAAAGAAAGU

GCUUCCUUUUAGAGGGUUACCGUUUGAGA;

mature sequence:
(SEQ ID NO: 68)
AAAGUGCUUCCUUUUAGAGGGUU;

nucleotide sequence complementary to mature sequence:
(SEQ ID NO: 69)
5'-AACCCTCTAAAAGGAAGCACTTT-3';

24) 585:
stem-loop sequence:
(SEQ ID NO: 70)
UGGGGUGUCUGUGCUAUGGCAGCCCUAGCACACAGAUACGCCCAGAGAAAGCCUGAAC

GUUGGGCGUAUCUGUAUGCUAGGGCUGCUGUAACAA;

mature sequence:
(SEQ ID NO: 71)
UGGGCGUAUCUGUAUGCUA;

nucleotide sequence complementary to mature sequence:
(SEQ ID NO: 72)
5'-TAGCATACAGATACGCCCA-3';

25) 621:
stem-loop sequence:
(SEQ ID NO: 73)
UAGAUUGAGGAAGGGGCUGAGUGGUAGGCGGUGCUGCUGUGCUCUGAUGAAGACCCAU

GUGGCUAGCAACAGCGCUUACCUUUUGUCUCUGGGUCC;

mature sequence:
(SEQ ID NO: 74)
GGCUAGCAACAGCGCUUACCU;

nucleotide sequence complementary to mature sequence:
(SEQ ID NO: 75)
5'-AGGTAAGCGCTGTTGCTAGCC-3';

26) 542-5p:
stem-loop sequence:
(SEQ ID NO: 76)
CAGAUCUCAGACAUCUCGGGGAUCAUCAUGUCACGAGAUACCAGUGUGCACUUGUGAC

AGAUUGAUAACUGAAAGGUCUGGGAGCCACUCAUCUUCA;

mature sequence:
(SEQ ID NO: 77)
UCGGGGAUCAUCAUGUCACGAG;

nucleotide sequence complementary to mature sequence:
(SEQ ID NO: 78)
5'-CTCGTGACATGATGATCCCCGA-3';

-continued 27) 560:
stem-loop sequence:
(SEQ ID NO: 79)
UCCCCUCUGGCGGCUGCGCACGGGCCGUGUGAGCUAUUGCGGUGGGCUGGGGCAGAUG

ACGCGUGCGCCGGCCGGCCGCCGAGGGGCUACCGUUC;

mature sequence:
(SEQ ID NO: 80)
GCGUGCGCCGGCCGGCCGCC;

nucleotide sequence complementary to mature sequence:
(SEQ ID NO: 81)
5'-GGCGGCCGGCCGGCGCACGC-3';
and 28) 126:
stem-loop sequence:
(SEQ ID NO: 82)
CGCUGGCGACGGGACAUUAUUACUUUUGGUACGCGCUGUGACACUUCAAACUCGUACC

GUGAGUAAUAAUGCGCCGUCCACGGCA;

mature sequence:
(SEQ ID NO: 83)
CAUUAUUACUUUUGGUACGCG;

nucleotide sequence complementary to mature sequence:
(SEQ ID NO: 84)
5'-CGCGTACCAAAAGTAATAATG-3'.

Nucleic acids that provide for detection of the presence and/or level of a microRNA that is differentially expressed in a pre-cancerous HMEC can comprises a nucleotide sequence that is complementary to all or a portion of a target microRNA. For example, the nucleotide sequence 5'-CGCGTACCAAAAGTAATAATG-3' (SEQ ID NO: 84) is complementary to the mature sequence of the 126 microRNA.

Nucleic acid reagents that provide for detection of the presence and/or level of a microRNA that is differentially expressed in a pre-cancerous HMEC can have a length of from about 10 nucleotides to about 100 nucleotides (nt), e.g., from about 10 nt to about 15 nt, from about 15 nt to about 20 nt, from about 20 nt to about 25 nt, from about 25 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt.

In some embodiments, a subject nucleic acid reagent provides for detection of the presence and/or level of a microRNA that is differentially expressed in a pre-cancerous MEC is immobilized onto an insoluble support. In some embodiments, the reagents include two or more nucleic acid probes that provide for detection of the presence and/or level of two or more microRNAs that are differentially expressed in a pre-cancerous MEC. In some embodiments, the two or more nucleic acid probes that provide for detection of the presence and/or level of two or more microRNAs that are differentially expressed in a pre-cancerous MEC are immobilized onto an insoluble support.

Target Nucleic Acids

Target nucleic acids include nucleic acids that are abnormally expressed in a pre-cancerous epithelial cell, where the abnormal expression levels are thus associated with an increased risk of developing cancer (e.g., a carcinoma, e.g., breast cancer) and/or are associated with a pre-cancerous or cancerous state of a cell such as an epithelial cell and/or are indicative of the presence of a pre-cancerous cell in the individual. For example, abnormal expression levels of a target nucleic acid will in some cases be associated with abnormal levels of target mRNA and/or target polypeptide in an epithelial cell. Exemplary, non-limiting target nucleic acids are the nucleic acids listed in FIG. 14. Exemplary, non-limiting target nucleic acids are CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR, TRF2, activin, and MEK1/2. Exemplary, non-limiting target nucleic acids are CD73, CD138, notch receptor-3, CD90, BMI-1, and Cox-2 nucleic acids.

In some embodiments, abnormal levels of a target mRNA that, when present in a cell, are associated with a precancerous or cancerous state of the cell, are levels that are significantly higher or lower than normal levels of the target mRNA found in a non-cancerous cell of the same cell type. In some embodiments, abnormal levels of a target mRNA that, when present in a test cell, are indicative of the presence of a cancerous cell in the individual from whom the test cell was obtained, are levels that are significantly higher or lower than normal levels of the target mRNA typically found in the test cell in an individual who does not have cancer.

An abnormally high level of a target mRNA that, when present in a cell, is associated with a precancerous or cancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the target mRNA in a non cancerous cell of the same cell type, e.g., an epithelial cell.

For example, an abnormally high level of a target mRNA that, when present in an epithelial cell, is associated with a precancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the target mRNA in a non-cancerous epithelial cell.

An abnormally low level of a target mRNA that, when present in a cell, is associated with a precancerous or cancerous state of the cell, is a level that is about 75% or less, about 60% or less, about 50% or less, about 25% or less, or about 10% or less, than the level of the target mRNA in a non cancerous cell of the same cell type For example, an abnormally low level of a target mRNA that, when present in an epithelial cell, is associated with a precancerous state of the epithelial cell, is a level that is about 75% or less, about 60% or less, about 50% or less, about 25% or less, or about 10% or less, than the level of the target mRNA in a non-cancerous epithelial cell.

Sources of Target Nucleic Acids

Where the detection methods involve detection of a target nucleic acid, the target nucleic acids are detected in samples obtained from a tissue comprising cells. In some embodiments, the cells are obtained from a tissue suspected of comprising cancer cells.

The source of the tissue will depend, at least in part, on the type of pre-cancerous epithelial cell that is being detected. For example, target nucleic acids can be obtained from lung tissue (for detection of a pre-cancerous lung epithelial cell); from pancreas; from prostate; etc.

In the context of breast cancer, the source of target nucleic acid is breast tissue. In some embodiments, the tissue is a breast biopsy. In other embodiments, the tissue is an axillary lymph node tissue. In the context of breast cancer, suitable sources of target nucleic acids include breast cells and lymph node cells, e.g., cells obtained via fine needle aspiration biopsy; cells obtained via core needle biopsy; cells obtained from lymph nodes in the vicinity of the breast (e.g., axillary lymph nodes); and the like.

In the context of breast cancer, breast cancers that can be detected using a subject method include mammary carcinoma, adenocarcinoma, ductal carcinoma in situ, lobular (small cell) carcinoma, intraductal carcinoma, medullary breast cancer, mucinous breast cancer, tubular breast cancer, papillary breast cancer, Paget's disease, inflammatory breast cancer, and hormone dependent tumors of the breast.

Nucleic Acid Probes

The present invention provides detection, diagnostic, and staging methods, e.g., methods for detecting and diagnosing cancer (e.g., breast cancer and other carcinomas) in an individual; methods of identifying individuals at risk of developing cancer (e.g., breast cancer); and methods of staging cancer (e.g., breast cancer). The methods generally involve detecting an abnormal level of a target mRNA in a biological sample obtained from the individual. The subject methods can be carried out using a method involving nucleic acid hybridization, amplification, or both.

Nucleic acid hybridization can be carried out using a nucleic acid probe that detects a level of a target mRNA that is abnormally expressed in a pre-cancerous epithelial cell. Where abnormal expression of a target nucleic acid is to be detected, nucleic acid probes suitable for use include nucleic acid probes that hybridize to and provide for detection of a target nucleic acid that is overexpressed or underexpressed in an epithelial cell, e.g., a pre-cancerous epithelial cell. The present invention provides such nucleic acid probes Suitable nucleic acid probes are in some embodiments in the range of between 10-50 nucleotides long, such as 10 to 50, 12 to 45, 15 to 40, 20 to 35, 25 to 30 nucleotides, and the like. For example, probes will in some embodiments be in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest in some embodiments.

A suitable probe may be coupled to a label for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Exemplary fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. In some embodiments, the probe is attached to the solid support by a linker which serves to distance the probe from the solid support. The linker is in many embodiments at least 15-30 atoms in length, or at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. In some embodiments, polymers such as functionalized polyethylene glycol are used because they do not significantly interfere with the hybridization of probe to the target oligonucleotide. In some embodiments, the linked is polyethylene glycol.

The linkages between the solid support, the linker and the probe are normally not cleaved during removal of base protecting groups under basic conditions at high temperature. Examples of suitable linkages include carbamate and amide linkages.

Examples of suitable types of solid supports for immobilization of the oligonucleotide probe include controlled pore glass, glass plates, polystyrene, avidin-coated polystyrene beads, cellulose, nylon, acrylamide gel and activated dextran.

In some embodiments, methods of detecting a level of a target mRNA in a cell will involve amplifying the target nucleic acid, using a pair of nucleic acid primers.

In general, primers provide for amplification of a target nucleic acid to produce a target nucleic acid amplification product (also referred to as an "amplicon"). Primers will in some embodiments be used in conjunction with a nucleic acid probe. 5' primers generally bind to a region to provide for amplification of the target nucleic, and in many embodiments bind to a 5' portion of the target sequence. 3' primers generally bind to a sequence that is complementary to a 3' portion of the nucleic acid generated by extension from the 5' primer.

Target nucleotide sequences to which 5' and 3' primers hybridize will be separated from one another by from about 10 nucleotides to about 1000 nucleotides, e.g., from about 10 nucleotides to about 20 nucleotides, from about 20 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, or from about 500 nucleotides to about 1000 nucleotides.

The amplification product will in many embodiments have a length in a range of from about 30 nucleotides (or base pairs, bp) to about 1000 nucleotides (or base pairs), e.g., from about 30 bp to about 50 bp, from about 50 bp to about 60 bp, from about 60 bp to about 70 bp, from about 70 bp to about 80 bp, from about 80 bp to about 90 bp, from about 90 bp to about 100 bp, from about 100 bp to about 150 bp, from about 150 bp to about 200 bp, from about 200 bp to about 250 bp, from about 250 bp to about 300 bp, from about 300 bp to about 350 bp, from about 350 bp to about 400 bp, from about 400 bp to about 500 bp, from about 500 bp to about 600 bp, from about 700 bp, from about 700 bp to about 800 bp, from about 800 bp to about 900 bp, or from about 900 bp to about 1000 bp (e.g., about 1 kb).

In some embodiments, the primer sequences are in the range of between 10-75 nucleotides in length, such as 10 to 70 nucleotides, 12 to 65 nucleotides, 15 to 60 nucleotides, 20 to 55 nucleotides, 25 to 50 nucleotides, 30 to 45 nucleotides, and the like. In some embodiments, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest in some embodiments.

In some embodiments, the first and/or the second primer comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Nucleic Acid Arrays

In some embodiments, nucleic acid probe that provides for detection of a target nucleic acid is present in an array. A subject nucleic acid array comprises an array of probe nucleic acids immobilized on a solid support surface. Nucleic acid probes are generally oligonucleotides, e.g. oligonucleotides of at least about 12 nucleotides (nt), at least about 15 nt, at least about 18 nt, at least about 20 nt, at least about 25 nt, at least about 30 nt, at least about 40 nt, at least about 50 at least about, at least about 60 nt, or longer. Such an array may comprise a series of oligonucleotides, each of which can specifically hybridize to a different target nucleic acid.

A variety of different array formats are known in the art, with a wide variety of different probe structures, substrate compositions and attachment technologies. Representative array structures of interest include those described in U.S. Pat. Nos. 6,919,211, 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

Essentially, any conceivable substrate for a subject nucleic acid may be employed. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is typically flat but may take on a variety of alternative surface configurations. For example, the substrate may contain raised or depressed regions on which the synthesis takes place. The substrate and its surface in many embodiments form a rigid support on which to carry out the hybridization reactions described herein. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In an exemplary embodiment, the substrate is flat glass or single-crystal silicon with surface relief features of less than 10 μm.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will in many embodiments be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. In many embodiments, the surface will contain reactive groups, which could be carboxyl, amino, hydroxyl, or the like. In many embodiments, the surface will be optically transparent and will have surface Si—OH functionalities, such as are found on silica surfaces.

A number of methods are available for creating microarrays of nucleic acids to be used in DNA hybridization assays. Exemplary are PCT Application Serial No. WO95/35505, published Dec. 28, 1995; U.S. Pat. No. 5,445,934, issued Aug. 29, 1995; and Drmanac et al. (1993) *Science* 260:1649-1652. Yershov et al. (1996) *Genetics* 93:4913-4918 describe an alternative construction of an oligonucleotide array. The construction and use of oligonucleotide arrays is reviewed by Ramsay (1998) supra. Methods of using high density oligonucleotide arrays are known in the art. For example, Milosavljevic et al. (1996) *Genomics* 37:77-86 describe DNA sequence recognition by hybridization to short oligomers.

The systems and kits of the subject invention may include the above-described arrays. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

Internal Control Nucleic Acids

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Synthesis of Primers and Probes

Primers and probes described above are designed based on target sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) *Tetrahedron* 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Biological Assay Reagents

The present invention provides reagents for use in a subject biological assay. For example, as described in more detail below, in some embodiments, a subject method involves contacting a test fibroblast obtained from a patient with a reporter epithelial cell; and determining the effect, if any, of the fibroblast on physical or functional property of the reporter epithelial cell. The present invention provides reagents and systems for carrying out such a biological assay.

System components can include one or more of a reporter epithelial cell; binding reagents (e.g., antibody reagents) for detecting the presence and/or level of markers present in a reporter epithelial cell; nucleic acid reagents for detecting the presence and/or level of a nucleic acid (e.g., an mRNA, a cDNA copy of an mRNA, etc.) in a reporter epithelial cell; components for assessing mobility of a reporter epithelial cell (e.g., ability to cross a membrane); reagents (e.g., as described above) for detecting epigenetic modification of a reporter epithelial cell (e.g., histone modification; DNA hypermethylation; etc.); reagents for detecting secretion or release of molecules from a test fibroblast; reagents for detecting a phenotypic change in a reporter cell; and reagents for detecting secretion or release from a reporter epithelial cell.

Suitable reporter epithelial cells include primary epithelial cells and immortalized epithelial cells (e.g., immortalized epithelial cell lines). In some embodiments, a reporter epithelial cell is a primary mammary epithelial cell, e.g., a primary human mammary epithelial cell. Primary human mammary epithelial cells can be obtained from a suitable source such as reduction mammoplasty. Reporter epithelial cells can be cultured as described in, e.g., Band and Sager (1989) *Proc. Natl. Acad. Sci. USA* 86:1249-1253; Hammond et al. (1984) *Proc. Natl. Acad. Sci. USA* 81:5435; and Romanov et al. (2001) *Nature* 409:633.

In some embodiments, a reporter epithelial cell is genetically modified with a nucleic acid comprising a nucleotide sequence encoding a polypeptide that provides a detectable signal. Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., *Science* 263(5148):802-805 (Feb. 11, 1994); an enhanced GFP (EGFP), Clontech-Genbank Accession Number U55762); a blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. *Curr. Biol.* 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, and 5,925,558; a GFP from species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like. Enzymes that catalyze production of a product that provides a detectable signal include, but are not limited to, luciferase, β-galactosidase, horse radish peroxidase, and alkaline phosphatase.

Genetically Modified vMEC

In some embodiments, a reporter epithelial cell is an isolated vMEC (e.g, a CD73+ MEC) that has been genetically modified with a nucleic acid comprising a nucleotide sequence encoding an oncogene. The present invention thus provides an isolated reporter epithelial cell, where the reporter epithelial cell is a CD73+ MEC that has been genetically modified with an exogenous nucleic acid comprising a nucleotide sequence encoding an oncogene. Suitable oncogenes include, but are not limited to, a ras family oncogene, a src family oncogene, Harvey murine sarcoma virus ras (v-Ha-ras), Kirsten murine sarcoma virus ras (v-Ki-ras), fyn, myc, erbB2, src, yes, sis, and the like.

In some embodiments, the oncogene is operably linked to a heterologous promoter. Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. In some embodiments, the heterologous promoter is a constitutive promoter. In other embodiments, the heterologous promoter is an inducible promoter. Suitable inducible promoters include, but are not limited to, a tetracycline-inducible promoter, a steroid-inducible promoter (e.g., a glucocorticoid-inducible promoter), and the like. A subject genetically modified, isolated vMEC is immortalized, but has not undergone cancerous transformation. In some embodiments, a subject genetically modified, immortalized vMEC is grown in medium containing 5% serum. In other embodiments, a subject genetically modified, immortalized vMEC is grown in medium containing 10% serum.

A subject genetically modified, isolated, immortalized vMEC is useful for detecting stromal components that has the capacity to induce a cancerous transformation of a vMEC, e.g., that has carcinogenic potential. A subject genetically modified, isolated, immortalized vMEC appears morphologically normal. Upon contact with a stromal component that has the capacity to induce a cancerous transformation of a vMEC, the genetically modified vMEC undergoes a change that is indicative of tumor progression. Such changes include, but are not limited to, increased motility; acquisition of mesenchymal features; increased telomerase activity; phenotypic changes associated with de novo methylation, e.g., methylation of a promoter region; anchorage-independent growth; genomic instability; and capacity for in vivo survival.

In some embodiments, a subject genetically modified, immortalized vMEC is further genetically modified with a nucleic acid comprising a nucleotide sequence encoding a protein that provides for a detectable signal. Suitable proteins include, but are not limited to, fluorescent proteins and enzymes (e.g., β-galactosidase, luciferase, horse radish peroxidase, alkaline phosphatase, etc.). Polypeptides that provide a detectable signal include fluorescent proteins, chromogenic proteins, enzymes that catalyze the production of a product that is luminescent, fluorescent, or colored, etc. Suitable fluorescent proteins are as described above (e.g., including a green fluorescent protein, a red fluorescent protein, a yellow fluorescent protein, etc.).

Detection Methods

The present invention provides methods of detecting a cell in a mammary tissue that is precancerous or has an increased likelihood of inducing a cancerous transformation in a neighboring mammary tissue cell. A subject detection method is useful in a variety of clinical applications, including imaging methods, diagnostic methods, prognostic methods, and monitoring methods, which are also provided.

A subject detection method generally involves detecting a mammary epithelial cell signature in a biological sample. In some embodiments, a biological sample is a sample that comprises cells, which can include living cells, dead cells, cells that have been treated for histochemical analysis, etc. In other embodiments, a biological sample is a liquid sample that may or may not include living cells, where liquid samples include bodily fluids such as nipple aspirate fluid, urine, blood, serum, plasma, and the like. In other embodiments, a biological sample is a liquid sample that may or may not include living cells, where the liquid sample is a lavage sample, e.g., a ductal lavage sample. In some embodiments, a biological sample has been treated prior to use in a subject detection method, e.g., by enrichment for one or more components (e.g., proteins, nucleic acids, etc.); removal of cells or cell debris; processing for histochemical analysis; and the like.

In some embodiments, a subject detection method provides for detection of a pre-cancerous mammary epithelial cell. Detection of a pre-cancerous MEC involves detection of an MEC signature, e.g., a signature that is indicative of a pre-cancerous MEC. An "MEC signature" includes, but is not limited to: 1) the presence and/or level of a selected protein or collection of proteins; 2) the presence or absence of a posttranslational modification of a selected protein or collection of proteins; 3) the presence of a chromatin modification; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

As an example, a subject method will in some embodiments involve administering a detectable labeled binding reagent, e.g., a detectably labeled antibody, to an individual; and detecting binding of the antibody reagent to a pre-cancerous mammary epithelial cell in the individual. Detecting binding of the antibody reagent to a pre-cancerous mammary epithelial cell in the individual can be carried out using standard methods, e.g., magnetic resonance imaging, histochemical analysis, and the like. As another example, in some embodiments a subject method will be carried out on a tissue sample obtained from an individual being tested, e.g., where the tissue sample, will be contacted with a specific binding reagent (e.g., an antibody reagent; a nucleic acid reagent, etc., as described above).

Detection of a pre-cancerous MEC is useful in a variety of clinical applications, including imaging methods, diagnostic methods, prognostic methods, and monitoring methods. For example, a subject imaging method provides for detection of a pre-cancerous MEC in a female individual, e.g., an individual who presents as "normal," e.g., an individual who would normally undergo a routine examination or screening procedure that would be carried out on an individual who is not considered at high risk for breast cancer. As another example, detection of a pre-cancerous MEC is useful in a diagnostic method, e.g., alone or in conjunction with a mammogram, magnetic resonance imaging (MRI), or other standard diagnostic test, to detect the presence of a pre-cancerous MEC in mammary tissue. As a further example, detection of a pre-cancerous MEC is useful in a prognostic method, e.g., following a procedure such as benign breast biopsy (BBB), to determine the need for a cancer treatment regimen such as chemotherapy. Finally, detection of a pre-cancerous MEC is useful in a monitoring method, e.g., to determine the efficacy of treatment for breast cancer, and/or to determine patient response to treatment for breast cancer.

It should be appreciated that a subject detection method can involve one, two, three, or more of the above-mentioned detection methods. In other embodiments, a subject method involves detecting two or more features of an MEC signature, e.g., a subject method can involve detecting two, three, four, five, or more of: 1) the presence and/or level of a selected protein or collection of proteins produced by an MEC; 2) the presence or absence of a posttranslational modification of a selected protein or collection of proteins in an MEC; 3) the presence of a chromatin modification in an MEC; 4) the level of a selected DNA or collection of DNA in an MEC; 5) the integrity of a selected DNA or collection of DNA in an MEC; 6) the methylation status of a selected DNA or collection of DNA in an MEC; 7) the presence and/or level of a selected mRNA or collection of mRNA in an MEC; 8) the presence and/or level of a selected microRNA or collection of microRNA in an MEC; and 9) secretion and/or release of a factor from an MEC:

Methods for Detecting a Variant Mammary Epithelial Cell

Methods for detecting a variant (e.g., pre-cancerous) mammary epithelial cell are provided. Detection of a pre-cancerous MEC involves detection of an MEC signature, e.g., a signature that is indicative of a pre-cancerous MEC. An "MEC signature" includes, but is not limited to, one or more of the following features: 1) the presence and/or level of a selected protein or collection of proteins; 2) the presence or absence of a posttranslational modification of a selected protein or collection of proteins; 3) the presence of a chromatin modification; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

In some embodiments, a subject detection method involves detection of a gene product (e.g., polypeptides; nucleic acids) produced by an MEC. In one embodiment, the methods involve contacting a sample with a probe specific for the gene product of interest (e.g., marker polypeptide). "Probe" as used herein in such methods is meant to refer to a molecule that specifically binds a gene product of interest (e.g., the probe binds to the target gene product with a specificity sufficient to distinguish binding to target over non-specific binding to non-target (background) molecules). "Probes" include, but are not necessarily limited to, antibodies (e.g., antibodies, antibody fragments that retain binding to a target epitope, single chain antibodies, and the like); polynucleotides (e.g., oligonucleotide probes); and other polypeptide, peptide, or molecule (e.g., receptor ligand) that specifically binds a target gene product of interest.

Subject detection methods include one or more of: 1) detecting the presence and/or level of a selected protein or collection of proteins in an MEC; 2) detecting the presence of posttranslational modifications of gene expression-controlling proteins in an MEC; 3) detecting the level of a selected DNA or collection of selected DNA in an MEC; 4) detecting the integrity of a selected DNA in an MEC; 5) detecting the methylation status of a selected DNA in an MEC; 6) detecting the presence and/or a level of a selected mRNA or collection of mRNA in an MEC; 7) detecting the presence and/or level of a selected microRNA in an MEC; and 8) detecting secretion and/or release of a molecule (e.g., a protein, a nucleic acid, an ion, etc.) from an MEC; and 9) detecting a physical, morphological, or functional change in an MEC when contacted with a test fibroblast.

In some embodiments, the method for detecting the presence or absence of a pre-cancerous epithelial cell in a subject includes detecting a pattern of gene product expression present in a biological sample obtained from a subject; and comparing the pattern of gene product expression from the biological sample to a library of gene product expression pattern known to be indicative of the presence or absence of a pre-cancerous epithelial cell, wherein the comparing indicates the presence or absence of a pre-cancerous epithelial cell.

The probe and sample suspected of having the gene product of interest are contacted under conditions suitable for binding of the probe to the gene product. For example, contacting is generally for a time sufficient to allow binding of the probe to the gene product (e.g., from several minutes to a few hours), and at a temperature and conditions of osmolarity and the like that provide for binding of the probe to the gene product at a level that is sufficiently distinguishable from background binding of the probe (e.g., under conditions that minimize non-specific binding). Suitable conditions for probe-target gene product binding can be readily determined using controls and other techniques available and known to one of ordinary skill in the art.

As such, in some embodiments, the pattern of gene product expression will be detected and compared to the library of gene product expression patterns known to be indicative of the presence or absence of a pre-cancerous epithelial cell. In certain embodiments, the assessment of gene product expression of a single gene product will provide a preliminary result and will be followed up with the assessment of at least a second gene product expression.

The present invention also provides a method for monitoring progression of a pre-cancerous epithelial cell in a subject by detecting a first pattern of expression of gene products present in a biological fluid sample obtained from a subject at a first time point, wherein said first pattern is indicative of a pre-cancerous epithelial cell; detecting a second pattern of expression of gene products present in a biological sample obtained from a subject at a second time point; and comparing the first and second patterns of expression of gene products from the biological samples, wherein the comparing provides for monitoring of the progression of the pre-cancerous epithelial cell from the first time point to the second time point.

In certain embodiments, the method of monitoring progression of a pre-cancerous epithelial cell in a subject will include detecting a pattern of expression of gene products present in a biological sample obtained from a subject at more than two time points, such as three or more. In general, the time points for detecting a pattern of expression of gene products can be separated by any amount of time that is desired. For example, the first time point and second time point can be separated by about 3 months, about 6 months, or about 1 year or more, such as about 3 or more years.

In general, it will be appreciated by one of skill in the art that the duration of time between the first time point and the second time point must be sufficient to provide for a monitoring of the progression of the pre-cancerous epithelial cell.

In certain embodiments, a subject detection method provides for monitoring the progression of a pre-cancerous epithelial cell in an individual. In some embodiments, the monitoring of the pre-cancerous epithelial cell in the subject is conducted without concomitant treatment for cancer. In such embodiments, the method of monitoring will provide information as to the status of the pre-cancerous epithelial cell, which information is used to determine whether treatment is warranted, to determine the type of treatment that should be initiated, and/or the treatment regimen. In some embodiments, monitoring is carried out once a year, every 6 months, every 4 months, every 3 months, or once per month.

The monitoring of the pre-cancerous epithelial cell in the subject can be conducted in parallel with a preventive approach (e.g., to remove precursors) and/or a treatment regimen for a cancer, e.g., a carcinoma. In such embodiments, the method of monitoring the pre-cancer or cancer during treatment will provide information of whether the treatment is improving the condition, or having no effect or an adverse effect on the condition. In such embodiments, the first time point may be either just before, concurrent with, or just after the in initiation of a treatment regimen and the second time point may be a time point following a desired treatment period. For example, in such embodiments, the second time point may be about 6 month or more following initiation of treatment, including about 1 year, about 2 years, or more. For example, the detection of the pattern of expression of gene products present in a biological sample obtained from the subject may be determined about once every 6 months to monitor progression of the disease and efficacy of the treatment regimen.

In general, methods of the invention involving detection of a gene product (e.g., polypeptides or polynucleotides). The probe and sample suspected of having the gene product of interest are contacted under conditions suitable for binding of the probe to the gene product. For example, contacting is generally for a time sufficient to allow binding of the probe to the gene product (e.g., from several minutes to a few hours), and at a temperature and conditions of osmolarity and the like that provide for binding of the probe to the gene product at a level that is sufficiently distinguishable from background binding of the probe (e.g., under conditions that minimize non-specific binding). Suitable conditions for probe-target gene product binding can be readily determined using controls and other techniques available and known to one of ordinary skill in the art.

The detection methods can be provided as part of a kit. Thus, the invention further provides kits for detecting the presence/absence and/or a level of expression of a marker of the invention, and/or a polypeptide in a human biological sample. The kits of the invention for detecting a marker polypeptide generally comprise a moiety that specifically binds the polypeptide, which may be a specific antibody. The kit may optionally provide additional components that are useful in the procedure, including, but not limited to, buffers, developing reagents, labels, reacting surfaces, means for detection, control samples, standards, instructions, and interpretive information.

Detecting the Presence and/or Level of a Selected Polypeptide or Collection of Polypeptides In some embodiments, a subject detection method involves detecting the presence and/or levels of a selected polypeptide or collection of polypeptides produced by an MEC. The methods generally involve use of a probe to detect the polypeptide(s). In these embodiments, the probe is an antibody or other polypeptide, peptide, or molecule (e.g., receptor ligand) that specifically binds a target polypeptide of interest.

In some embodiments, a subject detection method involves detecting the presence and/or level of one or more of the polypeptides listed in FIG. 14. In some embodiments, a subject detection method involves detecting the presence and/or level of one or more of: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a subject detection method involves detecting the presence and/or level of one or more of: CD73, CD138, notch receptor-3, CD90, BMI-1, and COX-2. In some embodiments, a subject detection method involves detecting the presence and/or level of CD73, CD138, notch receptor-3, CD90, BMI-1, and COX-2. In some embodiments, a subject detection method involves detecting the presence and/or level of Ki67 and p16. In some embodiments, a subject detection method involves detecting the presence and/or level of Ki67 and COX-2. In some embodiments, a subject detection method involves detecting the presence and/or level of Ki67, p16, and COX-2.

The selected polypeptides (also referred to herein as "biomarkers"), or collection of selected polypeptides, can be detected by any suitable method. Detection paradigms that can be employed to this end include enzymatic methods, including immunological-based methods, optical methods, electrochemical methods (voltametry and amperometry techniques), atomic force microscopy, and radio frequency methods, e.g., multipolar resonance spectroscopy. It is to be understood that the present invention is not limited to a particular detection method. However, in some embodiments detection is by, for example, fluorescent detection, spectrometric detection, chemiluminescent detection, matrix assisted laser desorption-time-of flight (MALDI-TOF) detection, high pressure liquid chromatographic detection, charge detection, mass detection, radio frequency detection, and light diffraction detection. Exemplary detection methods that are suitable for use with the subject methods are described herein.

In some embodiments, detection a selected polypeptide or collection of polypeptides is by use of capture reagents specific to the polypeptides. In some embodiments, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different polypeptides can be mixed in the same place, or they can be attached to solid phases in different physical or addressable locations. For example, one can load multiple columns with derivatized beads, each column able to capture a single polypeptide. Alternatively, one can pack a single column with different beads derivatized with capture reagents against a variety of polypeptides, thereby capturing all the polypeptide analytes in a single place. Accordingly, antibody-derivatized bead-based technologies, such as Multi-Analyte Profiling (xMAP™) technology of Luminex (Austin, Tex.) can be used to detect the polypeptide(s).

Luminex xMAP™ is based on polystyrene particles (microspheres) that are internally labeled with two different fluorophores. When excited by a 635-run laser, the fluorophores emit light at different wavelengths, e.g., 658 and 712 nm. By varying the 658-nm/712-nm emission ratios, the beads are individually classified by the unique Luminex 100 IS analyzer. A third fluorophore coupled to a reporter molecule allows for quantification of the interaction that has occurred on the microsphere surface. The Luminex xMAP™ technology is described, for example, in U.S. Pat. Nos. 5,736,330, 5,981,180, and 6,057,107, all of which are specifically incorporated by reference.

In yet another embodiment, the surfaces of biochips can be derivatized with the capture reagents directed against specific polypeptides. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound thereto.

Immunoassays

Any of a variety of known immunoassay methods can be used for detection, including, but not limited to, immunoassay, using an antibody specific for the polypeptide, e.g., by enzyme-linked immunosorbent assay (ELISA), radioimmunoassay (RIA), immunohistochemistry; and the like; and functional assays for the encoded polypeptide, e.g., binding activity or enzymatic activity.

In some embodiments, a subject detection method involves detecting the presence and/or level of one or more of: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a subject detection method involves detecting the presence and/or level of one or more of: CD73, CD138, notch receptor-3, CD90, BMI-1, and COX-2. In some embodiments, a subject detection method involves detecting the presence and/or level of CD73, CD138, notch receptor-3, CD90, BMI-1, and COX-2. In some embodiments, a subject detection method involves detecting the presence and/or level of Ki67 and p16. In some embodiments, a subject detection method involves detecting the presence and/or level of Ki67 and COX-2. In some embodiments, a subject detection method involves detecting the presence and/or level of Ki67, p16, and COX-2.

For example, an immunofluorescence assay can be easily performed on a biological sample obtained from a patient, e.g., a tissue biopsy. It is also possible to perform such assays in plasma.

To increase the sensitivity of the assay, the immunocomplex may be further exposed to a second antibody, which is labeled and binds to the first antibody, which is specific for the encoded polypeptide. Typically, the secondary antibody is detectably labeled, e.g., with a fluorescent marker. The cells which express the encoded polypeptide will be fluorescently labeled and easily visualized under the microscope. See, for example, Hashido et al. (1992) *Biochem. Biophys. Res. Comm.* 187:1241-1248.

As will be readily apparent to the ordinarily skilled artisan upon reading the present specification, the detection methods and other methods described herein can be varied. Such variations are within the intended scope of the invention. For example, in the above detection scheme, the probe for use in detection can be immobilized on a solid support, and the test sample (e.g., biological sample obtained from a patient) contacted with the immobilized probe. Binding of the test sample to the probe can then be detected in a variety of ways, e.g., by detecting a detectable label bound to the test sample.

Thus generally the methods comprise: a) contacting a sample comprising an MEC with an antibody specific for one or more of: CD73, CD 138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2; and b) detecting binding between the antibody and molecules of the sample. The level of antibody binding (either qualitative or quantitative) indicates that the MEC is pre-cancerous. For example, where the marker polypeptide is present at a level greater than that associated with a negative control level, the MEC is pre-cancerous, and the patient is susceptible to or at risk of developing breast cancer.

Suitable controls include a sample known not to contain the marker polypeptide; a sample contacted with an antibody not specific for the marker polypeptide; a sample having a level of polypeptide that is elevated in a cancerous epithelial cell. A variety of methods to detect specific antibody-antigen interactions are known in the art and can be used in the method, including, but not limited to, standard immunohistological methods, immunoprecipitation, an enzyme immunoassay, and a radioimmunoassay.

In general, the specific antibody will be detectably labeled, either directly or indirectly. Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. In some embodiments, an antibody reagent comprises, covalently linked to the antibody reagent, a protein that provides for a detectable signal. Suitable proteins include, but are not limited to, fluorescent proteins and enzymes (e.g., β-galactosidase, luciferase, horse radish peroxidase, alkaline phosphatase, etc.). For example, suitable proteins include fluorescent proteins, chromogenic proteins, enzymes that catalyze the production of a product that is luminescent, fluorescent, or colored, etc.

Suitable fluorescent proteins include, but are not limited to, a green fluorescent protein (GFP; Chalfie, et al., *Science* 263(5148):802-805 (Feb. 11, 1994); an enhanced GFP (EGFP), e.g., Genbank Accession Number U55762); a blue fluorescent protein; an enhanced yellow fluorescent protein; a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, and 5,925,558; a GFP from species such as *Renilla reniformis*, *Renilla mulleri*, or *Ptilosarcus guernyi*, as described in, e.g., WO 99/49019 or Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

Other suitable detectable labels include fluorescent dyes, e.g., Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls, and to appropriate standards.

In some embodiments, a subject detection method involves use of an array of specific binding reagents, e.g., an antibody reagent array. An array can be created by spotting captures agents onto a substrate (e.g., glass, nitrocellulose, etc.) and attaching those capture agents to the substrate. The antibody reagents can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena et al. (1995) *Science* 270(5235): 467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734. The antibody reagents utilized in the arrays can be of varying types and can include, for example, antibodies, including antibody fragments, aptamers, avimers, or peptidomimetics.

Common physical substrates for making protein arrays include glass or silicon slides, magnetic particles or other micro beads, functionalized with aldehyde or other chemical groups to help immobilize proteins. The substrate can also be coated with PLL (polylysine), nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

The variables in the immobilization of proteins include: type of capture agent (e.g., antibody reagent), nature of surface (including any pretreatment prior to use), and the immobilization method. Both adsorption and covalent attachment have been used for protein arrays. Orientation of the capture agent is very important in presenting it to the ligand or the surface in a functional state. Although covalent attachment using a variety of chemically activated surfaces (e.g., aldehyde, amino, epoxy) as well as attachment by specific biomolecular interactions (e.g., biotin-streptavidin) provide a stable linkage and good reproducibility, chemical derivatization of the surface may alter the biological activity of the capture agent and/or may result in multi-site attachment.

In one embodiment, antibody arrays are made with a non-contact deposition printer. The printer uses thermal ink jet heads that can print many solutions simultaneously to produce hundreds of spots of 50-60 μm in diameter with a spacing of 150 μm between spots. The droplet volume ranges between 35 pL to 1.5 nL. The heating element is made out of TaAl or other suitable materials, and is capable of achieving temperatures that can vaporize a sufficient volume of printing buffer to produce a bubble that will push out a precise volume of the antibody solution on the substrate. Selection of printing buffer is important, in that the buffer accomplishes the following: increases printing efficiency (measure of the number of spots that are printed to the total number of spots that are attempted), reduces sample spreading, promotes uniform delivery, stabilizes the capture agents that are being printed, reduces sample drying, and increases the visibility of the printed spots. In addition to the printing buffer, other variables that affect printing include: size of the drops, the method of washing and drying the print head, and the speed at which the dispensing head moves. Various modifications may be within these conditions.

Immunohistochemical Assays

In some embodiments, a subject detection method is an immunohistochemical assay. See, e.g., U.S. Pat. No. 6,007, 996 for a discussion of various immunohistochemical methods. In general, the method involves contacting a sample comprising an MEC with an antibody specific for a target polypeptide (e.g., one or more of: CD73, CD13S, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2); and detecting binding, if any, of the antibody to an epitope(s) present in the MEC.

In general, the specific antibody will be detectably labeled, either directly or indirectly. Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. Other suitable detectable labels include fluorescent dyes, e.g., Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{1S}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

In some embodiments, a sample comprising an MEC is contacted with antibody reagent(s) or other binding reagent(s) specific for one or more of: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a sample comprising an MEC is contacted with antibody reagent(s) or other binding reagent(s) specific for one or more of: CD73, CD138, notch receptor-3, CD90, BMI-1, and COX-2. In some embodiments, a sample comprising an MEC is contacted with antibody reagent(s) or other binding reagent(s) specific for CD73, CD138, notch receptor-3, CD90, BMI-1, and COX-2. In some embodiments, a sample comprising an MEC is contacted with antibody reagent(s) or other binding reagent(s) specific for Ki67 and p16. In some embodiments, a sample comprising an MEC is contacted with antibody reagent(s) or other binding reagent(s) specific for Ki67 and COX-2. In some embodiments, a sample comprising an MEC is contacted with antibody reagent(s) or other binding reagent(s) specific for Ki67, p16, and COX-2.

In some embodiments, e.g., where two or more antibodies are used, each antibody being specific for a different target polypeptide, each of the two or more antibodies is detectably labeled with a different label, where the two or more different labels are distinguishable from one another.

Polypeptide Arrays

Polypeptide arrays provide a high throughput technique that can assay a large number of polypeptides in a sample. This technology can be used as a tool to test for expression of a marker polypeptide and detection of a pre-cancerous epithelial cell. In some embodiments, a subject array comprises a probe for detection of one or more of the polypeptides listed in FIG. 14. Of particular interest are arrays which comprise a probe for detection of one or more of the following polypeptides: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

A variety of methods of producing arrays, as well as variations of these methods, are known in the art and contemplated for use in the invention. For example, arrays can be created by spotting polypeptide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Samples of polypeptides can be detectably labeled (e.g., using radioactive or fluorescent labels) and then hybridized to the probes. Alternatively, the polypeptides of the test sample can be immobilized on the array, and the probes detestably labeled and then applied to the immobilized polypeptides. In most embodiments, the "probe" is detectably labeled. In other embodiments, the probe is immobilized on the array and not detectably labeled. In such embodiments, the sample is applied to the polypeptide array and bound gene products (e.g., peptides) are detected using secondary labeled probes.

Examples of such protein arrays are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

Detecting Posttranslational Modification of a Factor

In some embodiments, a subject detection method involves detecting posttranslational modification of one or more factors (e.g., polypeptides), present in a MEC, that control gene expression and/or that modulate chromatin, and/or that modulate DNA methylation. In some embodiments, a subject detection method involves detecting a posttranslational modification of a Polycomb group (PcG) repressor complex (e.g., modification of a PcG protein such as EED) and/or a posttranslational modification of a histone deacetylase. Posttranslational modifications of chromatin polypeptides include methylation and acetylation. In some embodiments, a subject detection method involves use of an antibody reagent that specifically binds a chromatin polypeptide, e.g., a chromatin epitope that is susceptible to posttranslational modification or that has been posttranslationally modified. A suitable antibody reagent is contacted with a sample comprising an MEC, or with a sample comprising MEC proteins, and binding, if any, of the antibody reagent to a chromatin polypeptide in the sample is detected. For example, in some embodiments, an antibody reagent specifically binds to a chromatin epitope(s) that is not modified, e.g., the antibody reagent binds specifically to a chromatin epitope that comprises only encoded amino acids. In other embodiments, an antibody reagent specifically binds to an acetylated chromatin polypeptide, e.g., the antibody reagents binds specifically to a chromatin epitope that is acetylated. In other embodiments, an antibody reagent specifically binds to a methylated chromatin polypeptide, e.g., the antibody reagents binds specifically to a chromatin epitope that is methylated. The antibody reagent can be detectably labeled, as described above Detecting Chromatin Modifications In some embodiments, a subject detection method involves detecting chromatin modification in an MEC. In some embodiments, a subject detection method involves detection of histone acetylation. Suitable detection methods include immunohistochemical methods; and other immunological methods (e.g., immunoprecipitation; protein blot assays; etc.).

Detecting Secreted or Released Molecules

In some embodiments, a subject detection method involves detecting molecules secreted or released from an MEC. For example, in some embodiments, an MEC is obtained from an individual and is cultured in vitro; and a profile of molecules secreted or released from the cultured MEC is detected. In other embodiments, a reporter MEC is cultured in vitro in the presence of a fibroblast obtained from an individual; and a profile of molecules secreted or released from the reporter MEC is detected. Molecules secreted or released from an MEC include, but are not limited to, proteins, nucleic acids, and ions.

Proteins that are secreted or released from an MEC can be detected as described above, using any number of different assay formats, including, e.g., immunological assays, where in some embodiments, an array of antibody reagents is used to detect two or more proteins secreted or released from an MEC.

Nucleic acids that are secreted or released from an MEC can be detected as described below, using a nucleic acid probe and/or a nucleic acid primer. For example, in some embodiments, an array of nucleic acid probes is used to detect two or more nucleic acids secreted or released from an MEC.

Ions that can be detected include, e.g., calcium ions, potassium ions, sodium ions, magnesium ions, chloride ions, hydrogen ions (pH), and the like. Suitable ion-indicating agents include fluorescent calcium indicators, e.g., fura dyes (e.g., fura-2, fura-4F, fura-5F, fura-6F, fura-FF, Fura Red), fluo dyes (e.g., fluo-3, flou-4), indo dyes (e.g., indo-1), rhodamine dyes (e.g., rhod-2, X-rhod-1), Oregon Green 488, Calcium Green, Calcium Crimson, and quin-2; membrane-permeant acetoxymethyl (AM) ester forms of any of the aforementioned fluorescent calcium indicators; membrane-impermeant salt forms of any of the aforementioned fluorescent calcium indicators; fluorescent sodium indicators, e.g., benzofuran isophthalate (SBFI), Sodium Green, CoroNa Green; fluorescent potassium indicators, e.g., PBFI, CD222; fluorescent magnesium indicators, e.g., Mag-Fluo-4, Mag-Fura-2, Mag-Fura-5, Mag-Fura-Red, Mag-indo-1, Mag-rho-2, Magnesium Green; fluorescent chloride indicators, e.g., trans-1,2-bis(4-[1'-MQ-1"-dimethyl-AQ-xylyl]-pyridinium)ethylene (Bis-DMXPQ), 7-(β-D-ribofuranosylamino)-pyrido[2,1-h]-pteridin-11-ium-5-olate (LZQ), Lucigenin, and a variety of 6-methoxyquinolinium derivatives such as 6-Methoxy-N-(3-sulfopropyl)quinolinium (SPQ), N-(Ethoxycarbonylmethyl)-6-methoxyquinolinium bromide (MQAE) and 6-Methoxy-N-ethylquinolinium iodide (MEQ); and fluorescent pH indicators, e.g., biscarboxyethyl-carboxyfluorescein (BCECF) and 2',7'-bis-(2-carboxypropyl)-5-(6-)-carboxyfluorescein (BCPCF). Other suitable methods and reagents include those described in, e.g., U.S. Patent Publication No. 2006/0148104.

Detecting the Presence and/or Level of an mRNA

In some embodiments, a subject detection method involves detecting the presence and/or level of a selected mRNA, or a collection of selected mRNA, in an MEC. In some embodiments, a cDNA copy of a selected mRNA, or cDNA copies of a collection of selected mRNA, is detected. In some embodiments, a subject detection method will involve nucleic acid hybridization with a nucleic acid probe, nucleic acid amplification with a nucleic acid primer pair, or both. Nucleic acid hybridization and nucleic acid amplification methods are known to those skilled in the art. Exemplary nucleic acid hybridization and nucleic acid amplification methods are discussed in detail below. The following provides detail of exemplary nucleic acid-based methods for detection, and examples of how such can be adapted for use in the methods of the invention.

In some embodiments, a subject method for detecting the presence and/or level of an mRNA, a collection of mRNA, in an MEC involves contacting, under stringent hybridization conditions, a subject nucleic acid probe with a target nucleic acid in a sample; and detecting the level of target mRNA in the sample. In some embodiments, where the detected level of target mRNA indicates that target mRNA is overexpressed or underexpressed in the cell, the cell is considered precancerous. In some embodiments, a cDNA copy of a target mRNA is generated. In some embodiments, the target nucleic acid (mRNA or cDNA copy) is amplified using a nucleic acid primer pair.

In some embodiments, a subject method involves detecting, in an MEC (or a nucleic acid sample obtained from an MEC), the presence and/or level of one or more mRNAs (or a cDNA copy thereof) listed in FIG. 14. In some embodiments, a subject method involves detecting, in an MEC (or a nucleic acid sample obtained from an MEC), the presence and/or level of one or more of the following mRNA (or cDNA copy thereof): CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject method involves detecting, in an MEC (or a nucleic acid sample obtained from an MEC), the presence and/or level of two or more (e.g., two, three, four, five, or more) of the following mRNA (or cDNA copy of an mRNA): CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject method involves detecting, in an MEC (or a nucleic acid sample obtained from an MEC), the presence and/or level of two, three, four, five, or all of CD73, CD138, notch receptor-3, CD90, BMI-1, and COX-2 mRNAs (or cDNA copies of same). In some embodiments, a subject method involves detecting, in an MEC (or a nucleic acid sample obtained from an MEC), the presence and/or level of Ki67, COX-2, and p16 mRNA (or cDNA copies of same). In some embodiments, a subject method involves detecting, in an MEC (or a nucleic acid sample obtained from an MEC), the presence and/or level of two, three, four, five, or all of CD73, CD138, notch receptor-3, CD90, BMI-1, and COX-2 mRNAs (or cDNA copies of same). In some embodiments, a subject method involves detecting, in an MEC (or a nucleic acid sample obtained from an MEC), the presence and/or level of Ki67 and COX-2 mRNA (or cDNA copies of same). In some embodiments, a subject method involves detecting, in an MEC (or a nucleic acid sample obtained from an MEC), the presence and/or level of Ki67 and p16 mRNA (or cDNA copies of same).

A number of methods are available for analyzing nucleic acids for the presence and/or level of a specific nucleic acid in a cell, or in a sample comprising nucleic acids obtained from a cell (e.g., a cell lysate, etc.). The mRNA can be assayed directly. In some embodiments, an mRNA is detected by microarray analysis; see, e.g., U.S. Patent Publication No. 2007/0009915.

In some embodiments, an mRNA is reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33.

In some embodiments, the method involves contacting the sample under stringent hybridization conditions with a subject nucleic acid probe and detecting binding, if any, of the probe to a target nucleic acid in the sample. A variety of nucleic acid hybridization methods are well known to those skilled in the art, and any known method can be used. In many embodiments, the nucleic acid probe will be detectably labeled.

Where a subject method involves detecting a level of a target nucleic acid in a cell, the method will in some embodiments include amplification of the target nucleic acid, forming a target amplification product; and can further include a step of hybridizing the target amplification product with a nucleic acid probe.

In some embodiments, the method involves contacting a sample (e.g., under stringent hybridization conditions) with a subject nucleic acid primer pair, where the primer pair, under conditions that permit primer-initiated nucleic acid amplification, amplifies any target nucleic acid present in the sample, generating an amplification product (where amplification product is generated when target nucleic acid present in the sample).

Conditions that permit primer-initiated nucleic acid amplification and catalytic nucleic acid activity are well known to those skilled in the art, and include the presence of a DNA polymerase; deoxynucleotide triphosphates; and magnesium ions. Suitable reaction conditions are well known to those skilled in the art of nucleic acid amplification. The DNA polymerase is generally one that has high affinity for binding at the 3'-end of an oligonucleotide hybridized to a nucleic acid strand. The DNA polymerase is generally one that has little or no 5'-≥ 3' exonuclease activity so as to minimize degradation of primer, termination or primer extension polynucleotides. The DNA polymerase is generally one that has little to no proofreading activity. In many embodiments, the DNA polymerase is thermostable, e.g., is catalytically active at temperatures in excess of about 75° C. DNA polymerases that are suitable for use in a subject method include, but are not limited to, DNA polymerases discussed in U.S. Pat. Nos. 5,648,211 and 5,744,312, which include exo Vent (New England Biolabs), exo Deep Vent (New England Biolabs), Bst (BioRad), exo Pfu (Stratagene), Bca (Panvera), sequencing grade Taq (Promega); thermostable DNA polymerases from *Thermoanaerobacter thermohydrosulfuricus*; and the like. In some embodiments, the reaction mixture includes an RNAse H.

Magnesium ions are typically present in the reaction mix in a concentration of from about 1 mM to about 100 mM, e.g., from about 1 mM to about 3 mM, from about 3 mM to about 5 mM, from about 5 mM to about 10 mM, from about 10 mM to about 25 mM, from about 25 mM to about 50 mM, from about 50 mM to about 75 mM, or from about 75 mM to about 100 mM.

Usually the reaction mixture will comprise four different types of dNTPs corresponding to the four naturally occurring bases are present, i.e. dATP, dTTP, dCTP and dGTP. In the subject methods, each dNTP will typically be present at a final concentration in the reaction, ranging from about 10 µM to 5000 µM, e.g., from about 10 µM to about 50 µM, from about 50 µM to about 100 µM, from about 100 µM to about 200 µM, from about 200 µM to about 500 µM, from about 500 µM to about 1000 µM, from about 1000 µM to about 2000 µM, from about 2000 µM to about 3000 µM, from about 3000 µM to about 4000 µM, or from about 4000 µM to about 5000 µM. In some embodiments, each dNTP will be present at a final concentration in the reaction of from about 20 µM to 1000 µM, from about 100 µM to about 200 µM, or from about 50 µM to about 200 µM.

The amplification reaction mixture typically includes an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed. The divalent cation may be magnesium, manganese, zinc and the like, where the cation will typically be magnesium. Any convenient source of magnesium cation may be employed, including $MgCl_2$, Mg-acetate, and the like. Representative buffering agents or salts that may be present in the buffer include Tris, Tricine, HEPES, MOPS and the like, where the amount of buffering agent will typically range from about 5 to 150 mM, from about 10 to 100 mM, or from about 20 to 50 mM, where in certain embodiments the buffering agent will be present in an amount sufficient to provide a pH ranging from about 6.0 to 9.5, e.g., pH 7.3 at 72° C. Other agents which may be present in the buffer medium include chelating agents, such as EDTA, EGTA and the like.

Each primer nucleic acid is present in the reaction mixture at a concentration of from about 50 nM to about 900 nM, e.g., the 3' primer and the 5' primer nucleic acid are each independently present at a concentration of from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 400 nM, from about 400 nvI to about 500 nM, from about 500 nM to about 600 nM, from about 600 nM to about 700 nM, from about 700 nM to about 800 nM, or from about 800 nM to about 900 nM.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2', 7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one embodiment, a subject method involves amplifying nucleic acids from a sample, which amplifying step follows a reverse transcription step to provide a cDNA template for amplification. In some embodiments, the level of a target mRNA can be indicated, where overexpression or underexpression of a target mRNA indicates a cancerous or precancerous cell. In general, amplification-based methods involve reverse transcription of mRNA in a sample and amplifying the resulting cDNA from the sample using a primer and at least one other primer, as described above, and assessing the amplified nucleic acids.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect target nucleic acid (e.g., to detect a level of target mRNA; etc.) in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, e.g. by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stearothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. PCR is typically carried out with a commercially available thermal cycler, e.g., Perkin Elmer.

RNAs encoding a deacylase of interest can be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) PCR Meth. App. 4:80-84.

The fluorogenic 5' nuclease assay, known as the TAQMAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of a target nucleic acid as described herein can be used in TAQMAN™ analyses to detect a level of target mRNA in a biological sample. Analysis is performed in conjunction with thermal cycling by monitoring the generation of fluorescence signals. The assay system dispenses with the need for gel electrophoretic analysis, and has the capability to generate quantitative data allowing the determination of, for example, the level of target mRNA (e.g., to detect the presence of a pre-cancerous epithelial cell; etc.).

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention provides methods for amplifying a target nucleotide sequence using a nucleic acid polymerase having 5' to 3' nuclease activity, one or more primers capable of hybridizing to the target sequence or its extension product, and an oligonucleotide probe capable of hybridizing to the target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is in some embodiments a fluorescein dye and the quencher molecule is in some embodiments a rhodamine dye.

The target nucleic acids described herein may also be used as a basis for transcription-mediated amplification (TMA) assays. TMA provides a method of identifying target nucleic acids present in very small amounts in a biological sample. Such nucleic acids may be difficult or impossible to detect using direct assay methods. In particular, TMA is an isothermal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid from the biological sample of interest (e.g., breast tissue; axillary lymph node tissue; etc.); and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. In some embodiments, an exogenous RNAse H, such as *E. coli* RNAse H, is added, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al.

(eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. In some embodiments, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a deacylase-encoding nucleic acid as described herein, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

Oligonucleotides will in some embodiments be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The target nucleic acids described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent, design of the assays described herein is subject to a great deal of variation, and many formats are known in the art. The above descriptions are merely provided as guidance and one of skill in the art can readily modify the described protocols, using techniques well known in the art.

Detection Using Nucleic Acid Arrays

In some embodiments, a subject method of detecting a target nucleic acid involves detection of the target nucleic acid in a sample of nucleic acids that is labeled with at least a first and a second distinguishable detectable label. In some embodiments, the method includes the following steps a) contacting a nucleic acid probe for a target nucleic acid with the sample under conditions sufficient for specific binding to occur between the probe and the target nucleic acid; and b) identifying the amount of the first and second labels in the resultant target nucleic acid/probe complex, thereby determining the amount of the target nucleic acid in the sample.

For example, in some embodiments, the method involves: a) contacting a probe for a target nucleic acid with a sample of nucleic acids under conditions sufficient for duplex nucleic acids to be produced between the probe and the target nucleic acid, and b) identifying the amount of the first and second labels in the resultant duplex nucleic acid.

In an exemplary microarray assay, a microarray is hybridized with differentially labeled RNA or DNA populations derived from two different samples. For example, RNA (either total RNA or poly $A^+$ RNA) is isolated from cells or tissues of interest and is reverse transcribed to yield cDNA. Labeling can be performed during reverse transcription by incorporating a labeled nucleotide in the reaction mixture. Various labels can be used; for example, the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluor while cDNA derived from a second sample (representing, for example, a different cell type, tissue type, or growth condition) is labeled with the second fluor. Similar amounts of labeled material from the two samples are cohybridized to the microarray. In the case of a microarray assay in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

In certain embodiments, the nucleic acid is extracted from a source (e.g., a cell, group of cells, tissue, culture, etc.) of interest, and includes RNA (e.g., unspliced RNA or mRNA, etc.), or DNA (e.g., genomic DNA of a nucleus or organelle, etc.). In certain embodiments, the sample is a genetic copy of the nucleic acid extracted from a source, such as cDNA, amplified DNA or RNA, or a nucleic acid that contains modified nucleotide residues (e.g., amino-ally nucleotides). Nucleic acid compositions suitable for labeling in the subject methods are well known in the art, and their further description may be found in several publications, including Brumbaugh et al (Proc Natl Acad Sci USA 85, 5610-4, 1988), Hughes et al. (Nat Biotechnol 19, 342-7, 2001), Eberwine et al (Biotechniques. 20:584-91, 1996), Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.).

In some embodiments, the sample contains labeled nucleic acid, where individual nucleic acid molecules within the sample are labeled with at least two, (e.g., two, three, four, five, six, seven or eight or more) detectably distinguishable labels. At least 2, at least about 4, at least about 6, at least about 8, at least about 10, at least about 15, at least about 20, at least about 25, at least about 30, or at least about 40 or at least about 50 or more of each distinguishable detectable label may associated with a single nucleic acid molecule. In certain embodiments, however, particularly those that involve separately labeling two portions of the same sample and mixing the labeled portions together to make a labeled sample, individual nucleic acid molecules within the sample may be labeled with only one type of label.

Labels of interest include directly detectable and indirectly detectable non-radioactive labels such as fluorescent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In some embodiments, the label is a directly detectable label. Directly detectable labels of particular interest include fluorescent labels.

Suitable fluorescent labels include a fluorophore moiety. Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, RI 10, Eosin, JOE, R6G, Tetramethylrhodamine, TAMRA, Lissamine, ROX, Napthofluorescein, Texas Red, Napthofluorescein, Cy3, and Cy5, etc.

As mentioned above, the labels used in the subject methods are distinguishable, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, NJ), Quasar 570 and Quasar 670 (Biosearch Technology, Novato CA), Alexafluor555 and Alexafluor647 (Molecular Probes, Eugene, OR), BODIPY V-1002 and BODIPY V1005 (Molecular Probes, Eugene, OR), POPO-3 and TOTO-3 (Molecular Probes, Eugene, OR), and POPRO3 TOPRO3 (Molecular Probes, Eugene, OR). Further suitable distinguishable detectable labels may be found in Kricka et al. (*Ann Clin Biochem.* 39:114-29, 2002).

In general, at least two distinguishable labels are covalently attached to nucleic acids in a sample. Means for labeling nucleic acids are generally well known in the art (e.g. Brumbaugh et al Proc Natl Acad Sci USA 85, 5610-4, 1988; Hughes et al. Nat Biotechnol 19, 342-7, 2001, Eberwine et al Biotechniques. 20:584-91, 1996, Ausubel, et al, Short Protocols in Molecular Biology, 3rd ed., Wiley & Sons, 1995 Sambrook, et al, Molecular Cloning: A Laboratory Manual, Third Edition, 2001 Cold Spring Harbor, N.Y. and DeRisi et al. Science 278:680-686, 1997; Patton W F. Electrophoresis. 2000 21:1123-44; MacBeath G. Nat Genet. 2002 32 Suppl:526-32; and Biotechnol Prog. 1997 13:649-58). These means usually involve either direct chemical modification of the analyte, or a labeled nucleotide that is incorporated into a nucleic acid by nucleic acid replication, e.g., using a polymerase.

Chemical modification methods for labeling a nucleic acid sample can include incorporation of a reactive nucleotide into a nucleic acid, e.g., an amine-allyl nucleotide derivative such as 5-(3-aminoallyl)-2'-deoxyuridine 5'-triphosphate, using an RNA-dependent or DNA-dependent DNA or RNA polymerase, e.g., reverse transcriptase or T7 RNA polymerase, followed by chemical conjugation of the reactive nucleotide to a label, e.g. a N-hydroxysuccinimdyl of a label such as Cy-3 or Cy5 to make a labeled nucleic acids (Brumbaugh et al Proc Natl Acad Sci USA 85, 5610-4, 1988 and Hughes et al. Nat Biotechnol 19, 342-7, 2001). Such chemical conjugation methods may be combined with RNA amplification methods (e.g. those of Eberwine et al Biotechniques. 20:584-91, 1996), to produce labeled DNA or RNA.

Suitable labels may also be incorporated into a sample by means of nucleic acid replication, where modified nucleotides such as modified deoxynucleotides, ribonucleotides, dideoxynucleotides, etc., or closely related analogues thereof, e.g. a deaza analogue thereof, in which a moiety of the nucleotide, typically the base, has been modified to be bonded to the label. Modified nucleotides are incorporated into a nucleic acid by the actions of a nucleic acid-dependent DNA or RNA polymerases, and a copy of the nucleic acid in the sample is produced that contains the label. Methods of labeling nucleic acids by a variety of methods, e.g., random priming, nick translation, RNA polymerase transcription, etc., are well generally known in the art (see, e.g., Ausubel, et al, Short Protocols in Molecular Biology, 3rd ed., Wiley & Sons, 1995 Sambrook, et al, Molecular Cloning: A Laboratory Manual, Third Edition, 2001 Cold Spring Harbor, N.Y. and DeRisi et al. Science 278:680-686, 1997).

In some embodiments of the invention, a nucleic acid sample is labeled using a mixture of labels. In other words, two or more distinguishably detectable labels are mixed together, usually in a single vessel or tube, sometimes in equal proportions, in a single labeling reaction for a sample. The two or more labels may be for the same nucleotide e.g. "T" or "U", or a mixture of two, three or four nucleotides. In certain embodiments, however, if the samples are identical (e.g. they are two portions of a sample, or two nucleic acids samples made from the same source), the samples may be labeled separately and combined to make a labeled sample. As such, the subject methods do not involve labeling two different samples (e.g. samples from two different tissues, times, or conditions), each with distinguishable label, and mixing the samples together.

Once labeled, the sample is usually applied to a substrate that includes at least one probe, and incubated under conditions suitable for an analyte/probe complex, e.g. a nucleic acid duplex (i.e. a RNA/RNA, DNA/RNA, or DNA/DNA duplex) to be formed between a probe and a labeled nucleic acid in the sample, if such a labeled nucleic acid is present. In other words, the labeled nucleic acid sample is incubated with a substrate that contains at least one probe under conditions suitable for binding of the labeled nucleic acid to the probe. In certain embodiments, the substrate that includes the probe is an array of probes, where each probe is contained in a feature of the array, and where an array includes at least about 20, at least about 50, at least about 100, at least about 200, at least about 500, at least about 1,000, at least about 2,000, at least about 5,000, at least about 10,000, at least about 20,000, at least about 50,000, or up to about 100,000 or more features. Arrays used in the subject methods may have known amounts of probes present in a feature of the array. For example, if the concentration of a probe in a solution of probe to be deposited as known, and, the volume of the probe solution that is deposited in a feature is known, an amount of probe present in a feature of an array may be known.

After incubation, labeled sample that is not bound with a probe is typically washed away from the substrate, and the substrate, now including the labeled nucleic acid/probe duplexes, is scanned. The amount of each label associated with features of the array (each feature containing, e.g., a target nucleic acid/probe complex or a probe if no target nucleic acid is present) is then determined. In most embodiments, the substrate is scanned in two channels corresponding to the distinguishing features of the probes, such that the amounts of each label associated with each feature is determined independently (i.e. without interference) from other labels. In certain embodiments, scanning results in two scans, one for each channel, and usually represents a pixilated image of the substrate that reflects the amount of label associated with the features of the substrate. For example, each pixel of the image is accorded a signal level that represents the level of brightness of the label signal. As mentioned above, scanning methods are well known in the art (e.g., DeRisi et al. Science 278:680-686, 1997), and several suitable scanners are commercially available from Perkin-Elmer, Agilent, or Axon Instruments, etc., and are described in U.S. Pat. Nos. 5,091,652; 5,760,951, 6,320,196 and 6,355,934), the disclosures of which are herein incorporated by reference.

Detecting the Presence and/or Levels of a microRNA

In some embodiments, a subject method involves detecting the presence and/or levels of a microRNA synthesized by an MEC. MicroRNAs that can be detected using a subject method include, but are not limited to, mir 196b (HoxA9), (p14), 328, 30A-3P, 125b, 30E-3P, 680, 134, 604, 128b, 128a, 331, 520F, 299-3P, 520H, 510, 365, 520G, 9, 324-3P, 351, 125A, 764-5P, 302D, 520D, 652, 520C, 350, 585, 621, 542-5P, 560, 126, and 341.

MicroRNAs (miRNAs) are encoded by genes, which encode transcripts containing short double-stranded RNA hairpins. MiRNAs are transcribed as longer precursors, termed pre-miRNAs, which can be 50 to 80 nucleotides in length, and which are sometimes found in clusters and frequently found in introns. Upon transcription, miRNAs undergo nuclear cleavage by an RNase 111 endonuclease, producing the 60-70-nt stem-loop precursor miRNA (pre-miRNA) with a 5' phosphate and a 2-nt 3 overhang. The pre-miRNAs are cleaved by Dicer about two helical turns away from the ends of the pre-miRNA stem loop, producing double-stranded RNA with strands that are approximately the same length (21 to 24 nucleotides), and possess the characteristic 5'-phosphate and 3'-hydroxyl termini. One of the strands of this short-lived intermediate accumulates as the mature miRNA and is subsequently incorporated into a ribonucleoprotein complex, the miRNP. MiRNAs interact with target niRNAs at specific sites to induce cleavage of the message or inhibit translation.

Detection of microRNAs can be carried out using any of a variety of methods. One approach uses stem-loop reverse transcription (RT) followed by TaqMan PCR analysis (Chen et al. Nucleic Acids Res. 2005;33(20), e179). This method includes reverse transcription at low temperature. Another approach is to use a composite primer for reverse transcription which includes a gene-specific portion and a tail sequence used for PCR amplification (Raymond et al. RNA. 2005 Nov.; 11(11):1737-44). Another approach, described in U.S. Patent Publication No. 2007/0077582) is based on using a target miRNA as a primer for extension by DNA polymerase on a specific oligonucleotide template; the specific oligonucleotide sequence is longer than the target miRNA sequence and contains at its 3'-end a sequence complementary to target miRNA, and a spacer sequence adjacent to that complementary sequence, which is used in subsequent signal amplification. Also suitable for use is a microarray analysis method as described in, e.g., U.S. Patent Publication No. 2007/0009915. A quantitative RT-PCR approach that can be used in the mirVana™ method (Ambion).

DNA Detection Methods

In some embodiments, a subject detection method involves detecting the levels and/or integrity and/or methylation status and/or packaging of a selected DNA, or collection of DNA, present in an MEC.

Detecting a Level of a Selected DNA

In some embodiments, a subject detection method involves detecting the level of a selected DNA in an MEC. For example, in some embodiments, a variant MEC (e.g., an MEC that is pre-cancerous) has a deletion of all or part of one or more of chromosome 3p, chromosome 5p, chromosome 6p, chromosome 8p, chromosome 11q, chromosome 16q, and chromosome 22. In other embodiments, a variant MEC (e.g., an MEC that is pre-cancerous) has an amplification or all or a part of one or more of c-myc, her2/neu, or cyclin D1.

Detecting deletion of all or part of a DNA can be carried out using any of a number of well-established methods. In some embodiments, deletion is detected by histochemical analysis. In some embodiments, deletion is detected via metaphase karyotype analysis of the chromosomes present in an MEC. Suitable methods of detecting a DNA deletion include, but are not limited to, array comparative genomic hybridization, fluorescent in situ hybridisation (FISH), quantitative multiplex PCR, Southern blotting, multiplex amplifiable probe hybridization (MAPH), multiplex amplifiable probe hybridization (MLPA), and the like. See, e.g., White et al. (2003) *J. Med. Genetics* 40:e113; and Edgley et al. (2002) *Nucl. Acids Res.* 30:e52;

In some embodiments, detecting a DNA deletion is carried out by use of restriction endonucleases that cleave outside of a gene comprising a deletion, e.g., where one restriction endonuclease cleaves at a site 5' of the deletion and a second restriction endonuclease cleaves 3' of the deletion, such that a restriction fragment is generated that is shorter than the length of a restriction fragment generated using the same restriction endonucleases, using as a substrate the same gene without a deletion.

As another example, amplification using primer pairs spanning the deletion will result in different sized products corresponding to the deleted and undeleted (e.g., control) gene, which can be distinguished on the basis of size (e.g., by gel electrophoresis). These primer pairs can be used individually or in a nested PCR experiment. It will also be apparent to one of skill that hybridization methods (e.g., Northern hybridization) or RNAse protection assays using nucleic acid probe specific for the gene (e.g., a control, undeleted gene), or a nucleic acid probe specific for a region flanking the gene, can be used to detect and distinguish undeleted (control) genes and deleted variants.

Detecting amplification of all or part of a DNA can be carried out using any of a number of well-established methods.

Representational Oligonucleotide Microarray Analysis (ROMA) detects genomic amplifications and deletions with boundaries defined at a resolution of ~50 kb. See, e.g., Lucito et al. (2003) *Genome Res.* 13:2291-2305_A ROMA method can be used to detect amplification or deletion of all or a portion of a selected DNA. In another embodiment, a method such as comparative genomic hybridization (CGH) is used. See, e.g., U.S. Pat. No. 7,011,949. CGH is a method for detecting deletions and amplifications in one sample of genomic DNA relative to another individual sample; the method involves comparing the intensity of hybridization of microarray features to each target sample, each labeled with different fluorescent dyes In another embodiment, a method as described in U.S. Patent Publication No. 2006/0129331 is used.

In some embodiments, karyotype or other chromosomal analysis using gene-specific nucleic acid probes is carried out to detect amplification (i.e., change in copy number), deletion (including total deletion, partial deletion), insertion, substitution, or changes in the chromosomal location (e.g., translocation) of a selected gene. For example, alterations to a selected gene are identified by karyotype analysis, using any of a variety of methods known in the art. One useful technique is in situ hybridization (ISH). For example, when in situ hybridization techniques are used for karyotype analysis, a detectable or detectably-labeled probe is hybridized to a chromosomal sample in situ to locate a selected gene sequence. ISH can comprise one or more of the following steps: (1) fixation of the tissue, cell or other biological structure to be analyzed; (2) prehybridization treatment of the biological structure to increase accessibility of target DNA (e.g., denaturation with heat or alkali), and to reduce nonspecific binding (e.g., by blocking the hybridization capacity of repetitive sequences, e.g., using human genomic DNA); (3) hybridization of one or more nucleic acid probes (e.g., conventional nucleic acids, PNAs, or other nucleic acid analogs) to the nucleic acid in the biological structure or tissue; (4) posthybridization washes to remove nucleic acid fragments not bound in the hybridization; and, (5) detection of the hybridized nucleic acid fragments. The reagent used in each of these steps and their conditions for use can vary, depending on the particular application. It will be appreciated that these steps can be modified in a variety of ways well known to those of skill in the art.

In one embodiment of ISH, a gene-specific probe is labeled with a fluorescent label (fluorescent in situ hybridization; "FISH"). In some embodiments, it is desirable to use dual color fluorescent in situ hybridization, in which two probes are utilized, each labeled by a different fluorescent dye. A test probe that hybridizes to the selected sequence of interest is labeled with one dye, and a control probe that hybridizes to a different region is labeled with a second dye. A nucleic acid that hybridizes to a stable portion of the chromosome of interest, such as the centromere region, can be used as the control probe. In this way, one can account for differences between efficiency of hybridization from sample to sample.

Detecting Integrity of a Selected DNA

In some embodiments, a subject detection method involves detecting the integrity of a selected DNA in an MEC, e.g., detecting one or more of: an aneuploidy; telomeric content; a translocation; an aberrant pattern; and the like. Aberrant patterns in DNA include, but are not limited to "firestorms" (e.g., multiple closely spaced amplicons); "sawtooth" patterns (e.g., characterized by many narrow segments of duplication and deletion); and the like. See, e.g., Hicks et al. (2006) *Genome Res.* 16:1465-1479.

Detecting Methylation Status of a Selected DNA

In some embodiments, a subject detection method involves detecting the methylation status of a DNA. For example, in some embodiments, a subject detection method involves detecting the methylation status of a selected promoter, e.g., a p16 promoter, e.g., a p16$^{INKK4a}$ promoter.

Various methods can be used to determine the methylation status of a selected DNA. For example, indirect methods for DNA methylation pattern determinations at specific loci that have been developed rely on techniques that alter the genomic DNA in a methylation-dependent manner before an amplification event. There are two primary methods that have been utilized to achieve this methylation-dependent DNA alteration. The first is digestion by a restriction enzyme that is affected in its activity by 5-methylcytosine in a CpG sequence context. The cleavage, or lack of it, can subsequently be revealed by Southern blotting or by PCR. The other technique that has received recent widespread use-is the treatment of genomic DNA with sodium bisulfite. Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. The resulting sequence difference has been detected using standard DNA sequence detection techniques, primarily PCR.

An exemplary method involves use of a bisulfite treatment-based method followed by a PCR reaction to analyze specific loci within the genome. There are two principally different ways in which the sequence difference generated by the sodium bisulfite treatment can be revealed. The first is to design PCR primers that uniquely anneal with either methylated or unmethylated converted DNA. This technique is referred to as "methylation specific PCR" or "MSP". See, e.g., U.S. Pat. No. 5,786,146. The method used by all other bisulfite-based techniques (such as bisulfite genomic sequencing, COBRA and Ms-SNuPE) is to amplify the bisulfite-converted DNA using primers that anneal at locations that lack CpG dinucleotides in the original genomic sequence. In this way, the PCR primers can amplify the sequence in between the two primers, regardless of the DNA methylation status of that sequence in the original genomic DNA. This results in a pool of different PCR products, all with the same length and differing in their sequence only at the sites of potential DNA methylation at CpGs located in between the two primers. The difference between these methods of processing the bisulfite-converted sequence is that in MSP, the methylation information is derived from the occurrence or lack of occurrence of a PCR product, whereas in the other techniques a mix of products is always generated and the mixture is subsequently analyzed to yield quantitative information on the relative occurrence of the different methylation states. A method such as described in U.S. Pat. No. 7,186,512 is also suitable for use.

In some embodiments, the methods involve contacting a genomic sample of DNA with a modifying agent that modifies unmethylated cytosine (e.g., sodium bisulfite), to produce a converted nucleic acid; (b) amplifying the converted nucleic acid by means of oligonucleotide primers in the presence of one or a plurality of specific oligonucleotide probes, where the one or the plurality of the oligonucleotide primers or the specific probe(s) is/are capable of distinguishing between unmethylated and methylated nucleic acid (e.g., a CpG-specific probe capable of distinguishing between unmethylated and methylated nucleic acid); and (c) detecting, in real-time during the amplification, the methylated nucleic acid based on amplification-mediated probe displacement. See, e.g., U.S. Pat. No. 7,112,404. Amplification and detection can occur simultaneously as measured by fluorescence-based real-time quantitative PCR ("RT-PCR") using specific, dual-labeled dual label TaqMan® oligonucleotide probes. The displaceable probes can be specifically designed to distinguish between methylated and unmethylated CpG sites present in the original, unmodified nucleic acid sample. Sodium-bisulfite readily reacts with the 5,6-double bond of cytosine, but not with methylated cytosine, to produce a sulfonated cytosine intermediate that undergoes deamination under alkaline conditions to produce uracil. Because Taq polymerase recognizes uracil as thymine and 5-methylcytidine (m5C) as cytidine, the sequential combination of sodium bisulfite treatment and PCR amplification results in the ultimate conversion of unmethylated cytosine residues to thymine (C→U→T) and methylated cytosine residues ("mC") to cytosine (mC→mC→C). Thus, sodium-bisulfite treatment of genomic DNA creates methylation-dependent sequence differences by converting unmethylated cyotsines to uracil, and upon PCR the resultant product contains cytosine only at positions where methylated cytosine occurs in the unmodified nucleic acid.

In some embodiments, the specific primers are designed to be substantially complementary to each strand of the genomic locus of interest. Typically, one primer is complementary to the negative, (−) strand of the locus (the "lower" strand of a horizontally situated double-stranded DNA molecule) and the other is complementary to the positive (+) strand ("upper" strand). In some embodiments, the primers are designed to overlap potential sites of DNA methylation (CpG nucleotides) and specifically distinguish modified unmethylated from methylated DNA. This sequence discrimination can be based upon the differential annealing temperatures of perfectly matched, versus mismatched oligonucleotides. In some embodiments, primers are typically designed to overlap from one to several CpG sequences. In other embodiments, e.g., in a quantitative embodiment, the primers do not overlap any CpG sequences.

Proteomics Analysis

In some embodiments, a subject detection method involves a proteomics analysis of an MEC. In some embodiments, an antibody reagent array is used, where the array comprises antibody reagents specific for two or more of the proteins listed in FIG. 14. In some embodiments, an antibody reagent array is used, where the array comprises antibody reagents specific for two or more of: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In other embodiments, a polypeptide array is used. Polypeptide arrays provide a high throughput technique that can assay a large number of polypeptides in a sample. This technology can be used as a tool to test for expression of a marker polypeptide and detection of a pre-cancerous epithelial cell. Of particular interest are arrays which comprise a probe for detection of one or more of the following polypeptides: CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

A variety of methods of producing arrays, as well as variations of these methods, are known in the art and contemplated for use in the invention. For example, arrays can be created by spotting polypeptide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Samples of polypeptides can be detectably labeled (e.g., using radioactive or fluorescent labels) and then hybridized to the probes. Alternatively, the polypeptides of the test sample can be immobilized on the array, and the probes detectably labeled and then applied to the immobilized polypeptides. In most embodiments, the "probe" is detectably labeled. In other embodiments, the probe is immobilized on the array and not detectably labeled. In such embodiments, the sample is applied to the polypeptide array and bound gene products (e.g., peptides) are detected using secondary labeled probes.

Examples of such protein arrays are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828. Proteomics applications include those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803, the disclosures of which are herein incorporated by reference.

As noted above, in some embodiments, an antibody reagent array is used to detect proteins produced by an MEC (e.g. a variant MEC), where the array comprises antibody reagents specific for two or more of: CD73, CD138, notch receptor-3, CD90, BMI-1, COX-2, Ki67, p16, IGF2, YKL-40, EGF-R, a jun, PCNA, jnk, cyclin B1, c-kit, STAT3, cyclin D1, PI3K, MAPK, MAPKK, DDR2, TRF2, activin, and MEK1/2. Thus, e.g., use of an array of a plurality of distinct binding agents ("protein-binding agents" or "protein-binding reagents"), wherein each binding agent includes at least an epitope binding domain of an antibody molecule, is contemplated. The arrays employed in the subject methods can have a plurality of probe spots, each made up of a distinct binding agent (i.e., a plurality of copies of distinct binding agent molecule) stably associated with the surface of a solid support.

Each probe composition of a protein-binding reagent arrays is made up of multiple copies of a binding agent, where each binding agent includes at least an epitope binding domain of antibody. By epitope binding domain is meant a region or portion of an antibody molecule that specifically binds to an antigen, more particularly a determinant or epitope of a given antigen. As such, in some embodiments, the protein-binding reagents are antibodies, including specific antigen binding fragments and mimetics thereof. Where antibodies are the binding agent, they may be derived from polyclonal compositions, such that a heterogeneous population is used, where antibodies differing by specificity are each immobilized on the substrate surface; or monoclonal compositions, in which a homogeneous population of identical antibodies that have the same specificity for the target analyte, e.g., protein, are each immobilized on the substrate surface. As such, the binding agent may be either a monoclonal or a polyclonal antibody in certain embodiments.

In yet other embodiments, the binding agent making up the subject probe compositions is an antibody binding fragment or mimetic, where these fragments and mimetics have the requisite binding affinity for the target analyte, e.g., protein. For example, antibody fragments, such as Fv, F(ab)z and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies, i.e., they include the epitope binding domain (which means the whole domain or a least a functional portion thereof) of an antibody specific for the particular analyte. Such recombinantly produced antibody fragments generally include at least the $V_H$ and $V_L$ domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art. The binding agents typically have a strong affinity for their analyte, where this affinity is at least about $10^{-6}$, usually at least about $10^{-8}$ and typically ranges from about $10^{-8}$ to about $10^{-13}$, usually from about $10^{-9}$ to about $10^{-12}$, where the affinity is the affinity as measured following immobilization of the antibody onto the surface using the binding affinity assay described in Pellequer, J. L., Van Regenmortel, M. H., J Endocrinol, 139, (3) 495-501.

The probe spots made up of the binding agents as described above and present on the array may be any convenient shape, and can be circular, ellipsoid, oval or some other analogously curved shape. The total amount or mass of molecules present in each spot will be sufficient to provide for adequate binding and detection of analytes during the assay in which the array is employed. The total mass of binding agents in each spot can be at least about 10 pg, at least about 100 pg, or at least about 1 ng, where the total mass may be as high as 20 ng or higher. In some embodiments, the total mass of binding agent in each spot does not exceed about 10 ng, or does not exceed about 5 ng. Where the target protein is detectably labeled, the copy number of all of the individual binding agents in a spot will be sufficient to provide enough binding sites for tagged target molecule (e.g., protein being detected) to yield a detectable signal, and can range from about 100 fluorescence units (FU) to about 65500 FU, or from about 250 FU to about 45000 FU.

Where the probe spot has an overall circular dimension, the diameter of the spot can range from about 10 to about 5,000 μm, from about 20 to about 1,000 μm, or from about 50 to about 500 μm. The surface area of each spot can be at least about 100 μm$^2$, at least about 200 μm$^2$, or at least about 400 μm$^2$, and may be as great as about 25 mm$^2$ or greater; in some embodiments, the surface area of each spot does not exceed about 5 mm$^2$, or about 1 mm$^2$. The density of binding agents "probe" spots on the array, as well as the overall density of probe and non-probe spots (where the latter are described in greater detail below) may vary greatly. As used herein, the term spot refers to any spot on the array surface that is made up of binding agents, whether control or probe binding agents, and as such includes both probe spots and non-probe spots. The density of the probe spots on the solid surface is at least about 5/cm$^2$ and usually at least about 10/cm$^2$ and may be as high as about 100/cm$^2$, about 200/cm$^2$, about 300/cm$^2$, about 500/cm$^2$, about 1000/cm$^2$, about 5000/cm$^2$ or higher, but in many embodiments does not exceed about 1000/cm$^2$, and in these embodiments usually does not exceed about 500/cm$^2$ or about 400/cm$^2$ in many embodiments, and in certain embodiments does not exceed about 300/cm$^2$. The spots may be arranged in a spatially defined and physically addressable manner, in any convenient pattern across or over the surface of the array, such as in rows and columns so as to form a grid, in a circular pattern, and the like, where generally the pattern of spots will be present in the form of a grid across the surface of the solid support.

In the subject arrays, the spots of the pattern are stably associated with or immobilized on the surface of a solid support, where the support may be a flexible or rigid support. By "stably associated" it is meant that the binding agents of the spots maintain their position relative to the solid support under incubation (e.g., binding) and washing conditions, as described below. As such, the individual binding agent members that make up the spots can be non-covalently or covalently stably associated with the support surface based on technologies well known to those of skill in the art. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot binding agents and a functional group present on the surface of the rigid support, where the functional group may be naturally occurring or present as a member of an introduced linking group. In some embodiments, the binding agents making up the spots on the array surface, are covalently bound to the support surface, e.g., through covalent linkages formed between moieties present on the binding agents, e.g., amines, and the substrate surface, etc, as may be present on a glass substrate, e.g., aminated glass. See e.g., the specific covalent attachment protocol exemplified below.

As mentioned above, the array is present on either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the subject arrays are sufficient to provide physical support and structure to the polymeric targets present thereon under the assay conditions in which the array is employed, particularly under high throughput handling conditions. Furthermore, when the rigid supports of the subject invention are bent, they are prone to breakage.

The solid supports upon which the subject patterns of spots are presented in the subject arrays may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.01 mm to 2 mm and more usually from about 0.01 to 1 mm. Thus, in one representative embodiment the support may have a micro-titer plate format, having dimensions of approximately 125×85 mm. In another representative embodiment, the support may be a standard microscope slide with dimensions of from about 25×75 mm.

The substrates of the protein-binding reagent arrays can be fabricated from a variety of materials. The materials from which the substrate is fabricated should ideally exhibit a low level of non specific binding during binding events. In some embodiments, a material is used that is transparent to visible and/or UV light. For flexible substrates, materials of interest include: nylon, both modified and unmodified, nitrocellulose, polypropylene, and the like. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g., nylon or nitrocellulose, etc.

The substrates of the subject arrays comprise at least one surface on which the pattern of spots is present, where the surface may be smooth or substantially planar, or have irregularities, such as depressions or elevations. The surface on which the pattern of spots is present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, polyacrylamides, and the like, where the polymers may be hetero- or homopolymeric, and may or may not have separate functional moieties attached thereto, e.g. conjugated.

In certain embodiments, e.g., where the binding agent is a whole antibody or analogous structure, an antibody universal binding layer is present on the substrate surface, e.g., covalently bound to the substrate surface, which layer acts as a linking group or tethering element between the antibody binding agent in the substrate surface and serves to tether the antibody binding agent to the substrate surface. The basic principle is to utilize proteins and ligands with affinity towards antibodies (including but not limited to Protein A, Protein G, Protein L, Protein LA) which are covalently immobilized to a glass, plastic or any other type of surfaces. After the immobilization of the universal binding layer, the antibody binding agents are deposited on the same locations and reversibly immobilized. The universal binding layer of affinity ligands thus forms a layer which protects the consequently bound antibodies from detrimental surface effects. An additional benefit is the directed mode of immobilization as compared to that of direct covalent attachment of the antibodies to activated surfaces. This results in 100% availability of the antigen binding sites on the antibodies for consequent detection of antigens. It also provides universal conditions for binding, since the formation of ligand/antibody complex is obtained under mild physiological conditions where as covalent immobilization of proteins is often performed under conditions that might be detrimental to their biological activity.

The total number of spots on the substrate will vary depending on the number of different probe spots (binding agent probe compositions) one wishes to display on the surface, as well as the number of non probe spots, e.g., control spots, orientation spots, calibrating spots and the like, as may be desired depending on the particular application in which the subject arrays are to be employed. Generally, the pattern present on the surface of the array will comprise at least about 10 distinct spots, usually at least about 20 spots, and more usually at least about 50 distinct spots, where the number of distinct spots may be as high as 10,000 or higher, but will usually not exceed about 5,000 distinct spots, and more usually will not exceed about 3,000 distinct spots and in many instances will not exceed about 2,000 distinct spots. In certain embodiments, each distinct probe spot or probe composition is presented in duplicate, i.e. so that there are two duplicate probe spots displayed on the array for a given target. The number of probe spots present in the array will typically make up a substantial proportion of the total number of spots on the array, where in many embodiments the number of probe spots is at least about 50 number %, usually at least about 80 number % and more usually at least about 90 number % of the total number of spots on the array. As such, in many embodiments the total number of spots on the array ranges from about 10 to about 20,000, usually from about 20 to about 10,000 and more usually from about 100 to 5,000.

In the arrays of the subject invention (particularly those designed for use in high throughput applications, such as high throughput analysis applications), a single pattern of probe spots may be present on the array or the array may comprise a plurality of different spot patterns, each pattern being as defined above. When a plurality of different spot patterns are present, the patterns may be identical to each other, such that the array comprises two or more identical spot patterns on its surface, or the spot patterns may be different, e.g. in arrays that have two or more different sets of probes present on their surface, e.g., an array that has a pattern of spots corresponding to first population of target analytes and a second pattern of spots corresponding to a second population of analytes. Where a plurality of spot patterns are present on the array, the number of different spot patterns is at least 2, at least 6, or at least 24 or 96, where the number of different patterns will generally not exceed about 384.

Where the array includes a plurality of spot patterns on its surface, the array can include a plurality of reaction chambers, wherein each chamber has a bottom surface having associated therewith a pattern of spots and at least one wall, usually a plurality of walls surrounding the bottom surface. See e.g. U.S. Pat. No. 5,545,531, the disclosure of which is herein incorporated by reference. Of particular interest in many embodiments are arrays in which the same pattern of spots in reproduced in 24 or 96 different reaction chambers across the surface of the array.

Within any given pattern of spots on the array, there may be a single spot that corresponds to (i.e., specifically binds to) a given analyte target or a number of different spots that correspond to the same analyte, where when a plurality of different spots are present that correspond to the same analyte, the probe compositions of each spot that corresponds to the same analyte may be identical or different. In other words, a plurality of different analytes are represented in the pattern of spots, where each analyte may correspond to a single spot or a plurality of spots, where the probe compositions among the plurality of spots corresponding to the same analyte may be the same or different. Where a plurality of spots (of the same or different composition) corresponding to the same analyte is present on the array, the number of spots in this plurality will be at least about 2 and may be as high as 10; and in some embodiments will not exceed about 5. In some embodiments, any given analyte is represented by only a single type of probe spot, which may be present only once or multiple times on the array surface, e.g. in duplicate, triplicate etc.

The number of distinct or different probe spots present on the array, and therefore the number of different analytes represented on the array, is at least about 2, usually at least about 10 and more usually at least about 20, where in many embodiments the number of different analytes represented on the array is at least about 50, or at least about 100. The number of different analytes represented on the array may be as high as 5,000 or higher, and in some embodiments will not exceed about 3,000 or about 2,500. An analyte is considered to be represented on an array if it is able to specifically bind to one or probe compositions on the array.

The arrays employed in the subject methods may be fabricated using any convenient protocol, where the protocol may vary depending on the nature of the substrate, the nature of any intervening surface layer, e.g., whether or not a universal binding layer is present, and the nature of the binding agents. Where the substrate is a glass substrate or analogous material, typically the surface of the substrate is first activated to provide for functional groups suitable for use in the covalent bonding, either directly or through a linking group, of the binding agent. For example, glass surfaces may be aminated so as to display amine functional groups via silanization, according to well known surface chemistry protocols. In many embodiments, the binding agent is then immobilized on the functionalized surface, e.g., through direct or indirect covalent bonding, e.g., by non-covalent binding to a covalently bound universal binding layer of molecules, as described above. In some embodiments a surface activation agent is used, e.g., an agent that provides a linking group capable of forming a covalent linkage between aminated moieties, such as PIDTC and DVS.

Following surface preparation, e.g., surface activation, a binding agent composition is immobilized on the substrate surface to produce a spot of the array. The binding agent composition can be an aqueous composition. In some embodiments, the concentration ranges of the deposited binding agent composition is at least about 0.1 mg/mL, or at least about 0.2 mg/mL, where the concentration may be as great as 1 mg/mL or greater. The purity of the binding agent composition typically is at least about 90%, at least about 95%, or at least about 97% pure.

The binding agent composition is deposited on the array surface using any convenient protocol. In many embodiments, the binding agent composition is applied using a pin or analogous deposition device. Also of interest are pipette devices, ink jet devices, etc., which are extensively described in the array preparation art. The particular device and protocol employed to spot the subject binding agents is not critical, so long as it results in a functional probe spot, i.e., a probe spot that specifically binds to its target analyte.

Following deposition of the binding agent compositions to produce the pattern of probe spots on the array, the surface is then contacted with a blocking agent in order to block non-specific binding sites on the array surface. Any convenient blocking agent may be employed, where representative blocking agents include, but are not limited to, nonfat milk, BSA, gelatin, preimmune serum and the like, where standard blocking protocols may be employed.

Following preparation and blocking, as described above, the array is typically stored for a period of time prior to use. The array may be stored in any convenient format, including both dry and wet formats, so long as the activity of the array, i.e., the binding ability of the probe spots on the array for their specific analytes, is not adversely affected. By not adversely affected is meant that the sensitivity of the array does not change with respect to a given analyte as compared to the array immediately following blocking by a value that exceeds about 10 fold, and usually does not change by a value that exceeds about 5 fold. In many embodiments, the period of time for which the array is stored prior to use in the subject methods, described in greater detail below, is at least about 2 days, usually at least about 6 months and more usually at least about 9 months and may be as long as about 1 year or longer, where the array is typically not stored for a period that exceeds about 6 months prior to use.

The sample that is contacted with the substrate surface may vary greatly, depending upon the nature of the assay to be performed. In general, the sample is an aqueous fluid sample. The amount of fluid sample also varies with respect to the nature of the device, the nature of the sample, etc. In many embodiments, the amount of sample that is contacted with the substrate surface ranges from about 1 µl to about 5 ml, e.g., from about 1 µl to about 5 µl, from about 5 µl to about 10 µl, from about 10 µl to about 25 µl, from about 25 µl to about 50 µl, from about 50 µl to about 100 µl, from about 100 µl to about 500 µl, from about 500 µl to about 1 ml, or from about 1 ml to about 5 ml.

The fluid sample can be a cell lysate; a cell lysate that has been processed by one or more steps, e.g., removal of cellular debris, and the like; a cell fraction; a cell culture supernatant (e.g., the medium in which a cell is cultured in vitro; the fluid surrounding a cell in vivo; and the like. In obtaining the fluid sample, the initial physiological source (e.g., tissue, collection of cells, etc.) may be subjected to a number of different processing steps, where such processing steps might include tissue homogenation, protein extraction and the like, where such processing steps are known to the those of skill in the art. Of particular interest in many embodiments is the use of cellular extracts as the sample.

In certain embodiments, the initial fluid sample derived from a particular source, e.g., a cell extract, may be subjected to a fractionation protocol that reduces the complexity of the protein composition of the sample. By reduce the complexity is meant that the total mass of all of the proteins in the sample is reduced by at least about 10 fold, by at least about 100 fold, or at least about 1000 fold.

In certain embodiments, the fractionation protocol employed is one that reduces the amount of highly abundant proteins in the sample. In this embodiment, a pool of covalently attached antibodies, e.g., one or more columns of antibodies, is employed for enrichment of antigen analytes of interest from an initial sample, e.g., whole cell extracts. After reversible adsorption of the antigens of interest on the multi-antibody column, the non adsorbed material is washed away with washing buffer and the specifically retarded antigens are eluted and collected for further labeling and incubation with the array containing binding agent spots for the antigen/analytes of interest, e.g., the same antibodies that were used for initial enrichment. In this manner, the initial sample is fractionated so as to reduce the complexity and enrich the sample for the analytes of interest.

In some embodiments, the analytes of interest (e.g., proteins) present in the sample are labeled prior to contact with the array. By labeled is meant that the analytes are modified to be joined to, either covalently bonded to or stably but non-covalently bound to, a member of a signal producing system and are thus detectable, either directly or through combined action with one or more additional members of a signal producing system. Examples of directly detectable labels include isotopic and fluorescent moieties. Isotopic moieties or labels of interest include $^{32}P$, $^{33}P$, $^{35}S$, $^{125}I$, $^{3}H$, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like.

The analytes (e.g., proteins produced by an MEC, e.g., a variant MEC) can be labeled according to any convenient protocol, where the particular protocol employed may vary greatly with respect to the overall assay protocol being practiced and the nature of the specific label. For example, where the analytes are labeled with detectably labeled antibodies, e.g., fluorescently labeled antibodies, the labeling protocol typically comprises contacting the analyte with the labeled antibodies and incubating the sample under conditions sufficient for the labeled antibody to specifically bind to the analyte in the sample. In these embodiments, the labeled antibodies employed as labeling reagents are specific for an epitope of the analyte that is available for binding even when the analyte is bound to a probe spot on the array surface.

The functional moiety of the functionalized labels may vary greatly, and is chosen in view of the functional moiety present on the analytes in the sample, e.g., amine groups on the proteins analytes present in the sample. In other words, the functional moiety present on the functionalized label must be one that reacts with the functional moiety present on the analyte to produce a covalent bond between the analyte and the label. Representative functional moieties that may be present on the label include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like.

In certain embodiments where the analytes are labeled prior to contact with the array, the sample preparation protocol employs a single type of buffer for both the cellular extraction and labeling steps. In other words, a single buffer composition is employed in both the extraction step, where the proteins of the cell are separated from other cellular components/structures, and in the labeling step, where the analytes present in extract are labeled with a detectable label. The single extraction/labeling buffer employed in these embodiments is one that provides for high extraction efficiency, where high extraction efficiency is meant at least about 90% or at about 95% (by weight) of the proteins are extracted with the extaction/labeling buffer, as compared to the amount of proteins extracted by SDS boiling. In addition, the buffer is a buffer that extracts proteins from all cellular compartments/locations. This single cellular extract/ labeling buffer can be characterized by including detergents and other components, when present, that are free of primary amines. Representative detergents employed that may be present in the buffer include, but are not limited to: octyl-β-D-glucopyranoside (ODG), NP-40, Ernpigen, Pluronic, and the like. The amount of each detergent present in the extraction/labeling buffer may vary, but typically ranges from about 0.01% to about 10%, from about 0.05% to about 5%, or from about 0.1% to about 2%. In addition, the pH of the buffer is selected such that it provides for suitable conditions for both cellular extraction and labeling. As such, the pH can range from about 7 to about 12, or from about 8 to about 10.

Following sample preparation and any analyte labeling, where desired, the analyte containing fluid sample is contacted with the array of binding agents and contact is maintained under sufficient conditions and for a period of time sufficient for binding of analyte to specific binding pair members on the array surface to occur. For example, the array and analyte containing sample are incubated together for at least about 10 min., usually at least about 20 min., and more usually at least about 30 min., where the incubation time may be as long as about 480 min. or longer, and in some embodiments, incubation does not exceed about 60 min. During incubation, the array and sample are maintained at a temperature that typically ranges from about 20° C. to about 28° C., usually from about 22° C. to about 26° C. In many embodiments, the array and sample are subjected to mixing or agitation during the incubation step.

During incubation, the pH of the liquid medium is maintained at a value ranging from about 6.5 to about 8.5, or from about 7.0 to about 8.0. Also present may be one or more buffers, e.g., Tris, sodium citrate and the like; salts, e.g., NaCl, sodium sulfate, and the like; surfactants/surfactants, e.g., Pluronics, Tweens, glycerol, ethylene glycol, etc.

While the contact of the array and analyte containing fluid medium, as well as metal chelating polysaccharide, may be accomplished using any convenient protocol, in many embodiments, the initial sample is first pre-incubated with an incubation buffer that includes the metal ion chelating polysaccharide to produce a preincubated analyte containing sample, which preincubated sample is then contacted with the array for the incubation period. In these embodiments, the incubation buffer employed at least includes the metal ion chelating polysaccharide as described above. In addition, the incubation buffer typically includes a number of additional components, including buffering agents, salts, surfactants, etc.

Following incubation, non-array bound components of the analyte containing medium contacted with the array surface during incubation are separated or removed from the surface. This separation step can be accomplished using one or more washing steps, in which the array surface is contacted and separated from, including flushed with, one or more different fluid compositions.

The array surface can subjected to a sequential washing protocol, in which the array surface is washed with a plurality of distinct washing solutions. The number of different washings employed in these embodiments varies, but typically ranges from about 3 to 10, usually from about 5 to 9 and more usually from about 6 to 8, where in certain embodiments, 7 distinct washings are employed. In these embodiments, the series of different washing mediums employed provides a modulation or change in the nature of the washing medium and components therein, e.g., in order to subject the array surface to a sequential or step-wise change or modulation of conditions, e.g., amount/type of detergent, salt concentration, buffering agent, additives, etc. In these embodiments, the different washing conditions to which the array is subjected during the sequential wash protocol are ones that provide for a decrease in background and cross-reactivity during detection, and therefore an increase in signal to noise ratio and/or selectivity, so as to provide the sensitive results discussed above. In certain embodiments, the washing conditions are ones that provide for an increase in signal to noise ratio and/or selectivity of at least about 2-fold, at least about 5-fold, or at least about 10 fold and compared to a control assay in which only a single wash step with a wash fluid that is the same as the incubation fluid is performed. In certain embodiments, the sequential wash protocol is characterized by initially employing a high salt wash, e.g., to remove electrostatically bound molecules, followed by sequential use of wash fluids of decreasing detergent composition, and/or a change of buffers, e.g., from Tris to sodium citrate.

If the analytes in the sample (e.g., proteins produced by an MEC) are not labeled prior to incubation, as described above, they are labeled at some point prior to detection. As such, the surface bound analytes can be labeled following incubation and an initial wash step, e.g., where the labels are labeled antibodies capable of binding to already surface bound analytes. Alternatively, the labels can be functionalized to covalently bind to any molecule displaying a corresponding functional group, e.g., a primary amine. In these embodiments, the sample incubated array is contacted with the labeling composition under conditions sufficient for labeling to occur. An initial signal is then obtained from the array, followed by a washing step to remove bound analytes and other components. A second signal is then obtained. This second signal is then subtracted from the initial signal to obtain a final signal that is representative or related to the amount of analyte bound to the array, which signal is employed as described below to derive the amount of analyte in the sample.

Following washing, the array surface is read or scanned for the presence of binding complexes between analytes in the assayed sample and binding agents of the probe spots of the array. In other words, analyte/binding agent complexes on the surface of the array are detected.

Any convenient protocol may be employed for detecting the binding agents on the array surface. Many different protocols for detecting the presence of surface bound binding complexes are known to those of skill in the art, where the detection method may be qualitative or quantitative depending on the particular application in which the subject method is being performed, where the particular detection protocol employed may or may not use a detectable label. Representative detection protocols that may be employed include those described in WO 00/04389 and WO 00/04382; the disclosures of which are herein incorporated by reference. Representative non-label protocols include surface plasmon resonance, total internal reflection, Brewster Angle microscopy, optical waveguide light mode spectroscopy, surface charge elements, ellipsometry, etc., as described in U.S. Pat. No. 5,313,264, the disclosure of which is herein incorporated by reference. Alternatively, detectable label based protocols, including protocols that employ a signal producing system, may be employed. The particular protocol employed varies, depending on the nature of the label that is employed. Where fluorescent labels are employed, any convenient fluorescence scanner device, i.e., fluorimeter, may be employed, where numerous such devices and methods for their use are known to those of skill in the art.

Following detection of the surface bound binding complexes, the presence of any surface bound binding complexes is then related to the presence of the one or more analytes in the sample. In many embodiments, the signal intensity value obtained for any binding complex is quantitatively related to the presence of the corresponding analyte in the sample, so as to provide a quantitative determination of the analyte amount in the sample. This relating step is readily accomplished in that the position on the array at which a particular surface bound complex is located indicates the identity of the analyte or protein, since the binding agent for the protein is attached to a known specific location on the array. Thus, this relating step merely comprises determining the location on the array on which a binding complex is present, comparing that location to a reference that provides information regarding the correlation of each location to a particular analyte and thereby deriving the identity of the analyte in the sample. In sum, the location of the surface bound binding complexes is used to determine the identity of the one or more analytes of interest in the sample.

By way of further illustration, the following representative protein assay is summarized. Where one is interested in assaying a sample for the presence of 100 different proteins, an array displaying a collection of 100 different antibody binding agents is prepared, where each different antibody binding agents in the collection specifically binds to a different protein member of the 100 different proteins being assayed. The array is then contacted with the sample being assayed under conditions sufficient for binding complexes to be produced between the probe binding agent spots and their corresponding target proteins in the sample. Any resultant binding complexes on the surface of the array are then detected and the location of the detected binding complexes is used to determine which of the 100 proteins of interest is present in the sample.

In certain embodiments, two or more physiological sources, e.g., cell extracts (e.g., MEC cell extracts, variant MEC cell extracts, etc.), are assayed according to the above protocols in order to generate analyte profiles for the two or more sources that may be compared. In such embodiments, analyte containing sample may be separately contacted to identical arrays or together to the same array under binding conditions, depending on whether a means for distinguishing the patterns generated by the different populations of analytes is employed, e.g. distinguishable labels, such as two or more different emission wavelength fluorescent dyes, such as Cy3 and Cy5, two or more isotopes with different energy of emission, such as $^{32}P$ and $^{33}P$, gold or silver particles with different scattering spectra, labels which generate signals under different treatment conditions, like temperature, pH, treatment by additional chemical agents, etc., or generate signals at different time points after treatment.

Biological Assays

In some embodiments, a subject detection method is a biological assay, to detect one or more of a morphological, physiological, or functional characteristic of an MEC. Biological assays include, e.g., an assay involving contacting a reporter epithelial cell with a test fibroblast obtained from a patient; and determining the effect, if any, of the test fibroblast on the reporter epithelial cell.

A biological assay includes an assay that detects one or more of: 1) the presence and/or level of markers present in a reporter epithelial cell; 2) the presence and/or level of a nucleic acid (e.g., an mRNA, a eDNA copy of an mRNA, etc.) in a reporter epithelial cell; 3) mobility of a reporter epithelial cell (e.g., ability to cross a membrane); 4) epigenetic modification of a reporter epithelial cell (e.g., histone modification; DNA hypermethylation; etc.); 5) secretion or release of molecules from a test fibroblast; 6) secretion or release of molecules from a reporter epithelial cell; and 7) phenotypic changes.

The present invention provides a method of detecting an effect of a component of stroma on tumor progression in a variant human mammary epithelial cell (vMEC). The method generally involves: a) contacting a test stomal component with a vMEC in vitro; and b) determining the effect, if any, of the test stromal component on a cell characteristic of the vMEC, wherein a test stromal component that induces a cell characteristic change in the vMEC that is indicative of tumor progression indicates that the test stromal component has carcinogenic potential.

In some embodiments, a variant (pre-cancerous) HMEC is immortalized by genetically modifying the cell in vitro with a construct encoding a constitutively active oncogene, e.g., constitutively active Ha-Ras V12, to generate an immortalized variant HMEC. The variant HMEC is contacted in vitro with a test fibroblast or other component of the stroma. The effect, if any, of the fibroblast on a cell characteristic of the immortalized vHMEC is determined. Where the immortalized vMEC exhibits an altered cell characteristic in the presence of the test fibroblast, the test fibroblast is considered to be pre-cancerous or cancerous, or to have carcinogenic potential. Cell characteristics include, but are not limited to, increased motility; acquisition of mesenchymal features; increased telomerase activity; phenotypic changes associated with de novo methylation, e.g., methylation of a promoter region; anchorage-independent growth; genomic instability; and capacity for in vivo survival.

In some embodiments, the cell characteristic is acquisition of mesenchymal features, e.g., the reporter epithelial cell undergoes an epithelial-to-mesenchymal transition (EMT). Features that are characteristic of EMT include down-regulation of genes such as those encoding cellular adhesion molecules, and up-regulation of mesenchymal markers. Gene products that are down-regulated (e.g., are present, if at all, at reduced levels) include, but are not limited to, E-cadherin, β1-integrin, and cytokeratin. Gene products that are up-regulated include, but are not limited to, N-cadherin, fibronectin, and twist. Changes in the level of a gene product can be detected as described above, e.g., using an above-described method for detecting a change in protein level and/or using an above-described method for detecting a change in an mRNA level.

In other embodiments, the cell characteristic is a morphological change. For example, the reporter epithelial cell can acquire a spindle shaped morphology. In other embodiments, the cell characteristic is increased motility of the reporter epithelial cell. Motility can be assessed using any known assay, e.g., an assay as described in Valster et al. (2005) *Methods* 37:208. For example, a transwell migration assay can be used. The transwell migration assay has been amply described in the art; see, e.g., McKinnon et al. (2001) *J. Clin. Endocrinol. Metab.* 86:3665; Redmond et al. (1999) *Thromb. Haemost.* 81:293; and Seton-Rogers et al. (2004) *Proc. Natl. Acad. Sci. USA* 101:1257.

Suitable reporter epithelial cells include primary epithelial cells and immortalized epithelial cells (e.g., immortalized epithelial cell lines). In some embodiments, a reporter epithelial cell is a primary mammary epithelial cell, e.g., a primary human mammary epithelial cell. Primary human mammary epithelial cells can be obtained from a suitable source such as reduction mammoplasty. Reporter epithelial cells can be cultured as described in, e.g., Band and Sager (1989) *Proc. Natl. Acad. Sci. USA* 86:1249-1253; Hammond et al. (1984) *Proc. Natl. Acad. Sci. USA* 81:5435; and Romanov et al. (2001) *Nature* 409:633. In some embodiments, the reporter epithelial cell is a subject immortalized vHMEC, as described above.

In some embodiments, a reporter epithelial cell is genetically modified with a nucleic acid comprising a nucleotide sequence encoding a polypeptide that provides a detectable signal. Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., *Science* 263(5148):802-805 (Feb. 11, 1994); an enhanced GFP (EGFP), Clontech-Genbank Accession Number U55762); a blue fluorescent protein (BFP; 1. Quantum Biotechnologies, Inc. 1801 de Maisonneuve Blvd. West, 8th Floor, Montreal (Quebec) Canada H3H 139; 2. Stauber, R. H. *Biotechniques* 24(3):462-471 (1998); 3. Heim, R. and Tsien, R. Y. *Curr. Biol.* 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, and 5,925,558; a GFP from species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like. Enzymes that catalyze production of a product that provides a detectable signal include, but are not limited to, luciferase, β-galactosidase, horse radish peroxidase, and alkaline phosphatase.

Detecting Altered Metabolism

In some embodiments, a subject method of detecting a pre-cancerous MEC involves use of a method that detects a cell with altered metabolism (e.g., altered glucose metabolism; altered protein synthesis, e.g., incorporation of amino acids into proteins; altered nucleic acid synthesis, e.g., altered incorporation of nucleotides into nucleic acids; etc.). It has been found that a pre-cancerous MEC (e.g., a vHMEC) exhibits altered metabolism, e.g., an altered metabolism characteristic of a cancer cell. For example, a pre-cancerous MEC exhibits increased glucose metabolism, compared to a normal, non cancerous MEC. In some embodiments, the methods involve administering to in individual being tested an agent that is selectively taken up by a pre-cancerous MEC, compared to a normal, non-cancerous MEC. For example, the agent is taken up by a pre-cancerous MEC, and is substantially not taken up by a normal, non-cancerous MEC. The agent can be imaged using, e.g., Positron Emission Tomography (PET), computer-assisted tomography (CT), magnetic resonance imaging (MRI), and the like.

In some embodiments, a subject method involves imaging an individual for the presence of an agent that selectively labels cells with altered (e.g., increased) glucose metabolism, where a pre-cancerous MEC selectively takes up the agent. An example of such an agent is the positron-emitting $^{18}$F-labeled fluorodeoxyglucose (FDG), or a glucose derivative as described in U.S. Pat. No. 5,904,915, e.g., a halogenated glucose derivative, where the halogen is a radioisotope of a halogen atom.

In other embodiments, a subject method involves imaging an individual for the presence of an agent that selectively labels cells with altered (e.g., increased) protein synthesis, where a pre-cancerous MEC selectively takes up the agent. An example of such an agent is $^{11}$C-methionine.

In other embodiments, a subject method involves imaging an individual for the presence of an agent that selectively labels cells with altered (e.g., increased) DNA synthesis, where a pre-cancerous MEC selectively takes up the agent. An example of such an agent is $^{18}$F-thymidine.

Imaging Methods

As noted above, a subject detection method is useful in an imaging method. For example, detection (e.g., detection of an MEC signature) can be carried out in the context of risk assessment, where the analysis can be carried out on a woman who is considered to be at low risk of developing breast cancer, or on a woman who is considered at greater risk of developing breast cancer.

In some embodiments, a biological sample from a patient is subjected to an above-described detection method. Detection of an MEC signature that is indicative of a pre-cancerous MEC provides an indication of an increased risk of breast cancer. For example, in some embodiments, detection of an MEC signature that is indicative of a pre-cancerous MEC provides an indication that the individual from whom the biological sample was obtained has an at least about 25%, at least about 50%, at least about 75%, at least about 2-fold, at least about 5-fold, or at least about 10-fold, or higher, increased risk of developing breast cancer within the next year, within the next 5 years, or within the next 10 years, compared to the risk of developing breast cancer in an individual not having the MEC signature.

In some embodiments, a biological sample is a sample that comprises cells, which can include living cells, dead cells, cells that have been treated for histochemical analysis, etc. In other embodiments, a biological sample is a liquid sample that may or may not include living cells, where liquid samples include bodily fluids such as nipple aspirate fluid, urine, blood, serum, plasma, and the like. In other embodiments, a biological sample is a liquid sample that may or may not include living cells, where the liquid sample is a lavage sample, e.g., a ductal lavage sample. In some embodiments, a biological sample has been treated prior to use in a subject detection method, e.g., by enrichment for one or more components (e.g., proteins, nucleic acids, etc.); removal of cells or cell debris; processing for histochemical analysis; and the like.

In some embodiments, where an MEC signature indicative of a pre-cancerous MEC is detected, monitoring of the individual on a regular basis will be recommended. For example, where an MEC signature indicative of a pre-cancerous MEC is detected, the individual will be monitored yearly, twice yearly, three times per year, or four times per year, where the monitoring will include one or more of carrying out a subject detection method, MRI, and the like.

Diagnostic Methods

As noted above, a subject detection method is useful in a diagnostic method. For example, detection (e.g., detection of an MEC signature) can be carried out following, or in conjunction with, another diagnostic assay, such mammography, magnetic resonance imaging (MRI) of breast tissue and/or axillary lymph node tissue, etc.

In some embodiments, a subject detection method is carried out on a woman who is considered to be at high risk of developing breast cancer. In other embodiments, a subject detection method is carried out on a woman who has undergone mammography or MRI, where the mammogram indicates the presence, or the possible presence, of cancerous breast tissue.

Prognostic Methods

As noted above, a subject detection method is useful in a prognostic method. In some embodiments, a subject prognostic method is carried out on an individual who has undergone a benign breast biopsy. In some embodiments, a subject prognostic method is carried out on an individual who has been diagnosed with ductal carcinoma in situ. The methods generally involve carrying out a subject detection method on such individuals. In these embodiments, a subject detection method can provide for a determination of the likelihood that an individual will go on to develop a malignant breast cancer. If such a determination is made, then treatment for cancer may be recommended, or further monitoring may be recommended.

In some embodiments, subject method provides for determination of the likelihood that an individual diagnosed with ductal carcinoma in situ (DCIS) will develop a malignant breast cancer. In some embodiments, the methods involve detecting an MEC signature, e.g., detecting a gene product produced by an MEC, e.g., detecting one or more of the gene products listed in FIG. 14, e.g., detecting one or more of CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2 gene products, as described in detail above. In some embodiments, the methods involve detecting an MEC signature, e.g., detecting one or more of the following proteins: CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin and MEK1/2. In some embodiments, the methods involve detecting one or more of CD73, CD138, notch receptor-3, CD90, BMI-1, and COX-2 polypeptides. In some embodiments, the methods involve detecting one or more of COX-2, Ki67, and p16 polypeptides.

In some embodiments, subject method provides for determination of the likelihood that an individual with a benign breast biopsy (BBB) will develop a malignant breast cancer. In some embodiments, the methods involve detecting an MEC signature, e.g., detecting a gene product produced by an MEC, e.g., detecting one or more of CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2 gene products, as described in detail above. In some embodiments, the methods involve detecting an MEC signature, e.g., detecting one or more of the following proteins: CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2. In some embodiments, the methods involve detecting one or more of CD73, CD138, notch receptor-3, CD90, BMI-1, and COX-2 polypeptides. In some embodiments, the methods involve detecting one or more of COX-2, Ki67, and p16 polypeptides.

Monitoring Method

As noted above, a subject detection method is useful in a monitoring method, e.g., monitoring efficacy of a breast cancer treatment; monitoring patient response to a breast cancer treatment; etc. In some embodiments, a subject monitoring method involves carrying out a subject detection method on an individual who has undergone, or is undergoing, one or more treatments for breast cancer, where the treatments include, e.g., cancer chemotherapy, radiation therapy, a biological therapy (e.g., antibody treatments, etc.), and surgery (e.g., mastectomy, lumpectomy, etc.). A subject monitoring method can be carried out before the beginning of any such treatment and/or during the course of a treatment regimen, and/or following a treatment regimen. For example, a subject monitoring method can be carried out at the end of a treatment regimen, and at various time intervals thereafter, to monitor patient response to the treatment, and/or to monitor the efficacy of the treatment.

Carcinomas

The methods are useful for detecting, and/or staging, and/or grading a wide variety of cancers, including carcinomas. Carcinomas that can be detected using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Computer-Based Systems and Methods

The invention also provides a variety of computer-related embodiments. Specifically, the automated means for performing the methods described above may be controlled using computer-readable instructions, i.e., programming. Accordingly, in some embodiments the invention provides computer programming for analyzing and comparing a pattern of gene product expression present in a biological sample obtained from a subject to a library of gene product expression patterns known to be indicative of the presence or absence of a pre-cancerous epithelial cell, wherein the comparing indicates the presence or absence of a pre-cancerous epithelial cell.

In another embodiment, the invention provides computer programming for analyzing and comparing a first and a second pattern of expression of gene products from biological samples takes from a subject in at least two different time points, wherein the first pattern is indicative of a pre-cancerous epithelial cell, and/or progression from a pre-cancerous epithelial cell to a cancerous epithelial cell. In such embodiments, the comparing provides for monitoring of the progression of the pre-cancerous epithelial cell or for monitoring progression of a carcinoma from the first time point to the second time point.

In yet another embodiment, the invention provides computer programming for analyzing and comparing a pattern of gene product expression from a biological sample to a library of gene product expression patterns known to be indicative of the presence or absence of a carcinoma, wherein the comparing providing a differential diagnosis between a benign carcinoma, and an aggressive carcinoma, e.g., the gene product expression pattern provides for staging and/or grading of a carcinoma.

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of gene product expression for a sample). This information received can be stored at least temporarily in a database, and data analyzed in comparison to a library of gene product expression patterns known to be indicative of the presence or absence of a pre-cancerous epithelial cell, or known to be indicative of a stage and/or grade of a carcinoma.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the library of gene product expression patterns known to be indicative of the presence or absence of a pre-cancerous epithelial cell) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where gene product expression data for a biological sample obtained from a subject is to be input by a user (e.g., a technician or someone performing the activity assays)) and transmitted to a remote site to a second computer processor for analysis (e.g., where the pattern of gene expression is compared to a library of gene product expression patterns known to be indicative of the presence or absence of a pre-cancerous epithelial cell), where the first and second computer processors are connected by a network, e.g., via an intranet or internet). The system can also include a user component(s) for input; and a reviewer component(s) for review of data, and generation of reports, including detection of a pre-cancerous epithelial cell, staging and/or grading of a carcinoma, or monitoring the progression of a pre-cancerous epithelial cell or a carcinoma. Additional components of the system can include a server component(s); and a database(s) for storing data (e.g., as in a database of report elements, e.g., a library of gene product expression patterns known to be indicative of the presence or absence of a pre-cancerous cell and/or known to be indicative of a grade and/or a stage of a carcinoma, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one embodiment, the architecture is provided as a database-centric user/server architecture, in which the user application generally requests services from the application server which makes requests to the database (or the database server) to populate the activity assay report with the various report elements as required, especially the assay results for each activity assay. The server(s) (e.g., either as part of the application server machine or a separate RDB/relational database machine) responds to the user's requests.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the methods described herein, including detection of a pre-cancerous epithelial cell, staging and/or grading of a carcinoma, or monitoring the progression of a pre-cancerous epithelial cell or a carcinoma. Where the computer-readable medium contains a complete program for carrying out the methods described herein, the program includes program instructions for collecting, analyzing and comparing a pattern of gene product expression patterns from a biological sample (e.g., a biopsy sample) obtained from a subject to a library of gene product expression patterns known to be indicative of the presence or absence of a pre-cancerous epithelial cell, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data may be carried out at the remote site to provide for detection of a pre-cancerous epithelial cell, staging and/or grading of a carcinoma, or monitoring the progression of a pre-cancerous epithelial cell or a carcinoma. The computer-readable storage medium can also be provided in combination with one or more reagents for carrying out one or more of the activity assays (e.g., control compounds, cells, probes, arrays, or other activity assay test kit components).

Kits and Systems

Also provided by the subject invention are kits for practicing the subject methods, as described above, including detection of a cancerous or pre-cancerous epithelial cell, differential diagnosis malignant versus benign cancer, or monitoring the progression of a cancer. The subject kits include at least one or more of: a probe or primer for detection of a marker polynucleotide, a marker polypeptide, or an anti-marker polypeptide antibody. Other optional components of the kit include: restriction enzymes, control primers and plasmids; nucleic acid or polypeptide standards; buffers; reaction mixtures (e.g., for carrying out the assay); enzymes (e.g., DNA polymerase, reverse transcriptase, and the like); cells; and the like. The various components of the kit may be present in separate containers or certain compatible components may be precombined into a single container, as desired.

Kits for Detecting a Target Nucleic Acid

A subject kit comprises a pair of nucleic acids (primer pairs), one or more nucleic acid probes, or both, where the primer pairs and probes are suitable for use in a subject method, as described above. The nucleic acids will in some embodiments be present in a suitable storage medium, e.g., buffered solution, typically in a suitable container. The kit includes the primers and/or probes, and may further include a buffer; reagents (e.g., for polymerase chain reaction (e.g., deoxynucleotide triphosphates (dATP, dTTP, dCTP, and dGTP), a thermostable DNA polymerase, a buffer suitable for polymerase chain reaction, a solution containing $Mg^{2+}$ ions (e.g., $MgCl_2$), and other components well known to those skilled in the art for carrying out a polymerase chain reaction)). The kit may further include instructions for use of the kit, which instructions may be provided in a variety of forms, e.g., as printed information, on a compact disc, and the like. The kit may further include reagents necessary for extraction of DNA (or mRNA) from a biological sample (e.g., breast biopsy, axillary lymph node biopsy, etc.) from an individual. The kit may further include reagents necessary for reverse transcription of an mRNA, to make a cDNA copy of the mRNA.

The kit may further include positive and negative controls. An example of a positive control is a target nucleic acid that includes a region that will be amplified by primer pairs included in the kit. An example of a negative control is a nucleic acid (e.g., an albumin-encoding nucleic acid) that will not be amplified by nucleic acid primers included in the kit. The kits are useful in diagnostic applications, as described in detail above. A subject kit is useful to determine whether a target mRNA is present at higher or lower than normal levels in an epithelial cell.

A kit will in some embodiments provide a standard for normalization of a level of a target polynucleotide to a standard, e.g., a level of a glucose-6-phosphate dehydrogenase polynucleotide (e.g, a G6PDH mRNA or cDNA copy of a G6PDH mRNA).

Exemplary kits include at least one primer, at least two primers (a 5' and a 3' primer), or at least two primers and a probe, as described above. Also included in the subject kits may be buffers, dNTPs, and controls, (e.g., positive and negative control nucleic acids) for performing the subject methods. Primers in the subject kits may be detectably labeled or unlabeled).

Kits for Detecting a Target Polypeptide

A subject kit for detecting a target polypeptide comprises one or more anti-target polypeptide antibody reagents. For example, a subject kit will include antibody reagent(s) specific for a polypeptide that is included in an MEC signature (e.g., a variant MEC signature). In some embodiments, the antibody will comprise a detectable label. In some embodiments, the antibody will be bound to an insoluble support, e.g., a bead (e.g., a polystyrene bead, a magnetic bead, etc.); a plastic surface (e.g., the well of an ELISA plate); a membrane (e.g., a test strip; a polyvinylpyrrolidone membrane; a nitrocellulose membrane; etc.); and the like.

A subject kit can further include, if desired, one or more of various conventional components, such as, for example, containers with one or more buffers (e.g., wash buffers), detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized.

A kit will in some embodiments provide a standard for normalization of a level of a target polypeptide to a standard, e.g., a level of an actin polypeptide, a level of a GAPDH polypeptide, etc. A kit will in some embodiments further include negative controls, e.g., antibodies specific for a non-target polypeptide; and the like.

Kits may also include components for conducting western blots (e.g., pre-made gels, membranes, transfer systems, etc.); components for carrying out ELISAs (e.g., 96-well plates; plates containing wells in multiples of 96); components for conducting immunohistochemical analysis of a tissue sample; and the like.

Additional Components

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

Methods for Isolating vMEC

The present invention provides methods for isolating vMEC, e.g., a human vMEC (vHMEC), from a sample that comprises, in addition to vMEC, one or more other cell types, e.g., one or more of MEC, fibroblasts, and the like. The methods generally involve contacting the sample comprising a mixed cell population comprising a vMEC with a specific binding reagent that binds specifically to CD73, where the specific binding reagent binds CD73 present on the cell surface of a vMEC present in the sample, forming a complex between the specific binding reagent and the vMEC; and separating the complex from the sample. In some embodiments, the specific binding reagent is immobilized on an insoluble support.

In some embodiments, the specific binding reagent is an antibody specific for CD73. In these embodiments, the method generally involves contacting a sample comprising a mixed cell population comprising a vMEC with an anti-body specific for CD73, where the anti-CD73 antibody binds CD73 present on the cell sin-face of a vMEC present in the sample, forming a complex between the specific binding reagent and the vMEC; and separating the complex from the sample. In some embodiments, the anti-CD73 antibody is immobilized on an insoluble support.

Suitable insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (RIA), and the like); sheets, e.g., nylon, nitrocellulose, and the like; and chips, e.g., $SiO_2$ chips such as those used in microarrays.

The separation step is carried out in any of a varied of ways, depending in part on the nature of the insoluble support to which the anti-CD73 antibody is bound. In some embodiments, an anti-CD73 antibody is immobilized on the surface of a magnetic bead, and the separation step comprises applying a magnetic field to the sample comprising a complex formed between the anti-CD73 antibody and a vMEC. In other embodiments, an anti-CD73 antibody is immobilized on the surface of a plastic bead, and the separation step comprises low-speed centrifugation.

A subject method of isolating a vMEC from a mixed cell population comprising a vMEC can include one or more washing steps. For example, a washing step can be included after the formation of a complex between an anti-CD73 antibody and a vMEC, and before and/or after the separation step.

A subject method of isolating a vMEC from a mixed cell population yields a substantially pure vMEC cell population, e.g, a cell population comprising at least about 75%, at least about 80%, at least about 85%, at least about 90%, at least about 95%, at least about 98%, or at least about 99% vMEC. The vMEC are $CD73^r$, and are morphologically normal (e.g., do not exhibit a cancerous morphology).

The present invention further provides a CD73 binding reagent, e.g., a reagent that specifically binds CD73, immobilized on the surface of an insoluble support. A subject immobilized CD73 binding reagent is useful for isolating a vMEC from a mixed population of cells comprising a vMEC. In some embodiments, the CD73 binding reagent is an antibody that binds specifically to CD73.

Suitable insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (RIA), and the like); sheets, e.g., nylon, nitrocellulose, and the like; and chips, e.g., $SiO_2$ chips such as those used in microarrays.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Markers Associated with Pre-Cancerous ("Variant") Mammary Epithelial Cells Breast cancer affects one out of eight women in the U.S., and it is the second leading cause of cancer deaths in U.S. women. This work focused on understanding the early events of breast cancer development; specifically, events that can cause normal cells to transition to cancer cells. A model culture system of growing normal mammary epithelial cells (HMEC) was employed to identify molecular events leading to early transformation. When normal human mammary epithelial cells (HMEC) are grown in serum-free conditions in vitro, majority of the cells enter a growth arrest after 10 to 20 population doublings. However, a subpopulation of the cells, "variant" HMEC (vHMEC), continues to grow for an additional 30 to 50 population doublings when the bulk of the normal HMEC are arrested (FIG. 1). All vHMEC grown from women of various ages, parities, and genetic backgrounds share silencing of $p16^{INK4a}$ expression via promoter-hypermethylation. $p16^{INK4a}$ is a key cyclin-dependent kinase (CDK) inhibitor that inhibits CDK4/6-cyclinD activity, and which activity is needed to phosphorylate RB thereby allowing cells to pass through the G1/S phase of the cell cycle. Loss of $p16^{INK4a}$ activity has been found in 31 percent of all human breast cancers and loss of $p16^{INK4a}$ confers many characteristics associated with malignancy in vHMEC. $p16^{INK4a}$ loss in vHMEC is sufficient to induce centrosome dysfunction leading to genomic abnormalities and it also results in hypermethylation of HOXA9 transcriptional regulatory region and silencing of HOXA9 expression which may be preventing vHMEC from undergoing normal differentiation. Moreover, vHMEC contain a subpopulation of cells that express high levels of cyclooxgenase-2 (COX-2). The presence of COX-2 provides several "hallmarks" of cancers to vHMEC, such as resistance to apoptosis, increase chemo-attraction, motility, and invasion that may lead to initiation of angiogenesis. COX-2 overexpression has been shown to be sufficient to induce mammary tumors in mice. Cells with silenced p16INK4A via promoter hypermethylation exist in normal mammary tissue and that COX-2 overexpressing cells overlap in areas of tissues containing $p16^{INK4a}$-silenced cells.

It was hypothesized that vHMEC exist in normal mammary tissue and that these cells are likely candidates to be breast cancer precursors in vivo. To test this hypothesis, expression micro-array analysis comparing vHMEC vs. HMEC was performed. From the micro-array analysis, 26 potential cell surface markers were screened that may distinguish vHMEC from normal HMEC via fluorescent activated cell sorting (FACS). Markers were identified that facilitate the prospective isolation of a subpopulation of cells from normal mammary reduction tissues having extended growth characteristics which phenocopies cultured vHMEC.

FIG. 2. Marker expression on vHMEC and HMEC A) FACS analysis profiles of CD73, CD90, CD138, and Notch receptor-3 expression on vHMEC (blue) and HMEC (green) is shown. Cultured vHMEC and HMEC from mammary reductions were trypsinized to single cells incubated with anti-CD73-PE, -CD90-APC, CD138-FITC, and -notch receptor-3-FITC antibodies and analyzed by FACS. Immunocytochemistry of vHMEC and HMEC with anti-CD73 and anti-CD90 antibodies. Cells were grown on coverslips, fixed and stained with anti-CD73 and -CD90 antibodies followed by anti-mouse-FITC secondary antibodies and fluorescent signal was visualized by confocal microscopy. Cell nuclei were stained with Hoechst dye (blue) and CD73 and CD90 expression shown in green. Cell distribution of vHMEC (blue) and HMEC (green) co-stained with anti-CD73 and -CD90 antibodies. Cultured vHMEC and HMEC from mammary reductions were trypsinized to single cells, incubated with anti-CD73-PE and -CD90-APC antibodies and analyzed by FACS.

Figure 3:
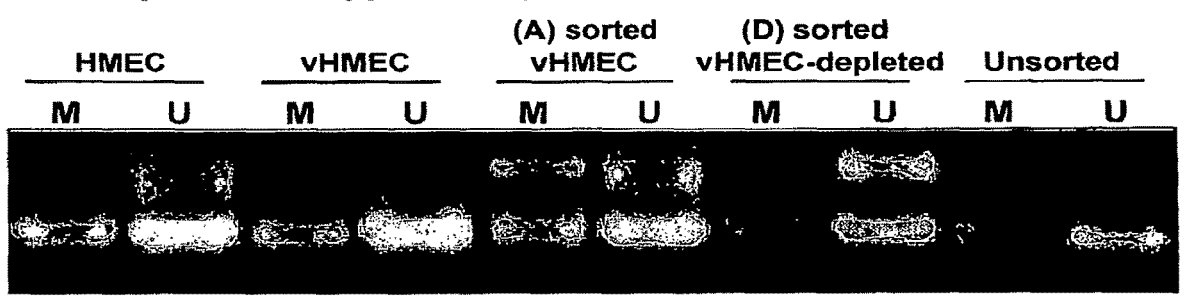
FIG. 3 depicts $p16^{INKK4a}$ promoter methylation status in HMEC and vHMEC cells.

FIG. 3. $p16^{INK4a}$ promoter methylation specific PCR (p16 MSP) indicated that cells in the CD73$^+$CD90$^-$ (vHMEC) population exhibited $p16^{INK4a}$ promoter hypermethylation, whereas $p16^{INK4a}$ promoter methylation was not detected in the CD73$^-$CD90$^+$ (vHMEC-depleted) or unsorted population. Cells that were sorted as indicated previously were cultured for 10 to 22 days, trypsinized, and frozen as pellets. Genomic DNA was extracted from cells, bisulfate treated, and subjected to p16 MSP. M represents a PCR reaction using p16-promoter-methylation specific PCR primers, and U represents a PCR reaction using unmethylated promoter PCR primers.

Figure 4:
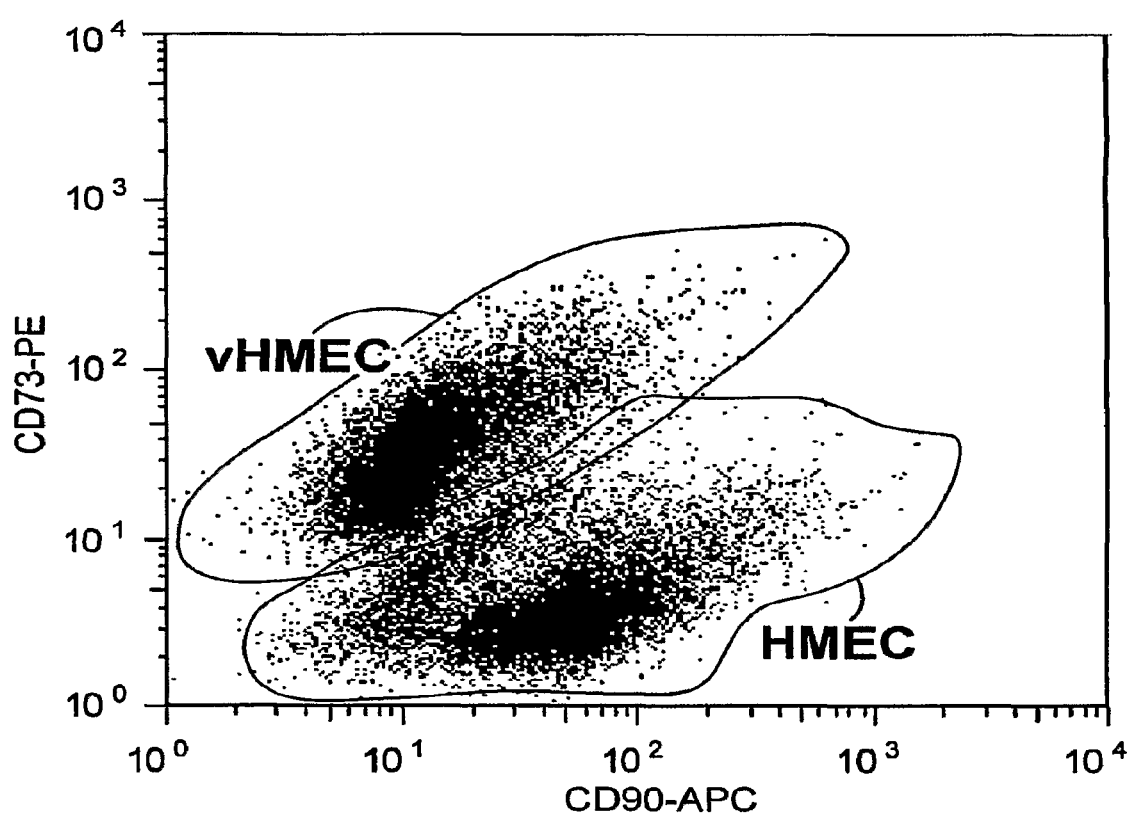
FIG. 4 depicts isolation of $CD73^+CD90^-$ vHMEC from disease-free mammary reduction tissue.

FIG. 4. Isolation of vHMEC from disease-free mammary reduction tissues: Mammary reduction tissues were digested to single cells and cells were incubated with anti-CD73-PE and -CD90-APC antibodies and subjected to FACS. Scatter plot representing total cell population and the gates used to isolate the designated subpopulations are shown. Cells were first gated for small cells based on forward and side scatter, and small cells were further separated by designated gates as shown. Percentage of cells sorted from each population is as indicated. Cells exhibited extended growth resided in CD73$^+$CD90$^-$ (vHMEC), whereas CD73$^-$CD90$^+$ population (vHMEC-depleted) entered a proliferation plateau within a short period of time.

Figure 5:
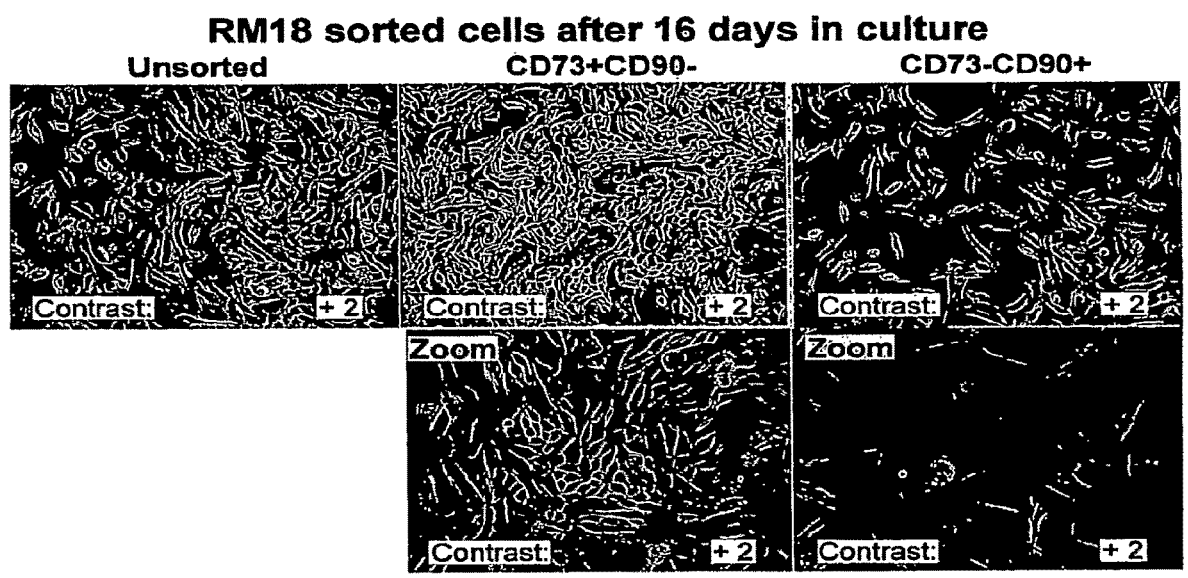
FIG. 5 depicts unsorted HMEC, $CD73^+CD90^-$ vHMEC, and $CD73^+ CD90^+$ HMEC from mammary-reduction tissue, cultured in vitro.

FIG. 5. Cells that were sorted based on the gates as shown in FIG. 4 were grown in culture, and growth curves of the sorted cells are shown. Total population doublings were determined after every passage of the cells. Phase contrast pictures of sorted CD73$^+$CD90$^-$ and CD73$^-$CD90$^+$ cells are shown. After 16 days of culturing CD73$^+$CD90$^+$ cells remained small shiny and continued to grow, whereas CD73$^-$CD90$^+$ cells were large, flat, vacuolated, and appeared senescent.

Figure 6:
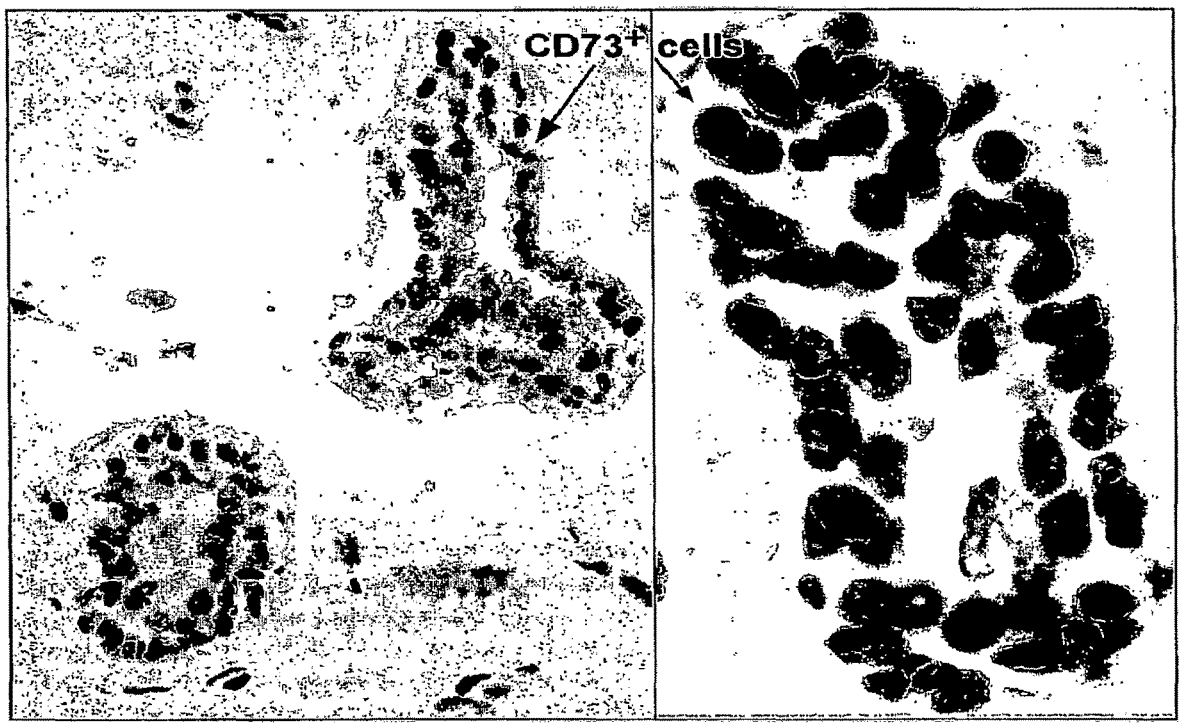
FIG. 6 depicts paraffin-embedded section of normal mammary tissue stained with anti-CD73 antibody.

FIG. 6. CD73 positive cells are predominantly located at the basal region. Paraffin-embedded sections of normal mammary tissue were stained with anti-CD73 antibody. Cells expressing CD73 are brown, whereas CD73 negative cells are light blue. Arrows indicate sample areas that contain CD73 positive cells. The right panel is a magnified area of the same tissue section as the left panel.

The data indicate that: 1) variant HMEC (vHMEC) can be distinguished by markers CD73$^{high}$, CD138$^{high}$, Notch Receptor-3$^{high}$, and CD90$^{low}$; 2) CD73$^+$CD90$^-$ cell population isolated from normal mammary reduction tissues have vHMEC growth characteristics, whereas CD73$^-$CD90$^+$ population is devoid of vHMEC; and 3) normal HMEC can acquire vHMEC growth characteristics by reducing p16 expression.

Example 2: Abrogated Stress Response Distinguishes Basal-Like Tumors and DCIS with Worse Prognosis Material and Methods Cells and cell culture. Human mammary epithelial cells (HMEC) and variant HMEC (vHMEC) were isolated from reduction mammoplasties (RM) of multiple individuals RM13, RM 15, RM16, RM18, RM21. Cells were propagated in modified MCBC 170 media (MEGM, BioWhittaker) as previously described ((Hammond, Ham et al. 1984; Romanov, Kozakiewicz et al. 2001)). All experiments were conducted with exponentially growing HMEC between population doublings 7 to 10, and exponentially growing mid-passage vHMEC between population doublings 20 to 34. Non-tumorigenic immortalized 184A1 breast cells were a kind gift from M. Stampfer (Lawrence Berkeley National Laboratories). Breast cancer cell lines T47D, SKBr3, BT549 and MDA-MB-231 were obtained from the ATCC.

DNA constructs. DNA constructs used in this study are as follows: pMSCV, pMSCV-shp16 (G. Hannon and S. Lowe, Cold Spring Harbor Laboratories); pLXSN, pLXSN-HPV 16 E7 (D. Galloway, Fred Hutchinson Cancer Center); pMKO, pMKO-shRb (W. Hahn, Harvard Medical School and Dana-Farber Cancer Institute), pBabe; pBabe-cyclinD1 (O. Tetsu, UCSF Cancer Center), pBabe, pBabe-hTert (K. Collins, UC-Berkeley); LXSP and LXSP-COX-2 (D. Dixon, Vanderbilt University Medical Center). All constructs were packaged in Phoenix A cells for viral propagation. To generate stable cell lines we exposed HMEC, vHMEC or breast cell lines to viral supernatant containing 8 µg/ml Polybrene (Sigma). Cells containing stable DNA integration were selected in medium containing 4 µg/ml puromycin (pMSCV, pMKO, and LXSP constructs), 50 µg/ml G418 (LXSN constructs) or 20 µg/nil hygromycin (pBabe). Where indicated, cell lines were imaged using a standard phase contrast microscopy.

Western Blot. Total protein (15-20 µg) lysates were electrophoretically separated by SDS-PAGE and transferred onto polyvinylidene difluoride (PVDF) membranes according to standard procedures. Antisera against COX-2 (160107; Cayman Chemical, MI), Rb (554136, BD Pharmingen), p16 (16P07 Neomarkers), E2F1 (sc-251 Santa Cruz), cyclinD1 (2926, Cell Signaling), p53 (se-126, Santa Cruz), p21 (SC-6246 Santa Cruz) were used according to manufacturers protocols.

Tumor samples. The primary gene expression analyses were performed on a cohort of 130 primary breast cancers from UC San Francisco and California Pacific Medical Center. Details of this cohort have been previously described. (Chin, DeVries et al. 2006) Raw microarray data and additional sample information is available (e.g_., available on the Internet at http://followed by cancer.lbl.gov/breastcancer/data.php). Paraffin-embedded tumor samples corresponding to 61 of the 130 cases were obtained with Institutional Review Board approval and analyzed by immunohistochemistry.

Gene expression profiling analyses The 130 UCSF/CPMC CEL files were background adjusted and normalized using RMA Express (available on the Internet at http:// followed by rmaexpress.bmbolstad.com/). Nearest centroid determination was performed using BRB Arraytools (available on the Internet at http://followed by linus.nci.nih.gov-fBRB-ArrayTools.html). Hierarchical clustering analyses were performed using Cluster 3.0 (available on the Internet at http://followed by bonsai.ims.u-tokyo.ac jp/-mdehoon/sofware/cluster/software.htm) on median-centered log expression values using Pearson correlation and centroid linkage. Clustered data was visualized using Java Treeview (on the Internet at http://followed by jtreereview.sourceforge.net/).

Derivation of molecular subtypes The recently defined 1300-gene "Intrinsic/UNC" gene set, derived from Agilent Human oligonucleotide platform data was cross-referenced to Affymetrix U133A to derive an intrinsic set for these studies. A subset of 1090 genes from the intrinsic/UNC genes represented on the U133A platform were additionally filtered for top 20% of variability within the 130 tumor set. This analysis resulted in 589 unique genes that are intrinsically variable and available for this analysis. Hierarchical clustering utilizing this set of 589 genes is shown in Table 7, below.

Molecular subtype classification was also determined through a nearest centroid based classifier. Hu et. al. derived a subset of 306 intrinsic genes that are conserved across microarray platforms. 297 of these genes are represented on the U133A platform. Based upon the 297-subset of training data available on the Internet (at http://followed by genome.unc.edu/pubsup/breasttumor) a nearest centroid class prediction analysis was performed on the 130 tumor samples with leave-one-out cross validation and probability calculated using the Bayesian Analog of Compound Covariate Predictor.

Pre-malignant samples. We analyzed a series of archival paraffin-embedded normal breast tissue specimens from reduction mammoplasties (n=47), tissue containing atypical ductal hyperplasia (n=33) and ductal carcinoma in situ (n=70). The DCIS samples comprise a subset of a large population-based cohort study among women in the San Francisco Bay Area diagnosed with DCIS and treated by lumpectomy alone between 1983 and 1996. *This patient population was followed for an average of* 12.4 years. All tissue was acquired with Institutional Review Board approval from the surgical pathology laboratory of the University of California, San Francisco and California Pacific Medical Center. Patients were identified through anonymous reference numbers in accordance with federal guidelines.

Tissue Preparation and Immunohistochemistry. Five-micron sections cut from formalin-fixed paraffin embedded tissue blocks were deparaffinized and rehydrated following standard protocol. After incubation with hydrogen peroxide, slides were microwaved in 1 mM EDTA, pH8, for antigen retrieval. Nonspecific protein binding was blocked with horse serum (Vectstain Elite ABC kit, Vector Labs). Sections were incubated with antisera against COX-2 (Dako M3617, 1/200), p16 (Neomarkers MS218, 1/150), Ki67 (Dako M7250, 1/80) overnight at 4° C. Antigen-antibody complexes were labelled using the Vectastain Elite ABC and following standard protocol (Vector Laboratories, CA) and visualised using 2.5% 3-amino-9-ethyl-carbazole in 50 mM acetate buffer pH5, with 0.05% hydrogen peroxide. Sections were counterstained in Mayers hematoxylin mounted in Crystal Mount (BMM02, American Mastertech). Once dry the sections were permanently mounted with a glass coverslip using cleannount (MMCLE1, American Mastertech).

Evaluation of immunohistochemistry staining. All staining was evaluated by light microscopy after examination of the entire slide and without knowledge of the patients' clinical information. Estimation of COX-2 protein expression was determined by COX-2 staining intensity on a 0, 1, 2, 3 scale (0—no staining, 1—weak; 2—moderate; 3—strong staining). p16 immunostaining was also scored on a 0, 1, 2, 3 scale based on the extent of immunopositive cells (0—no staining; 1→25% nuclear and/or cytoplasmic staining; 2-26-80% nuclear and/or cytoplasmic staining; 3→80% nuclear and/or cytoplasmic staining). Where indicated for both COX-2 and p16, high immunostaining reflects specimens that have a score of ≥2. Ki67 immunostaining was determined by manually counting immunopositive nuclei among a minimum of 1000 total nuclei in an average of three fields of view. Where indicated high Ki67 immunopositivity reflects specimens that contain a minimum of 10% of nuclei positive for Ki67.

Statistical analysis. Chi-square tests were used to test for associations between p16, COX-2, Ki67, nuclear grade and combinations therein with subsequent tumor development among women with DCIS. JMP-In statistical package (SAS Institute) was used for all analyses.

A Cox Proportional Hazards Model stratified by year of diagnosis was used to study the ability of four markers (grade and expression of Cox2, p16 and Ki67) to predict recurrence during follow-up. Controls were matched to cases by year of diagnosis. There were too few cases and controls for several of the years of diagnosis, so years were grouped as shown in Table 1 for the stratified analyses. First we analyzed that biomarkers separately and then in combinations of two factors. There were too few cases to warrant finer breakdowns of combinations of factors. Results are expressed as Hazard Ratios, which take time to recurrence, for cases, and follow-up time for controls into account.

TABLE 1

Years of recurrent diagnosis were grouped to stratify analysis

| year of dx | non-recur | recur | group |
|---|---|---|---|
| 1983 |  | 1 | 1 |
| 1984 | 3 | 1 | 1 |
| 1985 | 6 | 1 | 1 |
| 1986 | 3 | 2 | 2 |
| 1987 | 5 | 4 | 2 |
| 1988 | 3 | 5 | 3 |
| 1989 | 4 | 3 | 3 |
| 1990 | 10 | 5 | 4 |
| 1991 | 3 | 8 | 5 |
| 1992 | 2 | 1 | 6 |
| 1993 | 1 | 3 | 6 |
| 1994 | 1 | 1 | 6 |
| 1995 | 1 |  | 6 |
| 1996 | 3 | 2 | 6 |

Results

Determination of Risk for Subsequent Tumor Events in Women Diagnosed with DCIS and Treated with Lumpectomy Alone.

Our goal has been to evaluate potential predictive characteristics and their association with outcome in a population-based cohort of women in the San Francisco Bay Area diagnosed with DCIS between 1983 and 1996 and treated by lumpectomy alone. Similar to rates reported by others (Fisher et alSemOncol 2001; Cornfield et al. 2004 Cancer; Bijker et al 2006.JCO), ~225% of these women exhibited a subsequent tumor event within 10 years after surgical lumpectomy without additional therapy. In this study, a subsequent tumor event (also termed disease recurrence) was defined as a subsequent DCIS lesion or invasive cancer lesion diagnosed in the ipsilateral breast at least 6 months following the initial diagnosis of DCIS. In our previous study, we found 3 characteristics of DCIS lesions that were each associated with a higher risk for subsequent tumor development (Kerlikowske et al, 2003). These DCIS lesions were (1) detected in younger women (<50 years of age) (2) detected by palpation or (3) exhibited positive surgical margins. None of these characteristics provided a positive predictive value of more than 60%.

In the present study we used a subset of this population-based cohort (38 controls and 32 cases), followed for an average 12.4 years, to evaluate novel pathways that identify women that have an increased risk of developing subsequent tumor events (both DCIS and invasive cancer). These samples are a representative subset of the larger DCIS cohort previously described (Kerlikowske et al, 2003). In this study, we sought to understand the biological features that characterize DCIS lesions that portend a better or worse prognosis and improve the predictive power of defined biomarkers.

Histologic markers, such as nuclear grade, were the first to be examined in this cohort. Similar to our previous findings and that of others (Silverstein et al. 1995 Lancet; Barnes et al, 2000JP; Bijker et al, 2001 BrjC; Kerlikowske et al. 2003; Millis et al BJC2004), DCIS of high nuclear grade significantly increases the risk of developing a subsequent tumor event and inversely correlates with recurrence-free survival (HR 5.6, 95% CI 1.2 to 25.5, P=0.025 for high grade DCIS. However, although nuclear grade statistically stratifies a subpopulation of women with increased risk for a subsequent tumor event, a substantial fraction of women with high nuclear grade DCIS (36%, 9/25) do not develop subsequent disease. Likewise, 25% of women with low grade DCIS (3/12) experience subsequent disease. In other words, high nuclear grade has a positive predictive value of 64% and low nuclear grade has a negative predictive value of 75%.

To date, few molecular markers have been found that adequately predict which of the women initially diagnosed with DCIS have an increased risk of developing a subsequent tumor event. One of the first molecular markers that were considered in this study for risk stratification is a marker for proliferative index, Ki67. The level of Ki67 immunostaining was determined by manually counting immunopositive nuclei in a minimum of 1000 nuclei in an average of three fields of view. High Ki67 immunopositivity reflects specimens that contain a minimum of 10% of nuclei positive for Ki67. Similar to previous findings (Ringberg et al 2001; Barnes et al 2005; ClinCancerRes; Wilson et al 2006 BrJCancer;) examining the role of Ki67 measured as a single variable in modifying risk, we find that high Ki67 significantly stratifies women that develop a subsequent tumor (DCIS and invasive combined; P=0.011; Table 2) and predicts a reduced recurrence-free survival (HR 3.3, 95% CI 1.4 to 8.0, P=007; FIG. 7C) as compared to those that do not. However, a high proliferative index has a positive predictive value of 65% and a low proliferative index (Ki67 in less than 10% of nuclei) has a negative predictive value of 65%.

TABLE 2

| Marker | n | Control | Case | P-value |
|---|---|---|---|---|
| p16 | 70 | 50% (9/18) | 50% (9/18) | 0.672 |
| High |  | 56% (29/52) | 46% (23/52) |  |
| Low |  |  |  |  |
| p16 High | 18 | 0% (0/8) | 100% (8/8) | <0.001 |
| Ki67 High |  | 90% (9/10) | 10% (1/10) |  |
| K67 Low |  |  |  |  |
| p18 Low | 52 | 50% (9/18) | 50% (9/18) | 0.542 |
| Ki67 High |  | 59% (20/34) | 41% (14/34) |  |
| Ki67 Low |  |  |  |  |

TABLE 2-continued

| Marker | n | Control | Case | P-value |
|---|---|---|---|---|
| KI67 High | 70 | 35% (9/26) | 65% (17/26) | 0.011 |
| Low | | 66% (29/44) | 34% (15/44) | | p16 staining intensity with a score >2 is considered positive, Ki67 positive cases exhibited >10% nuclei immunopositivity. P-values were determined using Pearson Chi-quare test.

Deregulation of p16/Rb Increases the Risk of Subsequent Tumor Events Among Women Diagnosed with DCIS.

A well-recognized barrier to carcinogenesis is the induction of a senescent cellular response. Activated p16 signalling is a hallmark of the senescent cellular response pathway that induces a growth arrest in response to various cellular stressors such as genotoxic, oxidative, oncogenic or metabolic stress (see Mooi &c Peeper, 2006; Schmitt, 2003; Collado & Serrano, 2005; Campisi, 2005). This response is believed to be a crucial mechanism for controlling unchecked proliferation by limiting the propagation of damaged cells. One would predict that DCIS lesions expressing markers that are activated during a senescent cellular response, such as increased p16 expression, would be associated with fewer subsequent tumor events.

To determine if expression of this tumor suppressor pathway in DCIS lesions provides mechanistic insight about subsequent tumor events, we stained 70 samples of DCIS for p16 expression by immunohistochemistry, Immunostaining was scored on a 0, 1, 2, 3 scale where a score of 0 or 1 was considered low staining and a score of 2 or 3 was considered high. We find 26% (18/70) of DCIS lesions show high p16 staining (FIG. 7A, Table 3). This p16 immunopositivity is not associated with any clinicopathological variables such as nuclear grade or hormone receptor status (Table 3). Cases positive for p16 staining displayed moderate to intense p16 staining in the epithelium with varying degrees of lobular heterogeneity. At one extreme, a minority of cases, 28% (5/18) exhibited intense p16 staining in virtually all epithelial cells. The remaining p16 positive cases (13/18) exhibited heterogeneous immunopositivity in 26% to 80% of epithelial cells. The surrounding stromal compartment in a fraction of cases (10%) also exhibited p16 staining, primarily confined to fibroblasts surrounding cystic ducts. We would predict that high p16 expression induces a cellular growth arrest, and thus DCIS lesions overexpressing p16 would represent lesions that do not develop a subsequent recurrent disease. This prediction was not substantiated. We find that high p16 expression does not significantly stratify women at increased risk for developing a subsequent tumor event (DCIS and invasive cancer combined; FIG. 7A, Table 3). Furthermore, high p16 expression demonstrated no Paradoxically, overexpression of p16 can represent two different biological processes; a response to cellular stress (Mooi & Peeper, 2006; Schmitt, 2003; Collado & Serrano, 2005; Campisi, 2005)) or abrogation of functional Rb signalling (Serrano et al 1993; Nature; Bates S et al 1994 Oncogene; Parry et al 1995 EMBO;). Interestingly, inactivation of key Rb members leads to the upregulation of p16 due to unobstructed negative feedback regulation. The presence of proliferation can distinguish between these two situations. A cell that has maintained functional p16/Rb signalling will experience stress-induced overexpression of p16 that will cause a proliferative arrest characteristic of cellular senescence. On the other hand, a cell that has compromised the pRb pathway will experience a regulatory-induced over expression of p16 and can disregard the many stress signals that induce senescence and cellular arrest thereby allowing unimpeded proliferation and bypass of senescence.

Since high p16 expression can reflect two opposing phenotypes that can be distinguished by proliferation, we stained serial sections for Ki67. We found that 37% (26/70) and 63% (44/70) of the lesions within this cohort express high and low Ki67, respectively. Almost half (8/18) of DCIS lesions exhibiting high p16 levels also show high Ki67 index labelling (Table 2). We determined if this phenotype, representing deregulated p16/Rb signaling, identifies DCIS with worse prognosis. Our analysis demonstrated that all women with DCIS that show high p16 and high Ki67 develop a subsequent tumor (Table 2) and thus Ki67 significantly stratifies high p16 expressing lesions in women who develop a subsequent breast cancer (Wilcox on rank test; P=0.001, FIG. 7B) as compared to those that do not. Consequently, we calculate that women with DCIS that exhibit high p16 and high Ki67 have a substantially increased risk of developing a subsequent tumor (HR=21.8, 95% CI, 2.6 to 180; P=0.0001; FIG. 7B) as compared to women with lesions that show high p16 and low Ki67 labelling. In fact, DCIS lesions that show high p16 and low Ki67 index labelling identify benign lesions (90%, 9/10 are non-recurrent samples; Table 2). Therefore, proliferation is an obligate qualifier of p16 because the presence or absence of high Ki67 in lesions that show high p16 expression dictates their risk for developing subsequent disease (Wilcoxon rank test; P=0.426; FIG. 7D, Table 2). Moreover, women with DCIS that exhibit low p16 irrespective of Ki67 do not have a differential risk of developing recurrent disease (HR=1.1, 95% CI, 0.4 to 3.4; P=0.85). The high Ki67/high p16 phenotype is weighed toward higher grade lesions, such that 75% (6/8) are high grade DCIS and the remaining 25% (2/8) are intermediate grade (Table 3). Strikingly, lesions expressing high Ki67/high p16 phenotype

TABLE 3

| | n | p16+ | COX-2+ | Ki67+ | p16+/Ki67+ | COX-2+/Ki67+ | p16+/COX-2+/Ki67+ |
|---|---|---|---|---|---|---|---|
| ALL DCIS | | 26% (18/70) | 56% (39/70) | 37% (26/70) | 11% (8/70) | 26% (18/70) | 9% (6/70) |
| Nuclear Grade | | | | | | | |
| Low | 12 | 25% (3/12) | 67% (8/12) | 0% (0/12) | 0% (0/12) | 0% (0/12) | 0% (0/12) |
| intermediate | 32 | 22% (7/32) | 34% (11/32) | 25% (8/32) | 6% (2/32) | 13% (4/32) | 6% (2/32) |
| High | 26 | 31% (8/26) | 77% (20/26)) | 69% (18/26) | 23% (6/26) | 54% (14/26) | 15% (4/26) |
| P-value | | 0.742 | 0.004 | <0.001 | 0.046 | 0.003 | 0.013 | p16 and COX-2 staining intensity with a score >2 is considered positive, Ki67 positive cases exhibited >10% nuclei immunopositivity.
P-values were determined using Pearson Chi-quare test.

exhibit a positive predictive value of 100% and lesions expressing a low Ki67/high p16 phenotype have a negative predictive value of 90%.

FIG. 7A-D. p16 overexpression coupled with proliferation increases the risk of subsequent tumor events among women with DCIS. A) High p16 staining (immunopositivity score of ≥2) fails to stratify women with DCIS that develop subsequent disease (case versus control). Kaplan-Meier estimates of recurrence-free survival demonstrate that women with DCIS staining high or low for p16 immunopositivity develop subsequent disease at the same rate. Box plots and corresponding P-values were determined using Wilcoxon/Kruskal-Wallis rank of sums test. B) DCIS lesions high for p16 immunostaining and elevated Ki67 significantly stratify women that develop subsequent breast cancer from those that do not develop recurrent disease. Recurrence-free survival among women with DCIS that exhibit high p16 and high Ki67 (>10% of nuclei positive for Ki67) is significantly reduced compared to lesions that are high p16/low Ki67. C) Active proliferation measured by elevated Ki67 index labeling significantly stratifies women with DCIS that develop recurrent disease. DCIS with elevated Ki67 identifies women with decreased recurrence-free survival and increased risk for developing a subsequent tumor. Ki67 positivity was determined by counting a minimum of 1000 nuclei, with a score of >10% Ki67 nuclear staining considered positive. D) DCIS lesions with low p16 immunostaining irrespective of Ki67 labelling do not have a differential risk of developing subsequent disease. E) Immunohistochemistry staining for p16. Staining was scored on a 0, 1, 2, 3 scale with a score of ≥2 considered positive.

These data demonstrate that high p16 expression stratifies DCIS into two clinically significant populations. One population shows high p16 expression in presence of active proliferation, indicating deregulated p16/Rb signalling, and identifies DCIS lesions with worse prognosis. The second population shows high p16 in the absence of proliferation, indicating functional p16/Rb signaling, and identifies DCIS lesion with good prognosis. Interestingly, the tumor events that develop subsequent to DCIS with high p16 and high Ki67 are more often diagnosed as invasive breast cancer (62%). These data predict that the association of high p16 levels with a high Ki67 index will be well-represented in invasive tumors and that the association of high p16 levels with a low Ki67 index will be underrepresented in invasive tumors (since this phenotype is postulated to be a barrier to carcinogenesis). To test this prediction, we examined invasive tumors for the distribution of p16 overexpression and high Ki67 as a coupled phenotype.

High p16 mRNA Levels Defines the Basal-Like Subtype of Invasive Tumors

Previous reports have demonstrated that ipsilateral tumors that develop subsequent to DCIS share many histological and genetic alternations with the primary lesion (Millis et al. 2004 BrJCancer; Bijker et al 2001 BrJCancer;). For example, primary high grade DCIS is associated with the development of recurrent high grade DCIS or high grade invasive carcinoma. High concordance of genetic alterations demonstrated by loss of heterozygosity or comparative genomic hybridization between primary DCIS and subsequent recurrences also suggest a clonal relationship ((Lininger, Park et al. 1998; Waldman, DeVries et al. 2000). Given our finding that all DCIS lesions expressing high p16 and a high Ki67 index are followed by subsequent tumor formation and that these lesions are weighed toward invasive disease, one might predict that this phenotype would be reflected in invasive carcinomas.

To explore the subtype distribution of p16 overexpression, we examined gene expression profiles of 130 primary invasive breast tumors using Affymetrix U133A derived oligonucleotide microarray data generated at our institution (Chin et al, 2006). Recent studies have defined distinct molecular subtypes that display an intrinsic heterogeneity with prognostic significance for invasive tumors. Molecular subtypes were derived based upon a nearest centroid approach using molecular subtype training data as previously defined (see Materials and Methods) (Hu, Fan et al. 2006). Unsupervised clustering of these 130 samples with a set of intrinsically variable genes identifies luminal A, luminal B, normal-like, ERBB2 positive and basal-like clusters.

It was found that increased p16 mRNA preferentially characterizes the highly proliferative basal-like tumor subtype. The expression of the p16 gene is increased in the majority of basal-like tumors with 81% of basal-like samples showing p16 mRNA levels greater than 1.5-fold above the median. In addition, it was found that high p16 expression falls within a gene cluster comprised of many well-established basal-like genes, such as keratin 5, 17, SFRP5, and MMP-7. In keeping with the expected biology, the basal-like sample cluster that expresses high p16 mRNA is enriched for tumors with relatively low levels of Rb and cyclin D1 mRNA. Increased cyclin D1 levels were found to be most consistently elevated in the luminal 13 subtype.

To confirm the reproducibility of the observed differential subtype specificity of p16/Rb/Cyclin D1, we analyzed gene expression levels in four publicly available datasets from three different platforms. In each case, tumors with overexpression of p16 were consistently found to be classified as basal-like tumors. The low transcript levels of both Rb and cyclinD1 were also enriched in the basal-like tumor subtype.

These data demonstrate that transcriptional upregulation of p16 is a characteristic feature of highly proliferative basal-like tumors. Taken together with the observation that Rb transcript levels are among the lowest in this subgroup this suggests that loss of functional p16/Rb signalling may play a defining role in the biology of basal-like tumors. Overexpression of p16 does not simply reflect proliferating tumor cells since highly proliferating Luminal B tumors do not exhibit p16 levels above the median. Instead, the Luminal B subgroup of tumors commonly overexpresses cyclin D1. We demonstrate that deregulation of p16/Rb signalling, exemplified by overexpression of p16 in actively proliferating cells, define basal-like tumors and identify DCIS lesions with worse prognosis.

High COX-2 mRNA Levels are Enriched in Basal-Like Tumors

To further analyze p16 and explore gene expression interactions, hierarchical clustering was performed on top variable genes in 130 tumors. To select for genes with variable expression, we filtered those with >1.5 fold change from the median in at least 10% of samples and with a log intensity variation p<0.001, resulting in 6000 unique genes. To classify the 6000-gene clustering into molecular subtypes, tumors were grouped according to the sample clustering using the 589 intrinsic gene set. Members of the p16/Rb/cyclinD1 pathway did show variable expression, as well as many members of the E2F family. This analysis also demonstrates that among the variable genes, overexpression of COX-2 falls within the basal gene cluster along with the overexpression of p16. Our finding that COX-2 mRNA expression is enriched in basal-like tumors was exciting and of particular interest because we have previous shown that COX-2 is overexpressed in mammary epithelial cells with deregulated p16/Rb signalling (Crawford et al, Gauthier et al).

COX-2 mRNA levels were >1.5 fold above the median in 18% of the tumors analyzed with COX-2 overexpression distributed in two major subtype classes of tumors, basal-like and normal-like. We find that 50% (16/32) of basal-like and 33% (4/12) of normal-like tumors overexpress the COX-2 transcript. The basal and normal-like subtypes are known to share high levels of basal genes. Consistent with the subtype distribution of increased COX-2 mRNA, unsupervised hierarchical clustering demonstrates that COX-2 clusters with basal-like genes. In contrast, luminal tumors and ERBB2 positive tumors tend to express COX-2 mRNA levels below the median.

To determine if the prevalence of COX-2 overexpression in basal and normal-like tumors is unique to this tumor set, we analyzed four independent published microarray data sets across 3 different platforms. In each independent series, the highest levels of COX-2 mRNA were found within the basal-like tumors. Similar to the distribution in our original set of invasive tumors, the independent datasets also exhibited increased COX-2 in normal-like samples and lower levels of COX-2 gene expression in the majority of luminal and ERBB2 subtypes.

Concordance Between p16 or COX-2 mRNA and Protein Expression in Tumors

The low levels of COX-2 mRNA expression in ERBB2 positive tumors was perplexing because previous studies had demonstrated that, when assessed with immunohistochemistry, COX-2 protein levels were enriched in ERBB2 amplified tumors (Ristimaki et al, 2002 CancerRes 62:632; cho et al. 2005. Breast; Boland et al. 2004,BrJCancer 90:423;). Notably, microarray analyses of human tumor samples are typically average measurements of numerous cell types that often represent arbitrary units relative to a median value and fail to address post-transcriptional and post-translational regulation. Any one these reasons could underlie the discordance between mRNA levels and protein expression as determined by immunohistochemistry. To interpret the biological significance of microarray based measurements of mRNA expression in vivo, it is critical to relate thresholds of detection of mRNA by microarray to levels of protein expression as measured by immunohistochemistry. Further, it is important to determine the contributions of distinct cell types to overall levels of gene expression and the relative locations within different cellular compartments. To address these issues and to better understand p16 and COX-2 regulation in vivo, we performed p16 and COX-2 immunohistochemistry on paraffin-embedded tumor blocks representing 54 of the 130 tumors analyzed by microarray (FIG. 8A-D). These samples were chosen to represent all 5 molecular subtypes and span a continuum from the lowest to the highest levels of p16 and COX-2 microarray gene expression.

In samples of invasive tumors that showed elevated p16 via microarray analysis, immunopositivity was predominantly found in carcinoma cells. To a lesser extent, heterogeneous foci exhibiting p16 staining were detectable in the morphologically normal epithelial cells within or adjacent to the invasive tumor. Occasional p16 positivity was also observed in fibroblasts, predominantly those within desmoplastic appearing stroma. Cases with elevated COX-2 showed abundant staining within the carcinoma cells as well as in the morphologically normal epithelial. In rare cases, we found intense COX-2 staining in macrophages infiltrating and surrounding the invasive tumors. COX-2 staining was not observed in mesenchymal cells.

For p16, we observe a significant correlation (Wilcoxon rank of sums, P<0.0001) between mRNA levels by microarray and protein expression by IHC among all tumors analyzed (FIG. 8A). Basal tumors that express the highest levels of p16 mRNA showed intense pl 6 protein staining by immunohistochemistry (score 3+, FIG. 8B). We did observe a small fraction of ERBB2 positive tumors (2/8) that showed intense p16 staining despite having low levels of mRNA expression. This overall concordance between mRNA and protein suggests that p16 protein levels are primarily regulated at the transcriptional level and that p16 protein levels reflect the subtype specificity.

In contrast, evaluation of COX-2 demonstrated poor correlation (Wilcoxon rank of sums, P=0.161) between mRNA levels determined by microarray and protein levels determined by IHC among the tumors analyzed (FIG. 8C). In examining those cases with the highest levels of COX-2 mRNA, as defined by a greater than 2-fold increase over the median value, there is complete concordance as all showed high COX-2 immunoreactivity (FIG. 8D). Ten of the 54 invasive tumors show COX-2 mRNA levels greater than 2-fold above the median, eight of these cases are basal and the remaining two are classified as normal-like. In remaining cases (44/54), 10 of them exhibited relatively low mRNA detected by microarray analysis and were discordant with the elevated protein expression as measured by IHC (FIG. 8D). We found that 80% of the discordant samples were in the ErBB2 sub type.

The observation of high COX-2 protein expression by IHC in the absence of high COX-2 mRNA by microarray has a number of possible explanations including technical (i.e. inconsistent sampling of tumor tissue in microarray samples) and biological (i.e. post-transcriptional or post-translational regulation of COX-2). Inconsistent sampling of tumor tissue in microarray samples appears an unlikely explanation as all of the samples exhibiting low COX-2 mRNA still showed robust basal-like tumor microarray signatures (FIG. 8B,C). Furthermore, a number of the samples discordant for COX-2 showed concordant IHC and microarray elevations in p16. A biological explanation for the discrepant protein/IHC and mRNA/microarray levels for COX-2 is most likely given the particularly striking discordance in the ERBB2 positive tumors. The majority of ERRB2 tumors (75%, 6/8) showed high COX-2 immunoreactivity, yet none of these tumors showed elevated COX-2 mRNA (FIG. 8D). Many in vitro studies have demonstrated that COX-2 in addition to being regulated through de novo transcription is also often regulated by mRNA stabilization (Dixon, Kaplan et al. 2000; Ramsay, Ciznadija et al. 2003). While both these methods of regulation would be reflected in our gene expression analysis, post-translational regulation of COX-2 would not. These results suggest that ERBB2 positive invasive tumors target protein stabilization of COX-2 as a distinct and important mechanism of achieving COX-2 protein overeexpression.

FIG. 8A-D. Concordance between p16 or COX-2 mRNA and protein expression in tumors. A) There is good concordance between p16 mRNA expression determined by gene expression profiling and protein levels determined by immunohistochemistry. The correlation between the mRNA levels (expressed as log median centered) and high or low p16 immunostaining was determined using Wilcoxon rank of sums analysis. B) We determined the level of concordance among invasive tumor subtypes. The log median centered mRNA level of p16 for each sample analyzed is plotted as a continuous variable (red triangles) distributed by breast cancer subtype. The corresponding protein levels of p16 are plotted as immunohistochemistry scores 0,1, 2, or 3 (black squares). C) There is poor concordance between COX-2 mRNA and protein levels. The correlation between the mRNA levels (expressed as log median centered) and high or low COX-2 immunostaining was determined using Wilcoxon rank of sums analysis. D) We analyzed the discordance of mRNA (red triangles) and protein (black squares) levels of COX-2 in invasive tumors within different molecular subtypes determined by hierarchical clustering. The log median centered mRNA level of COX-2 for each sample analyzed is plotted as a continuous variable (red triangles) distributed by breast cancer subtype. The corresponding protein levels of COX-2 are plotted as immunohistochemistry scores 0,1, 2, or 3 (black squares).

COX-2 Overexpression Coupled with Proliferation Increases the Risk of Subsequent Tumor Events Among Women with DCIS.

Our findings that COX-2 mRNA levels are enriched in basal-like tumors and that COX-2 protein levels are elevated in both basal and ERBB2 positive tumors, led us to determine if elevated COX-2 protein expression in DCIS also portends a worse prognosis. In the 70 cases previous analyzed for p16 and Ki67, we stained serial sections for COX-2 for evaluation by immunohistochemistry. We determined the level of COX-2 staining on a 0,1,2,3 scale of immunopositivity. Representative COX-2 staining is illustrated in FIG. 9C). We considered a score of 0 or 1 to represent low staining and a score of 2 or 3 to be high immunostaining. We find that 56% ($39/70$) of DCIS lesions show high COX-2 protein levels (Table 3). To determine if expression of COX-2 in DCIS is clinically significant, we determined if cases with high COX-2 staining stratifies risk for developing subsequent disease. We find that high COX-2 immunopositivity by itself does not stratify risk for subsequent tumor formation and, similar to p16 overexpression by itself, is equally distributed among women that develop subsequent DCIS or invasive cancer (case) and those that do not (control; HR=1.0, 95% CI, 0.5 to 2.2, P=0.99; Table 4; FIG. 9A).

TABLE 4

| Marker | n | Control | Case | P-value |
|---|---|---|---|---|
| COX-2 | 70 | 56% (22/39) | 44% (17/39) | 0.689 |
| High | | 52% (16/31) | 48% (15/31) | |
| Low | | | | |
| COX-2 High Ki67 High | 39 | 27% (5/18) | 72% (13/18) | <0.001 |
| | | 81% (17/21) | 19% (4/21) | |
| K67 Low | | | | |
| COX-2 Low Ki67 High | 31 | 50% (4/8) | 50% (4/8) | 0.916 |
| | | 52% (12/23) | 48% (11/23) | |
| KI67 Low | | | | |
| Ki67 | 70 | | 65% (17/26) | 0.011 |
| High | | 35% (9/26) | | |
| Low | | 66% (29/44) | 34% (15/44) | |

COX-2 staining intensity with a score >2 is considered positive, Ki67 positive cases exhibited >10% nuclei immunopositivity. P-values were determined using Pearson Chi-quare test.

Since COX-2 expression in invasive tumors is found in actively proliferating cells, we determined the fraction of DCIS expressing high COX-2 and high Ki67. Almost half ($18/39$) of DCIS lesions showing high COX-2 also exhibit high Ki67 and is weighed toward higher grade lesions (Table 3). We determined if this phenotype (high COX-2 coupled with high Ki67) identifies DCIS lesions with worse prognosis. Indeed, stratifying high and low COX-2 DCIS lesions by proliferation identifies women with differential risk for recurrent disease. FIG. 6B demonstrates a significantly higher fraction of women (13 of 18) with DCIS showing high COX-2 and high Ki67 develop a subsequent tumor (Wilcoxon rank test; P=0.0002). We calculate a significant increased risk of developing a subsequent breast cancer and decreased recurrence-free survival when the primary DCIS lesion exhibits high COX-2 and high Ki67 labelling as compared to lesions that show high COX-2 and low Ki67 (HR=4.72, 95% CI, 1.0 to 22.1, P=0.0004; FIG. 9B, Table 4). Similar to our findings for p16, proliferation is an obligate qualifier of COX-2 because high Ki67 does not stratify low COX-2 expressing lesions (Wilcoxon rank test; P=0.925). Correspondingly, we do not observe a differential risk for recurrent disease in women that exhibit low COX-2 expressing DCIS irrespective of Ki67 (HR=0.86, 95% CI, 0.2 to 3.3, P=0.79). In examining the lesions that develop subsequent to DCIS that are immunopositive for both COX-2 and Ki67, we find that 8 of the 13 cases recur as invasive breast cancer. These data suggest that COX-2 and Ki67 immunopositive cells may identify an aggressive cellular phenotype.

FIG. 9A-C. COX-2 overexpression coupled with proliferation increases the risk of subsequent tumor events among women with DCIS. A) COX-2 staining intensity (score 0, 1, 2, or 3) fails to stratify women with DCIS that have a differential risk of developing recurrent disease. Recurrence-free survival is not different in women with DCIS that exhibits high or low for COX-2 immunopositivity (score of ≥2 was considered high). Box plots and corresponding P-values were determined using Wilcoxon/Kruskal-Wallis rank of sums test. B) DCIS lesions high for COX-2 immunostaining and elevated Ki67 significantly stratify women that develop subsequent breast cancer from those that do not develop subsequent disease. Recurrence-free survival among women with DCIS that exhibit high COX-2/high Ki67 is significantly reduced compared to lesions that are high COX-2/Low Ki67. C) DCIS lesions with low COX-2 immunostaining irrespective of Ki67 labelling do not have a differential risk of developing recurrent disease. D) Immunohistochemistry staining for COX-2. Staining was scored on a 0, 1, 2, 3 scale with a score of ≥2 considered positive.

Predicting Invasive Tumor Formation Using Molecular Markers

Figure 10:
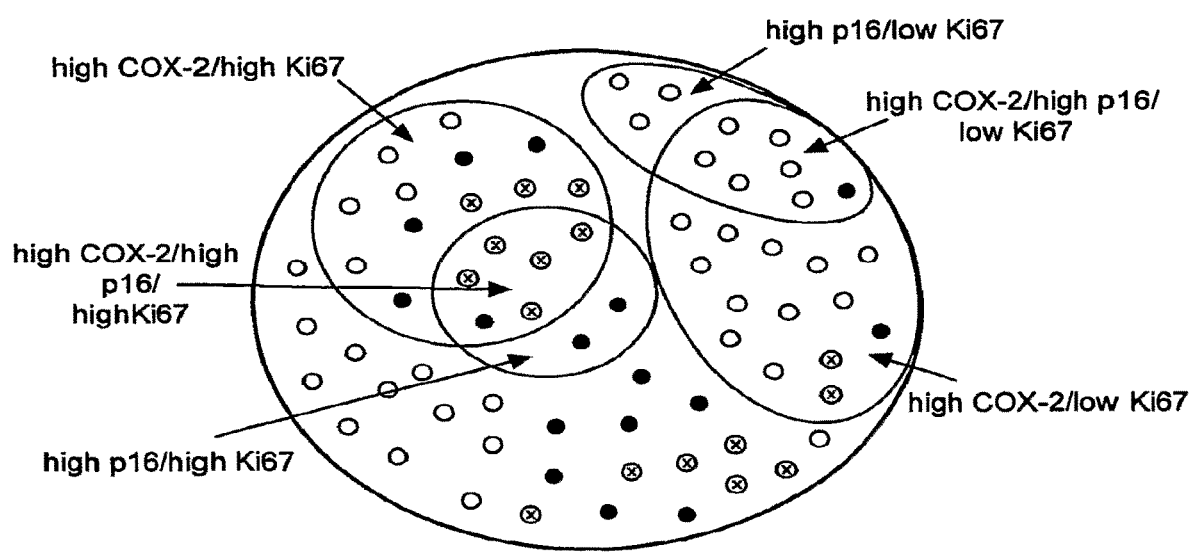
FIG. 10 is a diagram representing DCIS lesions expressing combinations of p16, COX-2 and Ki67.

These findings with COX-2 and Ki67 parallel our observations in examining the expression of p16 and Ki67. Given that 12% ($8/65$) of the DCIS lesions we examined from the UCSF cohort show high p16/high Ki67 and 25% ($16/65$) show high COX-2/high Ki67 (Table 3), we determined if one phenotype is enriched for the other. We find that 75% ($6/8$) of high 16/high Ki67 DCIS exhibits overexpression of COX-2, and 38% ($6/16$) of high COX-2/high Ki67 lesions show high p16 expression (FIG. 10). Strikingly, expression of all three markers, high p16, high COX-2, high Ki67, provides the first signature that is strong in predicting a subsequent invasive event over a non-invasive (DCIS) event. Since invasive lesions have the potential to invade and seed metastatic foci, this distinction is clinically relevant. Of the 6 DCIS lesion that overexpress all three markers, all develop a subsequent tumor event, 5 develop invasive breast cancer.

FIG. 10. Diagram representing DCIS lesions expressing combinations of p16, COX-2 and Ki67. High COX-2 and/or high p16 classifies two clinically different populations of cells in DCIS that can be stratified by proliferation. One population overexpresses COX-2 and/or p16 in the presence of proliferation and identifies women that develop subsequent DCIS (black circles) or invasive breast cancer (red circles). The second population overexpresses COX-2 and/or p16 in the absence of proliferation and identifies women that do not develop subsequent disease (open circles).

Similar to our observations that elevated p16 in the absence of proliferation identifies more benign lesions (Table 2), 81% (17/21) of women with high COX-2 and low Ki67 expressing lesions do not develop a subsequent tumor event (Table 4). Therefore, elevated levels of either p16 or COX-2 in the absence of proliferation suggest stress activation and identify a phenotype with more favourable prognosis. Equally intriguing, expression of high p16, high COX and low Ki67 marks a low risk of developing subsequent disease. We observe 7 DCIS lesions exhibiting high COX-2/high p16 and low Ki67, of which 6 do not develop a subsequent tumor event. The one sample that developed subsequent disease recurred as DCIS. These observations suggest high COX-2 and high p16 classifies two clinically different populations of cells in DCIS that can be stratified by proliferation. One population overexpresses COX-2 and/or p16 in the presence of proliferation and identifies lesions with poor prognosis. The second population overexpresses COX-2 and/or p16 absence of proliferation and identifies DCIS lesions with good prognosis (FIG. 10).

COX-2 Overexpression Causes Cell Cycle Arrest in Cells that Maintain Functional p16/Rb Signaling.

It is well appreciated that in vitro, cell cycle checkpoints are essential to preserve genomic stability. Overexpression of p16 in normal cells, induced by exogenous stressors or genetic manipulation, causes an irreversible cell cycle arrest and morphological changes characteristic of cellular senescence. It has been speculated that inactivation of this critical checkpoint in vivo would allow cells to propagate under unfavourable conditions that promote genomic instability and accelerate tumorigenesis. Our observations that abrogation of this checkpoint, reflected by high p16/high Ki67 expressing lesions in DCIS, portends a worse prognosis support this hypothesis.

These observations parallel our findings with COX-2 expression and elevated Ki67. We observe high COX-2 expressing DCIS lesions identify two distinct populations of cells, one that is quiescent and the other that is actively proliferating, that have different prognoses. These data prompted us to determine the cellular context that governs COX-2 and if it is associated with quiescence or proliferation. We investigated the S-phase fraction in a continuum of cell populations from normal to malignant engineered to constitutively overexpress COX-2 compared to vector control populations. 8-phase fraction was determined following a 4 h pulse of BrdU incorporation and flow cytometric analysis.

It was found that in normal cells, COX-2 inhibits cell proliferation while, in pre-malignant and malignant cells, overexpression of COX-2 subsists in the presence of ongoing proliferation. COX-2 expression was increased in normal human mammary epithelial cells (HMEC) generated from reduction mammoplasty tissue from 3 different individuals via expression of an exogenous COX-2 construct; it was found that sustained COX-2 overexpression significantly reduces the number of cycling cells (FIG. 11A). The diminished S-phase fraction of HMEC-COX-2 cells limits the proliferative capacity and reduces the lifespan of these cells in culture. These data parallel the finding when p16 was overexpressed in HMEC. In contrast, in non-tumorigenic cells that exhibit pre-malignant characteristics, both mortal (variant HMEC, vHMEC) and immortal (vHMEC-hTert and 184A1) as well as tumorigenic breast cancer cell lines (T47D, SKBr3, BT549 and MDA-MB-231), COX-2 overexpression neither induces nor diminishes proliferation (FIG. 11A). Functional p16/Rb signaling is one of the distinguishing features of normal cells compared to all other cells we examined. Therefore, it is hypothesized that COX-2 overexpression resulting in a cell cycle arrest is only observed in normal breast epithelial cells that retain functional p16/Rb signalling. All other cells that were examined have compromised p16/Rb signalling through diverse mechanisms including p16 hypermethylation (vHMEC, vHMEC-hTert, T47D), p16 deletion (MDA-MB-231), or Rb deletion (BT549). These analyses suggest cells with compromised p16/Rb signalling support COX-2 expression and its ensuing phenotypes in actively proliferating cells.

To extend this analysis, the differential response to COX-2 overexpression in HMEC versus a subpopulation of HMEC that have lost p16 expression through promoter hypermethylation (variant HMEC) was further explored. Constitutive expression of COX-2 in HMEC produced enlarged flattened cells that are growth arrested compared to vector control cells (FIG. 11B). In contrast, overexpression of COX-2 in cells lacking p16 (vHMEC) continued to proliferate without morphologic change (FIG. 11B). To characterize the molecular changes underlying the differential phenotypic response to COX-2 overexpression, cell lysates were probed for cell cycle regulatory proteins by immunoblotting. HMEC overexpressing COX-2 exhibited elevated protein levels of p16, p53 and p21 (FIG. 11C). This is in contrast to vHMEC where overexpression COX-2 did not alter the level of p53 or p21. Thus, COX-2 induces a cell-cycle arrest in p16 expressing cells while p16-silenced cells are refractive to COX-2-induced growth inhibition. This phenotype is also observed in cells that have abrogated all Rb family members. Targeted degradation of Rb, p107 and p130 (all three Rb family members) by HPV16-E7 in HMEC results in ongoing proliferation in the presence of COX-2 overexpression (FIG. 11B). Thus, COX-2 overexpression in cells with functional p16/Rb signalling induces a p16-dependent growth arrest, while cells with disrupted p16/Rb signalling continue to proliferate in the presence of COX-2 overexpression.

FIG. 11A-C. Overexpression of COX-2 in the absence or presence of proliferation is dependent on p16/Rb dysfunction. A) Cell populations with varying malignancy were retrovirally infected with a constitutive COX-2 expressing construct (COX-2) or an empty vector control (LXSP). Cells were pulsed for 4 h with BrdU and analyzed by flow cytometry following propidium iodide staining. The S-phase fraction of COX-2 expressing cells were compared to vector control cells and represented as fold increase of controls. B) Phase contrast micrographs of primary human mammary epithelial cells (HMEC), variant HMEC (vHMEC) lacking p16 expression and HMEC expressing HPV16-E7 retrovirally infected with a constitutive COX-2 expressing construct (COX-2) or an empty vector control (LXSP). C) We determined the molecular changes underlying the differential phenotypic response to COX-2 by probing cell lysates from COX-2 overexpressing and vector control HMEC and vHMEC for COX-2, p16, p53 and p21.

Deregulation of p16/Rb Signalling Causes COX-2 Overexpression.

Figure 12A:
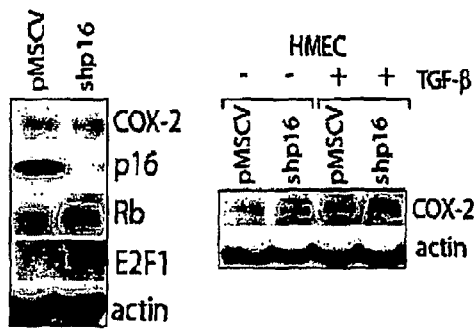
FIGS. 12A-E depict differential regulation of COX-2 by deregulation of distinct members of the p16/cyclin D1/Rb pathway.

The finding that the majority of high p16/high Ki67 DCIS lesions overexpress COX-2 suggests that deregulation of p16/Rb may drive COX-2 expression. To test this hypothesis, specific members of the p16/Rb pathway were genetically modulated, and the levels of COX-2 protein expression compared to HMEC that maintain p16 expression were determined. First, basal and induced COX-2 protein levels in HMEC lacking p16 activity were compared. Sequence specific silencing of p16 by retroviral infection of HMEC with a short hairpin RNA (shp16) downregulated p16 protein levels leading to the upregulation of both Rb and E2F1 compared to control HMEC infected with an empty pMSCV vector (FIG. 12A and Zhang et al. 2006). Basal levels of COX-2 expression did not change with the removal of p16 activity. However, exogenous induction of COX-2 by exposure to inducing stimuli (for example TGF-β) resulted in COX-2 upregulation in p16 silenced cells while vector control cells remain unresponsive. These results were observed in two independent reduction mammoplasties and three independent determinations after exposure to TGF-β. These findings demonstrate that while the basal levels of COX-2 protein remained unchanged with the removal of p16 activity, the genetic silencing of p16 sensitizes cells to exogenous COX-2 induction and demonstrates that a secondary event is necessary for COX-2 overexpression.

Figure 12B:
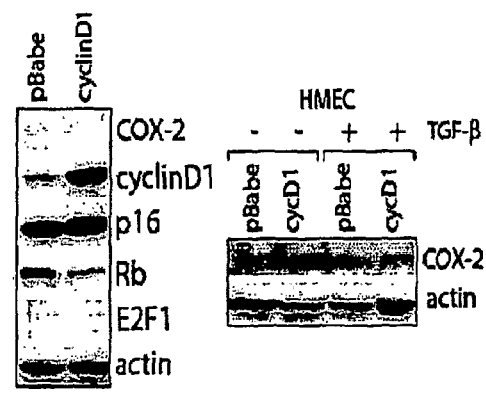
Figure 12C:
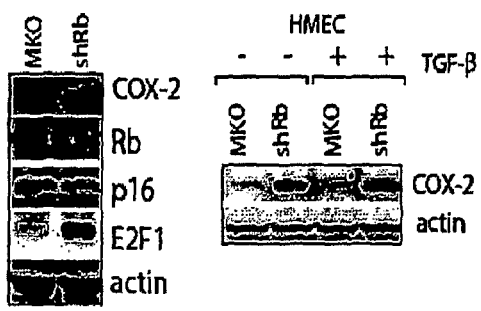
Figure 12D:
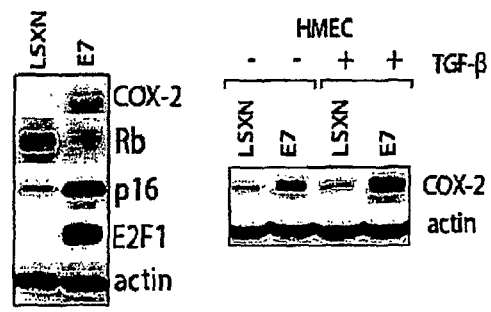
Figure 12E:
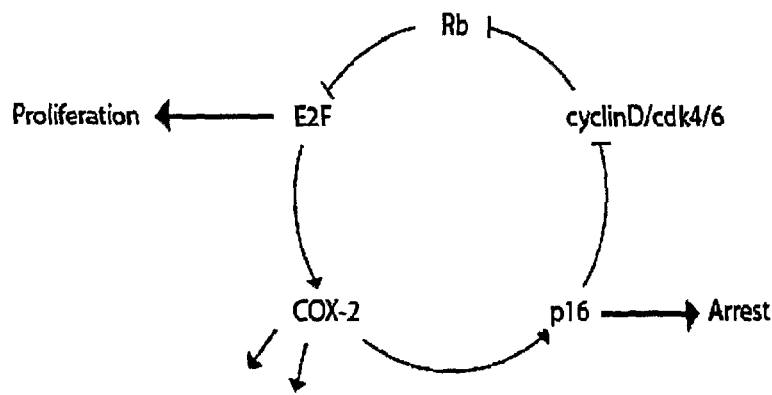

To extend this analysis, we determined how other alterations within this pathway, mutations common in cancer, affect COX-2 expression. We modulated the p16/Rb pathway by three additional methods, cyclin D1 overexpression, pRb downregulation, and expression of a viral oncoprotein, HPV 16-E7 and determined the effect on basal and exogenously-induced COX-2 protein levels. To determine if cyclin D1 induces and/or sensitizes cells to COX-2 induction, we measured COX-2 protein levels in HMEC engineered to stably express cyclin D1 under the regulation of an independent, constitutively active promoter. Cyclin D1 was introduced into cells generated from three different reduction mammoplasties and resulted in cyclin D1 protein overproduction similar in level to that measured in tumor cells. Overexpression of cyclin D1 alone did not cause hyperphosphorylation of Rb, and instead lead to a slight reduction in overall Rb protein levels (FIG. 12B). These results are consistent with previous findings (Lundberg et al, 1998) that overexpression of cyclin D1 is not sufficient for Rb inactivation. The absence of E2F1 upregulation following cyclin D1 overexpression supports our finding that Rb remains active. We demonstrate that overexpression of cyclin D1 did not induce basal COX-2 expression and failed to render cells sensitive to exogenous induction by TGF-β(FIG. 12B). These data suggest that cyclin D1 overexpression does not modulate Rb activity, does not alter basal levels of COX-2 expression or render cells sensitive to exogenous COX-2 induction. To determine if inactivation of Rb is sufficient for the upregulation of COX-2, we infected HMEC with a retrovirus containing a short hairpin RNA against Rb (shRb) and determined COX-2 protein levels in cells from two independent experiments. As anticipated, sequence specific silencing of Rb downregulated Rb protein levels and caused the upregulation of E2F1 compared to control HMEC infected with an empty pMKO vector (FIG. 12C). Viral transduction with shRb was integrated In these cells, both basal levels and exogenously induced levels of COX-2 protein were increased (FIG. 12C) supporting a central role for the loss of Rb in driving COX-2 overexpression. Similar to results obtained with Rb genetic silencing, expression of the human papilloma virus 16-E7 (HPV 16-E7) elevated both basal and induced levels of COX-2 protein (FIG. 12D). Stable expression of HPV16-E7 was performed in cells generated from three independent reduction mammoplasties. Mammary epithelial cells expressing HPV 16-E7 show downregulation of Rb and thus inactivation of Rb and consequently upregulation of E2F1 (FIG. 12D). HPV16-E7 is well characterized for its role as a transforming oncoprotein through targeted degradation of all three members of Rb family (Rb, p107 and p130) and driving E2F-dependent transactivation.

FIG. 12A-E. Deregulation of distinct members of the p16/cyclin D1/Rb pathway differentially regulate COX-2. A) To determine if p16 is necessary for the upregulation of COX-2, HMEC were retrovirally infected with a construct encoding a short hair-pin RNA against p16 (shp16) or an empty vector control construct (pMSCV). Cell lysates were probed by western blot for COX-2, p16, Rb and E2F1. To determine if genetic downregulation of p16 in HMEC are sensitive to the upregulate COX-2 in response to exogenous induction, cell lysates were probed for COX-2 by immunoblotting following 24 h exposure to 1 ng/ml TGF-β.B) To determine if cyclin D1 is necessary for COX-2 upregulation, HMEC were retrovirally infected with a constitutely expressing cyclin D1 construct (cycD1) or an empty vector control construct (pBabe). Cell lysates were probed by western blot for COX-2, cyclin D1, p16, Rb and E2F1. To determine if genetic upregulation of cyclin D1 in HMEC are sensitive to the upregulate COX-2 in response to exogenous induction, cell lysates were probed for COX-2 by immunoblotting following 24 h exposure to 1 ng/ml TGF-β. C) To determine if Rb is necessary for COX-2 upregulation, HMEC were retrovirally infected with a construct encoding a short hair-pin RNA against Rb (shRb) or an empty vector control construct (pMKO). Cell lysates were probed by western blot for COX-2, Rb, p16 and E2F1. To determine if genetic downregulation of Rb in HMEC are sensitive to the upregulate COX-2 in response to exogenous induction, cell lysates were probed for COX-2 by immunoblotting following 24 h exposure to 1 ng/ml TGF-β. D) To determine if Rb family members (Rb, p107 and p130) are necessary for the upregulation of COX-2, HMEC were retrovirally infected with HPV16-E7 or an empty vector control construct (pLSXN). Cell lysates were probed by western blot for COX-2, Rb, p16 and E2F1. To determine if genetic downregulation of all Rb family members in HMEC are sensitive to the upregulate COX-2 in response to exogenous induction, cell lysates were probed for COX-2 by immunoblotting following 24 h exposure to 1 ng/ml TGF-β. E) Diagram representing the connection between p16/Rb pathway and COX-2.

These data demonstrate that abrogation of p16/Rb signalling through genetic silencing of p16, Rb and Rb family members sensitizes cells to COX-2 upregulation. Thus, the propensity of COX-2 overexpression in DCIS lesions that exhibit high p16/high Ki67 may be a consequence of deregulation of the p16/Rb pathway.

p16 and COX-2 Overexpression can be Found in a Subset of Epithelial Cells in Normal Breast Tissue and Atypical Ductal Hyperplasias.

Figure 13:
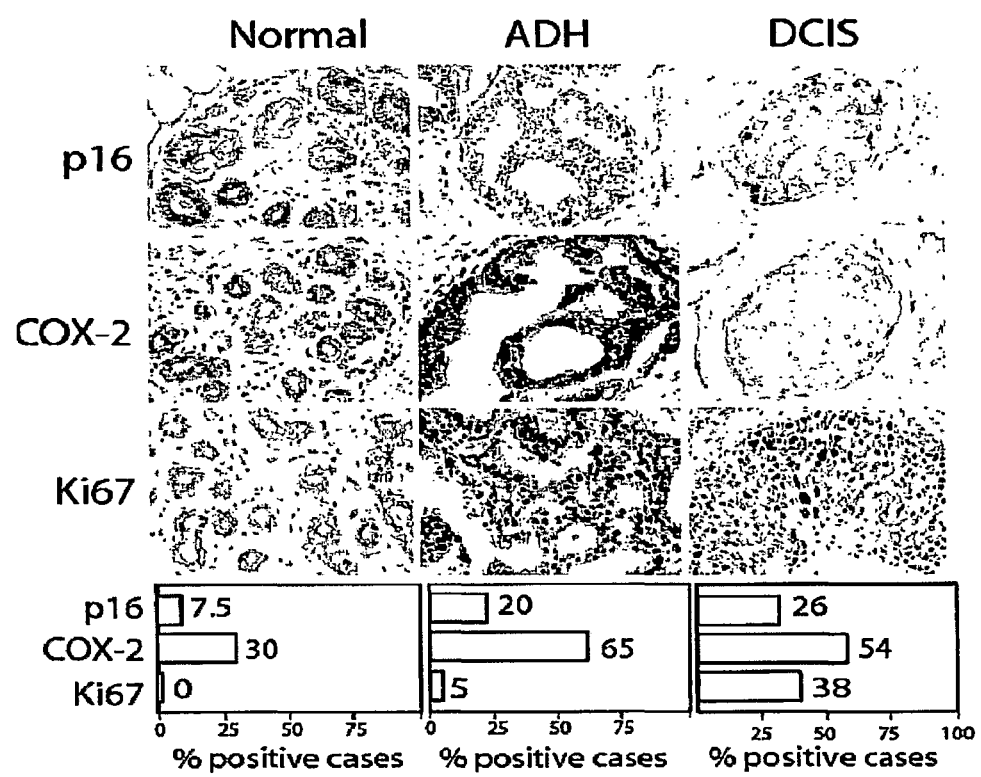
FIG. 13 depicts identification by p16 and COX-2 overexpression of a subset of epithelial cells in normal breast tissue and atypical ductal hyperplasias, for use in risk stratification.

We have described two cellular phenotypes that define a subset of invasive tumors and DCIS with worse prognosis. These findings prompted us to determine the prevalence of these phenotypes in normal breast tissue and in tissue biopsies diagnosed with atypical ductal hyperplasia (no DCIS present). We characterized p16 and COX-2 expression and proliferation index in normal breast biopsies (n=40) and atypical ductal hyperplasias (ADH; n=20). Representative p16 immunostaining in normal and ADH biopsies is shown in FIG. 13). We find that the majority of disease-free breast tissues exhibited low levels or were devoid of p16 expression while 7.5% of the cases displayed heterogeneous 16 staining in 25%-85% of the morphologically normal epithelium (Table 5). In examining a series of ADH lesions, we find 27% of cases showed heterogeneous p16 immunostaining, an increase as compared to disease-free tissue that did not reach statistical significance (Table 5; Pearson chi-square test P=0.394). Similar to our findings in DCIS, the surrounding stromal compartment in a fraction of cases (10%), both in normal tissue and tissue containing ADH also exhibited p16 staining in fibroblasts surrounding cystic ducts. For COX-2, we have previously demonstrated and illustrate here that approximately 20%-30% of tissue from disease-free women exhibit foci of cells with heterogeneous COX-2 staining in normal epithelium (FIG. 13; Crawford et al, 2004; Gauthier et al. 2005) and others have confirmed this observation (Boland et al. 2005).

FIGS. 13A and 13B. p16 and COX-2 overexpression identify a subset of epithelial cells in normal breast tissue and atypical ductal hyperplasias that may provide risk stratification. A) Representative of p16, COX-2 and Ki67 immunostaining in normal disease-free breast tissue, atypical ductal hyperplasia (ADH) and DCIS are illustrated. The bar graph demonstrates the percent positive cases for each biomarker. p16 and COX-2 staining intensity with a score ≥2 is considered positive. Ki67 immunostaining is considered positive in cases exhibiting more that 10% nuclei immunopositivity. B)To determine if p16 and/or COX-2 is correlated with proliferation, we evaluated p16 and COX-2 immunopositive staining (score of ≥2 was considered high) with the percent Ki67 nuclear positivity expressed as a continuous variable in normal, ADH and DCIS. Box plots and corresponding P-values were determined using Wilcoxon/Kruskal-Wallis rank of sums test.

In ADH lesions, we find 65% of lesions (13/20) stain positive for COX-2 (Table 5) a significant increase as compared to disease-free breast tissue, p=0.01). In examining the relationship between p16 and COX-2, we observe concomitant overexpression in 2.5% (1/40) of normal tissue devoid of disease (Table 6). In ADH and DCIS, we observe ~10% (2/20) and 19% (13/70) lesions overexpress both p16 and COX-2, respectively (Table 6).

it remains to be determined if elevated levels of coincident overexpression of p16 and COX-2 (2.5% in isolated normal lobules and 10% of ADH cases) may facilitate genomic instability and provide a selection pressure for clonal outgrowth. If these cells manifest the same tumorigenic proclivity as those that overexpress COX-2 and p16 in DCIS, we would predict that women from which these types of biopsies are obtained would exhibit subsequent disease.

As discussed above, the recently defined 1300-gene "Intrinsic/UNC" gene set, derived from Agilent Human oligonucleotide platform data was cross-referenced to Affymetrix U133A to derive a intrinsic set for these studies. A subset of 1090 genes from the intrinsic/UNC genes represented on the U133A platform were additionally filtered for top 20% of variability within the 130 tumor set. This analysis resulted in 589 unique genes that are intrinsically variable and available for this analysis. Hierarchical clustering utilizing this set of 589 genes is shown in FIG. 14. The genes listed in FIG. 14 are differentially expressed in vHMECs, and allow one to distinguish HMEC (e.g., normal, or non-pre-cancerous HMEC) from vHMEC.

Example 3: Extracellular Signaling and Intracellular Ras Activation Cooperate to Modulate Endothelial-to-Mesenchymal Transition (EMT) and De Novo Methylation in Human Mammary Epithelial Cells Over fifty percent of human breast carcinomas express elevated levels of normal Ha-Ras 3, and expression of oncogenic Ras is one of the components required for transformation of HMEC 2. As described in Example 1, a subpopulation of HMEC that display tumorigenic phenotypes was isolated from disease-free women; these "variant HMEC" appear to have engaged the process of malignant transformation. Stable expression of constitutively active Ha-Ras V12 into these cells led to their immortalization.

TABLE 5

| Epithelium | p16+ | COX-2+ | Ki67+ | p16+/Ki67+ | COX-2+/Ki67+ | p16+/COX-2+/Ki67+ |
|---|---|---|---|---|---|---|
| Normal | 7.5% (93/40) | 30% (12/40) | 0% (0/40) | 0% (0/40) | 0% (0/40) | 0% (0/40) |
| ADH | 20% (4/20) | 65% (13/20) | 5% (1/20) | 5% (1/20) | 0% (0/20) | 0% (0/20) |
| DCIS | 26% (18/70) | 56% (39/70) | 37% (26/70) | 11% (8/70) | 26% (18/70) | 9% (6/70) | p16 and COX-2 staining intensity with a score >2 is considered positive, Ki67 positive cases exhibited >10% nuclei immunopositivity.
P-values were determined using Pearson Chi-quare test.

TABLE 6

| Epithelium | p16 High | p16 Low | P-value |
|---|---|---|---|
| Normal | 2.5% (1/40) | 27.5% (11/40) | 0.605 |
| COX-2 high | 5% (2/40) | 65% (26/40) | |
| COX-2 low | | | |
| ADH | 10% (2/20) | 55% (11/20) | 0.481 |
| COX-2 high | 10% (2/20) | 25% (5/20) | |
| COX-2 low | | | |
| DCIS | 19% (13/70) | 37% (26/70) | 0.101 |
| COX-2 high | 7% (5/70) | 37% (26/70) | |
| COX-2 low | | | | p16 and COX-2 staining intensity with a score >2 is considered positive. P-values were determined using Pearson Chi-quare test.

In our analysis of DCIS, we demonstrated that proliferation was an obligate qualifier for p16 and COX-2 in determining which lesions have worse prognosis. In ADH, we observe only 1 case of 20 that exhibits coupled high Ki67 and high p16 staining (Table 5). There were no examples of high Ki67/high COX-2 staining in ADH lesions. However, These immortalized variant HMEC (vHMEC) are a valuable model of pre-malignant mammary epithelia to study the effects of stromal components on mammary tumor progression.

In order to examine the effect of oncogenic stress on the behavior of vHMECs, vHMECs were transduced with a retroviral construct encoding constitutively active Ha-Ras V12. Unlike normal cells, vHMEC expressing oncogenic ras failed to undergo a proliferative arrest. Since the microenvironment can modulate characteristics of epithelial cells, the possibility that extracellular signaling might cooperate with intracellular Ras activation in altering the phenotypes of vHMEC was tested. To mimic secretory aspects of the extracellular environment, both vHMEC carrying control vector and vHMEC expressing Ha-Ras V12 were exposed at agonesence to media containing 0.5% serum. It was found that extracellular stimulation resulting from the presence of 0.5% serum was sufficient to cause immortalization of vHMEC expressing Ha-Ras but not control vHMEC.

It was observed that HMEC-Ras cells undergo a morphological change, and acquire mesenchymal features, when co-cultured with carcinoma-associated fibroblasts, as well as with certain BRCA1 mutant fibroblasts. In contrast, this morphological change was not observed when HMEC-Ras are co-cultured with normal fibroblasts. Since HMEC-Ras cells respond differentially to normal and cancer stroma, they can be used as a reporter cell line for the sensing of stromal signals.

vHMEC are Resistant to Ha-Ras-Induced Proliferative Arrest and Display Chromosomal Abnormalities.

To test the effect of oncogenic stress on primary HMEC and vHMEC exhibiting p16 promoter hypermethylation, cells were retrovirally transduced with constitutively active Ha-rasV 12. Expression of Ha-rasV 12 was confirmed by immunoblot analysis (FIG. 15A). Despite oncogenic ras expression, vHMEC failed to undergo a proliferative arrest as seen normal HMEC (FIG. 15B), and previously shown in normal fibroblasts. Instead, they continued to grow, and did so until entering agonescence, a period of heightened growth and apoptosis.

In order to determine whether the resistance to ras-induced proliferative arrest was associated with alterations in genomic integrity, a chromosomal analysis of vHMEC expressing Ha-rasV 12 or the control vector was performed. The results indicate that upon continued propagation, vHMEC-ras cells became increasingly genomically unstable as evidenced by the accumulation of a number of chromosomal abnormalities, including structural abnormalities, telomeric associations and alterations in ploidy (FIG. 15C). These chromosomal abnormalities do not appear to be due to centrosome dysfunction as no differences in centrosome number were detected between the cell populations.

FIGS. 15A-C. vHMEC are resistant to Ha-ras-induced proliferative arrest and display chromosomal abnormalities. A. Immunoblot analysis demonstrating Ha-rasV 12 expression in HMEC and vHMEC following retroviral transduction with pLXSP3-Ha-rasV12 (r) or the control pLXSP3 vector (v). Constructs were expressed in HMEC and vHMEC derived from five different individuals. A representative blot is shown along with actin as a loading control. B. Cell cycle analysis and corresponding growth curves of HMEC and vHMEC expressing Ha-rasV 12 or control vector demonstrating that the number of cells in S-phase dropped from 33.8% to 8.8% following Ha-rasV 12 expression in HMEC, but remained the same in vHMEC. HMEC underwent a proliferative arrest in response to oncogenic ras, while vHMEC continued to proliferate. C. Chromosomal analysis of vHMEC-vector and vHMEC-ras cells. Control vHMEC (vector) and vHMEC expressing oncogenic Ha-RasV 12 (ras) were harvested at different passages, as indicated, and processed for metaphase analysis. Standard G-banding karyotypic analysis was performed on at least fifty metaphase spreads for each cell population. The number of abnormalities observed are presented as percentages. "Total" refers to all structural abnormalities and telomeric associations, not including numerical abnormalities. "Structural" refers to all deletions, duplications, rings, marker chromosomes, chromatid exchanges and translocations. "TAS" refers to telomeric associations. "Aneuploidy" refers to additions or deletions of whole chromosomes.

Combined Serum-Induced Extracellular Signaling and Intracellular Ras Activation Leads to Immortalization of vHMEC and Upregulation of Telomerase Activity.

Since the microenvironment can modulate the characteristics of epithelial cells, we tested the possibility that extracellular signaling might cooperate with intracellular ras activation in altering the behavior of vHMEC. Studies have shown that the gene expression pattern of cultured primary fibroblasts in response to serum exposure resembles that of a wounding response, and that this wound-response signature is strongly predictive of metastasis and progression for a variety of carcinomas. Chang et al. (2004) *PLoS Biol.* 2:E7. Studies were initiated by exposing both vHMEC carrying control vector (vHMEC-vector) and vHMEC expressing Ha-rasV12 (vHMEC-ras) at agonesence to media containing 0.5% or 10% serum. It was found that extracellular stimulation resulting from the presence of either 0.5% serum (vHMEC-ras0.5) or 10% serum (vHMEC-ras10) was sufficient to cause immortalization of vHMEC-ras but not control vHMEC (FIG. 16A, left graph).

To address whether constitutive extracellular stimulation resulting from the exposure to serum is required for the continued proliferation of vHMEC-ras0.5 and vHMEC-ras10, serum stimulation was withdrawn by placing these cells into mammary epithelial growth media (MEGM) without serum. It was found that both cell populations were capable of continued proliferation under these conditions, indicating that once immortalization is initiated by extracellular serum stimulation, the proliferation is independent of continued serum stimulation (FIG. 16A, middle and right graphs). Consistent with this, once immortalized, vHMEC expressing Ha-rasV 12 displayed an increase in telomerase activity (FIG. 16B).

Figure 16A:
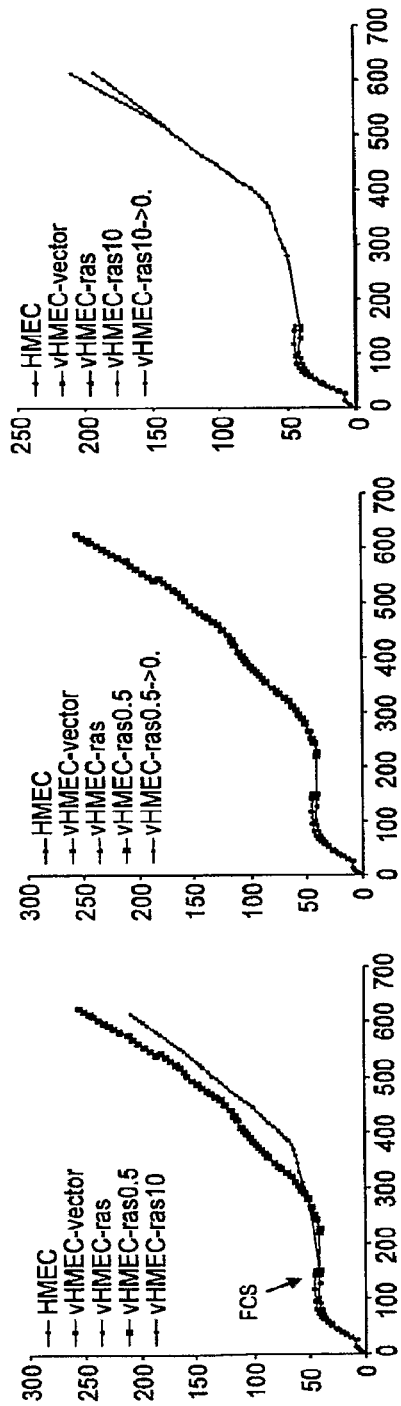
FIGS. 16A and 16B depict the effect of serum-induced extracellular signaling and intracellular ras activation on immortalization of vHMEC (FIG. 16A) and vHMEC telomerase activity (FIG. 16B).
Figure 16B:
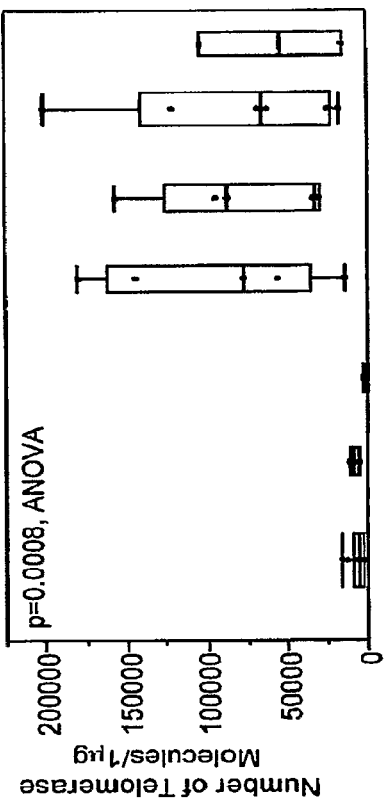

FIGS. 16A and 16B. Serum-induced extracellular signaling and intracellular ras activation leads to immortalization of vHMEC and increased telomerase activity. A. Growth curves of vHMEC expressing Ha-rasV 12 or control vector in the absence or presence of 0.5% or 10% serum. Arrow indicates time at which serum was added (day 150). vHMEC cultured in the presence of both 0.5% (vHMEC-ras0.5) and 10% (vHMEC-ras10) serum resumed proliferation and began being passaged again after 93 and 129 days, respectively (left graph). Both vHMEC-ras0.5 and vHMEC-ras10 continued to proliferate in the absence of serum (vHMEC-ras0.5→0; middle graph) and vHMEC-ras10→0; right graph) once they were immortalized B. Telomerase activity assay. Telomerase activity was measured using the Quantitative Telomerase Detection Kit from Allied Biotech and is represented as the amount of telomerase activity in 1 μg of lysate compared to the TDA standard provided in the kit. Each sample was analyzed in triplicate. A no template control, heat inactivated sample, and cell lysates from telomerase positive (MDA MB231) and telomerase negative (U2OS) cells were included with each experiment.

Extracellular Signaling and Intracellular Ras Activation Cooperate to Induce EMT.

Although vHMEC expressing oncogenic ras upregulated telomerase activity and became immortalized in the presence of both 0.5% and 10% serum, the cells grown in 10% serum underwent a distinguishing change in morphology that was not observed in the presence of 0.5% serum (FIG. 17A, first panel). In the presence of 10% serum, the cells assumed a mesenchymal appearance suggestive of an epithelial to mesenchymal transition (EMT). This mesenchymal phenotype did not require constitutive extracellular serum stimulation, as it was maintained upon serum withdrawal (FIG. 17A, second panel). The epithelial phenotype of ras-expressing vHMEC grown in 0.5% serum (vHMEC-ras0.5), and the mesenchymal phenotype of the same cells grown in 10% serum (vHMEC-ras10), were manifested both on plastic (2D) and in matrigel (3D). The epithelial vHMEC-ras0.5 formed mammospheres, while the mesenchymal vHMEC-ras10 retained their spindle morphology when cultured alone in matrigel (FIG. 17A, third panel). In addition, when the epithelial vHMEC-ras0.5 were co-cultured in 3D with normal human mammary fibroblasts derived from reduction mammoplasties, they were capable of forming ductal structures reminiscent of breast ducts in vivo. In contrast, the mesenchymal vHMEC-ras10 retained their spindle morphology under the same co-culture conditions (FIG. 17A, fourth panel).

EMT Occurs De Novo and is Accompanied by Molecular Alterations and Epigenetic Modifications at the E-Cadherin Locus.

EMT is characterized by a downregulation of cellular adhesion molecules, and an upregulation of mesenchymal markers. Since E-cadherin is a critical mediator of cell-cell contacts, loss of its expression is a characteristic feature of EMT. In addition, studies have shown that cell lines in which E-cadherin is irreversibly suppressed as a result of promoter methylation appear mesenchymal. Lombaerts et al. (2006) Br. J. Cancer 94:661. Since the mesenchymal appearance of vHMEC-ras10 appears to be irreversible (as it is maintained in the absence of extracellular serum stimulation), the hypothesis that epigenetic alterations may be involved in downregulating the expression of epithelial markers in these cells was tested.

Epigenetic modifications in the promoter region of E-cadherin were tested using both direct sequencing and methylation-specific PCR. MCF7 and MDA-MB-231 cells were used as negative and positive controls for methylation of E-cadherin, respectively. Consistent with the morphological appearance of the cells, methylation of the E-cadherin promoter was observed in the mesenchymal vHMEC-ras10, but not in the epithelial vHMEC-ras0.5 cells (FIG. 17B, lanes 1-4). This methylation pattern was also maintained after the cells were switched to no (0.5→0) or low (10→0.5) serum growth conditions (FIG. 17B, lanes 5-8), consistent with the maintenance of their morphology under those conditions. Interestingly, the E-cadherin promoter was unmethylated in early passage vHMEC-ras10 despite the fact that these cells appeared mesenchymal (FIG. 17B, lanes 11-14). This suggests that the emergence of vHMEC-ras exhibiting mesenchymal characteristics is unlikely due to the selection of a rare pre-existing population of vHMEC. Rather, the acquisition of mesenchymal features is likely to be the consequence of an active molecular process within vHMEC-ras10.

The protein 14-3-3σ is another mammary epithelial-specific marker that is often downregulated in breast cancer and methylated in fibroblasts, but unmethylated and expressed and in epithelial cells. Moreira et al. (2005) Mol. Cell. Proteomics 4:555; and Sato et al. (2006) Cancer Lett. 236:105. Consistent with the fact that all the cells are of epithelial origin, the promoter region of this gene remained unmethylated as detected by methylation-specific PCR (FIG. 17B). In addition, since E-cadherin is not methylated in human mammary fibroblasts (FIG. 17D), vHMEC-ras10 cells that have acquired a mesenchymal phenotype can be distinguished from fibroblasts on the basis of their E-cadherin methylation. Thus, together the data suggest that the mesenchymal appearing vHMEC-ras10 originated from mammary epithelial cells, not contaminating mammary fibroblasts.

To directly test the hypothesis that EMT is the result of an active process within vHMEC-ras10, two independent clones of vHMEC-ras0.5 (clone1 and clone2) were isolated, and the clones were exposed to media containing 10% serum. Both clones initially appeared epithelial in morphology (FIG. 17C) and expressed E-cadherin (FIG. 17D), as did all the vHMEC exhibiting an epithelial morphology, namely the parental vHMEC, vHMEC-vector, vHEMC-ras and vHMEC-ras0.5 from which the clones were isolated (FIG. 17D). However, after continued exposure to media containing 10% serum, both clones gradually acquired a mesenchymal morphology, their E-cadherin promoter became methylated (FIG. 17C), and E-cadherin expression was lost (FIG. 17D). Coincident with the loss of E-cadherin expression, the acquisition of mesenchymal morphology was associated with upregulation of the mesenchymal marker, N-cadherin as well as upregulation of fibronectin, demonstrating a functional consequence of the acquisition of a mesenchymal phenotype (FIG. 17D). In contrast, all vHMEC exhibiting an epithelial morphology expressed E-cadherin, but only very low levels of N-cadherin and fibronectin (FIG. 17D). This demonstrates that the changes in cellular morphology and methylation observed in vHMEC-ras exposed to 10% serum are the result of an EMT and occur de novo.

FIGS. 17A-D. Extracellular signaling and intracellular ras activation cooperate to modulate cellular morphology and methylation. A. Photomicrographs of vHMEC-ras grown in 0.5% serum (ras0.5), top panel, or 10% serum (ras10), bottom panel, both in 2D and 3D. Photos of 2D cultures represent the cells grown in their original concentration of serum (0.5% and 10%), as well as after they were switched to no serum (0.5→0 and 10→0). Photos of 3D cultures represent the cells grown alone or in combination with normal fibroblasts derived from a reduction mammoplasty (+RMF). Photos were taken at 10× magnification after 7 days in culture. B. Methylation-specific PCR (MSP) analysis of E-cadherin and 14-3-3σ on PCR products from bisulfite-modified DNA isolated from vHMEC-ras cells grown in 0.5%, 10%, 0.5≥0%, or 10≥0.5% serum as well as early passage vHMEC-ras0.5 (E0.5) and two early passage vHMEC-ras10 cells (E10). Bisulfite-modified DNA from MCF7 and MDA-MB-231 cells was used as unmethylated and methylated control templates, respectively for E-cadherin, while bisulfite-modified DNA from MDA-MB-231 and MDA-MB-435 served as unmethylated and methylated controls for 14-3-36. Also included is a water control (no template). Product sizes from methylated or unmethylated sequences of E-cadherin were 116 bp and 97 bp, respectively, while product sizes for the methylated and unmethylated sequences of 14-3-3s were 107 bp. Molecular weight markers are indicated on the left in base pairs. C. MSP analysis of E-cadherin and 14-3-3σ on two early (C1-E and C2-E) and late (C1-L and C2-L) passage clones isolated from vHMEC-ras0.5. Human mammary fibroblasts (HMF) were used as a positive control for methylation of 14-3-3σ. Photomicrographs of the early and late passage (P) clones analyzed for methylation are shown below the gel and depict the early epithelial and late mesenchymal morphology of the cells. Cells were photographed at 10× magnification. D. Immunoblot analysis of molecular markers associated with EMT, including fibronectin (Fn), N-cadherin (N-cad), and E-cadherin (E-cad) was performed on cell lysates prepared from parental vHMEC (par), vHMEC-vector (vec), vHMEC-ras (ras), vHMEC-ras0.5 (0.5), early and late passage vHMEC-ras10 (10E and 10L), early and late passage clone 1 (C1-E and C1-L), and early and late passage clone 2 (C2-E and C2-L). Actin is shown as a loading control.

TGFβ Cooperates with Oncogenic Ras to Induce EMT in Immortalized vHMEC.

Figure 18B:
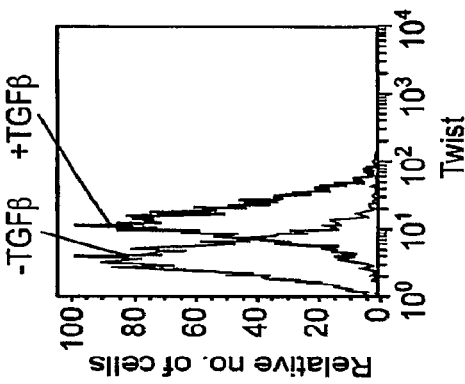
FIGS. 18A-D depict the effect of TGFβ on EMT in vHMEC-ras0.5 cells.
Figure 18A:
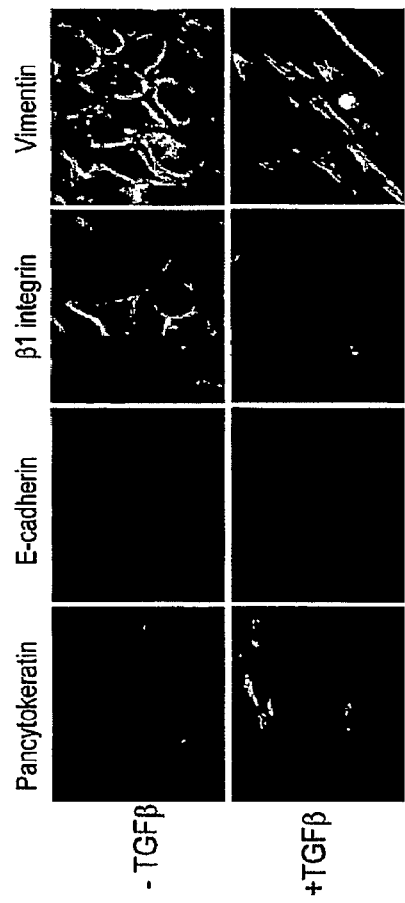
Figure 18D:
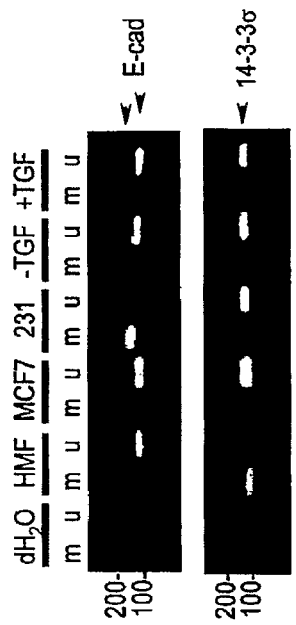
Figure 18C:
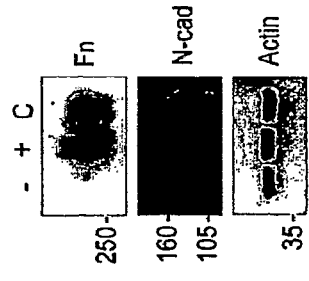

Having observed that extracellular signaling induced by 10% serum can cooperate with intracellular ras activation to induce EMT in vHMEC, it was then asked whether appropriate growth factor stimulation could induce EMT in the immortalized vHMEC-ras0.5 cells which had maintained their epithelial morphology. TGFβ has been shown to play a critical role in the induction of EMT. Thiery et al. (2003) *Curr. Opinion Cell. Biol.* 15:740; and Zavadil et al. (2005) *Oncogene* 24:5764. vHMEC-ras0.5 cells were treated with TGFβ and the expression of molecular markers associated with EMT was assessed by immunofluorescence, flow cytometry, and immunoblot analysis. Within 48 h of treatment, the cells began to undergo a morphological change, which became clearly manifested by 72 h. This morphological change was associated with a diminution in cytokeratin expression and disruption of both cell-cell and cell-matrix contacts, as evidenced by the loss of E-cadherin and β1-integrin expression, respectively (FIG. 18A). Coincident with the loss of epithelial marker expression was an upregulation in the expression of the mesenchymal markers, twist (FIG. 18B), N-cadherin, and fibronectin (FIG. 18C). Vimentin is another molecular marker often upregulated following EMT. Although immunofluorescence staining indicated that it is endogenously expressed in vHMEC, its expression pattern following TGFβ treatment clearly reflects the reorganization of the epithelial cell morphology into a mesenchymal one (FIG. 18A).

Unlike the EMT observed in cells exposed to 10% serum, TGFβ-induced EMT is reversible. Consistent with that, methylation of the E-cadherin promoter in these cells following TGFβ treatment was not observed; however, methylation of the E-cadherin promoter was observed in MDA-MB-231 cells, which were used as a positive control (FIG. 18D). As expected, the promoter of the epithelial marker 14-3-3σ remained unmethylated in all the epithelial cells, and methylated in the human mammary fibroblasts, which were used as a positive control (FIG. 18D).

FIGS. 18A-D. TGFβ induces EMT in vHMEC-ras0.5 cells without modulating methylation of E-cadherin. A. Inununofluorescence analysis. Cells were treated with 2 ng/ml TGFβ for 72 h, and immunostained for pancytokeratin, E-cadherin, β 1-integrin, and vimentin. B. Flow cytometric analysis of twist expression before (green curve) and after (purple curve) treatment with 2 ng/ml TGFβ for 72 h. C. Immunoblot analysis of the mesenchymal markers fibronectin (Fn) and N-cadherin (N-cad) was performed on cell lysates prepared from vHMEC-ras0.5 that were either untreated (−) or treated (+) with 2 ng/ml TGFβ for 72 h. Cell lystates prepared from human mammary fibroblasts were used as a positive control (C) and actin is shown as a loading control. D. MSP analysis of E-cadherin and 14-3 3σ was conducted on the PCR products of bisulfite-treated DNA isolated from vHMEC-ras0.5 untreated (−TGF) or treated (+TGF) with 2 ng/ml TGFβ for 96 h as described in FIGS. 3B and C. Bisulfite-modified DNA from MCF7 and MDA-MB-231 cells was used as unmethylated and methylated control templates, respectively for E-cadherin, while bisulfite-modified DNA from MDA-MB-231 and human mammary fibroblasts (HMF) served as unmethylated and methylated controls for 14-3-3s. Also included is a water control (no template).

TGFβ-Induced EMT is Associated with Enhanced Motility in vHMEC-Ras0.5 Cells.

To determine whether the morphological change in vHMEC-ras0.5 following TGFβ treatment was associated with increased motility, confluent cell monolayers were scratched with a pipet tip, and the ability of the cells to migrate into the denuded area was assessed using time-lapse microscopy. It was found that although vHMEC-ras0.5 cells were very motile, the mesenchymal phenotype induced by TGFβ treatment led to an increase in directed migration, which allowed these cells to fill in the denuded area faster than untreated cells.

A transwell invasion assay was used to examine the invasive behavior of vHMEC-control, non-immortalized vHMEC-ras, vHMEC-ras0.5, vHMEC-ras10 in response to serum. It was found that regardless of the stimulus, vHMEC-ras10 were significantly more invasive than all other vHMEC. These data suggest that extracellular stimulation provided by either serum can initiate EMT in immortalized vHMEC and that acquisition of this mesenchymal phenotype is associated with increased invasive ability.

Immortalized vHMEC Expressing Oncogenic Ras are Capable of Anchorage—Independent Growth and can Survive and Proliferate In Vivo.

Figure 19:
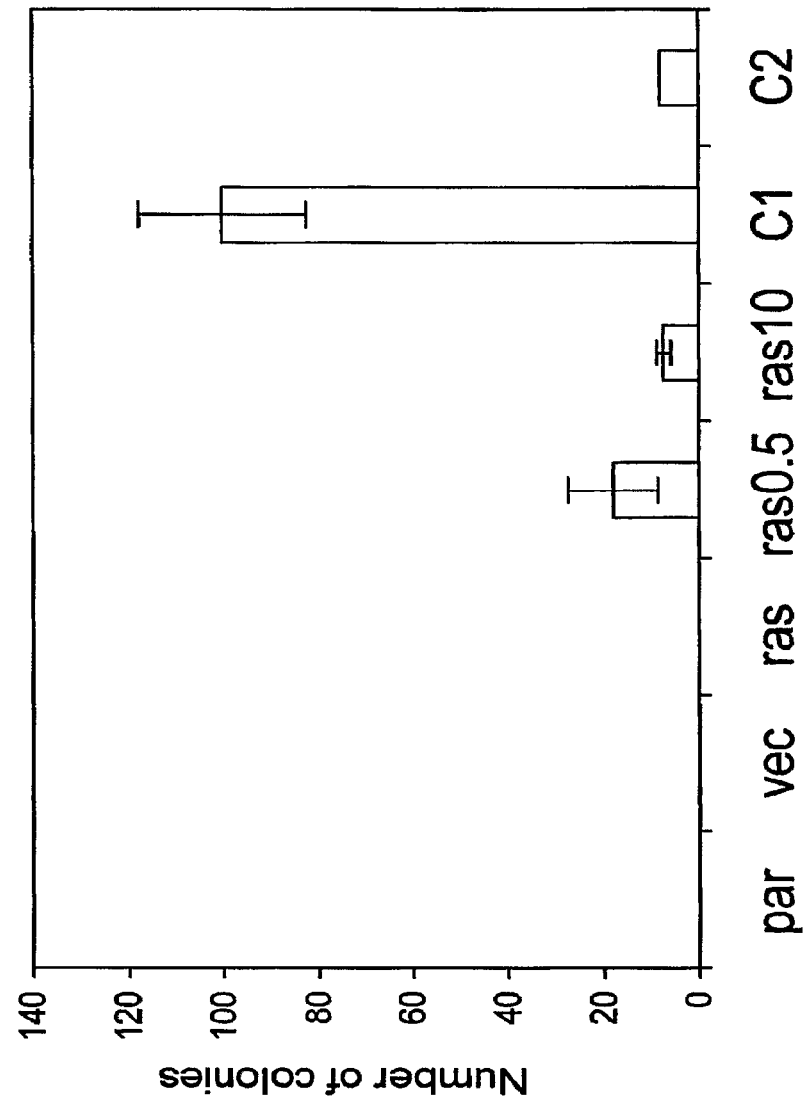
FIG. 19 depicts anchorage independent growth of vHMEC immortalized with Ha-ras.

Since the immortalized vHMEC expressing oncogenic ras exhibited phenotypic and functional changes associated with targeted DNA methylation that are typically observed during tumor progression, it was asked if these cells had any tumorigenic potential. Anchorage-independent growth is the best in vitro correlate of tumorigenicity, therefore, it was first examined whether vHMEC expressing oncogenic ras could grow in soft agar. As shown in FIG. 19, the parental, vector control, and non-immortalized vHMEC-ras cells failed to grow in soft agar. In contrast, the immortalized vHMEC-ras0.5 and vHMEC-ras10 as well as the two clones isolated from vHMEC-ras0.5 cells displayed some, albeit weak, capacity for anchorage-independent growth, suggesting that they may have some tumorigenic potential.

FIG. 19. vHMEC immortalized with Ha-ras are capable of anchorage independent growth. Soft agar colony assay. Parental vHMEC (par), vHMEC-vector (vec), vHMEC-ras (ras), vHMEC-ras0.5 (ras0.5), vHMEC-ras10 (ras10), clone 1 (C1), and clone 2 (C2) were plated in 35 mm dishes at a concentration of 50 000 cells per dish, in triplicate. After 14 days, colonies were counted manually in eight different fields. The data are presented as the average of the sum of 8 different fields counted.

Example 4: Overexpression of TRF2 Results in Activin A-Dependent Induction of COX-2 In Vitro and In Vivo Materials and Methods Tissue Samples: High (n=7) and low (n=8) grade+one unknown non-recurrent ductal carcinoma in situ (DCIS) specimens were obtained with institutional review board approval from the surgical pathology laboratory at the University of California, San Francisco. Patients were identified through anonymous reference numbers in accordance with federal guidelines.

Telomere Content Determination: A 5 μm tissue section was stained with hematoxylin and eosin and cellular morphology was evaluated. This reference slide was used to guide microdissection of 6×25 μm sections. Microdissection was performed using a Leica AS-LMD microdissection microscope on slides stained with methyl-green following standard procedures. DNA was purified from populations enriched for DCIS using proteinase K and chloroform/phenol. DNA was quantitated using Picogreen dye following the manufacturer's protocol (Invitrogen). Telomere content was determined as described previously (Fordyce et al, 2005). Briefly, DNA was denatured and fixed to positively charged membrane using a vacuum apparatus and then hybridized to a labeled telomere-specific probe $(TTAGGG)_4$ (IDT). The tagged probe was detected using an antibody conjugated to alkaline phosphatase and a chemiluminescent substrate, CDP-STAR (New England Biolabs). Blots were exposed to film, and the intensity of each spot was determined using Image Quant software (Molecular Dynamics). Samples were analyzed in triplicate. Data is expressed as a percentage of placental DNA.

Tissue Preparation and Immunohistochemistry (including evaluation): Five-micron sections were cut form paraffin-embedded tissue blocks adjacent to sections used for telomere content determination. Tissue sections were deparaffinized and rehydrated using standard protocols. Microwave antigen retrieval was accomplished using 0.001 M EDTA, pH=8 for COX-2, 0.01 M citrate for γH2AX and Antigen Unmasking Solution (Vector Laboratories) for TRF2. Antiserum against COX-0.2 (1:200, Dako), γH2AX (1:150, Upstate) and TRF2 (1:20, Imgenex) was incubated on tissue sections for ~16 hrs at 4° C. Antigen-antibody complexes were labeled using the Vectastain Elite ABC following standard protocols (Vector Laboratories, CA) and visualized using 2.5% 3-amino-9-ethyl-carbazole in 50 mM acetate buffer pH5, with 0.05% hydrogen peroxide. Sections were counterstained in Mayers hematoxylin mounted in Crystal Mount (BMM02, American Mastertech). Once dry, the sections were permanently mounted with a glass coverslip using clearmount (MMCLEI, American Mastertech). A blocking step (0.01% Triton×1000 for 1 hr) was added to this protocol prior to addition of the primary antibody for the TRF2 staining.

The degree of γH2AX, COX-2 or TRF2 staining intensity was evaluated in a blinded fashion. For COX-2, staining intensity was examined by light microscopy and was scored as low to absent (1), moderate (2) or strong (3) in the majority of either DCIS or adjacent normal tissue. For the purpose of the study, COX-2 expression scored as 2 or 3 was considered high. TRF2 and γH2AX expression was evaluated by counting the number of positive nuclei in a minimum of 500 cells. The mean level of positive cells for either TRF2 (29%) or γH2AX (27%) was used to stratify the tissues into high and low groups.

Cell Culture: Human mammary epithelial cells (vHMEC) were isolated from reduction mammoplasty (RM) of four individuals RM9, RM15, RM16 and RM18. HMEC undergo a spontaneous proliferation barrier between 8 and 12 population doublings. Variant human mammary epithelial cells (vHMEC) escape this growth barrier and have silenced p16 through promoter methylation. Cells were propagated in 2D cultures in modified MCBD 170 media (MEGM, Lonza) as previously described (Romanov et al, 2001; Hammond et al 1984). All experiments were performed on exponentially growing early passage vHMEC (between 13 to 20 population doublings); RM9, 15, 16 and 18 cease to expand in cell number at population doublings 45, 60, 50 and 53, respectively. Activin A (Sigma) and the p38 inhibitor, SB203580, (Sigma) were added to culture media for 48 and 24 hours (respectively) prior to harvest at the doses shown in FIGS. 3 and 4. The same amount of solvent for each molecule was added to the culture media for controls.

Wound Closure Assay: Wound closure assays were performed as previously described (Dumont et al, 2003 JBC). Cells were plated in duplicate wells of a 6-well plate at $2\times10^5$ each and allowed to proliferate until confluent. Confluent cell monolayers were wounded by manually scrapping the cells with a pipette tip and an ocular ruler was used to verify the widths of the resulting wounds. Media was replaced and wound closure was monitored by microscopy.

Expression of TRF2: The TRF2 gene was excised from the pLPC construct using Hind III and EcoRI and inserted into the pWPI *lenti* viral expression vector. The TRF2-pWP construct was packaged in 293T cells for viral propagation. *Lenti*-viral supernatant was diluted 1:1 with MEGM media containing polybrene (8 μg/ml; Sigma) and added to vHMEC for 4 to 6 hrs. Infection efficiency was monitored using GFP expression, which was driven from the same promoter via an IRES sequence.

Quantitative PCR: Total RNA was isolated from cells and cDNA synthesized using standard methods. cDNA was subsequently used for quantitative real-time PCR using the standard curve method. Primer-probe sets for COX-2 (Hs00153133), TRF2 (Hs00194619) and activin A (Hs00170103) were obtained from ABI (location). The expression of GUSB (IDT), an external control, was used to normalize for variances in input eDNA.

Western Blotting, ELISA and Immunofluorescence: Cell pellets were lysed in T-PER buffer (Pierce). Cell lysates were fractioned in gradient polyacrylamide gels (4-20%) and transferred to Hybond-P (Amersham Biosciences) membranes using standard procedures. Antibodies against COX-2 (1:200, Cayman), phospho-p38, (1:200, Cell Signaling) were used according to manufacturers' protocols. Activin A protein levels were measured using the Duo-Set Activin ELISA kit (R&D Systems) following the manufacturer's directions. Parental vHMEC or cells over expresing vector or TRF2 were plated in 6-well dishes at $1\times10^5$ in duplicate. Media was replaced the following day and allowed to condition for 72 hours prior to analysis. Levels of activin A were determined in cells from all four donors. For immunocytochemistry, $5\times10^4$ cells were seeded directly onto glass cover slips and fixed in 4% paraformaldehye (PFA) for 15 minutes at room temperature and stored in 0.01% PFA at 4° C. Cover slips were treated with anti-TRF2 antibody (1:100, Imgenex) or anti-γH2AX (1:1000, Upstate) following the manufacturer's protocols. Nuclei were counterstained using Dapi (Molecular probes, location) and visualized using a LSM450 Zeiss confocal microscope. The mean fluorescent intensity of γH2AX signal (voxels) in each nucleus was determined with the Volocity 4.0.0 software package (Improvision) on Z-stacks.

Statistical Methods: ANOVA was used to test the relationship between gene expression or activin protein levels in the vHMEC treatment groups (parent, vector and TRF2 over-expressing cells). The relationship between telomere content and COX-2, γH2AX and TRF2 staining intensity was examined using a T-test. Chi-Square test was used to evaluate the relationship between staining intensity for TRF2 and COX-2 and γH2AX. The Jmp statistical package (SAS Institute) was used for all analyses.

Results

Figure 20:
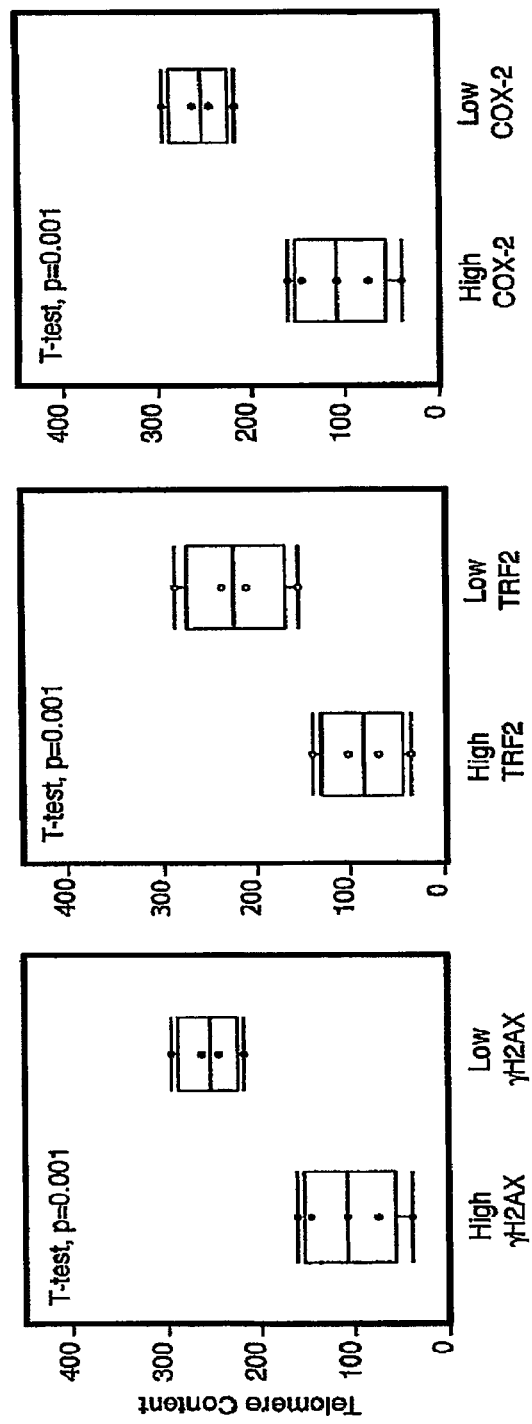
FIG. 20 depicts association of telomere Content with COX-2 expression.

Telomere Content is Inversely Associated with γH2AX, TRF2 and COX-2 Expression in DCIS. Fifteen high and low grade non-recurrent DCIS lesions ductal carcinoma in situ (DCIS) lesions were microdissected and used for DNA purification. Telomere content, a proxy for telomere length, was measured in the nine lesions from which sufficient DNA was obtained. Telomere content ranged from 39 to 417% of the placental standard. Telomere content was not associated with patient age at surgery, ethnicity, menopausal status, DCIS grade or tumor size. To determine if the reduced telomere content measured in this cohort was associated with a DNA damage response, we evaluated the levels of γH2AX, a DNA damage marker, with immunohistochemistry on serial sections of the DCIS lesions. As shown in FIG. 20, telomere content was inversely associated with the proportion of γH2AX positive nuclei in the DCIS lesion (T-test, p=0.001).

Exogenous expression of the telomere binding protein, TRF2, results in progressive telomere shortening. De Lange (2002) *Oncogene* 21:532; de Lange (2005) *Genes Dev.* 19:2100; Smogorzewska et al. (2000) *Mol. Cell. Biol.* 20:1659; and Oh et al. (2005) *Am. J. Pathol.* 166:73. It was determined if there was an association between telomere content and TRF2 in our DCIS cohort. The proportion of TRF2 positive nuclei in DCIS lesions was evaluated in 14 of 15 cases. Telomere content was measured in 8 of these cases. As shown in FIG. 20, TRF2 expression was higher in the in DCIS lesions with low telomere content than in lesions with high telomere content (T-test, p=0.001). TRF2 expression was associated with the proportion of cells in the DCIS lesion expressing γH2AX ($X^2$, p=0.005).

The observation that increases in COX-2 expression coincides with telomere loss and genomic instability in primary variant human mammary epithelial cells (vHMEC) in vitro, suggested that there might be a relationship between loss of telomere homeostasis and COX-2. It was postulated that the increase in γH2AX positive nuclei in DCIS lesions with reduced telomeres is indicative of loss of telomere homeostasis. The levels of COX-2 expression were evaluated, using immunohistochemistry in the DCIS cohort. Strikingly, there was a significant relationship between telomere content and the degree of COX-2 staining in the DCIS lesion (T-test, p=0.004). The degree of COX-2 and γH2AX expression were directly associated with each other ($X^2$, p<0.0001). Likewise, there was a statistically significant relationship between TRF2 expression and COX-2 ($X^2$, p=0.005). None of COX-2, γH2AX, and TRF2 were associated with any of the other parameters evaluated in this study. These data show that the reduced telomere content observed in the DCIS lesions is inversely associated with the induction of a DNA damage response, and the expression of TRF2 and COX-2.

FIG. 20: Telomere Content is Associated with COX-2 Expression. COX-2 and γH2AX levels were evaluated using immunohistochemistry. For COX-2, lesions were scored as low to absent (1), moderate (2) or strong (3) in the majority of either DCIS or adjacent normal tissue. For the purpose of the study, COX-2 expression scored as 2 or 3 was considered high. The number of γH2AX positive nuclei were manually counted and expressed as a percentage of the total number of nuclei within a region of DCIS. The mean percentage of γH2AX positive nuclei (27%) was used to stratify lesions. Telomere content, a proxy for telomere length was measured in DCIS following microdissection and is expressed as percentage of placental control. Box plots show the relationship between telomere content and either γH2AX (right) or COX-2 (left) when DCIS lesions are stratified into two groups (high or low staining intensity).

Exogenous Expression of TRF2 in vHMEC. To more directly access if changes in telomere length or structure can induce COX-2, an in vitro model system was used. The observation that TRF2 expression is associated with telomere content in this DCIS cohort is consistent with previous reports showing that exogenous expression of TRF2 results in telomere loss (de Lange supra; Smogorzewska et al. supra; Oh et al, 2005, supra). TRF2 is also an integral component of multiple protein complexes localized to the telomere and is important for the formation of the unique DNA loop at the extreme ends of the telomere (de Lange, supra). Exponentially growing early-passage (PD<15) variant human mammary epithelial cells (vHMEC) purified from four donors were mock infected or infected with *lenti* virus containing vector alone (pWP) or vector plus the TRF2 gene. Infection efficiency was monitored using GFP expression driven by an IRES sequence. TRF2 mRNA (ANOVA, p=0.0002) and protein levels were significantly up regulated in vHMEC infected with TRF2 containing *lenti* virus when compared to parent and vector controls. Over expression of proteins can result in altered localization. It was verified that TRF2 was confined to the nucleus using immunofluorescence. The rates of proliferation and number of population doublings for parent, vector and TRF2 over expressing cells from all four donors were evaluated using growth curve analysis. Consistent with previous reports, cells expressing TRF2 underwent slightly fewer population doublings than vector and parental controls, but had similar rates of cell replication, particularly at early passages. Flow cytometry for BrDu and propidium iodide was used to evaluate the proportion of cells in each phase of the cell cycle in cells over expressing TRF2 and parent and vector controls. There was no change in the proportion of cells in any phase of the cell cycle in parental vHMEC compared to cells infected with vector alone or over expressing TRF2.

Figure 21:
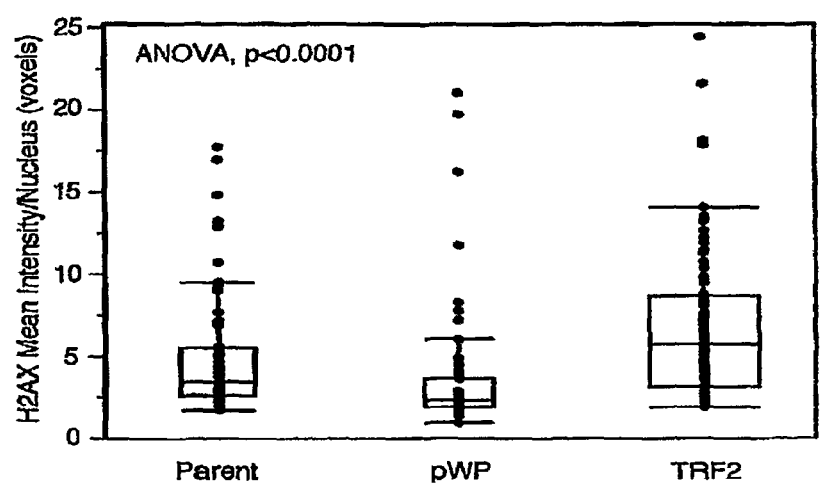
FIG. 21 depicts up-regulation of γH2AX in vHMEC expressing TRF2.

Previous reports have shown that over expression of TRF2 leads to a preferential enrichment of single strand breaks at the telomeres and increased telomere loss. It was postulated that over expression of TRF2 would result in accumulation of the DNA damage marker γH2AX in vitro. vHMEC over expressing either TRF2 wt or vector and parental controls were grown on glass cover slips, fixed and treated with antiserum against γH2AX. The mean fluorescent intensity of γH2AX in vHMEC with or without TRF2 wt was determined. As shown in FIG. 21, there was a statistically significant increase in the mean number of γH2AX voxels in cells over expressing TRF2 (ANOVA, p<0.0001). Thus, exogenous expression of TRF2 up-regulates γH2AX in vHMEC and recapitulates the increase in γH2AX observed in DCIS with reduced telomeres.

FIG. 21: γH2AX is Up Regulated in vHMEC Expressing TRF2. Levels of γH2AX were determined using immunofluorescence with an anti-γH2AX antibody (Upstate). ILevels of γH2AX expression were determined using Z-stacks obtained on a confocal microscope. The mean intensity of γH2AX voxels/nucleus were determined using Volocity software (company) in vHMEC from two donors.

COX-2 is Up Regulated in vHMEC expressing TRF2 in a Phospho-p38 Dependent Manner. Since COX-2 levels were associated with both telomere content and the levels of γH2AX expression in the DCIS cohort, the level of COX-2 in vHMEC over expressing TRF2 was evaluated. COX-2 mRNA and protein levels were evaluated using Q-PCR and immunoblotting, respectively. COX-2 mRNA levels were increased approximately two fold in vHMEC over expressing TRF2 (ANOVA, p=0.002, FIG. 22a). Likewise, COX-2 protein levels were increased in vHMEC over expressing TRF2 when compared to parental and vector controls. Next, it was determined if the increase in COX-2 observed in TRF2 over expressing vHMEC was able to induce a phenotype associated with COX-2 expression. Previous reports have shown that COX-2 expression enhances cell motility. A cell wounding assay was used to evaluate the motility of vHMEC over expressing TRF2 compared to vector and parental controls from two donors. Confluent monolayers in duplicate wells were manually wounded with a sterile pipette tip. After ensuring that the width of the wounds was similar, cells were monitored with microscopy for 12 hours. Cells over expressing TRF2 were able to fill the wound in 8 hours, while parent and vector controls required approximately 12 hours (FIG. 22c), demonstrating a modest, but consistent increase in cell motility.

Figure 22A:
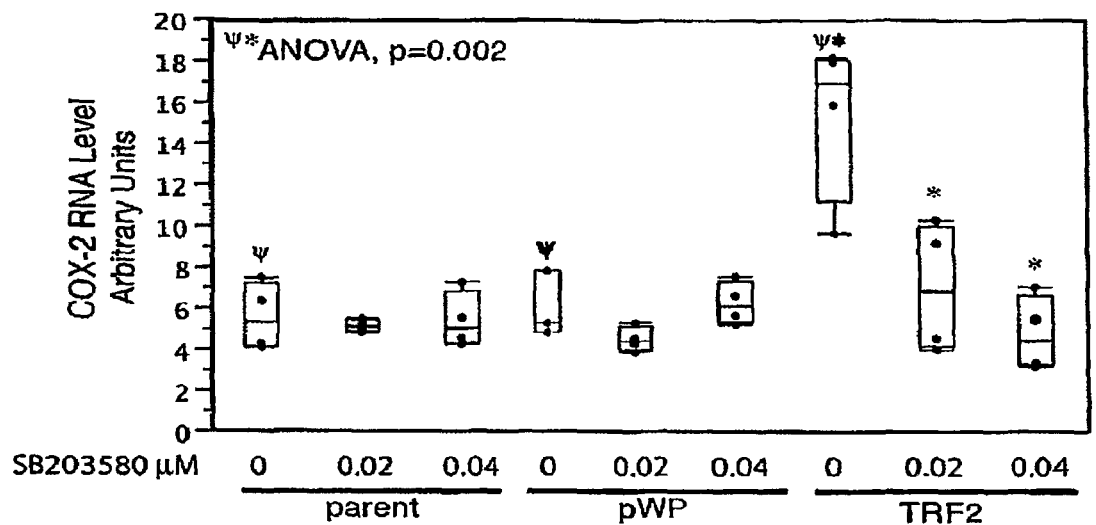
FIGS. 22A-C depict the effect of over-expressing TRF2 on COX-2 in vHMEC.
Figure 22B:
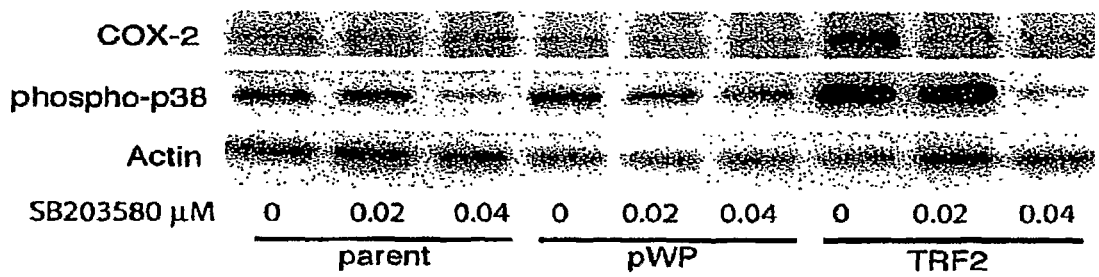

It has previously been shown that the increase of COX-2 observed in late-passage vHMEC is dependent on the MAPK, p38. Here it is shown that the activated phospho-p38 is up-regulated in early passage vHMEC cells over expressing TRF2 (FIG. 22b). To determine if phospho-p38 is necessary for the induction of COX-2 in response to TRF2, early passage parent, vector, and TRF2 over expressing vHMEC were treated with the phospho-p38 inhibitor SB203580. As shown in FIGS. 22A and 22B, inhibition of phospho-p38 lead to a marked decrease in COX-2 mRNA (ANOVA, p=0.002) and protein levels in cells expressing TRF2. This finding demonstrates that expression of TRF2 is able to induce COX-2 in a phospho-p38 dependent manner in vHMEC.

Figure 22C:
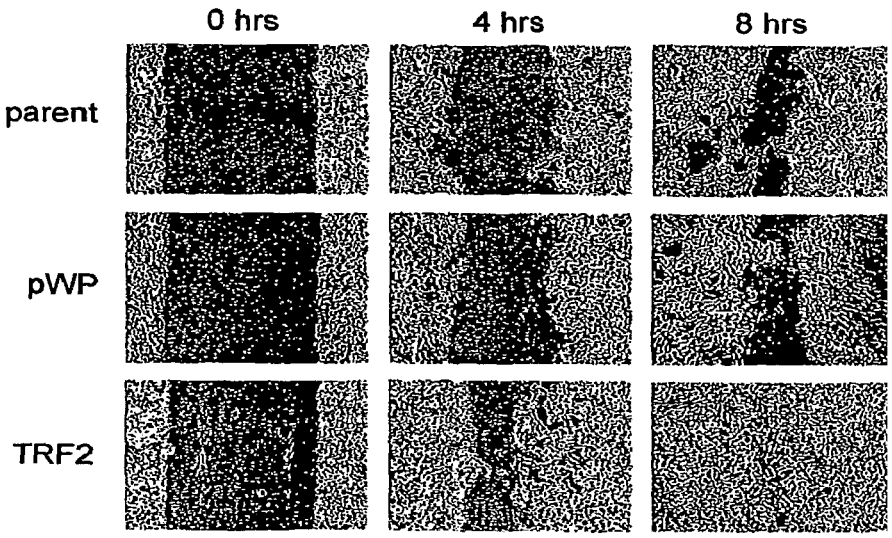

FIGS. 22A-C: COX-2 is Induced in vHMEC Over Expressing TRF2 and is Dependent on p38. A, Box plot showing the levels of COX-2 mRNA as measured with Q-PCR in untreated parental vHMEC or vHMEC over expressing either vector (pWP) or TRF2, or treated with the phospho-p38 inhibitor SB203580 for 24 hrs at the indicated doses. Inset is p-value comparing either parent, vector and TRF2 cells or cells treated with SB203580 to untreated controls. B, Representative immunoblot showing COX-2, phospho-p38 and actin (loading control) for the conditions described in A. C, Representative example of wounding assay showing parent vHMEC and vHMEC over expressing vector or TRF2 at 0, 4 and 8 hrs following wounding.

Figure 23A:
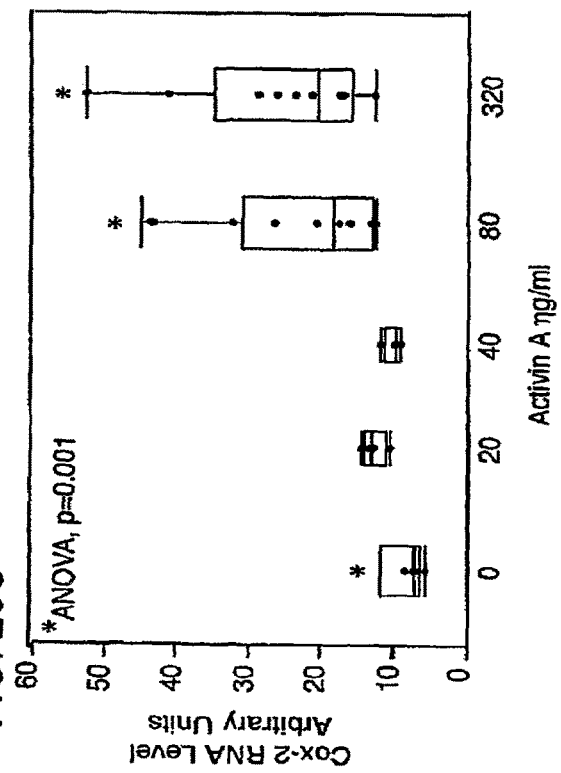
FIGS. 23A-D depict up-regulation of Activin A in vHMEC and the effect of up-regulation of Activin A on COX-2.

Activin A Induces COX-2 Up-regulation in vHMEC. A variety of signal transduction pathways can lead to the activation (and phosphorylation) of p38. To further elucidate the mechanisms by which TRF2 induces COX-2 in vHMEC, microarrays were used to screen for modulators of p38 activity. Activin A, a member of the TGF-β superfamily, was up regulated in vHMEC over expressing TRF2 when compared to parent and vector controls. Previous reports have demonstrated that binding of activin A to its receptor can lead to the phosphorylation and activation of p38. Activin A is a homodimer of the activin βA subunits. The activin βA monomer can also form a heterodimer with inhibin a, to produce the activin A antagonist, inhibin A. Microarray analysis demonstrated that inhibin a was not differentially expressed in vHMEC over expressing TRF2 when compared to controls. The results of the microarray analysis were validated using Q-PCR. As shown in FIG. 23a, activin βA was significantly up regulated in cells over expressing TRF2 (ANOVA, p=0.03).

Figure 23B:
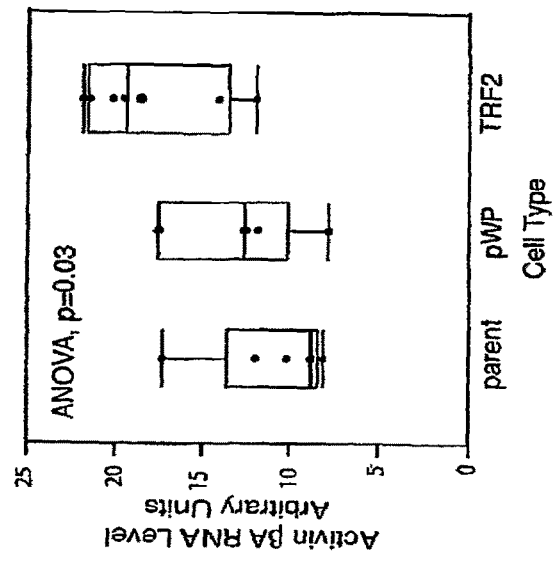

Activin A protein levels were measured using ELISA (FIG. 23b). Mean levels of activin A protein in condition media from parental vHMEC or vector controls was 1.3 ng/ml and 1.7 ng/ml, respectively. In contrast, the mean level of activin A in conditioned media from vHMEC expressing TRF2 was 4.4 ng/ml, an approximately 5-fold increase (p<0.0001, ANOVA). These data demonstrate that activin A is up regulated in vHMEC over expressing TRF2.

Figure 23C:
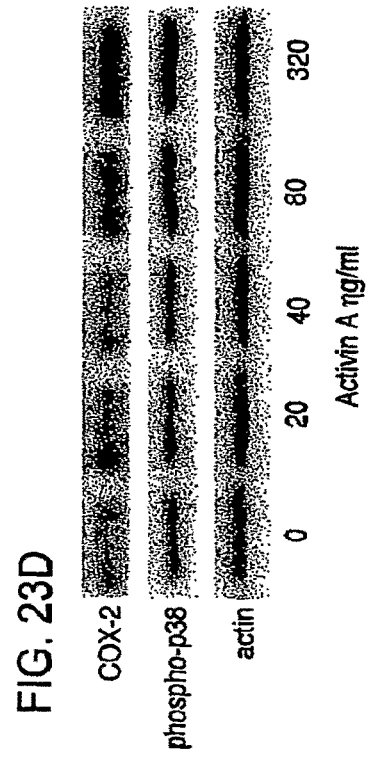
Figure 23D:
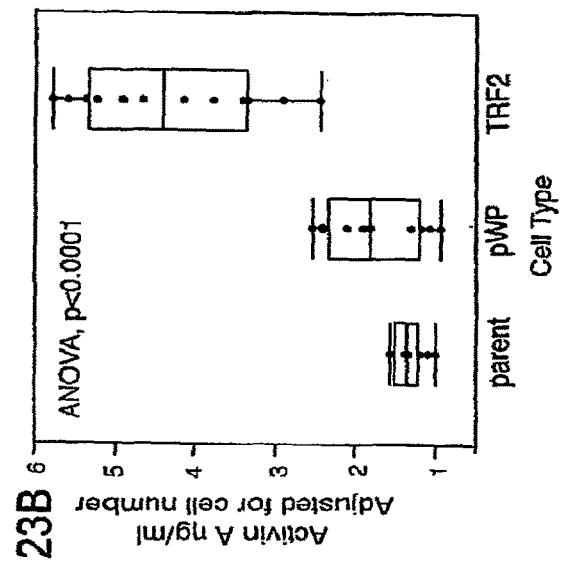

To determine if activin A was sufficient to induce COX-2 expression we treated vHMEC from two donors in duplicate experiments with exogenous activin A. As shown in FIG. 23c, exogenous activin A induced an approximately two-fold increase in COX-2 mRNA (ANOVA, p=0.001) and protein. Treatment with exogenous activin A also caused an increase in the levels of phospho-p38 (FIG. 23d). Since activin A is a secreted protein, it was reasoned that conditioned media from cells over expressing TRF2 should be able to induce COX-2 expression in vHMEC. Conditioned media from parent, vector and vHMEC over expressing TRF2 was collected from two donors and used to treat uninfected vHMEC obtained from three donors. COX-2 mRNA and protein were increased approximately two fold when vHMEC were treated with conditioned media from cells over expressing TRF2. Likewise, phospho-p38 levels were increased in vHMEC treated with conditioned media from cells over expressing TRF2. Taken together these data suggest that the induction of COX-2 expression observed in early-passage vHMEC over expressing TRF2 is driven by activin A.

FIGS. 23A-D: Activin A is Up Regulated in vHMEC and Induces COX-2. A. Box plot showing the levels of activin A mRNA measured using Q-PCR in parental vHMEC, or vHMEC over expressing vector (pWP) or TRF2 from 4 donors. p-value was calculated using ANOVA and is shown in the inset. B, Box plot showing the levels of activin A protein measured using ELISA in parental vHMEC or vHMEC over expressing vector (pWP) or TRF2 from 4 donors. Inset shows p-value calculated using ANOVA. C, vHMEC from 2 donors were treated with exogenous activin A for 48 hrs at the indicated doses. Box plot shows the levels of COX-2 mRNA as measured by Q-PCR. Inset shows p-values for untreated cells compared to the two highest doses of activin A. The experiment was performed in quadruplicate. D, Representative immunoblots showing the levels of COX-2, phospho-p38 and actin (loading control) for cells and treatments described in C.

Example 5: Cell Surface Markers that Identify Cancer Cell Precursors

Method & Materials
Screening of Markers

HMEC were trypsinized, washed, spun down, and counted. Cells were incubated in MEGM+2% FBS for 2 hours to regenerate cell surface markers. Cells were spun down, and incubated with anti-CD73-phycoerythrin (anti-CD73-PE; PE-conjugated antibody to CD73) (124, per $1 \times 10^6$ cells) for 30 min. Then cells were spun down and incubated with anti-CD90-allophycocyanin (anti-CD90-APC; APC-conjugated antibody to CD90) (1 µL per $1 \times 10^6$ cells). Following staining, cells were washed 3X with PBS and subjected by flow cytometry. Flow cytometry profiles were analyzed by Flowjo software.

Flow Sorting of Cells and Culturing of Cells

Human mammary tissue were digested as described (Romanov et al. (2001) *Nature* 409:633-7), and further digested to single cells as described (Liu et al. (2004) *Proc Natl Acad Sci USA* 101:4158-63). Cells were counted and incubated in MEGM+2% FBS for 2 hours. Cells were spun down, and incubated with CD73-PE (12 µL per $1 \times 10^6$ cells) for 30 min. Then cells were spun down and incubated with CD90-APC (1 µL per $1 \times 10^6$ cells) and anti-epithelial-specific antigen-fluorescein isothiocyanate (anti-ESA-FITC; FITC-conjugated antibody to ESA) (2 µL per $1 \times 10^6$ cells). Following staining, cells were washed 3X with PBS and subjected to flow cytometry. Cells were sorted by BD FAC Aria. Once cells were isolated, they were plated in a 12-well plate with 1 mL of MEGM. Cells were passaged once reached ~70% confluency, counted and population doublings (PD) was determined.

Methylation-Specific PCR (MSP)

Cells were sorted and mixed with $0.5 \times 10^5$ HeLa carrier cells. Genomic DNA was prepared, bisulfate treated, and subjected to methylation specific PCR.

Immunoblot

Cells were lysed by 1% SDS and 1% b-mecaptoethanol, and cell lysate was subjected to immunoblot analysis as described (Liu et al. (2003) *Oncogene* 22:9243-53). Anti-Bmi-1 antibody was purchased from Upstate Cell Technology.

Results

Based on microarray experiments, potential candidate markers were identified that are important for distinguishing cancer precursor cells from bulk epithelial cells. 19 cell surface markers were screened via flow cytometry. It was found that the markers CD73, CD138, CD90, CD133, and Notch receptor-3 clearly distinguished cultured vHMEC from HMEC. Expression of CD73, CD138, and Notch Receptor-3 in the vHMEC was increased by ~12-fold, ~5-fold, and ~6-fold respectively, as compared to HMEC (median vHMEC vs. HMEC; FIG. 24A), whereas expression of CD90 and CD133 in the vHMEC was decreased by ~7-fold, and ~3-fold respective relative to HMEC.

Figure 24B:
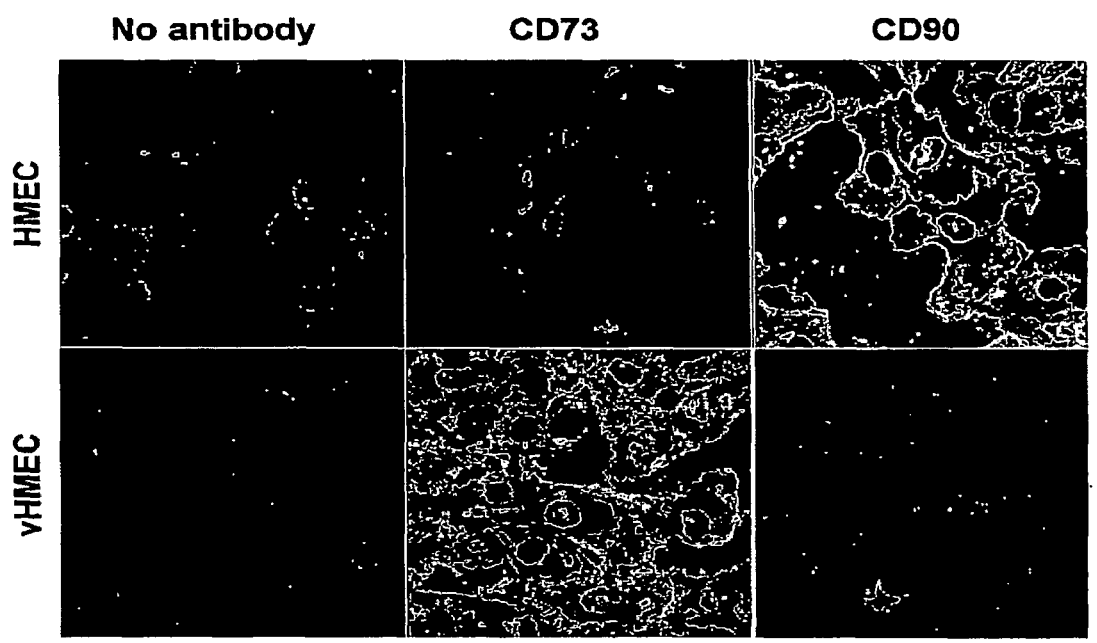

Immunocytochemical analysis of vHMEC and HMEC with anti-CD73 and anti-CD90 antibodies also showed results consistent with FACs analysis (FIG. 24B). Detectable levels of CD73 were seen in vHMEC but not in HMEC, and the localization of CD73 was predominantly on the cell surface. Likewise, only cell surface expression of CD90 was detected in HMEC, and not in vHMEC (FIG. 24B). When anti-CD73 and anti-CD90 antibodies were combined, the vHMEC population was easily distinguishable from the HMEC population; vHMEC were CD73$^+$ (FIG. 24C).

Figure 24C:
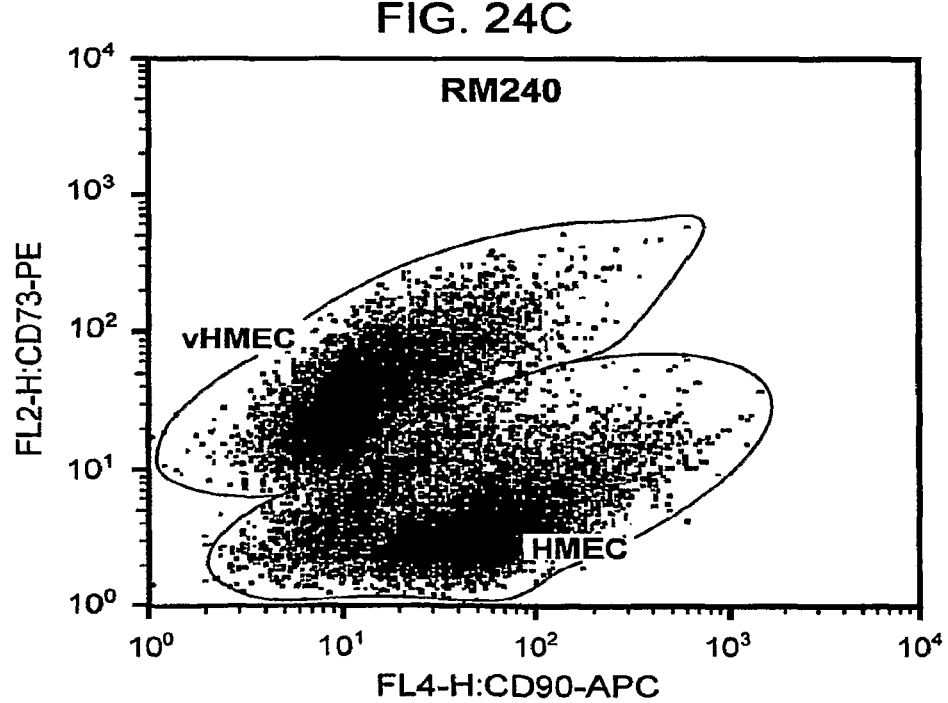

FIGS. 24A-C: (A) Histogram of flow cytometric analysis of CD73, CD90, CD138, Notch receptor-3, and p16 expression on vHMEC and HMEC is shown. Cultured vHMEC and HMEC from matched mammary reduction individual were trypsinized to single cells, incubated with anti-CD73, -CD90-APC, -CD138-FITC, Notch receptor-3-FITC, or -p16-PE antibodies, and analyzed by flow cytometry. (B) Immunocytochemistry of vHMEC and HMEC with anti-CD73 and anti-CD90 antibodies. Cells were grown on coverslips, fixed, and stained with anti-CD73 and -CD90 antibodies followed by anti-mouse-FITC secondary antibodies, and fluorescent signal was visualized by confocal microscopy. Cell nuclei were stained with Hoechst dye; and CD73 and CD90 expression was detected using antibodies. (C) Cell distribution of vHMEC and HMEC co-stained with anti-CD73 and -CD90 antibodies. Cultured vHMEC and HMEC from matched mammary reduction individual were trypsinized to single cells, incubated with anti-CD73-PE and -CD90-APC antibodies, and analyzed by flow cytometry.

Since the markers CD73 and CD90 distinguish the variant population in cultured cells, the markers were applied to mammary tissues that have not subjected to culturing conditions. Mammary tissue from five individuals were processed as described in (1) and further digested to single cells. Cells were incubated with antibodies to ESA (to identify epithelial cells), CD73, and CD90; and sorted by flow cytometry. Cells were gated as indicated and isolated.

To determine whether the isolated cells contained the distinguishing characteristic of vHMEC, methylation of the p16 promoter, methylation-specific PCR was performed on the various gated cells. 10,000 cells were isolated from each CD73CD90 fraction and diluted the cells into 5×10$^5$ carrier cells, HeLa cells. Genomic DNA was prepared, bisulfate converted, and subjected to methylation specific PCR. Methylation of the p16 promoter was detected in cell fractions with CD73+ epithelial cells, but not in bulk epithelial cell populations.

To determine if gated populations proliferated in a manner similar to that of vHMEC or HMEC, different sorted fractions were subjected to culturing. CD73+ cells grew for an extended time under conditions where the bulk population encountered a proliferative arrest. This evaluation was conducted with cells from 4 individuals.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

In addition to the items above, the following particular options are set forth:

1. An array of a plurality of distinct binding agents displayed on a surface of a solid support, wherein each of said binding agents comprises at least a specific epitope binding domain of an antibody that specifically binds a target protein that is differentially expressed in a pre-cancerous epithelial cell, wherein said target protein is selected from COX-2, Ki67, p16, CD73, CD138, notch receptor-3, CD90, BMI-1, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.
2. The array of 1, wherein said target protein is selected from COX-2, Ki67, and p16.
3. The array of 1, wherein said target protein is selected from CD73, CD138, notch receptor-3, CD90, BMI-1, and cyclooxygenase-2.
4. The array of 1, wherein the array comprises a binding agent that specifically binds CD73 and a binding agent that specifically binds CD90.
5. A set of distinct protein-binding agents, wherein each of said protein-binding agents comprises at least a specific epitope binding domain of an antibody that specifically binds a target protein that is differentially expressed in a pre-cancerous epithelial cell, wherein said target protein is selected from CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.
6. The set of 5, wherein each of said protein-binding agents comprises a detectable label.
7. The set of 6, wherein the detectable label is selected from gold, a fluorescent protein, a chromogenic protein, a fluorescent dye, an enzyme, and biotin.
8. The set of 7, wherein the fluorescent protein is a green fluorescent protein, a red fluorescent protein, a yellow fluorescent protein, or a blue fluorescent protein.
9. The set of 5, wherein said target protein is a cell surface protein.
10. A method of detecting a pre-cancerous mammary epithelial cell in a sample, the method comprising detecting one or more target proteins that are differentially expressed in a pre-cancerous epithelial cell.
11. The method of 10, wherein the one or more target proteins are selected from CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, TRF2, activin, and MEK1/2.
12. The method of 10, wherein the one or more target proteins is selected from COX-2, Ki67, and p16.

13. The method of 10, wherein the one or more target proteins are selected from CD73, CD138, notch receptor-3, CD90, BMI-1, and cyclooxygenase-2.
14. The method of 10, wherein the one or more target proteins are CD73 and CD90.
15. A method of determining the risk that a pre-cancerous mammary epithelial cell will become cancerous, the method comprising detecting one or more targeted proteins that are differentially expressed in a pre-cancerous epithelial cell.
16. The method of 15, wherein the one or more target proteins are selected from CD73, CD138, notch receptor-3, CD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.
17. The method of 15, wherein the one or more target proteins are selected from COX-2, Ki67, and p16.
18. The method of 15, wherein the one or more target proteins are selected from CD73, CD138, notch receptor-3, CD90, BMI-1, and cyclooxygenase-2.
19. The method of 15, wherein the one or more target proteins are CD73 and CD90.
20. A method of imaging a pre-cancerous mammary epithelial cell in an individual, the method comprising administering to the individual a detectably labeled antibody reagent that binds specifically to a target protein that is differentially expressed in a pre-cancerous mammary epithelial cell; and detecting binding of the antibody reagent to a pre-cancerous mammary epithelial cell in the individual.
21. A method of determining the risk that an individual will develop a malignant cancer, the method comprising detecting the level in a mammary epithelial cell obtained from the individual of a target polypeptide that is differentially expressed in a pre-cancerous mammary epithelial cell.
22. The method of 21, wherein the individual has been diagnosed with low-grade ductal carcinoma in situ.
23. The method of 21, wherein the individual has been diagnosed with high-grade ductal carcinoma in situ.
24. The method of 21, wherein the individual has been diagnosed as having a benign breast biopsy.
25. The method of 21, wherein the individual has been previously determined to be at high risk of developing a malignant cancer.
26. A method of detecting a pre-cancerous epithelial cell in an individual, the method comprising detecting a methylation status of a p16 promoter in the genome of an epithelial cell in a sample obtained from the individual, wherein the methylation status provides an indication of a pre-cancerous state of the epithelial cell.
27. An isolated, immortalized variant human mammary epithelial cell (vHMEC), wherein the vHMEC is CD73$^+$, and wherein the vHMEC is genetically modified to comprise a nucleic acid comprising a nucleotide sequence encoding an oncogene.
28. The isolated, immortalized vHMEC of 27, wherein the oncogene is v-Ha-ras.
29. The isolated, immortalized vHMEC of 28, wherein the nucleotide sequence encoding the oncogene is operably linked to a constitutive promoter.
30. The isolated, immortalized vHMEC of 27, wherein the vHMEC is further genetically modified with a nucleic acid comprising a nucleotide sequence encoding a protein that provides a detectable signal.
31. A method of detecting an effect of a component of stroma on tumor progression in a human mammary epithelial cell (HMEC), the method comprising:
a) contacting a test stomal component in vitro with an immortalized variant HMEC (vHMEC) according to 27; and
b) determining the effect, if any, of the test stromal component on a cell characteristic of the immortalized vHMEC,
wherein a test stromal component that induces a cell characteristic change in the immortalized vHMEC that is indicative of tumor progression indicates that the test stromal component has potential to induce tumor progression in an HMEC.
32. The method of 31, wherein the test stromal component is a fibroblast.
33. The method of 31, wherein the cell characteristic is a morphological change.
34. The method of 31, wherein the cell characteristic is acquisition of a mesenchymal feature.
35. The method of 31, wherein the cell characteristic is increased motility.
36. A method of isolating a variant human mammary epithelial cell (vHMEC) from a mixed cell population comprising a vHMEC, the method comprising:
a) contacting a mixed cell population comprising a vHMEC with an antibody specific for CD73, wherein the antibody binds to CD73 present on the surface of the vHMEC, forming a complex between the anti-CD73 antibody and the vMEC; and
b) separating the complex from the sample.
37. An array of a plurality of distinct nucleic acid binding agents displayed on a surface of a solid support, wherein each of said nucleic acid binding agents comprises a nucleotide sequence that specifically binds a target mRNA that is differentially expressed in a pre-cancerous epithelial cell, wherein said target mRNA is selected from CD73, CD138, notch receptor-3, CDD90, BMI-1, COX-2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.
38. A method of imaging a pre-cancerous mammary epithelial cell in an individual, the method comprising:
detecting in the individual a pre-cancerous mammary epithelial cell that has been labeled with an agent that provides for selective labeling of a cell that exhibits altered metabolism.
39. The method of 38, wherein said detecting comprises magnetic resonance imaging, positron emission tomography, or magnetic resonance imaging.

What is claimed is:

1. A method of treating breast cancer in a subject, comprising:
   collecting a biological sample from a subject having at least one of ductal carcinoma in situ (DCIS) or atypical ductal hyperplasias (ADH);
   detecting a mammary epithelial cell signature for the biological sample by contacting the biological sample with a composition comprising at least three detection reagents, wherein the at least three detection reagents comprise:
      a first detection reagent that binds to a first mammary epithelial cell structure, the first mammary epithelial cell structure selected from the group consisting of a p16 protein and an mRNA encoding the p16 protein, wherein the first detection reagent comprises an antibody, or a nucleic acid;
      a second detection reagent that binds to a second mammary epithelial cell structure, the second mammary epithelial cell structure selected from the group consisting of a Ki67 protein and an mRNA encoding the Ki67 protein, wherein the second detection reagent comprises an antibody, or a nucleic acid; and
      a third detection reagent that binds to a third mammary epithelial cell structure, the third mammary epithelial cell structure selected from the group consisting of a COX-2 protein and an mRNA encoding the COX-2 protein, wherein the third detection reagent comprises an antibody, or a nucleic acid,
   wherein each of the first, second and third detection reagents comprises a detectable label, and wherein the detectable labels of the first, second, and third detection reagents are different from each other;
   upon determining that the detected mammary epithelial cell signature comprises an elevated level of expression of each of the first, second and third mammary epithelial cell structures compared to respective control levels of expression of the first, second and third mammary epithelial cell structures, providing a treatment to the subject, wherein the treatment comprises:
      a) lumpectomy with an additional therapy; or
      b) mastectomy.

2. The method of claim 1, wherein the detectable label is selected from gold, a fluorescent protein, a chromogenic protein, a fluorescent dye, an enzyme, a biotin, a radioisotope and any combinations thereof.

3. The method of claim 1, wherein the biological sample is selected from the group consisting of a living cell, a dead cell, any non-cellular liquid samples comprising nipple aspirate fluid, and a lavage sample, and any combinations thereof.

4. The method of claim 1, wherein the biological sample comprises a mammary tissue sample.

5. The method of claim 1, wherein the first detection reagent comprises an antibody that binds to the p16 protein, and wherein the second detection reagent comprises an antibody that binds to the Ki67 protein.

6. The method of claim 1, wherein the first detection reagent comprises an antibody that binds to the p16 protein, wherein the second detection reagent comprises an antibody that binds to the Ki67 protein, and wherein the third detection reagent comprises an antibody that binds to the COX-2 protein.

7. The method of claim 1, wherein the first detection reagent comprises an antibody that binds to the p16 protein, and wherein the third detection reagent comprises an antibody that binds to the COX-2 protein.

8. The method of claim 1, wherein the second detection reagent comprises an antibody that binds to the Ki67 protein, and wherein the third detection reagent comprises an antibody that binds to the COX-2 protein.

9. The method of claim 1, wherein the at least three detection reagents consist essentially of the first, second and third detection reagents.

10. The method of claim 1, wherein the at least three detection reagents consist of the first, second and third detection reagents.

11. A method of treating breast cancer in a subject, comprising:
    collecting a biological sample from a subject having at least one of ductal carcinoma in situ (DCIS) or atypical ductal hyperplasias (ADH);
    detecting a mammary epithelial cell signature for the biological sample by contacting the biological sample with a composition comprising at least three detection reagents, wherein the at least three detection reagents, comprise:
       a first detection reagent that binds to a first mammary epithelial cell structure, the first mammary epithelial cell structure selected from the group consisting of a p16 protein and an mRNA encoding the p16 protein, wherein the first detection reagent comprises an antibody, or a nucleic acid;
       a second detection reagent that binds to a second mammary epithelial cell structure, the second mammary epithelial cell structure selected from the group consisting of a Ki67 protein and an mRNA encoding the Ki67 protein, wherein the second detection reagent comprises an antibody, or a nucleic acid; and
       a third detection reagent that binds to a third mammary epithelial cell structure, the third mammary epithelial cell structure selected from the group consisting of a COX-2 protein and an mRNA encoding the COX-2 protein, wherein the third detection reagent comprises an antibody, or a nucleic acid,
    wherein each of the first, second and third detection reagents comprises a detectable label, and wherein the detectable labels of the first, second, and third detection reagents are different from each other; and
    treating the subject with lumpectomy without additional therapy upon determining that the detected mammary epithelial cell signature comprises a reduced level of expression of at least one of the first, second and third mammary epithelial cell structures compared to respective control levels of expression of the first, second and third mammary epithelial cell structures.

12. The method of claim 11, wherein the detectable label is selected from gold, a fluorescent protein, a chromogenic protein, a fluorescent dye, an enzyme, a biotin, a radioisotope and any combinations thereof.

13. The method of claim 11, wherein the biological sample is selected from the group consisting of a living cell, a dead cell, any non-cellular liquid samples comprising nipple aspirate fluid, and a lavage sample, and any combinations thereof.

14. The method of claim 11, wherein the biological sample comprises a mammary tissue sample.

15. The method of claim 11, wherein the first detection reagent comprises an antibody that binds to the p16 protein, and wherein the second detection reagent comprises an antibody that binds to the Ki67 protein.

16. The method of claim 11, wherein the first detection reagent comprises an antibody that binds to the p16 protein, wherein the second detection reagent comprises an antibody that binds to the Ki67 protein, and wherein the third detection reagent comprises an antibody that binds to the COX-2 protein.

17. The method of claim 11, wherein the first detection reagent comprises an antibody that binds to the p16 protein, and wherein the third detection reagent comprises an antibody that binds to the COX-2 protein.

18. The method of claim 11, wherein the second detection reagent comprises an antibody that binds to the Ki67 protein, and wherein the third detection reagent comprises an antibody that binds to the COX-2 protein.

19. The method of claim 11, wherein the at least three detection reagents consist essentially of the first, second and third detection reagents.

20. The method of claim 11, wherein the at least three detection reagents consist of the first, second and third detection reagents.

21. A method of treating a subject having DCIS, the method comprising administering a treatment to a subject having DCIS and determined to have a mammary epithelial cell signature comprising an elevated level of expression of each of p16, Ki67, and COX-2 compared to respective control levels of expression of p16, Ki67, and COX-2, wherein the treatment comprises: a) a lumpectomy with an additional therapy; or b) a mastectomy.

* * * * *

SEQUENCE LISTING

<160> NUMBER OF SEQ ID NOS: 84

<210> SEQ ID NO 1

```
<211> LENGTH: 75
<212> TYPE: RNA
<213> ORGANISM: Homo sapiens

<400> SEQUENCE: 1 uggaguggggg gggcaggagg ggcucaggga gaaagugcau acagcccug gcccucucug      60 cccuuccguc cccug                                                      75

<210> SEQ ID NO 2
<211> LENGTH: 22
<212> TYPE: RNA
<213> ORGANISM: Homo sapiens

<400> SEQUENCE: 2
cuggcccucu cugcccuucc gu                                              22

<210> SEQ ID NO 3
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 3
acggaagggc agagagggcc ag                                              22

<210> SEQ ID NO 4
<211> LENGTH: 84
<212> TYPE: RNA
<213> ORGANISM: Homo sapiens

<400> SEQUENCE: 4 acugucggu gauuuaggua guuuccuguu guugggaucc accuuucucu cgacagcacg      60
acacugccuu cauuacuuca guug                                            84

<210> SEQ ID NO 5
<211> LENGTH: 21
<212> TYPE: RNA
<213> ORGANISM: Homo sapiens

<400> SEQUENCE: 5
uagguaguuu ccuguuguug g                                              21

<210> SEQ ID NO 6
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 6
ccaacaacag gaaactacct a                                              21

<210> SEQ ID NO 7
<211> LENGTH: 71
<212> TYPE: RNA
<213> ORGANISM: Homo sapiens

<400> SEQUENCE: 7
gcgacuguaa acauccucga cuggaagcug ugaagccaca gaugggcuuu cagucggaug      60
uuugcagcug c                                                          71
```

```
<210> SEQ ID NO 8
<211> LENGTH: 22
<212> TYPE: RNA
<213> ORGANISM: Homo sapiens

<400> SEQUENCE: 8
uguaaacauc cucgacugga ag                                              22

<210> SEQ ID NO 9
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 9
cttccagtcg aggatgttta ca                                              22

<210> SEQ ID NO 10
<211> LENGTH: 88
<212> TYPE: RNA
<213> ORGANISM: Homo sapiens

<400> SEQUENCE: 10
ugcgcuccuc ucagucccug agacccuaac uugugauguu uaccguuuaa auccacgggu     60
uaggcucuug ggagcugcga gucgugcu                                        88

<210> SEQ ID NO 11
<211> LENGTH: 22
<212> TYPE: RNA
<213> ORGANISM: Homo sapiens

<400> SEQUENCE: 11
ucccugagac ccuaacuugu ga                                              22

<210> SEQ ID NO 12
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 12
tcacaagtta gggtctcagg gt                                              22

<210> SEQ ID NO 13
<211> LENGTH: 92
<212> TYPE: RNA
<213> ORGANISM: Homo sapiens

<400> SEQUENCE: 13
gggcagucuu ugcuacugua aacauccuug acuggaagcu guaagguguu cagaggagcu     60
uucagucgga uguuuacagc ggcaggcugc ca                                   92

<210> SEQ ID NO 14
<211> LENGTH: 22
<212> TYPE: RNA
<213> ORGANISM: Homo sapiens

<400> SEQUENCE: 14
cuuucagucg gauguuuaca gc                                              22

<210> SEQ ID NO 15
```

```
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 15
gctgtaaaca tccgactgaa ag                                              22

<210> SEQ ID NO 16
<211> LENGTH: 82
<212> TYPE: RNA
<213> ORGANISM: Homo sapiens

<400> SEQUENCE: 16
ccugccgggg cuaaagugcu gacagugcag auaguggucc ucuccgugcu accgcacugu     60
ggguacuugc ugcuccagca gg                                              82

<210> SEQ ID NO 17
<211> LENGTH: 21
<212> TYPE: RNA
<213> ORGANISM: Homo sapiens

<400> SEQUENCE: 17
uaaagugcug acagugcaga u                                               21

<210> SEQ ID NO 18
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 18
atctgcactg tcagcacttt a                                               21

<210> SEQ ID NO 19
<211> LENGTH: 73
<212> TYPE: RNA
<213> ORGANISM: Homo sapiens

<400> SEQUENCE: 19
cagggugugu gacugguuga ccagagggggc augcacugug uucacccugu gggccaccua    60
gucaccaacc cuc                                                        73

<210> SEQ ID NO 20
<211> LENGTH: 21
<212> TYPE: RNA
<213> ORGANISM: Homo sapiens

<400> SEQUENCE: 20
ugugacuggu ugaccagagg g                                               21

<210> SEQ ID NO 21
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 21
ccctctggtc aaccagtcac a                                               21
```

```
<210> SEQ ID NO 22
<211> LENGTH: 94
<212> TYPE: RNA
<213> ORGANISM: Homo sapiens

<400> SEQUENCE: 22
agagcaucgu gcuugaccuu ccacgcucuc guguccacua gcaggcaggu uuucugacac      60
aggcugcgga auucaggaca gugcaucaug gaga                                  94

<210> SEQ ID NO 23
<211> LENGTH: 19
<212> TYPE: RNA
<213> ORGANISM: Homo sapiens

<400> SEQUENCE: 23
aggcugcgga auucaggac                                                   19

<210> SEQ ID NO 24
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 24
gtcctgaatt ccgcagcct                                                   19

<210> SEQ ID NO 25
<211> LENGTH: 84
<212> TYPE: RNA
<213> ORGANISM: Homo sapiens

<400> SEQUENCE: 25
ugugcagugg gaagggggc cgauacacug uacgagagug aguagcaggu cucacaguga       60
accggucucu uucccuacug uguc                                             84

<210> SEQ ID NO 26
<211> LENGTH: 22
<212> TYPE: RNA
<213> ORGANISM: Homo sapiens

<400> SEQUENCE: 26
ucacagugaa ccggucucuu uc                                               22

<210> SEQ ID NO 27
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 27
gaaagagacc ggttcactgt ga                                               22

<210> SEQ ID NO 28
<211> LENGTH: 82
<212> TYPE: RNA
<213> ORGANISM: Homo sapiens

<400> SEQUENCE: 28
ugagcuguug gauucggggc cguagcacug ucugagaggu uuacauuucu cacagugaac      60
cggucucuuu uucagcugcu uc                                               82
```

```
<210> SEQ ID NO 29
<211> LENGTH: 22
<212> TYPE: RNA
<213> ORGANISM: Homo sapiens

<400> SEQUENCE: 29
ucacagugaa ccggucucuu uu                                               22

<210> SEQ ID NO 30
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 30
aaaagagacc ggttcactgt ga                                               22

<210> SEQ ID NO 31
<211> LENGTH: 94
<212> TYPE: RNA
<213> ORGANISM: Homo sapiens

<400> SEQUENCE: 31
gaguuugguu uuguuggggu uuguucuagg uaugguccca gggaucccag aucaaaccag      60
gccccugggc cuauccuaga accaaccuaa gcuc                                  94

<210> SEQ ID NO 32
<211> LENGTH: 21
<212> TYPE: RNA
<213> ORGANISM: Homo sapiens

<400> SEQUENCE: 32
gccccugggc cuauccuaga a                                                21

<210> SEQ ID NO 33
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 33
ttctaggata ggcccagggg c                                                21

<210> SEQ ID NO 34
<211> LENGTH: 87
<212> TYPE: RNA
<213> ORGANISM: Homo sapiens

<400> SEQUENCE: 34
ucucaggcug ugacccucua aagggaagcg cuuucugugg ucagaaagaa aagcaagugc      60
uuccuuuuag aggguuaccg uuuggga                                          87

<210> SEQ ID NO 35
<211> LENGTH: 22
<212> TYPE: RNA
<213> ORGANISM: Homo sapiens

<400> SEQUENCE: 35
aagugcuucc uuuuagaggg uu                                               22
```

```
<210> SEQ ID NO 36
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 36
aaccctctaa aaggaagcac tt                                              22

<210> SEQ ID NO 37
<211> LENGTH: 63
<212> TYPE: RNA
<213> ORGANISM: Homo sapiens

<400> SEQUENCE: 37
aagaaauggu uuaccguccc acauacauuu ugaauaugua uguggaugg uaaaccgcuu      60 cuu                                                                   63

<210> SEQ ID NO 38
<211> LENGTH: 22
<212> TYPE: RNA
<213> ORGANISM: Homo sapiens

<400> SEQUENCE: 38 uauguggau gguaaaccgc uu                                               22

<210> SEQ ID NO 39
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 39
aagcggttta ccatcccaca ta                                              22

<210> SEQ ID NO 40
<211> LENGTH: 88
<212> TYPE: RNA
<213> ORGANISM: Homo sapiens

<400> SEQUENCE: 40
ucccaugcug ugaccucucua gaggaagcac uuucuguuug uugucugaga aaaacaaag     60 ugcuucccuu uagaguuacu guuuggga                                        88

<210> SEQ ID NO 41
<211> LENGTH: 22
<212> TYPE: RNA
<213> ORGANISM: Homo sapiens

<400> SEQUENCE: 41
acaaagugcu ucccuuuaga gu                                              22

<210> SEQ ID NO 42
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 42
actctaaagg gaagcacttt ga                                              22
```

```
<210> SEQ ID NO 43
<211> LENGTH: 74
<212> TYPE: RNA
<213> ORGANISM: Homo sapiens

<400> SEQUENCE: 43 guguguccu acucaggaga guggcaauca cauguaauua ggugugauug aaaccucuaa      60
gaguggagua acac                                                      74

<210> SEQ ID NO 44
<211> LENGTH: 23
<212> TYPE: RNA
<213> ORGANISM: Homo sapiens

<400> SEQUENCE: 44
uacucaggag aguggcaauc aca                                             23

<210> SEQ ID NO 45
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 45
tgtgattgcc actctcctga gta                                             23

<210> SEQ ID NO 46
<211> LENGTH: 87
<212> TYPE: RNA
<213> ORGANISM: Homo sapiens

<400> SEQUENCE: 46
accgcaggga aaaugaggga cuuuugggggg cagaugaguguu uccauuccac uaucauaaug    60
ccccuaaaaa uccuuauugc ucuugca                                         87

<210> SEQ ID NO 47
<211> LENGTH: 22
<212> TYPE: RNA
<213> ORGANISM: Homo sapiens

<400> SEQUENCE: 47
uaaugccccu aaaaauccuu au                                              22

<210> SEQ ID NO 48
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 48
ataaggattt tagggggcat ta                                              22

<210> SEQ ID NO 49
<211> LENGTH: 90
<212> TYPE: RNA
<213> ORGANISM: Homo sapiens

<400> SEQUENCE: 49
ucccaugcug ugaccucucua gaggaagcac uuucuguuug uugucugaga aaaacaaag      60 ugcuucccuu uagaguguua ccguuuggga                                      90
```

```
<210> SEQ ID NO 50
<211> LENGTH: 24
<212> TYPE: RNA
<213> ORGANISM: Homo sapiens

<400> SEQUENCE: 50
acaaagugcu ucccuuuaga gugu                                              24

<210> SEQ ID NO 51
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 51
acactctaaa gggaagcact ttga                                              24

<210> SEQ ID NO 52
<211> LENGTH: 83
<212> TYPE: RNA
<213> ORGANISM: Homo sapiens

<400> SEQUENCE: 52
cugacuaugc cuccccgcau ccccuagggc auugguguaa agcuggagac ccacugcccc       60
aggugcugcu gggggguugua guc                                              83

<210> SEQ ID NO 53
<211> LENGTH: 22
<212> TYPE: RNA
<213> ORGANISM: Homo sapiens

<400> SEQUENCE: 53
ccacugcccc aggugcugcu gg                                                22

<210> SEQ ID NO 54
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 54
ccagcagcac ctggggcagt gg                                                22

<210> SEQ ID NO 55
<211> LENGTH: 86
<212> TYPE: RNA
<213> ORGANISM: Homo sapiens

<400> SEQUENCE: 55
ugccagucuc uaggucccug agacccuuua accugugagg acauccaggg ucacagguga       60
gguucuuggg agccuggcgu cuggcc                                            86

<210> SEQ ID NO 56
<211> LENGTH: 23
<212> TYPE: RNA
<213> ORGANISM: Homo sapiens

<400> SEQUENCE: 56
ucccugagac ccuuuaaccu gug                                               23
```

```
<210> SEQ ID NO 57
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 57
cacaggttaa agggtctcag ggt                                            23

<210> SEQ ID NO 58
<211> LENGTH: 68
<212> TYPE: RNA
<213> ORGANISM: Homo sapiens

<400> SEQUENCE: 58
ccucuacuuu aacauggagg cacuugcugu gacaugacaa aaauaagugc uuccauguuu     60
gagugugg                                                             68

<210> SEQ ID NO 59
<211> LENGTH: 23
<212> TYPE: RNA
<213> ORGANISM: Homo sapiens

<400> SEQUENCE: 59
uaagugcuuc cauguuugag ugu                                            23

<210> SEQ ID NO 60
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 60
acactcaaac atggaagcac tta                                            23

<210> SEQ ID NO 61
<211> LENGTH: 87
<212> TYPE: RNA
<213> ORGANISM: Homo sapiens

<400> SEQUENCE: 61
ucucaagcug ugagucuaca aagggaagcc cuuucuguug ucuaaaagaa aagaaagugc     60
uucucuuugg uggguuacgg uuugaga                                        87

<210> SEQ ID NO 62
<211> LENGTH: 23
<212> TYPE: RNA
<213> ORGANISM: Homo sapiens

<400> SEQUENCE: 62
ucuacaaagg gaagcccuuu cug                                            23

<210> SEQ ID NO 63
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 63
cagaaagggc ttcccttgt aga                                             23
```

```
<210> SEQ ID NO 64
<211> LENGTH: 98
<212> TYPE: RNA
<213> ORGANISM: Homo sapiens

<400> SEQUENCE: 64
acgaauggcu augcacugca caacccuagg agagggugcc auucacauag acuauaauug      60
aauggcgcca cuaggguugu gcagugcaca accuacac                             98

<210> SEQ ID NO 65
<211> LENGTH: 23
<212> TYPE: RNA
<213> ORGANISM: Homo sapiens

<400> SEQUENCE: 65
aauggcgcca cuaggguugu gca                                             23

<210> SEQ ID NO 66
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 66
tgcacaaccc tagtggcgcc att                                             23

<210> SEQ ID NO 67
<211> LENGTH: 87
<212> TYPE: RNA
<213> ORGANISM: Homo sapiens

<400> SEQUENCE: 67
ucucaggcug ucguccucua gagggaagca cuuucuguug ucugaaagaa aagaaagugc      60
uuccuuuuag aggguuaccg uuugaga                                         87

<210> SEQ ID NO 68
<211> LENGTH: 23
<212> TYPE: RNA
<213> ORGANISM: Homo sapiens

<400> SEQUENCE: 68
aaagugcuuc cuuuuagagg guu                                             23

<210> SEQ ID NO 69
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 69
aaccctctaa aaggaagcac ttt                                             23

<210> SEQ ID NO 70
<211> LENGTH: 94
<212> TYPE: RNA
<213> ORGANISM: Homo sapiens

<400> SEQUENCE: 70
uggggugucu gugcuauggc agcccuagca cacagauacg cccagagaaa gccugaacgu      60
```
ugggcguauc uguaugcuag ggcugcugua acaa    94

<210> SEQ ID NO 71
<211> LENGTH: 19
<212> TYPE: RNA
<213> ORGANISM: Homo sapiens

<400> SEQUENCE: 71
ugggcguauc uguaugcua    19

<210> SEQ ID NO 72
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 72
tagcatacag atacgccca    19

<210> SEQ ID NO 73
<211> LENGTH: 96
<212> TYPE: RNA
<213> ORGANISM: Homo sapiens

<400> SEQUENCE: 73
uagauugagg aagggcuga gugguaggcg gugcugcugu gcucugauga agacccaugu    60
ggcuagcaac agcgcuuacc uuuugucucu gggucc    96

<210> SEQ ID NO 74
<211> LENGTH: 21
<212> TYPE: RNA
<213> ORGANISM: Homo sapiens

<400> SEQUENCE: 74
ggcuagcaac agcgcuuacc u    21

<210> SEQ ID NO 75
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 75
aggtaagcgc tgttgctagc c    21

<210> SEQ ID NO 76
<211> LENGTH: 97
<212> TYPE: RNA
<213> ORGANISM: Homo sapiens

<400> SEQUENCE: 76
cagaucucag acaucucggg gaucaucaug ucacgagaua ccagugugca cuugugacag    60
auugauaacu gaaaggucug ggagccacuc aucuuca    97

<210> SEQ ID NO 77
<211> LENGTH: 22
<212> TYPE: RNA
<213> ORGANISM: Homo sapiens

<400> SEQUENCE: 77
ucggggauca ucaugucacg ag    22

<210> SEQ ID NO 78
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 78
ctcgtgacat gatgatcccc ga                                          22

<210> SEQ ID NO 79
<211> LENGTH: 95
<212> TYPE: RNA
<213> ORGANISM: Homo sapiens

<400> SEQUENCE: 79
uccccucugg cggcugcgca cgggccgugu gagcuauugc gguggggcugg ggcagaugac    60 gcgugcgccg gccggccgcc gaggggcuac cguuc                               95

<210> SEQ ID NO 80
<211> LENGTH: 20
<212> TYPE: RNA
<213> ORGANISM: Homo sapiens

<400> SEQUENCE: 80
gcgugcgccg gccggccgcc                                             20

<210> SEQ ID NO 81
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 81
ggcggccggc cggcgcacgc                                             20

<210> SEQ ID NO 82
<211> LENGTH: 85
<212> TYPE: RNA
<213> ORGANISM: Homo sapiens

<400> SEQUENCE: 82
cgcuggcgac gggacauuau uacuuuuggu acgcgcugug acacuucaaa cucguaccgu    60
gaguaauaau gcgccgucca cggca                                          85

<210> SEQ ID NO 83
<211> LENGTH: 21
<212> TYPE: RNA
<213> ORGANISM: Homo sapiens

<400> SEQUENCE: 83
cauuauuacu uuugguacgc g                                           21

<210> SEQ ID NO 84
<211> LENGTH: 21
<212> TYPE: DNA
<213> ORGANISM: artificial sequence

```
<220> FEATURE:
<223> OTHER INFORMATION: synthetic oligonucleotide

<400> SEQUENCE: 84
cgcgtaccaa aagtaataat g                                          21
```